US011584789B2

(12) United States Patent
Chan-Hui et al.

(10) Patent No.: US 11,584,789 B2
(45) Date of Patent: Feb. 21, 2023

(54) MONOCLONAL ANTIBODIES DIRECTED AGAINST TRIMERIC FORMS OF THE HIV-1 ENVELOPE GLYCOPROTEIN WITH BROAD AND POTENT NEUTRALIZING ACTIVITY

(71) Applicants: Theraclone Sciences, Inc., Seattle, WA (US); International AIDS Vaccine Initiative, New York, NY (US); The Scripps Research Institute, La Jolla, CA (US)

(72) Inventors: Po-Ying Chan-Hui, Bellevue, WA (US); Steven Frey, Redmond, WA (US); Ole Olsen, Everett, WA (US); Jennifer Mitcham, Redmond, WA (US); Matthew Moyle, Redmond, WA (US); Sanjay K. Phogat, Frederick, MD (US); Dennis R. Burton, La Jolla, CA (US); Laura Marjorie Walker, San Diego, CA (US); Pascal Raymond Georges Poignard, San Diego, CA (US); Wayne Koff, Stony Brook, NY (US); Melissa Danielle De Jean De St. Marcel Simek-Lemos, Brooklyn, NY (US); Stephen Kaminsky, Bronx, NY (US)

(73) Assignees: INTERNATIONAL AIDS VACCINE INITIATIVE, INC., New York, NY (US); THE SCRIPPS RESEARCH INSTITUTE, La Jolla, CA (US); THERACLONE SCIENCES, INC., Seattle, WA (US)

( * ) Notice: Subject to any disclaimer, the term of this patent is extended or adjusted under 35 U.S.C. 154(b) by 268 days.

(21) Appl. No.: 17/082,322

(22) Filed: Oct. 28, 2020

(65) Prior Publication Data

US 2021/0040186 A1 Feb. 11, 2021

Related U.S. Application Data

(63) Continuation of application No. 16/513,859, filed on Jul. 17, 2019, now Pat. No. 10,865,234, which is a continuation of application No. 16/275,936, filed on Feb. 14, 2019, now Pat. No. 10,407,493, which is a continuation of application No. 15/918,343, filed on Mar. 12, 2018, now Pat. No. 10,239,934, which is a continuation of application No. 14/692,483, filed on Apr. 21, 2015, now Pat. No. 9,920,111, which is a continuation of application No. 12/726,245, filed on Mar. 17, 2010, now Pat. No. 9,051,362.

(60) Provisional application No. 61/285,664, filed on Dec. 11, 2009, provisional application No. 61/224,739, filed on Jul. 10, 2009, provisional application No. 61/165,829, filed on Apr. 1, 2009, provisional application No. 61/161,010, filed on Mar. 17, 2009.

(51) Int. Cl.
| | | |
|---|---|---|
| C07K 16/10 | (2006.01) |
| A61K 39/00 | (2006.01) |
| A61K 39/21 | (2006.01) |
| A61P 31/18 | (2006.01) |
| A61K 38/00 | (2006.01) |
| A61P 31/14 | (2006.01) |

(52) U.S. Cl.
CPC .......... *C07K 16/1045* (2013.01); *A61K 39/21* (2013.01); *A61P 31/14* (2018.01); *C07K 16/1063* (2013.01); *A61K 2039/505* (2013.01); *C07K 2317/56* (2013.01); *C07K 2317/565* (2013.01); *C07K 2317/76* (2013.01)

(58) Field of Classification Search
CPC .......... C07K 16/1063; C07K 2317/565; C07K 2317/76; A61K 2039/505; A61K 39/21
See application file for complete search history.

(56) References Cited

U.S. PATENT DOCUMENTS

| 6,815,201 B2 | 11/2004 | Pinter |
| 2007/0292390 A1 | 12/2007 | Dimitrov et al. |

OTHER PUBLICATIONS

Australian Examination Report dated Aug. 9, 2017, issued in Australian Application No. 2015234345.
European Search Report dated Oct. 9, 2017 issued in European Application No. 17173548.3.
Communication pursuant to Article 94(3) EPC dated Dec. 14, 2016, issued in European Application No. 10 722 810.8.

(Continued)

*Primary Examiner* — Barry A Chestnut
(74) *Attorney, Agent, or Firm* — Duane Morris LLP; Thomas J. Kowalski; Deborah L. Lu

(57) ABSTRACT

The invention provides a method for obtaining a broadly neutralizing antibody (bNab), including screening memory B cell cultures from a donor PBMC sample for neutralization activity against a plurality of HIV-1 species, cloning a memory B cell that exhibits broad neutralization activity; and rescuing a monoclonal antibody from that memory B cell culture. The resultant monoclonal antibodies are characterized by their ability to selectively bind epitopes from the Env proteins in native or monomeric form, as well as to inhibit infection of HIV-1 species from a plurality of clades. Compositions containing human monoclonal anti-HIV antibodies used for prophylaxis, diagnosis and treatment of HIV infection are provided. Methods for generating such antibodies by immunization using epitopes from conserved regions within the variable loops of gp120 are provided. Immunogens for generating anti-HIV1 bNAbs are also provided. Furthermore, methods for vaccination using suitable epitopes are provided.

31 Claims, 65 Drawing Sheets

Specification includes a Sequence Listing.

(56) References Cited

OTHER PUBLICATIONS

Brown, et al., Tolerance to single, but not multiple, amino acid replacements in antibody VH CDR2, Journal of Immunology (1996) 156:3285-3291.
Casadevall, et al., Immunoglobulin isotype influences affinity and specificity, PNAS (Jul. 2012) 109(31):12272-12273.
Center, et al., The Human Immunodeficiency Virus Type 1 gp120 V2 Domain Mediates gp41-Independent Intersubunit Contacts, Journal of Virology (May 2000) 74(10):4448-4455.
Fanning, et al., Development of the immunoglobulin repertoire, Clin. Immunol. Immunopath.,(1996) 79(1):1-14.
Koefoed, et al., Molecular characterization of the circulating anti-HIV-1 gp120-specific 8 cell repertoire using antibody phage display libraries generated from pre-selected HIV-1 gp120 binding PBLs, J. Immunol. Methods (2005) 297:187-201.
McKeating, et al., Characterization of Neutralizing Monoclonal Antibodies to Linear and Conformation-Dependent Epitopes within the First and Second Variable Domains of Human Immunodeficiency Virus Type 1 gp120, Journal of Virology (Aug. 1992) 67(8):4932-4944.
Moulard, et al., Broadly cross-reactive HIV-1-neutralizing human monoclonal Fab selected for binding to gp120-CD4-CCR5 comptexes. PNAS (May 2002) 99(10):6913-6918.
Pantophlet, et al., GP120: Target for neutralizing HIV-1 antibodies" Annual Review of Immunology (2006) 24:739-769.
Stiegler, et al., A potent cross-clade neutralizing human monoclonal antibody against a novel epitope on gp41 of human immunodeficiency virus type 1" AIDS Research and Human Retroviruses (Dec. 2001) 17(18):1757-1765.
Trkola, et al., Human monoclonal antibody 2G12 defines a distinctive neutralization epitope on the gp 120 glycoprotein of human immunodeficiency virus type 1, Journal of Virology (Feb. 1996) 70(2): 1100-1108.
Winkler, et al., Changing the antigen binding specificity by single point mutations of an anti-p24 (HIV-1) antibody. Journal of Virology (2000) 165:4505-4514.
Xiang, et al., Modification in framework region 1 results in a decreased affinity of chimeric anti-TAG72 antibody, Molecular Immunology (1991) 28(1-2):141-148.
Xiang, et al., Framework residues 71 and 93 of the chimeric 872.3 antibody are major determinants of the conformation of heavy-chain bypervariable loops, J. Mol. Biol.,(1995) 253:385-390.
Zhang, et al., Identification and Characterization of a New Cross-Reactive Human Immunodeficiency Virus Type 1-Neutralizing Human Monoclonal Antibody, Journal of Virology (Sep. 2004) 78(17):9233-9242.
Zhang, et al., Cross-reactive human immunodeficiency vims type 1-neutralizing human monoclonal antibody that recognizes a novel conformational epitope on gp41 and lacks reactivity against self-antigens, Journal of Virology (Jul. 2008) 82(14):6869-6879.
Zhang, et al., Novel Approaches for Identification of Broadly Cross-Reactive HIV-1 Neutralizing Human Monoclonal Antibodies and Improvement of Their Potency, Current Pharmaceutical Design (Jan. 2007) 13(2):203-212.
Johannes Scheid, et al., Broad diversity of neutralizing antibodies isolated from memory B cells in HIV-infected individuals, Nature (2009) vol. 458:636-640.

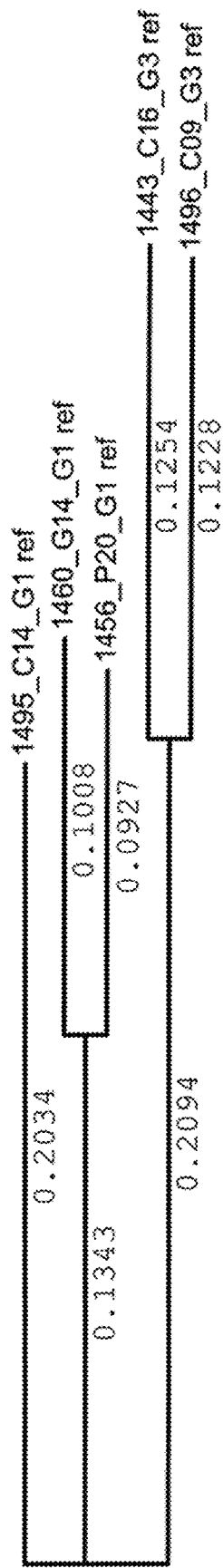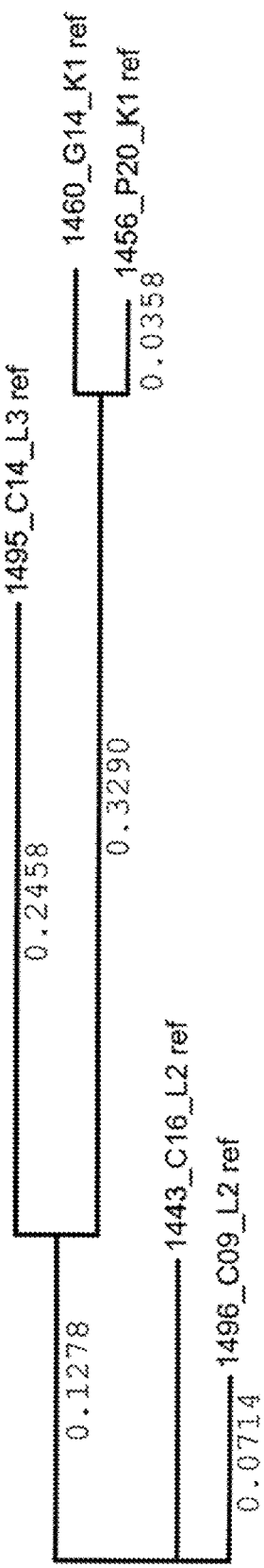
FIG. 1A  Heavy Chain Tree
FIG. 1B  Light Chain Tree

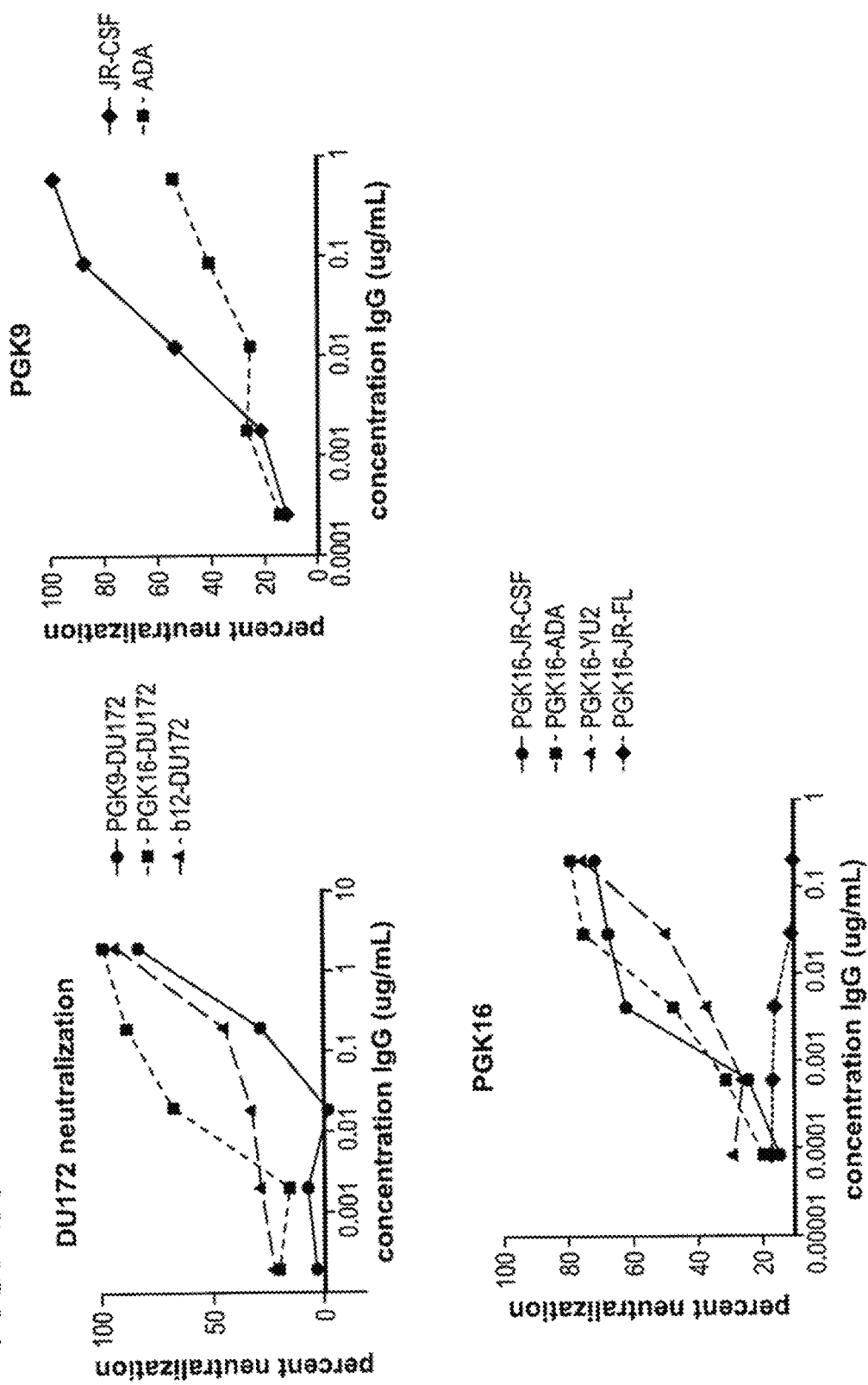
FIG. 4A  PG9 and PG16 Neutralization Assays

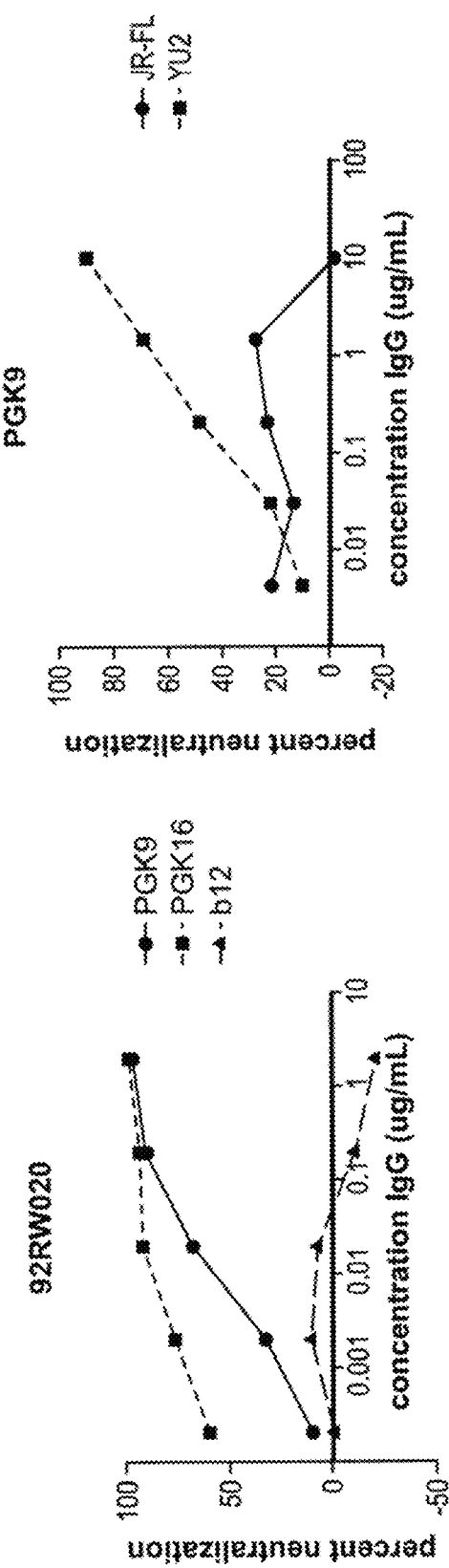

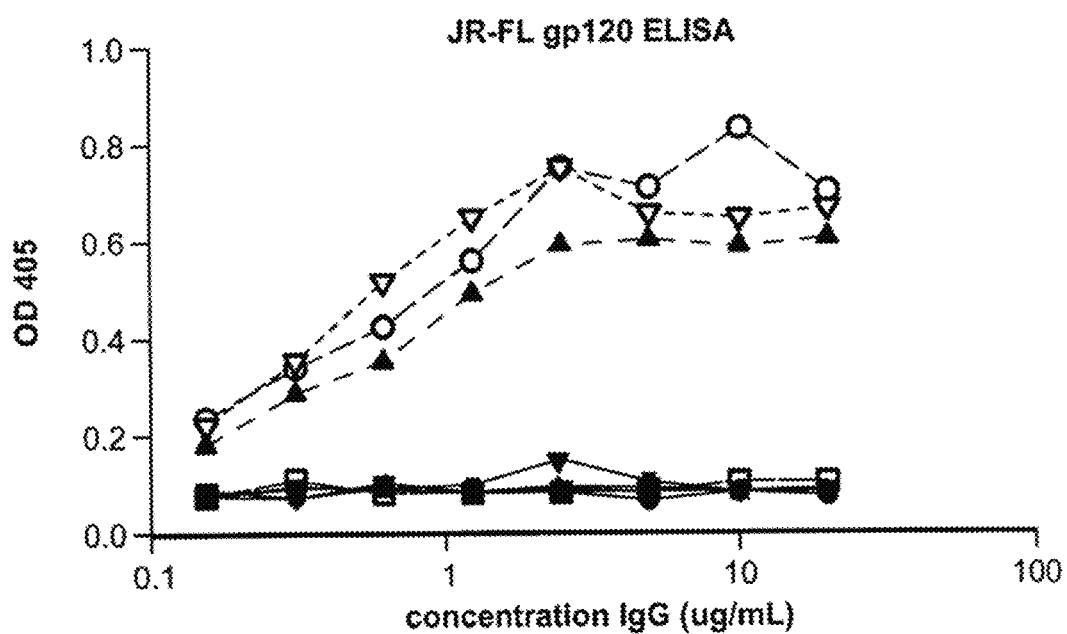

FIG. 6C
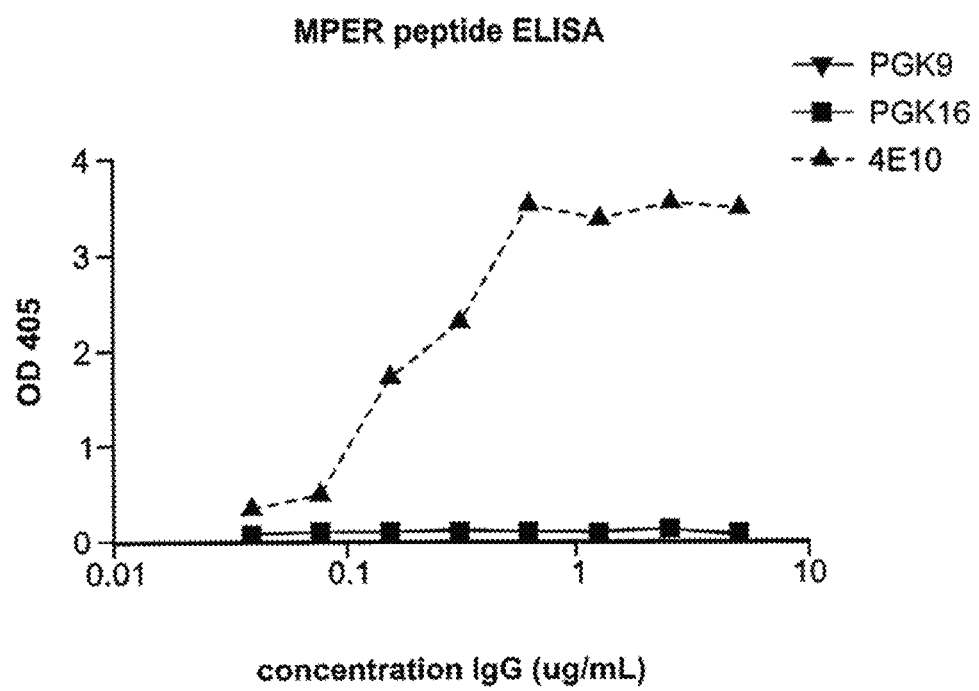
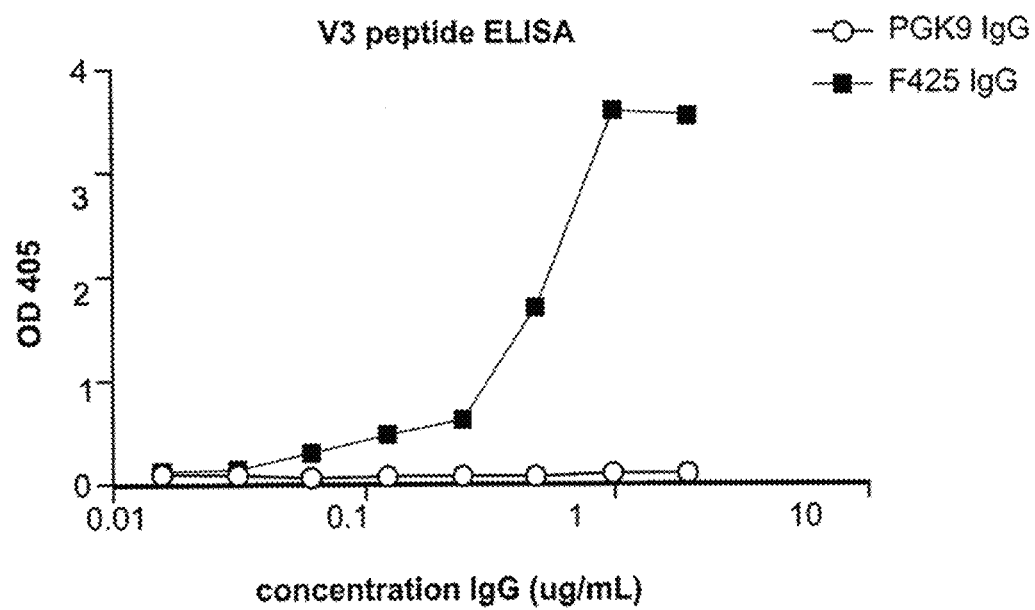

FIG. 8A
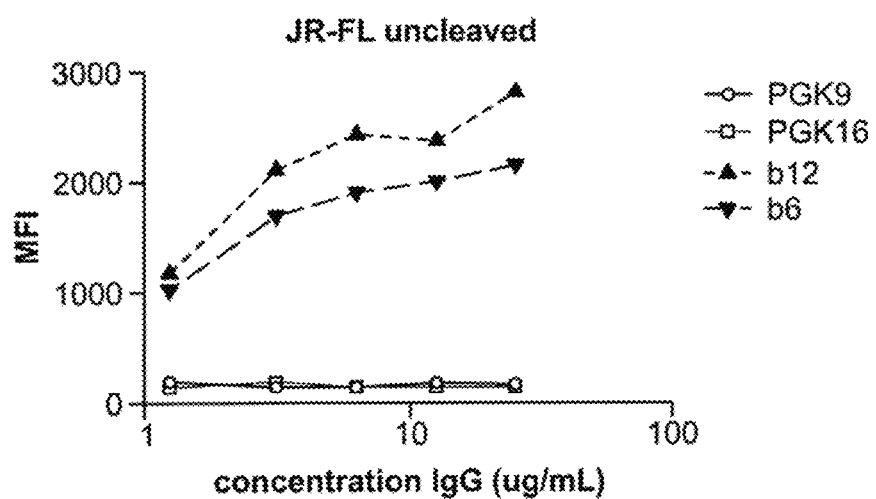
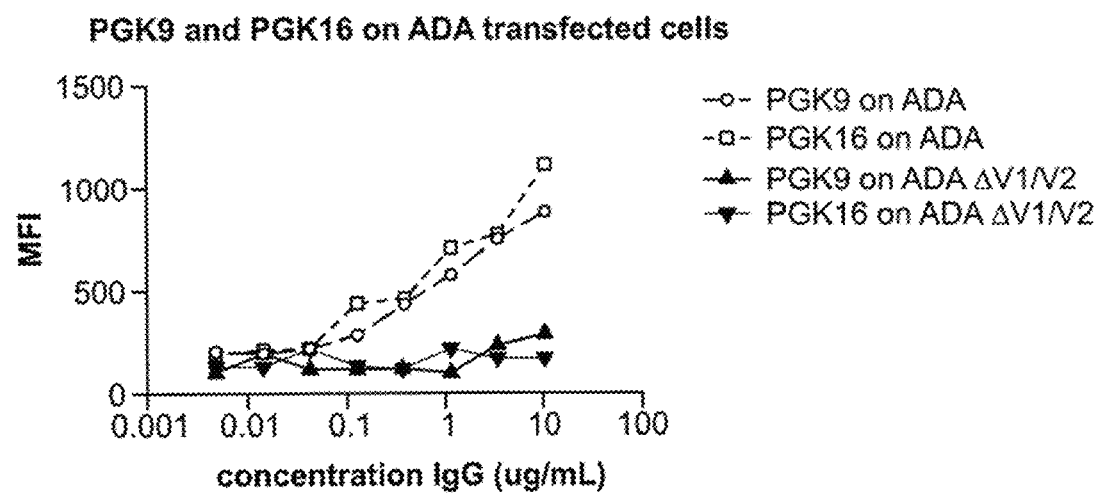

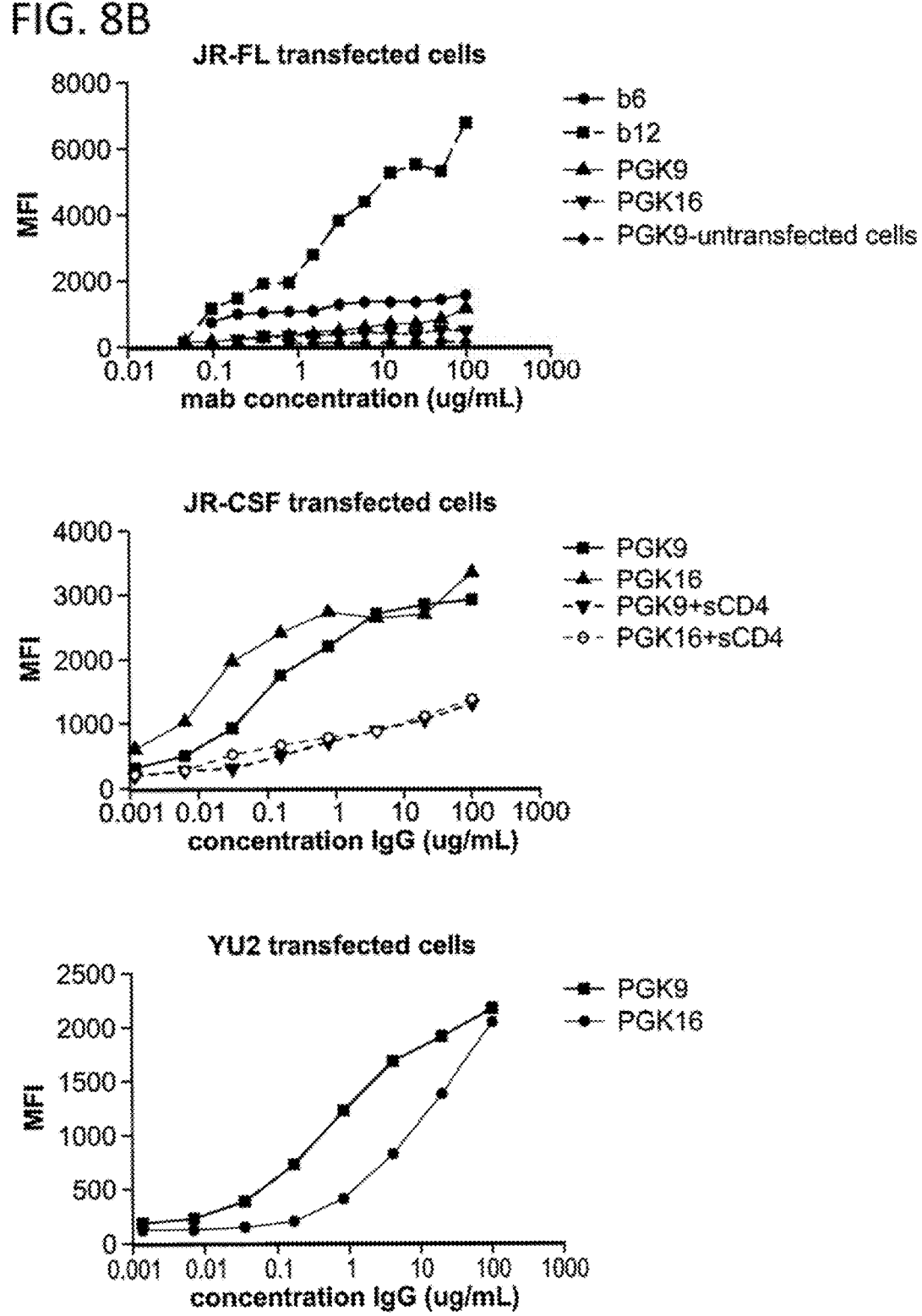

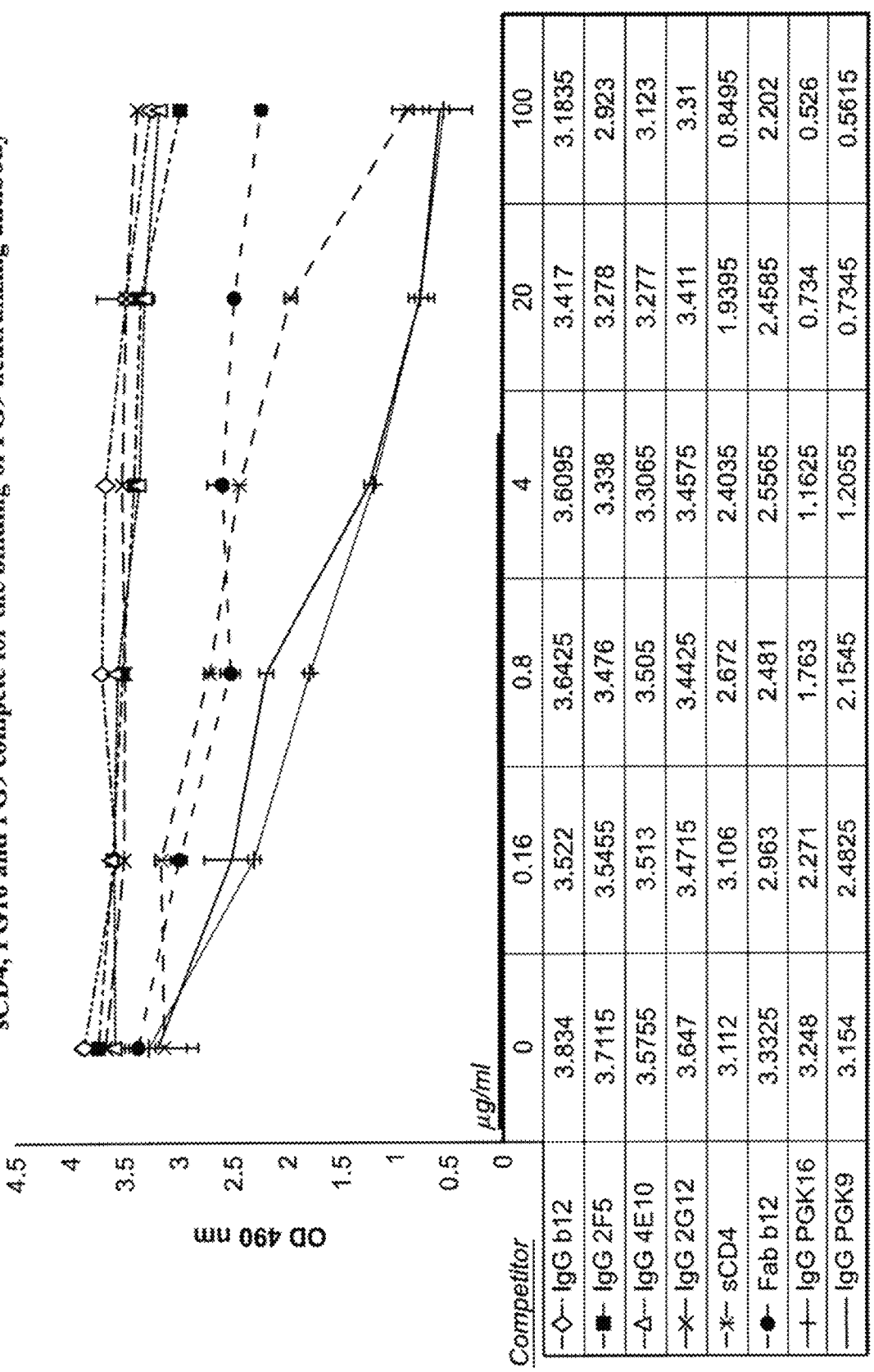

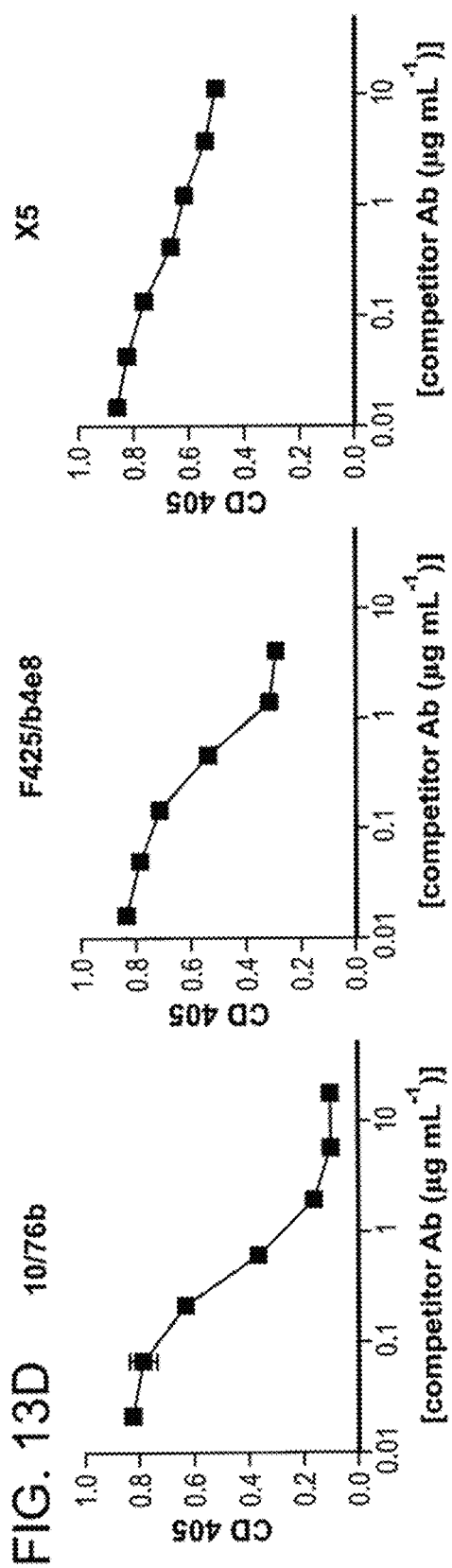
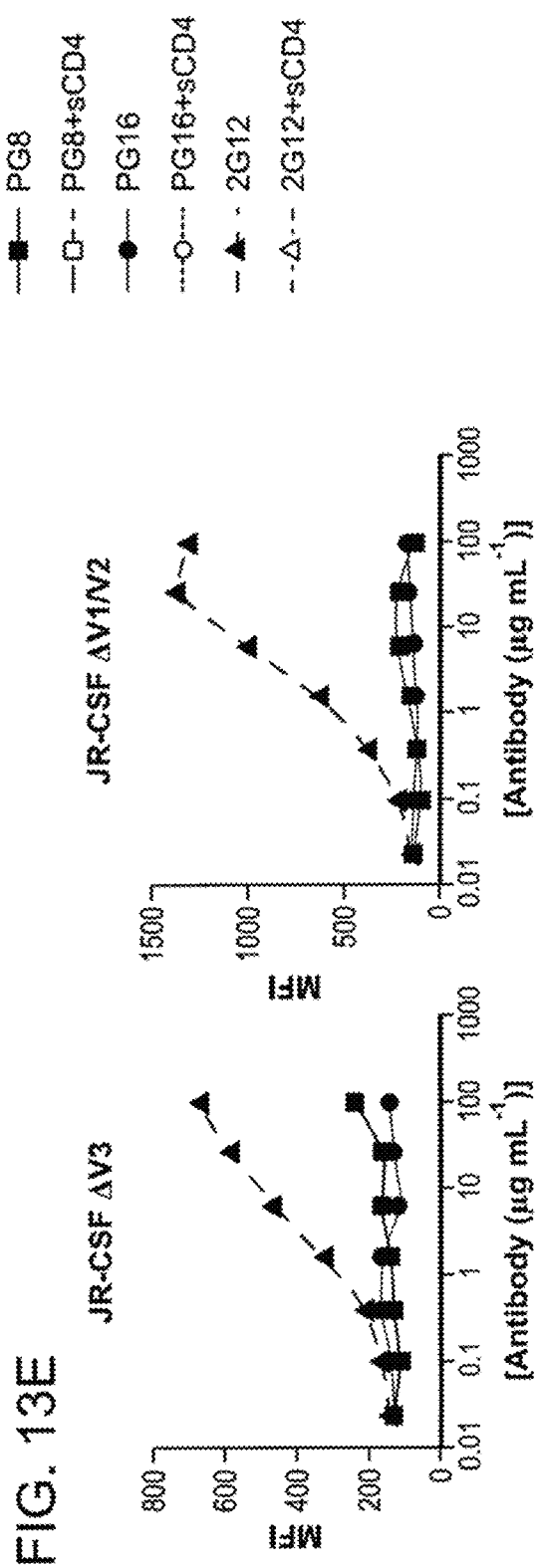
FIG. 13D
FIG. 13E

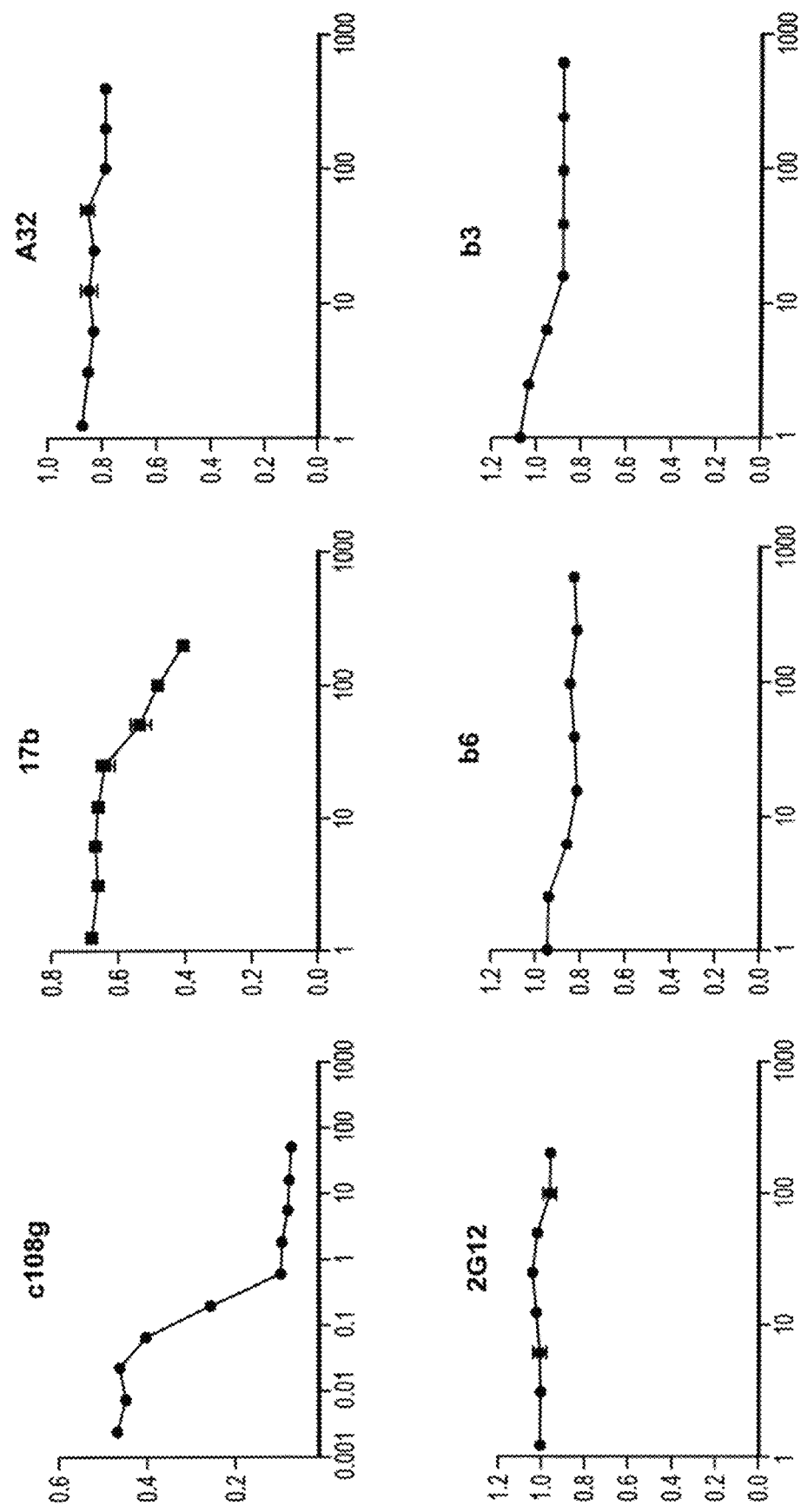

FIG. 22

| | | IC50 (µg/mL) | | | | |
|---|---|---|---|---|---|---|
| | Isolate | PGC14 | PG9 | PG16 | PGG14 | P20 |
| Clade A | 94UG103 | >50 | 0.17 | 0.008 | >50 | >50 |
| | 92RW020 | 23.60 | 0.06 | 0.004* | >50 | >50 |
| | 93UG077 | >50 | >50 | >50 | >50 | >50 |
| Clade B | 92BR020 | 0.64 | >50 | >50 | >50 | >50 |
| | APV-13 | >50 | >50 | >50 | >50 | >50 |
| | JRCSF | >50 | <0.0025 | <0.0025 | >50 | >50 |
| | APV-17 | >50 | 26.45 | >50 | >50 | 25.770 |
| | APV-6 | 7.41 | 0.09 | 0.18* | >50 | >50 |
| Clade C | 93IN905 | >50 | N/A | 0.10* | >50 | >50 |
| | IAVI-C18 | >50 | 0.05 | 0.007 | >50 | >50 |
| | IAVI-C22 | >50 | N/A | 0.069* | >50 | >50 |
| | IAVI-C3 | 9.50 | 12.91 | 14.80 | >50 | >50 |
| Clade D | 92UG024 | >50 | 10.96 | >50 | >50 | >50 |
| | 92UG005 | >50 | >50 | >50 | >50 | >50 |
| CRF01_AE | 92TH021 | >50 | 0.11 | 0.13* | >50 | >50 |
| | CMU02 | >50 | >50 | >50 | >50 | >50 |
| negative control | aMLV | >50 | >50 | >50 | >50 | >50 |

FIG. 23A

| | | Median IC$_{50}$ (µg/mL) against viruses neutralized with an IC$_{50}$ <50 µg/mL | | | | | | |
|---|---|---|---|---|---|---|---|---|
| Clade[a] | # viruses | b12 | 2G12 | 2F5 | 4E10 | PG9 | PG16 | PGC14 |
| A | 27 | 6.98 | 17.10 | 5.70 | 6.20 | 0.16 | 0.11 | 41.59 |
| B | 31 | 0.80 | 0.82 | 2.41 | 5.22 | 0.43 | 0.70 | 21.88 |
| C | 27 | 6.46 | 2.93 | 31.51 | 2.97 | 0.22 | 0.25 | 11.97 |
| D | 25 | 1.47 | 7.71 | 3.17 | 4.60 | 0.10 | 0.02 | 38.57 |
| CRF01_AE | 10 | 21.53 | >50 | 0.26 | 0.51 | 0.08 | 0.03 | >50 |
| CRF_AG | 10 | 10.40 | 0.95 | 0.64 | 1.42 | 0.80 | 0.03 | 45.10 |
| G | 15 | 3.07 | 31.03 | 1.24 | 1.44 | 0.29 | 1.21 | >50 |
| F | 15 | >50 | 9.23 | 1.78 | 2.30 | 0.09 | 0.08 | 25.71 |
| Total | 162 | 2.82 | 2.43 | 2.30 | 3.24 | 0.22 | 0.15 | 25.99 |

FIG. 23B

| Clade[a] | # viruses | % viruses neutralized with an IC$_{50}$ <50 μg/mL | | | | | | |
|---|---|---|---|---|---|---|---|---|
| | | b12 | 2G12 | 2F5 | 4E10 | PG9 | PG16 | PGC14 |
| A | 27 | 30 | 37 | 74 | 96 | 85 | 85 | 11 |
| B | 31 | 58 | 71 | 68 | 97 | 74 | 74 | 29 |
| C | 27 | 33 | 11 | 7 | 96 | 78 | 78 | 19 |
| D | 25 | 48 | 24 | 56 | 96 | 76 | 60 | 8 |
| CRF01_AE | 10 | 30 | 0 | 89 | 100 | 100 | 100 | 0 |
| CRF_AG | 10 | 30 | 50 | 80 | 100 | 80 | 60 | 10 |
| G | 15 | 13 | 20 | 80 | 100 | 87 | 73 | 7 |
| F | 15 | 0 | 21 | 87 | 100 | 67 | 64 | 13 |
| Total | 162 | 35 | 32 | 60 | 98 | 79 | 73 | 15 |

| Clade | # viruses | % viruses neutralized with an IC$_{50}$ <1.0 μg/mL | | | | | | |
|---|---|---|---|---|---|---|---|---|
| | | b12 | 2G12 | 2F5 | 4E10 | PG9 | PG16 | PGC14 |
| A | 27 | 0 | 4 | 4 | 0 | 70 | 63 | 0 |
| B | 31 | 32 | 39 | 23 | 0 | 45 | 42 | 3 |
| C | 27 | 7 | 0 | 0 | 11 | 56 | 48 | 0 |
| D | 25 | 12 | 8 | 12 | 8 | 48 | 44 | 0 |
| CRF01_AE | 10 | 11 | 0 | 88 | 80 | 70 | 70 | 0 |
| CRF_AG | 10 | 10 | 30 | 60 | 30 | 40 | 50 | 0 |
| G | 15 | 0 | 0 | 27 | 0 | 60 | 33 | 0 |

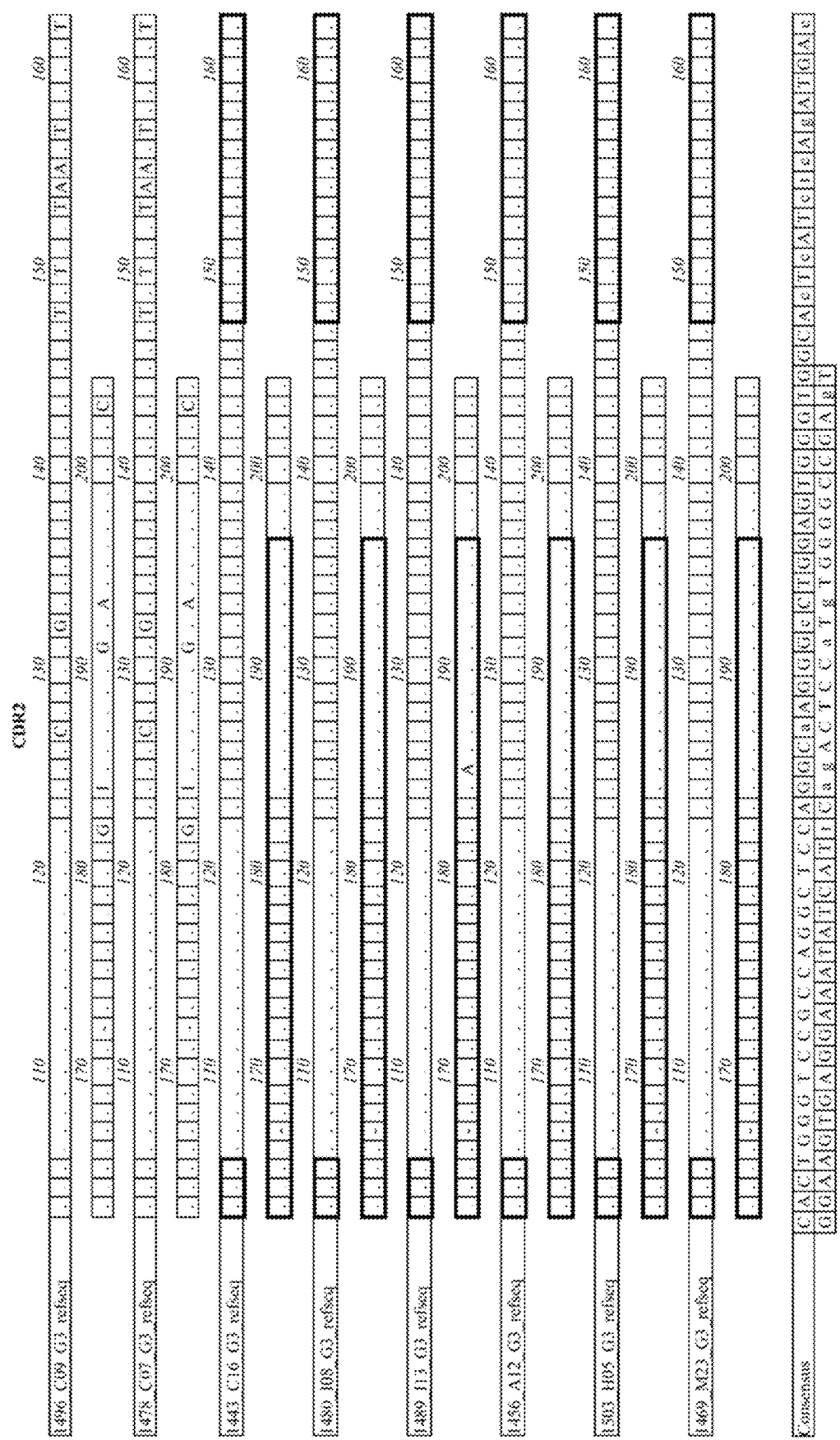

FIG. 29A

| B Cell Culture Hit Priority | Sample ID by B Cell Culture | | Primary B Cell Culture Screening | | | | Transfectant Screening for Recombinant Antibodies | | | | | |
|---|---|---|---|---|---|---|---|---|---|---|---|---|
| | | | Neutralization Index | | ELISA OD | | H & L Combinations | | Transfectant Quantitative ELISA | | Neutralization Index | |
| Rank | Plate | Well | JRCSF | SF162 | gp120 | gp41 | Heavy Chain Family | Light Chain Family | Average anti-gp-120 or anti-gp41 Conc* (µg/ml) | Average total IgG Conc (µg/ml) | JRCSF | SF162 |
| 1 | 1456 | P20 | 42.77 | 1.63 | | Neg | 1456 P20 γ1 | 1456 P20 κ1 | 4.03 | 4.62 | 0.80 | 9.57 |
| 1 | 1456 | P20 | 42.77 | 1.63 | | Neg | 1456 P20 γ1 | 1456 P20 κ1 | 4.03 | 4.62 | 0.80 | 9.57 |
| 1 | 1456 | P20 | 42.77 | 1.63 | | Neg | 1456 P20 γ1 | 1456 P20 κ1 | 4.03 | 4.62 | 0.80 | 9.57 |
| 1 | 1456 | P20 | 42.77 | 1.63 | | Neg | 1456 P20 γ1 | 1456 P20 κ1 | 4.03 | 4.62 | 0.80 | 9.57 |
| 2 | 1477 | B12 | 18.52 | 0.81 | Neg | | 1477 B12 γ3 | 1477 B12 λ2 | 0.04 | 3.23 | 13.25 | 1.20 |
| 2 | 1477 | B12 | 18.52 | 0.81 | Neg | | 1477 B12 γ3 | 1477 B12 λ2 | 0.04 | 3.23 | 13.25 | 1.20 |

FIG. 29B

| B Cell Culture Hit Priority | Sample ID by B Cell Culture | | Primary B Cell Culture Screening | | | | Transfectant Screening for Recombinant Antibodies | | | | | |
|---|---|---|---|---|---|---|---|---|---|---|---|---|
| | | | Neutralization Index | | ELISA OD | | H & L Combinations | | Transfectant Quantitative ELISA | | Neutralization Index | |
| Rank | Plate | Well | JRSCF | SF162 | gp120 | gp41 | Heavy Chain Family | Light Chain Family | Average anti-gp-120 or anti-gp41 Conc* (µg/ml) | Average total IgG Conc (µg/ml) | JRCSF | SF162 |
| 4 | 1443 | C16 | 179.12 | 1.11 | Neg | Neg | 1443 C16 γ1 | 1443 C16 λ2 | N/A | 0.63 | 2.96 | 0.86 |
| 4 | 1443 | C16 | 179.12 | 1.11 | Neg | Neg | 1443 C16 γ1 | 1443 C16 λ2 | N/A | 1.63 | 2.96 | 0.86 |
| 4 | 1443 | C16 | 179.12 | 1.11 | Neg | Neg | 1443 C16 γ3 | 1443 C16 λ2 | N/A | 3.50 | 115.86 | 0.88 |
| 5 | 1496 | C9 | 166.09 | 1.34 | Neg | Neg | 1496 C09 γ3 | 1496 C09 λ2 | N/A | 5.61 | 111.45 | 0.58 |
| 5 | 1496 | C9 | 166.09 | 1.34 | Neg | Neg | 1496 C09 γ3 | 1496 C09 λ3 | N/A | 5.73 | 115.76 | 0.63 |
| 5 | 1496 | C9 | 166.09 | 1.34 | Neg | Neg | 1496 C09 γ3 | 1496 C09 λ5 | N/A | 4.22 | 86.86 | 0.67 |
| 5 | 1496 | C9 | 166.09 | 1.34 | Neg | Neg | 1496 C09 | 1496 | N/A | 0.92 | 261.00 | 1.14 |

FIG. 29C

| B Cell Culture Hit Priority | Sample ID by B Cell Culture | | Primary B Cell Culture Screening | | | | Transfectant Screening for Recombinant Antibodies | | | | | |
|---|---|---|---|---|---|---|---|---|---|---|---|---|
| | | | Neutralization Index | | ELISA OD | | H & L Combinations | | Transfectant Quantitative ELISA | | Neutralization Index | |
| Rank | Plate | Well | JRSCF | SF162 | gp120 | gp41 | Heavy Chain Family | Light Chain Family | Average anti-gp-120 or anti-gp41 Conc* (µg/ml) | Average total IgG Conc (µg/ml) | JRCSF | SF162 |
| | | | | | | | γ3 | C09 λ7 | | | | |
| 6 | 1495 | C14 | 1.42 | 87.13 | | Neg | 1495 C14 γ1 | 1495 C14 λ1 | 160 | 2.66 | 1.67 | 56.48 |
| 6 | 1495 | C14 | 1.42 | 87.13 | | Neg | 1495 C14 γ1 | 1495 C14 λ3 | 2.20 | 3.34 | 1.67 | 84.87 |
| 6 | 1495 | C14 | 1.42 | 87.13 | | Neg | 1495 C14 γ1 | 1495 C14 λ3 | 2.20 | 3.34 | 0.80 | 84.87 |
| 6 | 1495 | C14 | 1.42 | 87.13 | | Neg | 1495 C14 γ1 | 1495 C14 λ3 | 2.20 | 3.34 | 0.80 | 84.87 |
| 6 | 1495 | C14 | 1.42 | 87.13 | | Neg | 1495 C14 γ1 | 1495 C14 λ3 | 2.20 | 3.34 | 0.80 | 84.87 |
| 6 | 1495 | C14 | 1.42 | 87.13 | | Neg | 1495 C14 γ1 | 1495 C14 λ3 | 2.20 | 3.34 | 0.80 | 84.87 |

FIG. 29D

| B Cell Culture Hit Priority | Sample ID by B Cell Culture | | Primary B Cell Culture Screening | | | | Transfectant Screening for Recombinant Antibodies | | | | | |
|---|---|---|---|---|---|---|---|---|---|---|---|---|
| | | | Neutralization Index | | ELISA OD | | H & L Combinations | | Transfectant Quantitative ELISA | | Neutralization Index | |
| Rank | Plate | Well | JRSCF | SF162 | gp120 | gp41 | Heavy Chain Family | Light Chain Family | Average anti-gp-120 or anti-gp41 Conc* (µg/ml) | Average total IgG Conc (µg/ml) | JRCSF | SF162 |
| 6 | 1495 | C14 | 1.42 | 87.13 | | Neg | 1495 C14 γ1 | 1495 C14 λ3 | 2.20 | 3.34 | 0.80 | 84.87 |
| 6 | 1495 | C14 | 1.42 | 87.13 | | Neg | 1495 C14 γ1 | 1495 C14 λ3 | 2.20 | 3.34 | 0.80 | 84.87 |
| 6 | 1495 | C14 | 1.42 | 87.13 | | Neg | 1495 C14 γ1 | 1495 C14 λ3 | 2.20 | 3.34 | 0.80 | 84.87 |
| 6 | 1495 | C14 | 1.42 | 87.13 | | Neg | 1495 C14 γ1 | 1495 C14 λ3 | 2.20 | 3.34 | 0.80 | 84.87 |
| 6 | 1495 | C14 | 1.42 | 87.13 | | Neg | 1503 C14 γ1 | 1503 C14 λ5 | 0.39 | 0.64 | 0.58 | 18.95 |
| 6 | 1495 | C14 | 1.42 | 87.13 | | Neg | 1503 C14 γ1 | 1503 C14 λ5 | 0.39 | 0.64 | 0.58 | 18.95 |
| 6 | 1495 | C14 | 1.42 | 87.13 | | Neg | 1503 C14 | 1503 | 0.39 | 0.64 | 0.58 | 18.95 |

FIG. 29E

| B Cell Culture Hit Priority | Sample ID by B Cell Culture | | Primary B Cell Culture Screening | | | | Transfectant Screening for Recombinant Antibodies | | | | | | |
|---|---|---|---|---|---|---|---|---|---|---|---|---|
| | | | Neutralization Index | | ELISA OD | | H & L Combinations | | Transfectant Quantitative ELISA | | Neutralization Index | |
| Rank | Plate | Well | JRSCF | SF162 | gp120 | gp41 | Heavy Chain Family | Light Chain Family | Average anti-gp-120 or anti-gp41 Conc* (µg/ml) | Average total IgG Conc (µg/ml) | JRCSF | SF162 |
| 10 | 1460 | G14 | 1.62 | 1.57 | | Neg | γ1 1460 G14 γ1 | C14 λ5 1460 G14 κ1 | 13.41 | 16.25 | 0.61 | 17.07 |
| 10 | 1460 | G14 | 1.62 | 1.57 | | Neg | 1460 G14 γ1 | 1460 G14 κ2 | 12.49 | 14.61 | 0.81 | 15.37 |

FIG. 29F

| B Cell Culture Hit Priority | Transfectant Screening for Recombinant Monoclonal Antibodies ||||||
|---|---|---|---|---|---|---|
| | Clonal H & L Combinations || Transfectant Quantitative ELISA || Neutralization Index ||
| Rank | Heavy Chain Clone | Light Chain Clone | Average anti-gp-120 or anti-gp41 Conc* (μg/ml) | Average total IgG Conc (μg/ml) | JRCSF | SF162 |
| 1 | 1456 P20 γ1 018 | 1456 P20 κ1 021 | 0.07 | 8.01 | 0.66 | 0.66 |
| 1 | 1456 P20 γ1 018 | 1456 P20 κ1 024 | 0.01 | 6.81 | 0.88 | 0.78 |
| 1 | 1456 P20 γ1 023 | 1456 P20 κ1 021 | 9.45 | 6.99 | 0.89 | 10.72 |
| 1 | 1456 P20 γ1 023 | 1456 P20 κ1 024 | 12.49 | 7.76 | 1.39 | 20.83 |
| 2 | 1477 812 γ3 017 | 1477 812 λ2 022 | 0.00 | 5.98 | 0.72 | 0.83 |
| 2 | 1477 812 γ3 023 | 1477 812 λ2 022 | 10.96 | 6.02 | 0.90 | 0.94 |
| 4 | 1443 C16 γ1 018 | 1443 C16 λ2 019 | 0.00 | 0.25 | 1.00 | 1.07 |
| 4 | 1443 C16 | 1443 C16 | 0.00 | 1.51 | 0.97 | 1.20 |

FIG. 29G

| B Cell Culture Hit Priority | Transfectant Screening for Recombinant Monoclonal Antibodies | | | | | |
|---|---|---|---|---|---|---|
| | Clonal H & L Combinations | | Transfectant Quantitative ELISA | | Neutralization Index | |
| Rank | Heavy Chain Clone | Light Chain Clone | Average anti-gp-120 or anti-gp41 Conc* (µg/ml) | Average total IgG Conc (µg/ml) | JRCSF | SF162 |
| | γ1 021 | λ2 019 | | | | |
| 4 | 1443 C16 γ3 023 | 1443 C16 λ2 019 | 0.00 | 6.38 | 55.62 | 0.67 |
| 5 | 1496 C09 γ3 017 | 1496 C09 λ2 017 | 0.00 | 8.80 | 282.47 | 1.10 |
| 5 | 1496 C09 γ3 017 | 1496 C09 λ3 024 | 0.00 | 12.31 | 227.65 | 0.94 |
| 5 | 1496 C09 γ3 017 | 1496 C09 λ5 023 | 0.00 | 0.00 | 1.21 | 0.86 |
| 5 | ND | ND | ND | ND | ND | ND |
| 6 | ND | ND | ND | ND | ND | ND |
| 6 | 1495 C14 γ1 017 | 1495 C14 λ3 017 | 0.00 | 0.00 | 0.89 | 0.97 |
| 6 | 1495 C14 γ1 017 | 1495 C14 λ3 018 | 0.20 | 1.43 | 0.91 | 7.97 |
| 6 | 1495 C14 γ1 | 1495 C14 λ3 023 | 0.22 | 1.65 | 0.89 | 9.90 |

FIG. 29H

| B Cell Culture Hit Priority | Transfectant Screening for Recombinant Monoclonal Antibodies ||||||
|---|---|---|---|---|---|---|
| | Clonal H & L Combinations || Transfectant Quantitative ELISA || Neutralization Index ||
| Rank | Heavy Chain Clone | Light Chain Clone | Average anti-gp-120 or anti-gp41 Conc* (µg/ml) | Average total IgG Conc (µg/ml) | JRCSF | SF162 |
| | 017 | | | | | |
| 6 | 1495 C14 γ1 020 | 1495 C14 λ3 017 | 0.00 | 0.00 | 0.86 | 0.81 |
| 6 | 1495 C14 γ1 020 | 1495 C14 λ3 018 | 12.61 | 3.76 | 1.26 | 95.15 |
| 6 | 1495 C14 γ1 020 | 1495 C14 λ3 022 | 13.03 | 3.95 | 0.91 | 105.92 |
| 6 | 1495 C14 γ1 024 | 1495 C14 λ3 017 | 0.00 | 0.00 | 1.07 | 0.79 |
| 6 | 1495 C14 γ1 022 | 1495 C14 λ3 018 | 4.65 | 2.30 | 1.13 | 60.60 |
| 6 | 1495 C14 γ1 022 | 1495 C14 λ3 022 | 5.91 | 3.18 | 0.89 | 39.85 |
| 6 | 1503 C14 γ1 017 | 1503 C14 λ5 020 | 0.00 | 0.00 | 0.84 | 0.68 |
| 6 | 1503 C14 γ1 | 1503 C14 λ5 020 | 0.00 | 0.00 | 0.95 | 0.65 |

FIG. 29I

| B Cell Culture Hit Priority | Transfectant Screening for Recombinant Monoclonal Antibodies | | | | | |
|---|---|---|---|---|---|---|
| | Clonal H & L Combinations | | Transfectant Quantitative ELISA | | Neutralization Index | |
| Rank | Heavy Chain Clone | Light Chain Clone | Average anti-gp-120 or anti-gp41 Conc* (µg/ml) | Average total IgG Conc (µg/ml) | JRCSF | SF162 |
| 6 | [shaded] | 1503 C14 λ5 02D | 0.00 | 0.00 | 0.99 | 0.87 |
| 10 | 1460 G14 γ1 023 | 1460 G14 κ1 017 | 17.37 | 12.44 | 1.64 | 39.43 |
| 10 | ND | ND | ND | ND | ND | ND |

FIG. 30

| Virus/Ab Incubation | | IC50 (ug/mL) Except Where Noted | | | | | | | | |
|---|---|---|---|---|---|---|---|---|---|---|
| | | SF162 | 94UG103 | 92BR020 | 93IN905 | IAVI_C22 | 92TH021 | JRCSF | NL43 | aMLV |
| 1 hour | 1443C16 | >50 | 0.0211 | >50 | 0.3302** | 0.1143* | 0.1362** | <0.0025 | <0.0025** | >50 |
| 18 hour | 1443C16 | >50 | 0.0085 | >50 | 0.2553* | 0.1064* | 0.0435 | <0.0025 | 4.9874* | >50 |
| 1 hour | 1456P20 | 0.1946 | >50 | >50 | >50 | >50 | >50 | >50 | 0.20 | >50 |
| 18 hour | 1456P20 | 0.0661 | >50 | >50 | 3.8384* | >50 | >50 | >50 | 0.05 | >50 |
| 1 hour | 1460G14 | 0.1789 | >50 | >50 | >50 | >50 | >50 | >50 | 0.17 | >50 |
| 18 hour | 1460G14 | 0.0573 | >50 | >50 | 3.1738* | >50 | >50 | >50 | 0.05 | >50 |
| 1 hour | 1495C14 | 0.0069 | >50 | 1.1697 | >50 | >50 | >50 | >50 | 0.35 | >50 |
| 18 hour | 1495C14 | <0.0025 | >50 | 0.2442 | 0.1456* | 13.3798 | >50 | >50 | 0.15 | >50 |
| 1 hour | 1496C09 | >50 | 0.3336 | >50 | 0.1444 | 24.8611 | 0.0612 | <0.0025 | 0.2944* | >50 |
| 18 hour | 1496C09 | >50 | 0.0942 | >50 | 0.0619 | 2.1073 | 0.0571 | <0.0025 | 38.03 | >50 |
| 1 hour | Z23 (1/dil'n) | 13521 | 188 | 616 | 369 | 340 | 175 | 438 | 4793 | <100 |
| 18 hour | Z23 (1/dil'n) | 66074 | 262 | 1292 | 1396 | 614 | 336 | 1054 | 9472 | <100 |

FIG. 31A

|  |  | PG9 | PG16 | PGC14 | PGG14 | PG20 | b12 | 2G12 | 2F5 | 4E10 |
|---|---|---|---|---|---|---|---|---|---|---|
| Clade A | 94UG103 | 0.1731 | 0.0080 | >50 | >50 | >50 | 3.54 | >50 | 3.79 | 9.7 |
|  | 92RW020 | 0.0637 | 0.0040*** | 28.5960 | >50 | >50 | >50 | 0.56 | 3.37 | 3.38 |
|  | 93UG077 | >50 | >50 | >50 | >50 | >50 | 41.12 | >50 | 4.45 | 11.15 |
| Clade B | 92BR020 | >50 | >50 | 0.6366 | >50 | >50 | 27.5 | 2.26 | >50 | 41.44 |
|  | APV-13 | >50 | >50 | >50 | >50 | >50 | >25 | 23.9 | 2.8 | 3.8 |
|  | APV-17 | 26.4465 | >50 | >50 | >50 | >50 | >25 | >50 | 2 | 5.1 |
|  | APV-6 | 0.0869 | 0.08*** | 7.4062 | >50 | 25.7798 | >25 | 5.3 | 0.1 | 0.4 |
|  | JRCSF | <0.0025 | <0.0025 | >50 | >50 | >50 | 0.16 | 0.66 | 3.36 | 6 |
| Clade C | 93IN905 | 0.1400 | 0.1016*** | >50 | >50 | >50 | 34.15 | >50 | >50 | 1.55 |
|  | IAVI-C18 | 0.0535 | 0.0067 | >50 | >50 | >50 | >50 | >50 | >50 | >50 |
|  | IAVI-C22 | 24.8600 | 0.0687** | 9.4999 | >50 | >50 | 3.6042 | >50 | >50 | 1.0229 |
|  | IAVI-C3 | 12.9103 | 14.8372 | >50 | >50 | >50 | 5.0000 | >50 | >50 | 5.0000 |
| Clade D | 92UG024 | 10.9552 | >50 | >50 | >50 | >50 | 49.06 | 0.59 | 1.27 | 1.32 |
|  | 92UG005 | >50 | >50 | >50 | >50 | >50 | >50 | >50 | 11.75 | 8.86 |
| CRF01_AE | 92TH021 | 0.1105 | 0.1273*** | >50 | >50 | >50 | 9.99 | >50 | 1.51 | 1.9 |
|  | CMU02 | >50 | >50 | >50 | >50 | >50 | 4.25 | >50 | 0.38 | 0.59 |
| Pos C | NL43 | N/A | <0.0025* | 0.3727 | 0.1717 | 0.1880 | 0.06 | 0.75 | 2.41 | 4.95 |
| Neg C | aMLV | >50 | >50 | >50 | >50 | >50 | >50 | >50 | >50 | >50 |

FIG. 31B

|  |  | PG9 | PG16 | b12 | 2G12 | 2F5 | 4E10 |
|---|---|---|---|---|---|---|---|
| Clade A | 94UG103 | 3.3726 | 15915 | 47.29 | >50 | 46.63 | >50 |
|  | 92RW020 | 6.5462 | >50 | >50 | 6.23 | 27.74 | 36.11 |
|  | 93UG077 | >50 | >50 | >50 | >50 | 33.44 | >50 |
| Clade B | 92BR020 | >50 | >50 | >50 | 24.09 | >50 | >50 |
|  | APV-13 | >50 | >50 | >50 | N/A | N/A | N/A |
|  | APV-17 | >50 | >50 | >50 | N/A | N/A | N/A |
|  | APV-6 | 1.3591 | 44.2600 | >50 | N/A | N/A | N/A |
|  | JRCSF | <0.0025 | 0.0130 | 1.17 | 5.38 | 25.31 | 44.07 |
| Clade C | 93IN905 | 1.8945 | >50 | >50 | >50 | >50 | 12.82 |
|  | IAVI-C18 | 0.8659 | 0.2074 | >50 | >50 | N/A | >50 |
|  | IAVI-C22 | >50 | >50 | 29.6187 | >50 | >50 | 16.405 |
|  | IAVI-C3 | >50 | >50 |  | >50 | N/A | N/A |
| Clade D | 92UG024 | >50 | >50 | >50 | 7.57 | 14.44 | 23.71 |
|  | 92UG005 | >50 | >50 | >50 | >50 | >50 | >50 |
| CRF01_AE | 92TH021 | 1.9071 | 23.4110 | >50 | >50 | 18.78 | 23.52 |
|  | CMU02 | >50 | >50 | 34.7 | >50 | 17.25 | 13.4 |
| Pos C | NL43 | N/A | >50 | 0.28 | 15.75 | 19.32 | 29.55 |
| Neg C | aMLV | >50 | >50 | >50 | >50 | >50 | >50 |

FIG. 32A

| Clade | Virus | IC50(µg/ml)[a] | | | | | | | IC50 (1/Dil'n)[b] |
|---|---|---|---|---|---|---|---|---|---|
| | | b12 | 2G12 | 2F5 | 4E10 | PG9 | PG16 | PGC14 | Donor Serum |
| A | MGRM-A-001 | >50 | >50 | >50 | 15.00 | >50 | >50 | >50 | <100 |
| | MGRM-A-002 | >50 | >50 | >50 | 6.45 | 0.02 | 0.004 | >50 | 804 |
| | MGRM-A-003 | >50 | >50 | 7.37 | 5.94 | 0.65 | 2.65 | >50 | <100 |
| | MGRM-A-004 | >50 | >50 | 7.49 | 3.14 | 0.02 | 0.04 | >50 | 523 |
| | MGRM-A-005 | 3.64 | >50 | 5.70 | 4.09 | 0.28 | 0.09 | >50 | 175 |
| | MGRM-A-006 | 13.52 | 13.15 | 15.73 | 9.87 | >50 | >50 | >50 | 131 |
| | MGRM-A-007 | >50 | >50 | 6.33 | 1.82 | 0.37 | 5.91 | >50 | 142 |
| | MGRM-A-008 | >50 | >50 | >50 | 7.59 | >50 | >50 | >50 | 142 |
| | MGRM-A-009 | 4.34 | 7.47 | 9.40 | 12.01 | 0.03 | 0.01 | >50 | 941 |
| | MGRM-A-0010 | >50 | 17.01 | 20.75 | 14.44 | 0.02 | 0.004 | >50 | 1430 |
| | MGRM-A-0011 | 4.01 | >50 | >50 | 2.88 | 0.02 | 0.24 | >50 | 404 |
| | MGRM-A-0012 | >50 | >50 | 2.36 | 4.27 | 11.10 | 20.72 | >50 | <100 |
| | MGRM-A-0013 | 7.04 | >50 | 0.66 | 1.46 | 0.16 | 0.09 | >50 | 350 |
| | MGRM-A-0014 | >50 | >50 | 1.43 | 1.74 | 0.62 | 20.53 | >50 | 158 |
| | 94UG103 | 6.92 | 48.12 | 1.92 | 4.97 | 0.24 | 0.04 | >50 | 350 |
| | 92RW020 | >50 | 0.48 | 3.36 | 4.54 | 0.08 | 0.28 | 45 | 282 |
| | 93UG077 | 46.95 | >50 | 3.30 | 10.80 | >50 | >50 | >50 | 206 |
| | 94KE105 | >50 | 7.22 | >50 | 7.63 | 29.56 | 6.13 | >50 | <100 |
| | 93RW029 | >50 | >50 | >50 | 15.52 | 1.19 | 3.83 | 42 | 256 |
| | 92RW009 | >50 | 26.14 | 39.08 | >50 | 0.03 | 0.11 | >50 | 254 |
| | 92UG031 | >50 | >50 | 3.81 | 4.94 | 3.08 | 0.43 | >50 | 259 |
| | 92RW026 | >50 | 17.20 | 8.63 | 12.80 | 0.27 | 0.03 | >50 | 361 |
| | 92UG037 | >50 | 45.24 | 3.24 | 8.84 | 0.02 | 0.01 | >50 | 1252 |
| | 92RW008 | 9.46 | 22.47 | 10.41 | 14.56 | 0.01 | 0.002 | 37 | 4067 |
| | 92RW021* | >50 | >50 | 4.16 | 4.87 | 0.05 | 0.11 | >50 | 316 |
| | VLGCA1 | >50 | >50 | 3.90 | 4.58 | 0.07 | 0.18 | >50 | 197 |
| | 92RW024 | >50 | >50 | 8.22 | 8.88 | 0.18 | 0.08 | >50 | 241 |

FIG. 32B

| Clade | Virus | IC50(µg/ml) | | | | | | | IC50 (1/Dil'n) |
|---|---|---|---|---|---|---|---|---|---|
| | | b12 | 2G12 | 2F5 | 4E10 | PG9 | PG16 | PGC14 | Donor Serum |
| B | 6535.3 (Acute) | 1.93 | 3.85 | 2.76 | 1.23 | 0.22 | 36.83 | 35 | 387 |
| | QH0692.42 (Acute) | 0.73 | 4.39 | 5.42 | 12.67 | >50 | >50 | >50 | <100 |
| | SC422661.8 (Acute) | 6.11 | 0.84 | >50 | 6.35 | 0.79 | 1.13 | >50 | 182 |
| | PVO.4 (Acute) | >50 | 0.80 | >50 | 18.32 | 4.01 | 5.43 | >50 | 171 |
| | TRO.11 (Acute) | >50 | 0.29 | >50 | 1.39 | 5.43 | 0.22 | >50 | 222 |
| | CAAN.A2 (Acute) | >50 | >50 | 23.05 | 17.89 | 5.67 | 8.83 | >50 | <100 |
| | TRJ0.58 (Acute) | >50 | >50 | >50 | 11.94 | 0.43 | 1.16 | >50 | 171 |
| | THR0.18 (Acute) | 3.62 | >50 | >50 | 4.68 | 12.39 | 1.34 | >50 | <100 |
| | 92BR020 | >50 | 4.84 | >50 | >50 | >50 | >50 | 4 | <100 |
| | APV_13 | >50 | 9.24 | 3.81 | 7.33 | >50 | >50 | >50 | <100 |
| | APV_17 | >50 | >50 | 4.61 | 10.53 | 14.59 | 24.78 | >50 | <100 |
| | APV_6 | >50 | 1.90 | 0.25 | 1.10 | 0.12 | 0.29 | 23 | 394 |
| | 93TH305 | 4.17 | 0.55 | 7.61 | 12.33 | 2.08 | 19.34 | 6 | 133 |
| | VLGCB3 | 0.15 | 7.90 | >50 | 5.76 | 0.02 | 0.40 | 21 | 244 |
| | JRCSF | 0.21 | 0.37 | 1.85 | 3.30 | 0.003 | 0.001 | 15 | 8425 |
| | NL43 | 0.17 | 0.49 | 2.02 | 4.67 | 0.32 | 0.02 | 40 | 1488 |
| | MGRM-Chronic-B-001 | 0.75 | 0.08 | 0.55 | 1.46 | >50 | >50 | >50 | <100 |
| | MGRM-Chronic-B-002 | 0.86 | >50 | 1.25 | 2.19 | 1.41 | 3.06 | >50 | 220 |
| | MGRM-Chronic-B-003 | >50 | 0.06 | 1.00 | 3.50 | 50.00 | 0.19 | >50 | 280 |
| | MGRM-Chronic-B-004 | 0.26 | 8.65 | 2.41 | 3.70 | 0.11 | 0.01 | >50 | 1316 |
| | MGRM-Chronic-B-008 | 2.82 | 0.55 | >50 | 16.70 | 6.66 | 0.73 | >50 | 140 |
| | MGRM-Chronic-B-010 | >50 | 1.50 | 0.96 | 1.69 | 0.004 | 0.01 | 27 | 1640 |
| | MGRM-Chronic-B-011 | 2.11 | >50 | 0.81 | 1.07 | >50 | >50 | >50 | 249 |
| | MGRM-Chronic-B-012 | >50 | 0.22 | 17.65 | 48.05 | 0.91 | 3.74 | >50 | 304 |
| | MGRM-Chronic-B-017 | 2.59 | >50 | >50 | 2.77 | 0.32 | 0.02 | >50 | 644 |
| | MGRM-Chronic-B-018 | 0.66 | >50 | 10.80 | 23.19 | 0.16 | 0.70 | >50 | 180 |
| | MGRM-Chronic-B-020 | 6.16 | 0.20 | 0.78 | 2.45 | >50 | >50 | >50 | <100 |
| | MGRM-Chronic-B-023 | >50 | 0.16 | 0.10 | 27.92 | 0.04 | 0.13 | >50 | 286 |
| | MGRM-Chronic-B-024 | >50 | >50 | >50 | 9.19 | 0.18 | 0.01 | >50 | 884 |
| | JRFL | 0.02 | 1.45 | 3.54 | 18.91 | >50 | >50 | >50 | <100 |
| | SF162 | 0.02 | 1.67 | 2.52 | 4.28 | >50 | >50 | <0.0025 | 9777 |

FIG. 32C

| Clade | Virus | IC50(µg/ml)[a] | | | | | | | IC50 (1/Dil'n)[b] |
|---|---|---|---|---|---|---|---|---|---|
| | | b12 | 2G12 | 2F5 | 4E10 | PG9 | PG16 | PGC14 | Donor Serum |
| C | MGRM-C-001 | >50 | 2.93 | >50 | 5.66 | >50 | 16.79 | >50 | 175 |
| | MGRM-C-002 | >50 | >50 | 44.68 | 18.19 | >50 | 28.30 | >50 | >100 |
| | MGRM-C-004 | 5.46 | >50 | >50 | 24.24 | 1.18 | 5.09 | >50 | 183 |
| | MGRM-C-005 | 2.66 | >50 | >50 | 16.41 | 2.98 | 2.55 | >50 | 306 |
| | MGRM-C-006 | >50 | >50 | >50 | 4.94 | 0.23 | 2.62 | >50 | 224 |
| | MGRM-C-007 | >50 | >50 | >50 | 5.84 | 0.09 | 0.05 | >50 | 598 |
| | MGRM-C-008 | 1.51 | >50 | >50 | 2.97 | >50 | >50 | >50 | 160 |
| | MGRM-C-009 | >50 | >50 | >50 | 0.56 | >50 | >50 | >50 | <100 |
| | MGRM-C-010 | >50 | >50 | >50 | 10.96 | 12.45 | >50 | >50 | <100 |
| | MGRM-C-012 | >50 | >50 | >50 | 0.44 | 0.24 | 0.48 | >50 | 432 |
| | MGRM-C-013 | >50 | >50 | 18.35 | 2.10 | >50 | >50 | >50 | 105 |
| | MGRM-C-014 | >50 | >50 | >50 | 2.48 | 0.64 | >50 | >50 | 124 |
| | MGRM-C-015 | 13.30 | 1.75 | >50 | 2.52 | 0.50 | 0.26 | >50 | 365 |
| | MGRM-C-017 | >50 | >50 | >50 | 1.47 | 1.52 | 1.80 | >50 | 190 |
| | MGRM-C-019 | >50 | >50 | >50 | 3.49 | 0.01 | 0.002 | 12 | 6894 |
| | MGRM-C-020 | >50 | 18.58 | >50 | 2.80 | >50 | >50 | >50 | <100 |
| | MGRM-C-022 | >50 | >50 | >50 | 5.71 | 0.19 | 0.25 | >50 | 126 |
| | MGRM-C-023 | 13.88 | >50 | >50 | 1.95 | 0.51 | 0.09 | >50 | 220 |
| | MGRM-C-024 | >50 | >50 | >50 | 22.61 | 0.22 | 0.04 | >50 | 494 |
| | MGRM-C-025 | >50 | >50 | >50 | 5.58 | 0.17 | 0.04 | >50 | 434 |
| | 93IN905 | 21.38 | >50 | >50 | 1.26 | 0.03 | 0.25 | 19 | 647 |
| | IAVIC_18 | >50 | >50 | >50 | >50 | 0.10 | 0.02 | >50 | 577 |
| | IAVI_C22 | 7.64 | >50 | >50 | 2.02 | 0.14 | 0.02 | 25 | 1002 |
| | IAVI_C3 | 0.94 | >50 | >50 | 2.85 | 1.45 | 9.55 | 12 | 443 |
| | 98IN022 | 0.42 | >50 | >50 | 0.53 | 0.006 | 0.003 | 9 | 2708 |
| | 93MW959 | >50 | >50 | >50 | 4.55 | 0.04 | 0.007 | >50 | 976 |
| | 97ZA012 | >50 | >50 | >50 | 4.70 | 1.27 | 2.55 | >50 | 188 |
| CRF08 BC | 98CN006 | >50 | >50 | >50 | 1.91 | >50 | >50 | >50 | 397 |
| CRF07 BC | 98CN009 | 1.52 | >50 | >50 | 2.46 | 1.07 | 5.76 | 43 | 289 |

FIG. 32D

| Clade | Virus | IC50(µg/ml)[a] | | | | | | | IC50 (1/Dil'n)[b] |
|---|---|---|---|---|---|---|---|---|---|
| | | b12 | 2G12 | 2F5 | 4E10 | PG9 | PG16 | PGC14 | Donor Serum |
| D | MGRM-D-001 | >50 | >50 | 0.63 | 1.84 | >50 | >50 | >50 | <100 |
| | MGRM-D-002 | >50 | >50 | 24.64 | 9.44 | 0.027 | 0.01 | 29 | 515 |
| | MGRM-D-003 | >50 | >50 | >50 | 2.49 | 0.02 | 0.01 | >50 | 363 |
| | MGRM-D-004 | >50 | >50 | 2.30 | 1.58 | 0.03 | 0.01 | >50 | 616 |
| | MGRM-D-005 | >50 | 25.06 | >50 | 35.16 | 0.59 | 19.66 | >50 | <100 |
| | MGRM-D-008 | >50 | >50 | >50 | 42.90 | 6.86 | >50 | >50 | <100 |
| | MGRM-D-0011 | 7.75 | 1.50 | >50 | 0.91 | 0.06 | 0.01 | >50 | 298 |
| | MGRM-D-0012 | 0.13 | >50 | 1.70 | 1.13 | 9.31 | 0.35 | >50 | <100 |
| | MGRM-D-0013 | >50 | >50 | 2.12 | 5.38 | 0.06 | 0.11 | >50 | <100 |
| | MGRM-D-0014 | >50 | >50 | 2.22 | 3.24 | 0.02 | 0.003 | 48 | 5127 |
| | MGRM-D-0016 | 1.12 | >50 | 9.85 | 15.45 | 0.10 | 0.02 | >50 | 364 |
| | MGRM-D-0018 | 1.39 | 0.12 | 4.05 | 3.90 | 0.02 | 0.004 | >50 | 883 |
| | MGRM-D-0019 | >50 | >50 | 0.14 | 0.04 | 0.03 | 0.01 | >50 | 497 |
| | MGRM-D-0020 | >50 | >50 | >50 | >50 | 2.03 | 16.27 | >50 | <100 |
| | MGRM-D-0021 | 5.23 | 22.98 | >50 | 13.26 | >50 | >50 | >50 | <100 |
| | MGRM-D-0022 | 17.63 | >50 | 8.45 | 16.92 | >50 | >50 | >50 | <100 |
| | MGRM-D-0024 | 5.92 | >50 | >50 | 3.60 | 0.03 | 0.02 | >50 | 239 |
| | MGRM-D-0026 | 1.55 | >50 | 4.37 | 2.95 | 17.51 | >50 | >50 | <100 |
| | MGRM-D-0028 | 0.78 | >50 | >50 | 1.28 | 4.39 | >50 | >50 | <100 |
| | MGRM-D-0029 | >50 | >50 | >50 | 5.30 | >50 | >50 | >50 | <100 |
| | 92UG024 | 45.64 | 0.42 | 0.95 | 2.17 | 1.91 | 23.98 | >50 | 112 |
| | 92UG005 | >50 | >50 | 8.61 | 7.46 | >50 | >50 | >50 | <100 |
| | 92UG046 | 0.07 | >50 | >50 | 12.15 | 0.64 | 1.42 | >50 | 114 |
| | 92UG001 | 1.01 | >50 | 12.98 | 13.58 | 41.79 | >50 | >50 | <100 |
| | 94UG114 | >50 | 13.92 | >50 | 9.72 | >50 | >50 | >50 | <100 |

FIG. 32E

| Clade | Virus | IC50 (µg/ml)[a] | | | | | | | IC50 (1/Dil'n)[] |
|---|---|---|---|---|---|---|---|---|---|
| | | b12 | 2G12 | 2F5 | 4E10 | PG9 | PG16 | PGC14 | Donor Serum |
| CRF01_AE | MGRM-AE-001 | 25.95 | >50 | 0.29 | 0.85 | 2.97 | 4.33 | >50 | <100 |
| | MGRM-AE-002 | 17.10 | >50 | 0.31 | 0.55 | 0.04 | 0.01 | >50 | 653 |
| | MGRM-AE-003 | >50 | >50 | 0.24 | 0.34 | 0.02 | 0.03 | >50 | 211 |
| | MGRM-AE-004 | >50 | >50 | 0.98 | 1.27 | 0.01 | 0.002 | >50 | 1773 |
| | MGRM-AE-005 | 0.63 | >50 | 0.14 | 0.47 | 0.16 | 0.02 | >50 | 233 |
| | MGRM-AE-006 | >50 | >50 | 0.18 | 0.23 | 0.05 | 0.03 | >50 | 151 |
| | MGRM-AE-007 | >50 | >50 | 0.07 | 0.45 | 0.11 | 0.04 | >50 | 176 |
| | MGRM-AE-008 | >50 | >50 | >50 | 0.94 | 10.58 | 3.25 | >50 | 141 |
| | 92TH021 | N/A | >50 | N/A | 1.17 | 0.09 | 0.10 | >50 | 192 |
| | CMU02 | 29.32 | >50 | 0.60 | 0.72 | 7.69 | 43.63 | >50 | 142 |
| CRF_AG | MGRM-AG-001 | 11.87 | 0.69 | 0.75 | 1.12 | 8.83 | 0.03 | >50 | 388 |
| | MGRM-AG-002 | 0.89 | 0.54 | 0.54 | 0.80 | 0.04 | 0.03 | >50 | 147 |
| | MGRM-AG-003 | >50 | >50 | 0.14 | 0.64 | 9.71 | >50 | >50 | <100 |
| | MGRM-AG-005 | >50 | >50 | >50 | 2.13 | 29.67 | >50 | >50 | 150 |
| | MGRM-AG-006 | >50 | 3.92 | 0.85 | 1.76 | >50 | >50 | >50 | <100 |
| | MGRM-AG-008 | >50 | >50 | 0.54 | 1.48 | 0.02 | 0.002 | 45 | 1518 |
| | MGRM-AG-009 | >50 | >50 | 24.80 | 31.39 | >50 | >50 | >50 | <100 |
| | MGRM-AG-011 | >50 | >50 | >50 | 1.36 | 0.01 | 0.002 | >50 | 1427 |
| | MGRM-AG-012 | 10.40 | 1.94 | 0.33 | 0.86 | 1.37 | 25.13 | >50 | <100 |
| | MGRM-AG-013 | >50 | 0.95 | 1.79 | 2.61 | 0.23 | 0.31 | >50 | <100 |
| G | MGRM-G-001 | >50 | >50 | 4.1 | 2.04 | 0.16 | 0.15 | >50 | <100 |
| | MGRM-G-004 | >50 | >50 | >50 | 1.47 | >50 | >50 | >50 | <100 |
| | MGRM-G-006 | >50 | >50 | 1.33 | 1.23 | 0.51 | 2.42 | >50 | 116 |
| | MGRM-G-009 | >50 | >50 | 7.21 | 1.34 | 4.90 | >50 | <50 | <100 |
| | MGRM-G-011 | >50 | >50 | 1.16 | 1.44 | 0.19 | 0.04 | >50 | 150 |
| | MGRM-G-013 | >50 | >50 | 0.59 | 1.15 | >50 | >50 | >50 | <100 |
| | MGRM-G-014 | >50 | >50 | 9.65 | 13.67 | 6.32 | 6.98 | >50 | <100 |
| | MGRM-G-015 | >50 | >50 | 0.43 | 1.07 | 1.51 | 5.33 | >50 | <100 |
| | MGRM-G-016 | >50 | >50 | 16.82 | 1.02 | 0.40 | 11.35 | >50 | <100 |
| | MGRM-G-017 | >50 | >50 | 0.60 | 1.14 | 0.03 | 0.02 | >50 | 453 |
| | MGRM-G-019 | 3.77 | 31.03 | >50 | 6.53 | 0.67 | 1.21 | <50 | <100 |
| | MGRM-G-024 | 2.38 | >50 | 1.07 | 1.57 | 0.07 | 0.01 | >50 | 236 |
| | MGRM-G-025 | >50 | 31.94 | >50 | 1.70 | >50 | >50 | >50 | <100 |
| | MGRM-G-027 | >50 | >50 | 0.28 | 1.19 | 0.01 | 0.01 | >50 | 351 |
| | MGRM-G-028 | >50 | 28.25 | 2.24 | 6.32 | 0.13 | 3.09 | <50 | <100 |

FIG. 32F

| Clade | Virus | IC50 (µg/ml)[a] | | | | | | | IC50 (1/Dil'n)[b] |
|---|---|---|---|---|---|---|---|---|---|
| | | b12 | 2G12 | 2F5 | 4E10 | PG9 | PG16 | PGC14 | Donor Serum |
| F | MGRM-F1-004 | >50 | >50 | 4.31 | 2.74 | 0.11 | 0.43 | >50 | 104 |
| | MGRM-F1-006 | >50 | >50 | 1.10 | 1.01 | 1.45 | 0.27 | >50 | <100 |
| | MGRM-F1-008 | >50 | >50 | 1.61 | 2.75 | >50 | >50 | >50 | <100 |
| | MGRM-F1-010 | >50 | N/A | 14.56 | 3.69 | 0.03 | 0.01 | >50 | 634 |
| | MGRM-F1-012 | >50 | 1.81 | >50 | 0.37 | 0.01 | 0.003 | >50 | 866 |
| | MGRM-F1-013 | >50 | >50 | 4.57 | N/A | 0.56 | N/A | 6 | 142 |
| | MGRM-F1-014 | >50 | >50 | 15.13 | 7.36 | 0.01 | 0.01 | >50 | 437 |
| | MGRM-F1-015 | >50 | >50 | 0.10 | 0.53 | >50 | >50 | >50 | <100 |
| | MGRM-F1-016 | >50 | >50 | 21.47 | 7.61 | 0.58 | 1.12 | >50 | <100 |
| | MGRM-F1-017 | >50 | >50 | >50 | 4.92 | >50 | >50 | >50 | <100 |
| | MGRM-F1-018 | >50 | >50 | 3.91 | 3.60 | 0.03 | 0.01 | >50 | 432 |
| | MGRM-F1-020 | >50 | >50 | 0.59 | 0.66 | 4.55 | 4.35 | >50 | <100 |
| | MGRM-F1-021 | >50 | 14.09 | 1.37 | 1.87 | >50 | >50 | 46 | <100 |
| | MGRM-F1-022 | >50 | >50 | 1.26 | 1.01 | 0.06 | 0.08 | >50 | 246 |
| | MGRM-F1-023 | >50 | 9.23 | 1.78 | 0.44 | >50 | >50 | >50 | 101 |
| neg. control | aMLV | >50 | >50 | >50 | >50 | >50 | >50 | >50 | <100 |

FIG. 33A

| Clade[a] | # viruses | Median IC$_{90}$ (µg/mL) against viruses neutralized with an IC$_{90}$ <50 µg/ml | | | | | | |
|---|---|---|---|---|---|---|---|---|
| | | b12 | 2G12 | 2F5 | 4E10 | PG9 | PG16 | PGC14 |
| A | 27 | 48.45 | 17.77 | 28.82 | 40.62 | 0.99 | 0.81 | >50 |
| B | 31 | 2.30 | 4.65 | 25.85 | 32.38 | 0.11 | 0.01 | 9.45 |
| C | 27 | 28.41 | 28.67 | >50 | 23.37 | 2.94 | 5.10 | >50 |
| D | 25 | 12.68 | 8.76 | 9.02 | 23.45 | 0.34 | 0.44 | >50 |
| CRF01_AE | 10 | 12.68 | >50 | 8.14 | 12.95 | 0.36 | 1.51 | >50 |
| CRF_AG | 10 | 16.97 | 7.04 | 13.49 | 15.78 | 0.28 | 1.86 | >50 |
| G | 15 | 23.62 | >50 | 17.54 | 16.67 | 1.91 | 1.96 | >50 |
| F | 15 | >50 | 21.49 | 17.77 | 7.64 | 0.25 | 0.55 | >50 |
| total | 162 | 20.30 | 13.27 | 17.54 | 23.37 | 0.36 | 1.16 | 9.45 |

FIG. 33B

| Clade[a] | # viruses | % viruses neutralized with an IC$_{90}$ <50 µg/ml | | | | | | |
|---|---|---|---|---|---|---|---|---|
| | | b12 | 2G12 | 2F5 | 4E10 | PG9 | PG16 | PGC14 |
| A | 27 | 4 | 4 | 33 | 22 | 74 | 41 | 0 |
| B | 31 | 45 | 52 | 45 | 23 | 42 | 26 | 6 |
| C | 27 | 15 | 4 | 0 | 41 | 52 | 41 | 0 |
| D | 25 | 28 | 12 | 12 | 20 | 44 | 36 | 0 |
| CRF01_AE | 10 | 11 | 0 | 67 | 70 | 60 | 60 | 0 |
| CRF_AG | 10 | 10 | 30 | 70 | 60 | 40 | 40 | 0 |
| G | 15 | 13 | 0 | 53 | 53 | 47 | 27 | 0 |
| F | 15 | 0 | 7 | 47 | 43 | 47 | 29 | 0 |
| total | 162 | 19 | 15 | 33 | 36 | 51 | 35 | 4 |

| Clade[a] | # viruses | % viruses neutralized with an IC$_{90}$ <1.0 µg/ml | | | | | | |
|---|---|---|---|---|---|---|---|---|
| | | b12 | 2G12 | 2F5 | 4E10 | PG9 | PG16 | PGC14 |
| A | 27 | 0 | 0 | 0 | 0 | 36 | 27 | 0 |
| B | 31 | 10 | 6 | 0 | 0 | 13 | 19 | 3 |
| C | 27 | 0 | 0 | 0 | 0 | 15 | 15 | 0 |
| D | 25 | 0 | 4 | 0 | 0 | 32 | 20 | 0 |
| CRF01_AE | 10 | 0 | 0 | 0 | 0 | 40 | 30 | 0 |
| CRF_AG | 10 | 0 | 0 | 0 | 0 | 30 | 10 | 0 |
| G | 15 | 0 | 0 | 0 | 0 | 13 | 7 | 0 |
| F | 15 | 0 | 0 | 0 | 0 | 33 | 21 | 0 |
| total | 162 | 2 | 2 | 0 | 0 | 25 | 18 | <1 |

FIG. 34A

| Mutation[a,b] | gp120 domain[c] | Fold IC50 increase relative to wild-type[d] | | Mutation[a,b] | gp120 domain[c] | Fold IC50 increase relative to wild-type[d] | |
|---|---|---|---|---|---|---|---|
| | | PG9 | PG16 | | | PG9 | PG16 |
| W112A | C1 | 1 | 1 | P299A | V3 (base) | 200 | 1400 |
| V120A | C1 | 2 | 1 | N301A | V3 (base) | 9 | 3 |
| K121A | C1 (V1/V2 stem) | 1 | 1 | N302A | V3 (stem) | 1 | 1 |
| L122A | C1 (V1/V2 stem) | 2 | 1 | R304A | V3 (stem) | 2 | 3 |
| L125A | C1 (V1/V2 stem) | 1 | 1 | K305A | V3 (stem) | 50 | 2800 |
| V127A | C1 (V1/V2 stem) | 30 | 57 | S306A | V3 (tip) | 1 | 1 |
| N134A | V1 | 5 | 23 | I307A | V3 (tip) | 10 | 3000 |
| N156A | C1 (V1/V2 stem) | 280 | 1500 | H308A | V3 (tip) | 3 | 1 |
| S158A | C1 (V1/V2 stem) | >2000 | >2000 | I309A | V3 (tip) | 9 | 150 |
| F159A | C1 (V1/V2 stem) | >2000 | >2500 | P313A | V3 (tip) | 1 | 1 |
| N160k | V2 | >2000 | >2500 | R315A | V3 (tip) | 1 | 1 |
| T162A | V2 | >2000 | >2500 | F317A | V3 (tip) | 3 | 1400 |
| I165A | V2 | 1 | 1 | Y318A | V3 (tip) | 2 | 1000 |
| R166A | V2 | 2 | 1 | T319A | V3 (tip) | 1 | 1 |
| D167A | V2 | 5 | 30 | T320A | V3 (tip) | 2 | 1 |
| K168A | V2 | 1 | 3 | E322A | V3 (stem) | 2 | 3 |
| K171A | V2 | 1 | 1 | D325A | V3 (stem) | 1 | 1 |
| E172A | V2 | 1 | 1 | H330A | V3 (base) | 1 | 1 |
| Y173A | V2 | 1400 | 1000 | N332A | V3 (base) | 1 | 1 |
| F176A | V2 | ≥5000 | ≥7000 | Q337A | C3 | 1 | 1 |
| Y177A | V2 | 1 | 5 | N339A | C3 | 1 | 1 |
| L179A | V2 | 1 | 3 | K343A | C3 | 1 | 1 |
| D180A | V2 | 1 | 4 | R350A | C3 | 1 | 1 |
| V181A | V2 | 200 | 250 | N355A | C3 | 9 | 3 |
| V182A | V2 | 1 | 3 | S365A | C3 | 2 | 3 |
| I184A | V2 | 1 | 1 | N386A | C3 | 1 | 1 |
| D185A | V2 | 1 | 1 | T388A | C3 | 1 | 1 |
| N188A | V2 | 3 | 3 | N392A | V4 | 7 | 23 |
| T190A | V2 | 2 | 4 | W395A | V4 | 1 | 1 |
| N197K | C2 (V1/V2 stem) | 1 | 1 | R419A | C4 | 3 | 3 |

FIG. 34B

| Mutation[a,b] | gp120 domain[c] | Fold IC50 increase relative to wild-type[d] | | Mutation[a,b] | gp120 domain[c] | Fold IC50 increase relative to wild-type[d] | |
|---|---|---|---|---|---|---|---|
| | | PG9 | PG16 | | | PG9 | PG16 |
| T198A | C2 (V1/V2 stem) | 2 | 1 | I420A | C4 | 9 | 11 |
| S199A | C2 (V1/V2 stem) | 2 | 1 | K421A | C4 | 1 | 1 |
| T202A | C2 (V1/V2 stem) | 1 | 1 | Q422A | C4 | 9 | 5 |
| F210A | C2 | 3 | 1 | I423A | C4 | 40 | 14 |
| I213A | C2 | 1 | 1 | I424A | C4 | 10 | 9 |
| N241A | C2 | 4 | 3 | I439A | C4 | 2 | 3 |
| N262A | C2 | 1 | 1 | T450A | C4 | 1 | 1 |
| N276A | C2 | 1 | 1 | L452A | C4 | 1 | 1 |
| N295A | C2 | 2 | 1 | P470A | V5 | 1 | 1 |
| T297A | V3 (base) | 1 | 1 | | | | |

FIG. 35

| Mutation[a,b] | gp120 domain[c] | Fold IC$_{50}$ increase relative to wild-type[d] | |
|---|---|---|---|
| | | PG9 | PG16 |
| V127A | C1 (V1/V2 stem) | 30 | 57 |
| N134A | V1 | 5 | 23 |
| N156A | C1 (V1/V2 stem) | 280 | 1500 |
| S158A | C1 (V1/V2 stem) | >2000 | >2000 |
| F159A | C1 (V1/V2 stem) | >2000 | >2500 |
| N160K | V2 | >2000 | >2500 |
| T162A | V2 | >2000 | >2500 |
| D167A | V2 | 5 | 30 |
| Y173A | V2 | 1400 | 1000 |
| F176A | V2 | >5000 | >7000 |
| V181A | V2 | 200 | 250 |
| P299A | V3 (base) | 200 | 1400 |
| K305A | V3 (stem) | 50 | 2800 |
| I307A | V3 (tip) | 10 | 3000 |
| I309A | V3 (tip) | 9 | 150 |
| F317A | V3 (tip) | 3 | 1400 |
| Y318A | V3 (tip) | 2 | 1000 |
| N392A | V4 | 7 | 23 |
| L420A | C4 | 9 | 11 |
| I423A | C4 | 40 | 14 |
| I424A | C4 | 10 | 9 |

FIG. 36

| 1443 C16 Sister mAbs | Gamma Chain Clone | Light Chain Clone | Antibody concentration (µg/ml) | JRCSF Neutralization Index |
|---|---|---|---|---|
| 1456 A12 | 1456_A12_G3_01_002 | 1456_A12_L2_01_023 | 0.006 | 0.90 |
| | | 1456_A12_L2_01_036 | 0.012 | 0.82 |
| | | 1456_A12_L2_01_040 | 0.016 | 2.79 |
| | 1456_A12_G3_01_004 | 1456_A12_L2_01_023 | <0.005 | 1.00 |
| | | 1456_A12_L2_01_036 | <0.005 | 1.02 |
| | | 1456_A12_L2_01_040 | 0.005 | 6.95 |
| 1469 M23 | 1469_M23_G3_01_005 | 1469_M23_L2_01_001 | 2.624 | 215.74 |
| | 1469_M23_G3_01_006 | | 0.000 | 10.05 |
| 1480 I08 | 1480_I08_G3_01_012 | 1480_I08_L2_01_005 | <0.005 | 10.34 |
| | 1480_I08_G3_01_016 | | 10 | 223.14 |
| | 1480_I08_G3_01_021 | | <0.005 | 2.98 |
| | 1480_I08_G3_01_032 | | <0.005 | 3.83 |
| | 1480_I08_G3_01_037 | | 34 | 1.36 |
| | 1480_I08_G3_01_055 | | <0.005 | 1.16 |
| 1489 I13 | 1489_I13_G3_01_003 | 1489_I13_L2_01_007 | 0.0008 | 2.02 |
| | 1489_I13_G3_01_004 | | 0.0009 | 22.86 |
| | 1489_I13_G3_01_007 | | 1.455 | 139.35 |
| 1503 H05 | 1503_H05_G1_01_001 | 1503_H05_L2_01_021 | 0.013 | 0.96 |
| | 1503_H05_G1_01_006 | | 0.000 | 3.75 |
| | 1503_H05_G3_01_005 | | 1.108 | 91.41 |
| | 1503_H05_G3_01_007 | | 0.567 | 155.54 |

MONOCLONAL ANTIBODIES DIRECTED AGAINST TRIMERIC FORMS OF THE HIV-1 ENVELOPE GLYCOPROTEIN WITH BROAD AND POTENT NEUTRALIZING ACTIVITY

RELATED APPLICATIONS

This application is a continuation of U.S. application Ser. No. 16/513,859 filed Jul. 17, 2019 now allowed, which is a continuation of U.S. application Ser. No. 16/275,936 filed Feb. 14, 2019, now U.S. Pat. No. 10,407,493, which issued on Sep. 10, 2019, which is a continuation of U.S. application Ser. No. 15/918,343, filed Mar. 12, 2018, now U.S. Pat. No. 10,239,934, which issued on Mar. 26, 2019, which is a continuation of U.S. application Ser. No. 14/692,483 filed Apr. 21, 2015, now U.S. Pat. No. 9,920,111, which issued on Mar. 20, 2018, which is a continuation of U.S. patent application Ser. No. 12/726,245 filed Mar. 17, 2010, now U.S. Pat. No. 9,051,362, which issued on Jun. 9, 2015, which claims the benefit of provisional applications U.S. Ser. No. 61/161,010, filed Mar. 17, 2009, U.S. Ser. No. 61/165,829, filed Apr. 1, 2009, U.S. Ser. No. 61/224,739, filed Jul. 10, 2009, and U.S. Ser. No. 61/285,664, filed Dec. 11, 2009, the contents of which are each herein incorporated by reference in their entirety.

GOVERNMENT SUPPORT

This invention was made with Government support under Grant No. AI033292 awarded by the National Institutes of Health. The Government has certain rights in the invention.

INCORPORATION BY REFERENCE

The contents of the text file named "37418507001USSeqList.txt," which was created on Oct. 21, 2010 and is 125 KB in size, are hereby incorporated by reference in their entirety.

FIELD OF THE INVENTION

The present invention relates generally to therapy, diagnosis and monitoring of human immunodeficiency virus (HIV) infection. The invention is more specifically related to human neutralizing monoclonal antibodies specific for HIV-1, such as broad and potent neutralizing monoclonal antibodies specific for HIV-1 and their manufacture and use. Broad neutralization suggests that the antibodies can neutralize HIV-1 isolates from different individuals. Such antibodies are useful in pharmaceutical compositions for the prevention and treatment of HIV, and for the diagnosis and monitoring of HIV infection and for design of HIV vaccine immunogens.

BACKGROUND OF THE INVENTION

AIDS was first reported in the United States in 1981 and has since become a major worldwide epidemic. AIDS is caused by the human immunodeficiency virus, or HIV. By killing or damaging cells of the body's immune system, HIV progressively destroys the body's ability to fight infections and certain cancers. People diagnosed with AIDS may get life-threatening diseases called opportunistic infections. These infections are caused by microbes such as viruses or bacteria that usually do not make healthy people sick. HIV is spread most often through unprotected sex with an infected partner. HIV also is spread through contact with infected blood. The human immunodeficiency virus (HIV) is the cause of acquired immune deficiency syndrome (AIDS) (Barre-Sinoussi, F., et al., 1983, Science 220:868-870; Gallo, R., et al., 1984, Science 224:500-503). There are currently 1.25 million people in the US infected with HIV-induced acquired immunodeficiency syndrome according to a Center for Disease Control report. The epidemic is growing most rapidly among minority populations and is a leading killer of African-American males ages 25 to 44. Accordingly, AIDS affects nearly seven times more African Americans and three times more Hispanics than whites. In recent years, an increasing number of African-American women and children are being affected by HIV/AIDS. With over 40 million people infected worldwide, the current global HIV pandemic ranks among the greatest infectious disease scourges in human history.

There is therefore a need for the efficient identification and production of neutralizing antibodies effective against multiple clades and strains of HIV as well as the elucidation of the target and antigenic determinants to which such antibodies bind.

SUMMARY OF THE INVENTION

The present invention provides a novel method for isolating potent, broadly neutralizing monoclonal antibodies against HIV. Peripheral Blood Mononuclear Cells (PBMCs) are obtained from an HIV-infected donor selected for HIV-1 neutralizing activity in the plasma, and memory B cells are isolated for culture in vitro. The B cell culture supernatants are then screened by a primary neutralization assay in a high throughput format, and B cell cultures exhibiting neutralizing activity are selected for rescue of monoclonal antibodies. It is surprisingly observed that neutralizing antibodies obtained by this method do not always exhibit gp120 or gp41 binding at levels that correlate with neutralization activity. The method of the invention therefore allows identification of novel antibodies with cross-clade neutralization properties.

The present invention provides human monoclonal antibodies specifically directed against HIV. In certain embodiments, the invention provides human anti-HIV monoclonal antibodies and sister clones thereof. For instance, an exemplary sister clone of the 1443_C16 (PG16) antibody is the 1503 H05 (PG16) antibody, the 1456 A12 (PG16) antibody, the 1469 M23 (PG16) antibody, the 1489 I13 (PG16) antibody, or the 1480_I08 (PG16) antibody.

Specifically, the invention provides an isolated anti-HIV antibody, wherein said antibody has a heavy chain with three CDRs including an amino acid sequence selected from the group consisting of the amino acid sequences of SGFTFHKYGMH (SEQ ID NO: 88), LISDDGMRKYHSDSMW (SEQ ID NO: 89), and EAGGPIWHDDVKYYDFNDGYYNYHYMDV (SEQ ID NO: 6), and a light chain with three CDRs that include an amino acid sequence selected from the group consisting of the amino acid sequences of NGTSSDVGGFDSVS (SEQ ID NO: 97), DVSHRPSG (SEQ ID NO: 95), and SSLTDRSHRI (SEQ ID NO: 41).

The invention provides an isolated anti-HIV antibody, wherein said antibody has a heavy chain with three CDRs including an amino acid sequence selected from the group consisting of the amino acid sequences of SGFTFHKYGMH (SEQ ID NO: 88), LISDDGMRKYHSDSMW (SEQ ID NO: 89), and EAGGPIWHDDVKYYDFNDGYYNYHYMDV (SEQ ID NO: 6), and a light chain with three CDRs that include an amino acid sequence selected from the group consisting of the amino acid sequences of NGTRSDVGGFDSVS (SEQ ID NO: 92), DVSHRPSG (SEQ ID NO: 95), and SSLTDRSHRI (SEQ ID NO: 41).

The invention provides an isolated anti-HIV antibody, wherein said antibody has a heavy chain with three CDRs including an amino acid sequence selected from the group consisting of the amino acid sequences of SGFTFHKYGMH (SEQ ID NO: 88), LISDDGMRKYHSDSMW (SEQ ID NO: 89), and EAGGPIWHDDVKYYDFNDGYYNYHYMDV (SEQ ID NO: 6), and a light chain with three CDRs that include an amino acid sequence selected from the group consisting of the amino acid sequences of NGTSRDVGGFDSVS (SEQ ID NO: 93), DVSHRPSG (SEQ ID NO: 95), and SSLTDRSHRI (SEQ ID NO: 41).

The invention provides an isolated anti-HIV antibody, wherein said antibody has a heavy chain with three CDRs including an amino acid sequence selected from the group consisting of the amino acid sequences of SGFTFHKYGMH (SEQ ID NO: 88), LISDDGMRKYHSNSMW (SEQ ID NO: 98), and EAGGPIWHDDVKYYDFNDGYYNYHYMDV (SEQ ID NO: 6), and a light chain with three CDRs that include an amino acid sequence selected from the group consisting of the amino acid sequences of NGTSSDVGGFDSVS (SEQ ID NO: 97), DVSHRPSG (SEQ ID NO: 95), and SSLTDRSHRI (SEQ ID NO: 41).

The invention provides an isolated anti-HIV antibody, wherein said antibody has a heavy chain with three CDRs including an amino acid sequence selected from the group consisting of the amino acid sequences of SGGTFSSYAFT (SEQ ID NO: 104), MVTPIFGEAKYSQRFE (SEQ ID NO: 105), and RAVPIATDNWLDP (SEQ ID NO: 102), and a light chain with three CDRs that include an amino acid sequence selected from the group consisting of the amino acid sequences of RASQTINNYLN (SEQ ID NO: 107), GASNLQNG (SEQ ID NO: 108), and QQSFSTPRT (SEQ ID NO: 42).

The invention provides an isolated anti-HIV antibody, wherein said antibody has a heavy chain with three CDRs including an amino acid sequence selected from the group consisting of the amino acid sequences of SGGTFSSYAFT (SEQ ID NO: 104), MVTPIFGEAKYSQRFE (SEQ ID NO: 105), and RRAVPIATDNWLDP (SEQ ID NO: 103), and a light chain with three CDRs that include an amino acid sequence selected from the group consisting of the amino acid sequences of RASQTINNYLN (SEQ ID NO: 107), GASNLQNG (SEQ ID NO: 108), and QQSFSTPRT (SEQ ID NO: 42).

The invention provides an isolated anti-HIV antibody, wherein said antibody has a heavy chain with three CDRs including an amino acid sequence selected from the group consisting of the amino acid sequences of SGGAFSSYAFS (SEQ ID NO: 110), MITPVFGETKYAPRFQ (SEQ ID NO: 111), and RAVPIATDNWLDP (SEQ ID NO: 102), and a light chain with three CDRs that include an amino acid sequence selected from the group consisting of the amino acid sequences of RASQTIHTYL (SEQ ID NO: 113), GASTLQSG (SEQ ID NO: 114), and QQSYSTPRT (SEQ ID NO: 43).

The invention provides an isolated anti-HIV antibody, wherein said antibody has a heavy chain with three CDRs including an amino acid sequence selected from the group consisting of the amino acid sequences of SGGAFSSYAFS (SEQ ID NO: 110), MITPVFGETKYAPRFQ (SEQ ID NO: 111), and RRAVPIATDNWLDP (SEQ ID NO: 103), and a light chain with three CDRs that include an amino acid sequence selected from the group consisting of the amino acid sequences of RASQTIHTYL (SEQ ID NO: 113), GASTLQSG (SEQ ID NO: 114), and QQSYSTPRT (SEQ ID NO: 43).

The invention provides an isolated anti-HIV antibody, wherein said antibody has a heavy chain with three CDRs including an amino acid sequence selected from the group consisting of the amino acid sequences of SGYSFIDYYLH (SEQ ID NO: 116), LIDPENGEARYAEKFQ (SEQ ID NO: 117), AVGADSGSWFDP (SEQ ID NO: 118), and a light chain with three CDRs that include an amino acid sequence selected from the group consisting of the amino acid sequences of SGSKLGDKYVS (SEQ ID NO: 120), ENDRRPSG (SEQ ID NO: 121), QAWETTTTFVF (SEQ ID NO: 44).

The invention provides an isolated anti-HIV antibody, wherein said antibody has a heavy chain with three CDRs including an amino acid sequence selected from the group consisting of the amino acid sequences of SGFDFSRQGMH (SEQ ID NO: 123), FIKYDGSEKYHADSVW (SEQ ID NO: 124), and EAGGPDYRNGYNYYDFYDGYYNYHYMDV (SEQ ID NO: 7), and a light chain with three CDRs that include an amino acid sequence selected from the group consisting of the amino acid sequences of NGTSNDVGGYESVS (SEQ ID NO: 126), DVSKRPSG (SEQ ID NO: 127), and KSLTSTRRRV (SEQ ID NO: 45).

The invention provides an isolated anti-HIV antibody, wherein said antibody has a heavy chain with three CDRs including an amino acid sequence selected from the group consisting of the amino acid sequences of SGFTFHKYGMH (SEQ ID NO: 88), LISDDGMRKYHSDSMW (SEQ ID NO: 89), EAGGPIWHDDVKYYDFNDGYYNYHYMDV (SEQ ID NO: 6), SGGTFSSYAFT (SEQ ID NO: 104), MVTPIFGEAKYSQRFE (SEQ ID NO: 105), RAVPIATDNWLDP (SEQ ID NO: 102), SGGAFSSYAFS (SEQ ID NO: 110), MITPVFGETKYAPRFQ (SEQ ID NO: 111), SGYSFIDYYLH (SEQ ID NO: 116), LIDPENGEARYAEKFQ (SEQ ID NO: 117), AVGADSGSWFDP (SEQ ID NO: 118), SGFDFSRQGMH (SEQ ID NO: 123), FIKYDGSEKYHADSVW (SEQ ID NO: 124), EAGGPDYRNGYNYYDFYDGYYNYHYMDV (SEQ ID NO: 7), LISDDGMRKYHSNSMW (SEQ ID NO: 98), wherein said antibody binds to and neutralizes HIV-1.

The invention provides an isolated anti-HIV antibody, wherein said antibody has a light chain with three CDRs that include an amino acid sequence selected from the group consisting of the amino acid sequences of NGTSSDVGGFDSVS (SEQ ID NO: 97), DVSHRPSG (SEQ ID NO: 95), SSLTDRSHRI (SEQ ID NO: 41), RASQTINNYLN (SEQ ID NO: 107), GASNLQNG (SEQ ID NO: 108), QQSFSTPRT (SEQ ID NO: 42), RASQTIHTYL (SEQ ID NO: 113), GASTLQSG (SEQ ID NO: 114), QQSYSTPRT (SEQ ID NO: 43), SGSKLGDKYVS (SEQ ID NO: 120), ENDRRPSG (SEQ ID NO: 121), QAWETTTTFVF (SEQ ID NO: 44), NGTSNDVGGYESVS (SEQ ID NO: 126), DVSKRPSG (SEQ ID NO: 127), KSLTSTRRRV (SEQ ID NO: 45), NGTRSDVGGFDSVS (SEQ ID NO: 92), NGTSRDVGGFDSVS (SEQ ID NO: 93), wherein said antibody binds to and neutralizes HIV-1.

The invention provides an isolated anti-HIV antibody, wherein said antibody has a heavy chain with three CDRs including an amino acid sequence selected from the group consisting of the amino acid sequences of SGFTFHKYGMH (SEQ ID NO: 88), LISDDGMRKYHSDSMW (SEQ ID NO: 89), EAGG- PIWHDDVKYYDFNDGYYNYHYMDV (SEQ ID NO: 6), SGGTFSSYAFT (SEQ ID NO: 104), MVTPIFGEAKYSQRFE (SEQ ID NO: 105), RRAVPIATDNWLDP (SEQ ID NO: 103), SGGAFSSYAFS (SEQ ID NO: 110), MITPVFGETKYAPRFQ (SEQ ID NO: 111), SGYSFIDYYLH (SEQ ID NO: 116), LIDPENGEARYAEKFQ (SEQ ID NO: 117), AVGADSGSWFDP (SEQ ID NO: 118), SGFDFSRQGMH (SEQ ID NO: 123), FIKYDGSEKYHADSVW (SEQ ID NO: 124), EAGGPDYRNGYNYYDFYDGYYNYHYMDV (SEQ ID NO: 7), LISDDGMRKYHSNSMW (SEQ ID NO: 98), wherein said antibody binds to and neutralizes HIV-1.

The invention provides an isolated anti-HIV antibody, wherein said antibody has a light chain with three CDRs that include an amino acid sequence selected from the group consisting of the amino acid sequences of NGTSSDVGGFDSVS (SEQ ID NO: 97), DVSHRPSG (SEQ ID NO: 95), SSLTDRSHRI (SEQ ID NO: 41), RASQTINNYLN (SEQ ID NO: 107), GASNLQNG (SEQ ID NO: 108), QQSFSTPRT (SEQ ID NO: 42), RASQTIHTYL (SEQ ID NO: 113), GASTLQSG (SEQ ID NO: 114), QQSYSTPRT (SEQ ID NO: 43), SGSKLGDKYVS (SEQ ID NO: 120), ENDRRPSG (SEQ ID NO: 121), QAWETTTTFVF (SEQ ID NO: 44), NGTSNDVGGYESVS (SEQ ID NO: 126), DVSKRPSG (SEQ ID NO: 127), KSLTSTRRRV (SEQ ID NO: 45), NGTRSDVGGFDSVS (SEQ ID NO: 92), NGTSRDVGGFDSVS (SEQ ID NO: 93), wherein said antibody binds to and neutralizes HIV-1.

The invention provides an isolated anti-HIV antibody or fragment thereof, wherein said antibody includes: (a) a $V_H$ CDR1 region comprising the amino acid sequence of SEQ ID NO: 88, 104, 110, 116, or 123; (b) a $V_H$ CDR2 region comprising the amino acid sequence of SEQ ID NO: 98, 89, 91, 105, 111, 117, or 124; and (c) a $V_H$ CDR3 region comprising the amino acid sequence of SEQ ID NO: 6, 102, 103, 118, or 7, wherein said antibody binds to and neutralizes HIV-1. In certain aspects, this antibody further includes: (a) a $V_L$ CDR1 region comprising the amino acid sequence of SEQ ID NO: 93, 92, 97, 94, 107, 113, 120, or 126; (b) a $V_L$ CDR2 region comprising the amino acid sequence of SEQ ID NO: 95, 108, 114, 121, or 127; and (c) a $V_L$ CDR3 region comprising the amino acid sequence of SEQ ID NO: 41, 42, 43, 44, or 45.

The invention provides an isolated fully human monoclonal anti-HIV antibody including: a) a heavy chain sequence comprising the amino acid sequence of SEQ ID NO: 31 and a light chain sequence comprising amino acid sequence SEQ ID NO: 32, or b) a heavy chain sequence comprising the amino acid sequence of SEQ ID NO: 33 and a light chain sequence comprising amino acid sequence SEQ ID NO: 34, or c) a heavy chain sequence comprising the amino acid sequence of SEQ ID NO: 35 and a light chain sequence comprising amino acid sequence SEQ ID NO: 36, or d) a heavy chain sequence comprising the amino acid sequence of SEQ ID NO: 37 and a light chain sequence comprising amino acid sequence SEQ ID NO: 38, or e) a heavy chain sequence comprising the amino acid sequence of SEQ ID NO: 39 and a light chain sequence comprising amino acid sequence SEQ ID NO: 40, or f) a heavy chain sequence comprising the amino acid sequence of SEQ ID NO: 140 and a light chain sequence comprising amino acid sequence SEQ ID NO: 96, or g) a heavy chain sequence comprising the amino acid sequence of SEQ ID NO: 48 and a light chain sequence comprising amino acid sequence SEQ ID NO: 51, or h) a heavy chain sequence comprising the amino acid sequence of SEQ ID NO: 54 and a light chain sequence comprising amino acid sequence SEQ ID NO: 57, or i) a heavy chain sequence comprising the amino acid sequence of SEQ ID NO: 60 and a light chain sequence comprising amino acid sequence SEQ ID NO: 32.

The invention provides a composition including any one of the isolated anti-HIV antibodies described herein.

Optionally, an anti-HIV human monoclonal antibody of the invention is isolated from a B-cell from an HIV-1-infected human donor. In some embodiments, the antibody is effective in neutralizing a plurality of different clades of HIV. In some embodiments, the antibody is effective in neutralizing a plurality of different strain within the same clade of HIV-1. In some embodiments, the neutralizing antibody binds to the HIV envelope proteins gp120, or gp41 or envelope protein on HIV-1 pseudovirions or expressed on transfected or infected cell surfaces. In some embodiments, the neutralizing antibody does not bind to recombinant or monomeric envelope proteins gp120, or gp41 or envelope protein on HIV-1 pseudovirions or expressed on transfected or infected cell surfaces but binds to natural trimeric forms of the HIV-1 Env proteins.

The present invention provides human monoclonal antibodies wherein the antibodies are potent, broadly neutralizing antibody (bNAb). In some embodiments, a broadly neutralizing antibody is defined as a bNAb that neutralizes HIV-1 species belonging to two or more different clades. In some embodiments the different clades are selected from the group consisting of clades A, B, C, D, E, AE, AG, G or F. In some embodiments the HIV-1 strains from two or more clades comprise virus from non-B clades.

In some embodiments, a broadly neutralizing antibody is defined as a bNAb that neutralizes at least 60% of the HIV-1 strains listed in FIGS. 32A-F. In some embodiments, at least 70%, or at least 80%, or at least 90% of the HIV-1 strains listed in FIGS. 32A-F are neutralized.

In some embodiments, a potent, broadly neutralizing antibody is defined as a bNAb that displays a potency of neutralization of at least a plurality of HIV-1 species with an IC50 value of less than 0.2 µg/mL. In some embodiments the potency of neutralization of the HIV-1 species has an IC50 value of less than 0.15 µg/mL, or less than 0.10 µg/mL, or less than 0.05 µg/mL. A potent, broadly neutralizing antibody is also defined as a bNAb that displays a potency of neutralization of at least a plurality of HIV-1 species with an IC90 value of less than 2.0 µg/mL. In some embodiments the potency of neutralization of the HIV-1 species has an IC90 value of less than 1.0 µg/mL, or less than 0.5 µg/mL.

Exemplary monoclonal antibodies that neutralize HIV-1 include 1496_C09 (PG9), 1443_C16 (PG16), 1456_P20 (PG20), 1460_G14 (PGG14), and 1495_C14 (PGC14) described herein. Alternatively, the monoclonal antibody is an antibody that binds to the same epitope as 1496_C09 (PG9), 1443_C16 (PG16), 1456_P20 (PG20), 1460_G14 (PGG14), and 1495_C14 (PGC14). Specifically, monoclonal antibodies PG9 and PG16 are broad and potent neutralizing antibodies. The antibodies are respectively referred to herein as HIV antibodies.

The invention provides a number of isolated human monoclonal antibodies, wherein each said monoclonal antibody binds to HIV-1 infected or transfected cells; and binds to HIV-1 virus. A neutralizing antibody having potency in neutralizing HIV-1, or a fragment thereof is provided. In some embodiments a neutralizing antibody of the invention exhibits higher neutralization index and/or a higher affinity for binding to the envelope proteins gp120, or gp41 than anti-HIV mAbs known in the art, such as the mAb b12. (Burton D R et al., Science Vol. 266. no. 5187, pp. 1024-1027). Exemplary monoclonal antibodies 1496_C09 (PG9), 1443_C16 (PG16), 1456_P20 (PG20), 1460_G14 (PGG14), and 1495_C14 (PGC14) exhibit binding to the envelope glycoprotein gp120, but not gp41, in an ELISA assay, however gp120 binding does not always correlate with neutralization activity against specific strains of HIV-1. In some embodiments, monoclonal antibodies, for example 1443_C16 (PG16) and 1496_C09 (PG9), display none or weak gp120 binding activity against a particular strain but bind to HIV-1 trimer on transfected or infected cell surface and/or virion and exhibit broad and potent neutralization activity against that strain of HIV-1.

In one aspect the antibody is a monoclonal antibody comprising one or more polypeptides selected from the group consisting of 1496_C09 (PG9), 1443_C16 (PG16), 1456_P20 (PG20), 1460_G14 (PGG14), and 1495_C14 (PGC14); comprising a heavy chain selected from the group consisting of the heavy chain of 1496_C09 (PG9), 1443_C16 (PG16), 1456_P20 (PG20), 1460_G14 (PGG14), and 1495_C14 (PGC14); comprising a heavy chain comprising a CDR selected from the group consisting of the CDRs of the heavy chain of 1496_C09 (PG9), 1443_C16 (PG16), 1456_P20 (PG20), 1460_G14 (PGG14), and 1495_C14 (PGC14); comprising a light chain selected from the group consisting of the light chain of 1496_C09 (PG9), 1443_C16 (PG16), 1456_P20 (PG20), 1460_G14 (PGG14), and 1495_C14 (PGC14); comprising a light chain comprising a CDR selected from the group consisting of the CDRs of the light chain of 1496_C09 (PG9), 1443_C16 (PG16), 1456_P20 (PG20), 1460_G14 (PGG14), and 1495_C14 (PGC14).

The invention relates to an antibody or a fragment thereof, such as Fab, Fab', F(ab')2 and Fv fragments that binds to an epitope or immunogenic polypeptide capable of binding to an antibody selected from 1496_C09 (PG9), 1443_C16 (PG16), 1456_P20 (PG20), 1460_G14 (PGG14), and 1495_C14 (PGC14). The invention also relates to immunogenic polypeptides encoding such epitopes.

Nucleic acid molecules encoding such antibodies, and vectors and cells carrying such nucleic acids are also provided.

The invention relates to a pharmaceutical composition comprising at least one antibody or fragment as recited herein, together with a pharmaceutically acceptable carrier.

The invention relates to a method of immunizing, preventing or inhibiting HIV infection or an HIV-related disease comprising the steps of identifying a patient in need of such treatment and administering to said patient a therapeutically effective amount of at least one monoclonal antibody as recited herein.

In a further aspect the HIV antibodies according to the invention are linked to a therapeutic agent or a detectable label.

Additionally, the invention provides methods for stimulating an immune response, treating, preventing or alleviating a symptom of an HIV viral infection by administering an HIV antibody to a subject In another aspect, the invention provides methods of administering the HIV antibody of the invention to a subject prior to, and/or after exposure to an HIV virus. For example, the HIV antibody of the invention is used to treat or prevent HIV infection. The HIV antibody is administered at a dose sufficient to promote viral clearance or eliminate HIV infected cells.

Also included in the invention is a method for determining the presence of an HIV virus infection in a patient, by contacting a biological sample obtained from the patient with an HIV antibody; detecting an amount of the antibody that binds to the biological sample; and comparing the amount of antibody that binds to the biological sample to a control value.

The invention further provides a diagnostic kit comprising an HIV monoclonal antibody.

The invention relates to a broadly neutralizing antibody (bNAb) wherein the antibody neutralizes at least one member of each clade with a potency greater than that of the bNAbs b12, 2G12, 2F5 and 4E10 respectively.

The invention relates to a broadly neutralizing antibody (bNAb) wherein the antibody does not bind monomeric gp120 or gp41 proteins of the HIV-1 env gene. The antibody binds with higher affinity to trimeric forms of the HIV-1 Env expressed on a cell surface than to the monomeric gp120 or artificially trimerized gp140. In some aspects, the antibody binds with high affinity to uncleaved HIV-1 gp160 trimers on a cell surface.

The invention relates to a broadly neutralizing antibody (bNAb) wherein the antibody binds an epitope within the variable loop of gp120, wherein the epitope comprises the conserved regions of V2 and V3 loops of gp120, wherein the epitope comprises N-glycosylation site at residue Asn-160 within the V2 loop of gp120, wherein the antibody binds an epitope presented by a trimeric spike of gp120 on a cell surface, wherein the epitope is not presented when gp120 is artificially trimerized. In some embodiments, the antibody does not neutralize the HIV-1 in the absence of N-glycosylation site at residue Asn-160 within the V2 loop of gp120.

The invention relates to a broadly neutralizing antibody (bNAb) selected from the group consisting of PG16 and PG9.

The invention relates to an antigen or an immunogenic polypeptide, or a vaccine comprising such antigen or immunogenic polypeptide, for producing a broadly neutralizing antibody (bNAb) by an immune response, the antigen comprising an epitope within the variable loop of gp120 according to the invention.

The invention relates to method for passive or active immunization of an individual against a plurality of HIV-1 species across one or more clades, the method comprising: providing a broadly neutralizing antibody (bNAb) wherein the bNAb neutralizes HIV-1 species belonging to two or more clades, and further wherein the potency of neutralization of at least one member of each clade is determined by an IC50 value of less than 0.005 µg/mL. In some embodiments, the antibody is selected from the group consisting of PG9 and PG16.

In some embodiments, the antibody is produced by active immunization with an antigen comprising an epitope within the variable loop of gp120, wherein the epitope comprises the conserved regions of V2 and V3 loops of gp120 or, wherein the epitope comprises an N-glycosylation site at residue Asn-160 within the V2 loop of gp120. In some aspects, the epitope is presented by a trimeric spike of gp120 on a cell surface, and the epitope is not presented when gp120 is monomeric or artificially trimerized.

Other features and advantages of the invention will be apparent from and are encompassed by the following detailed description and claims.

BRIEF DESCRIPTION OF THE DRAWINGS

FIG. 1A is a schematic tree diagram of Clustal W-aligned variable region sequences of heavy chains of the monoclonal antibodies.

FIG. 1B is a schematic tree diagram of Clustal W-aligned variable region sequences of light chains of the monoclonal antibodies.

FIG. 4A-4B is a series of graphs depicting the neutralization activity of monoclonal antibodies 1443_C16 (PG16) and 1496_C09 (PG9) to additional pseudoviruses not included in FIGS. 31A-B.

FIG. 6A-6C is a series of graphs depicting the results from ELISA binding assays of monoclonal antibodies 1443_C16 (PG16) and 1496_C09 (PG9) to HIV-1 YU2 gp140, JR-CSFgp120, membrane-proximal external regions (MPER) peptide of gp41 and V3 polypeptide.

FIG. 8A-8B is a graph depicting the results of a binding assay using monoclonal antibodies 1443_C16 (PG16) and 1496_C09 (PG9) to HIV-1 gp160 transfected cells.

FIG. 10B is a graph depicting the results of a competitive binding assay using monoclonal antibodies sCD4, PG16 and PG9, wherein the claimed antibodies compete for the binding of monoclonal antibody 1496_C09 (PG9) to pseudovirus but control antibodies b12, 2G12, 2F5 and 4E10 do not competitively bind to the pseudovirus.

FIG. 13A-13E is a series of graphs depicting the mapping the PG9 and PG16 epitopes. Competitor antibody is indicated at the top of each graph. 2G12 is included to control for cell surface Env expression. A: PG9 and PG16 compete with each other for cell surface Env binding and neither antibody competes with the CD4bs antibody b12 for Env binding. B: Ligation of cell surface Env with sCD4 diminishes binding of PG9 and PG16. 2G12 is included to control for CD4-induced shedding of gp120. C: sCD4 inhibits binding of PG9 to artificially trimerized gp140YU-2 as determined by ELISA. D: PG9 competes with 10/76b (anti-V2), F425/b4e8 (anti-V3) and X5 (CD4i) for gp120 binding in competition ELISA assays. E: PG9 and PG16 fail to bind variable loop deleted HIV-1JR-CSF variants expressed on the surface of 293T cells.

FIG. 14 is a series of graphs depicting the results of competition ELISA assays using the monoclonal antibody PG9.

FIG. 22 is a table depicting the results of testing for neutralization activity against a multi-clade 16-pseudovirus panel FIG. 23A-23B are tables depicting neutralization activities—breadth and potency, respectively—of PG9, PG16, and PGC14 as well as four control bNAbs as measured by IC50 values.

FIGS. 25A-25D depicts the Alignment of heavy chain coding sequences of the variable domain of 1443_C16 sister clones to 1443_C16 and 1496_C09. Kabat CDR sequences for the PG16 sister clones are highlighted in boxes.

FIGS. 29A-29I depicts the screening results of the monoclonal antibodies 1496_C09 (PG9), 1443_C16 (PG16), 1456_P20 (PG20), 1460_G14 (PGG14), and 1495_C14 (PGC14) during the course of their identification in the method described in this invention. The neutralization activity of each antibody and its corresponding binding reactivity to soluble recombinant gp120 or gp41, in the context of B cell culture supernatant and recombinant transfectant supernatants are illustrated. Boxes are color coded as follows: Lightest grey: suggested H &L pair for monoclonal antibody per priority well. Medium grey with black lettering: Denotes clones derived from same recombinant H or L chain pool of the priority well with identical sequences. Bolded: 1496_C09 λ3 clone 024 is likely a cross-contaminant in the recombinant DNA pool as it is identical to 1443_C16 λ2 019 in sequence. 1496_C09 λ2 017 sequence represents 21/22 clones in the pool. *Anti-gp120 and anti-gp41 concentrations were extrapolated from b12 and 2F5 standard curves in quantitative ELISA, respectively. N/A=not applicable because these hits were neither gp-120- nor gp-41 positive in B cell culture. ND=not done.

FIG. 30 depicts testing for neutralization of 6 additional HIV strains from clades A (94UG103), B (92BR020, JR-CSF), C (93IN905, IAVI_C22), and CRF01_AE (92TH021). (*plateau; flat inhibition curve—probably <0.0025 with plateau; *very long, shallow slope;****plateau with very long, shallow slope to curve)

FIG. 31A shows neutralization profiles (IC50 values) of monoclonal antibodies 1443_C16 (PG16), 1456_P20 (PG20), 1460_G14 (PGG14), 1495_C14 (PGC14) and 1496_C09 (PG9) and the known cross-clade neutralizing antibodies b12, 2G12, 2F5 and 4E10 on a diverse panel of 16 HIV pseudoviruses from different clades. (NA—Not Applicable; IC50: Inhibitory concentration to inhibit 50% of the virus)

FIG. 31B shows IC90 values of the monoclonal antibodies 1443_C16 (PG16) and 1496_C09 (PG9) and the known cross-clade neutralizing antibodies b12, 2G12, 2F5 and 4E10 on the same panel of pseudoviruses.

FIGS. 32A-32F depicts different viruses with boxes color coded as follows: White squares indicate an IC50 of >50 μg/mL, black squares indicate 50 μg/mL>IC50>10 μg/mL, lightest grey squares indicate μg/mL>IC50>1 μg/mL, medium grey squares indicate 1/mL>IC50>0.1 μg/mL, darker grey squares indicate IC50<0.01 μg/mL. N.D., not done; b White squares indicate an IC50 of <1:100 dilution, darkest grey squares indicate 1:50>IC50>1:150, lightest grey squares indicate 1:150>IC50>1:500, medium grey squares indicate 1:500>IC50>1:1000, darker grey squares indicate IC50>1:1000 dilution.

FIG. 33A depicts Neutralization Potency. Boxes are color coded as follows: White boxes indicate a medium potency of >50 μg/mL; darkest grey between 20 and 50 μg/mL; lightest grey between 2 and 20 μg/mL; medium grey between 0.2 and 2/mL; and darker grey<0.2 μg/mL. *CRF_07BC and CRF_08BC viruses not included in the clade analysis because there was only one virus tested from each of these clades.

FIG. 33B depicts Neutralization Breadth. Boxes are color coded as follows: white boxes indicate that no viruses were neutralized; darkest grey indicate 1 to 30% of viruses were neutralized; lightest grey indicate 30 to 60% of viruses were neutralized; medium grey indicate 60 to 90% of viruses were neutralized; and darker grey indicate 90 to 100% of viruses were neutralized. *CRF_07BC and CRF_08BC viruses not included in the clade analysis because there was only one virus tested from each of these clades.

FIGS. 34A-34B is a table depicting the neutralization activity of PG9 and PG16 against JR-CSF pseudovirus containing alanine point mutations. Experiments were performed in triplicate and values represent an average of at least three independent experiments. $^a$Amino acid number is based on the sequence of HIV-1HxB2. $^b$Boxes are color coded as follows: white boxes indicate that the amino acid is identical among 0 to 49% of all HIV isolates, light grey boxes indicate that the amino acid is identical among 50-90% of all HIV isolates, and dark grey boxes indicate that the amino acid is identical among 90-100% of all HIV isolates. Amino acid identity was determined based upon a sequence alignment of HIV-1 isolates listed in the HIV sequence database. $^c$C refers to constant domains and V refers to variable loops. $^d$Neutralization activity is reported as fold increase in IC50 value relative to WT JR-CSF and was calculated using the equation (IC50 mutant/IC50 WT). Boxes are color coded as follows: white: substitutions which had a negligible effect on neutralization activity' lightest grey: 4-9 fold IC50 increase; dark grey: 10-100 fold IC50 increase; darkest grey: >100 fold IC50 increase.

FIG. 35 is a table depicting the Alanine mutations that decrease PG9 and PG16 neutralization activity. $^a$Amino acid numbering is based on the sequence of HIV-1HxB2. $^b$Boxes are color coded as follows: white, the amino acid is identical among 0 to 49% of all HIV-1 isolates; light grey, the amino acid is identical among 50 to 90% of isolates; dark grey, the amino acid is identical among 90 to 100% of isolates. Amino acid identity was determined based on a sequence alignment of HIV-1 isolates listed in the HIV sequence database. [c]C refers to constant domains and V refers to variable loops. [d]Neutralization activity is reported as fold increase in IC50 value relative to WT JR-CSF and was calculated using the equation (IC50 mutant/IC50 WT. Boxes are color coded as follows: white, substitutions which had a negative effect on neutralization activity. light grey, 4-9 fold IC50 increase. medium grey, 10-100 fold IC50 increase. dark grey, >100 fold IC50 increase. Experiments were performed in triplicate and values represent an average of at least three independent experiments.

FIG. 36 is a table identifying 14443 C16 (PG16) sister clones. Note that the constant region of the 1456_A12 heavy chain clones used in transfection contains an error generated during the cloning process that lead to no full-length IgG production.

DETAILED DESCRIPTION OF THE INVENTION

Figure 2:
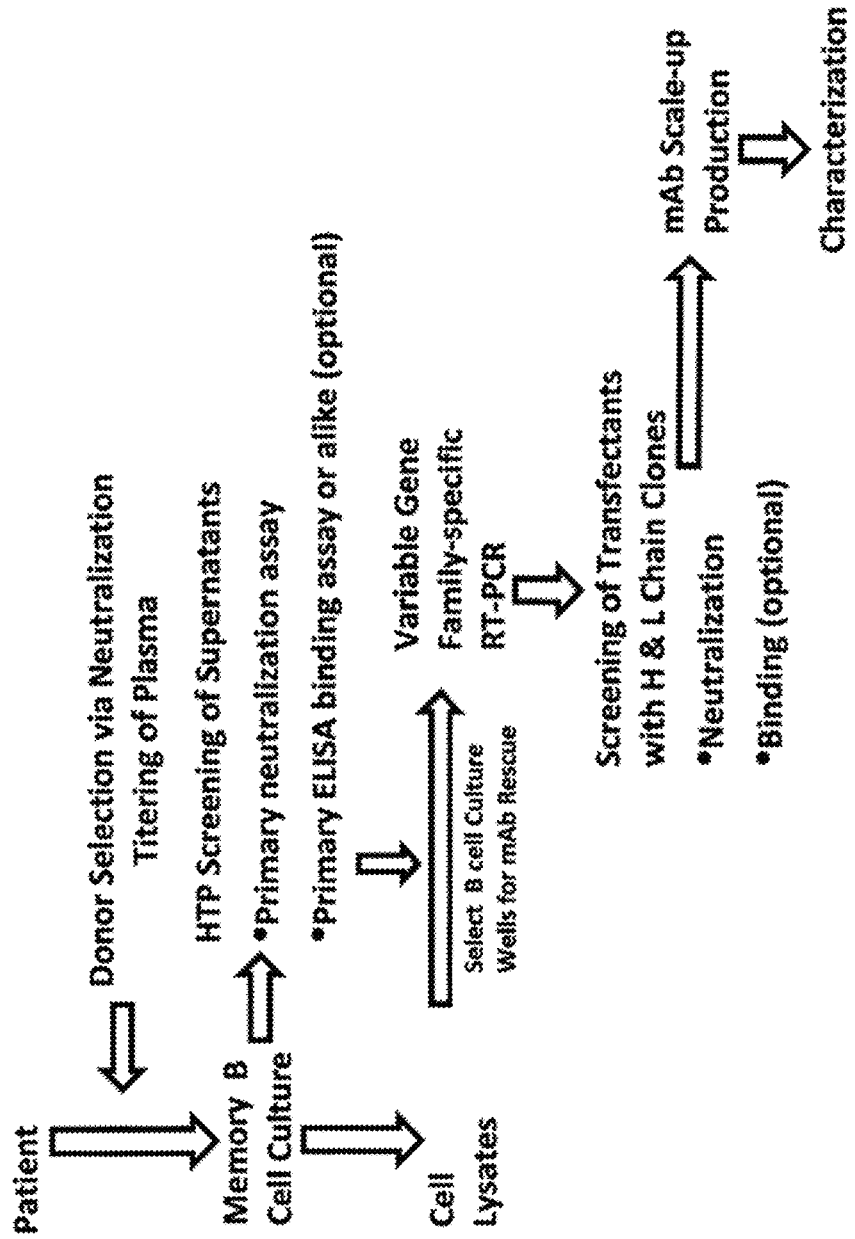
FIG. 2 is a flow chart of the process for isolation of monoclonal antibodies according to the invention.

In the sera of human immunodeficiency virus type 1 (HIV-1) infected patients, anti-virus antibodies can be detected over a certain period after infection without any clinical manifestations of the acquired immunodeficiency syndrome (AIDS). At this state of active immune response, high numbers of antigen-specific B-cells are expected in the circulation. These B-cells are used as fusion partners for the generation of human monoclonal anti-HIV antibodies. One major drawback to finding a vaccine composition suitable for more reliable prevention of human individuals from HIV-1 infection and/or for more successful therapeutic treatment of infected patients is the ability of the HIV-1 virus to escape antibody capture by genetic variation, which very often renders the remarkable efforts of the researchers almost useless. Such escape mutants may be characterized by a change of only one or several of the amino acids within one of the targeted antigenic determinants and may occur, for example, as a result of spontaneous or induced mutation. In addition to genetic variation, certain other properties of the HIV-1 envelope glycoprotein makes it difficult to elicit neutralizing antibodies making generation of undesirable non-neutralizing antibodies a major concern (see Phogat S K and Wyatt R T, Curr Pharm Design 2007; 13(2):213-227).

HIV-1 is among the most genetically diverse viral pathogens. Of the three main branches of the HIV-1 phylogenetic tree, the M (main), N (new), and O (outlier) groups, group M viruses are the most widespread, accounting for over 99% of global infections. This group is presently divided into nine distinct genetic subtypes, or clades (A through K), based on full-length sequences. Env is the most variable HIV-1 gene, with up to 35% sequence diversity between clades, 20% sequence diversity within clades, and up to 10% sequence diversity in a single infected person (Shankarappa, R. et al. 1999. J. Virol. 73:10489-10502). Clade B is dominant in Europe, the Americas, and Australia. Clade C is common in southern Africa, China, and India and presently infects more people worldwide than any other clade (McCutchan, F E. 2000. Understanding the genetic diversity of HIV-1. AIDS 14(Suppl. 3):S31-S44). Clades A and D are prominent in central and eastern Africa.

Neutralizing antibodies (NAbs) against viral envelope proteins (Env) provide adaptive immune defense against human immunodeficiency virus type 1 (HIV-1) exposure by blocking the infection of susceptible cells (Kwong P D et al., 2002. Nature 420: 678-682). The efficacy of vaccines against several viruses has been attributed to their ability to elicit NAbs. However, despite enormous efforts, there has been limited progress toward an effective immunogen for HIV-1. (Burton, D. R. 2002. Nat. Rev. Immunol. 2:706-713).

HIV-1 has evolved with an extensive array of strategies to evade antibody-mediated neutralization. (Barouch, D. H. Nature 455, 613-619 (2008); Kwong, P. D. & Wilson, I. A. Nat Immunol 10, 573-578 (2009); Karlsson Hedestam, G. B., et al. Nat Rev Microbiol 6, 143-155 (2008)). However, broadly neutralizing antibodies (bNAbs) develop over time in a proportion of HIV-1 infected individuals. (Leonidas Stamatatos, L. M., Dennis R Burton, and John Mascola. Nature Medicine (E-Pub: Jun. 14, 2009); PMID: 19525964.) A handful of broadly neutralizing monoclonal antibodies have been isolated from clade B infected donors. (Burton, D. R., et al. Science 266, 1024-1027 (1994); Trkola, A., et al. J Virol 69, 6609-6617 (1995); Stiegler, G., et al. AIDS Res Hum Retroviruses 17, 1757-1765 (2001)). These antibodies tend to display less breadth and potency against non-clade B viruses, and they recognize epitopes on the virus that have so far failed to elicit broadly neutralizing responses when incorporated into a diverse range of immunogens. (Phogat, S. & Wyatt, R. Curr Pharm Design 13, 213-227 (2007); Montero, M., van Houten, N. E., Wang, X. & Scott, J. K. Microbiol Mol Biol Rev 72, 54-84, table of contents (2008); Scanlan, C. N., Offer, J., Zitzmann, N. & Dwek, R. A. Nature 446, 1038-1045 (2007)). Despite the enormous diversity of the human immunodeficiency virus (HIV), all HIV viruses known to date interact with the same cellular receptors (CD4 and/or a co-receptor, CCR5 or CXCR4). Most neutralizing antibodies bind to functional regions involved in receptor interactions and cell membrane fusion. However, the vast majority of neutralizing antibodies isolated to date do not recognize more than one clade, therefore exhibiting limited protective efficacy in vitro or in vivo. (See Binley J M et al., 2004. J. Virol. 78(23):13232-13252). The rare broadly neutralizing human monoclonal antibodies (mAbs) that have been isolated from HIV+ clade B-infected human donors bind to products of the env gene of HIV-1, gp120 and the transmembrane protein gp41. (Parren, P W et al. 1999. AIDS 13:S137-S162). However, a well-known characteristic of the HIV-1 envelope glycoprotein is its extreme variability. It has been recognized that even relatively conserved epitopes on HIV-1, such as the CD4 binding site, show some variability between different isolates (Poignard, P., et al., Ann. Rev. Immunol. (2001) 19:253-274). Even an antibody targeted to one of these conserved sites can be expected to suffer from a reduced breadth of reactivity across multiple different isolates.

The few cross-clade reactive monoclonal antibodies known to date have been isolated by processes involving generation of panels of specific viral antibodies from peripheral blood lymphocytes (PBLs) of HIV-infected individuals, either via phage display, or via conventional immortalization techniques such as hybridoma or Epstein Barr virus transformation, electrofusion and the like. These are selected based on reactivity in vitro to HIV-1 proteins, followed by testing for HIV neutralization activity.

An antibody phage surface expression system was used to isolate the cross-clade neutralizing Fab (fragment, antigen binding) b12 occurring in a combinatorial library. The Fab b12 was screened by panning for envelope glycoprotein gp120 binding activity and neutralizing activity against the HIV-1 (HXBc2) isolate was observed. (Roben P et al., J. Virol. 68(8): 4821-4828(1994); Barbas C F et al., Proc. Natl.

Acad. Sci. USA Vol. 89, pp. 9339-9343, (1992); Burton D P et al., Proc. Natl. Acad. Sci. USA Vol. 88, pp. 10134-10137 (1991)).

Human B cell immortalization was used to isolate the cross-clade neutralizing monoclonal antibodies 2G12, 2F5, and 4E10 from HIV-infected individuals. The monoclonal antibody 2G12 binds to a glycotope on the gp120 surface glycoprotein of HIV-1 and had been shown to display broad neutralizing patterns. (Trkola A., et al., J. Virol. 70(2):1100-1108 (1996), Buchacher, A., et al., 1994. AIDS Res. Hum. Retroviruses 10:359-369). The monoclonal antibody 2F5 which had been shown to bind a sequence within the external domain of the gp41 envelope glycoprotein of HIV-1 was found to have broad neutralization properties. (Conley A J Proc. Natl. Acad. Sci. USA Vol. 91, pp. 3348-3352 (1994); Muster T et al., J. Virol. 67(11):6642-6647 (1993); Buchacher A et al., 1992, Vaccines 92:191-195). The monoclonal antibody 4E10, which binds to a novel epitope C terminal of the ELDKWA sequence in gp41 recognized by 2F5, has also been found to have potent cross-clade neutralization activity. (Buchacher, A., et al., 1994. AIDS Res. Hum. Retroviruses 10:359-369; Stiegler, G., et al., 2001. AIDS Res. Hum. Retroviruses 17(18):1757-1765)).

Other studies on antibody neutralization of HIV-1 (Nara, P. L., et al. (1991) FASEB J. 5:2437-2455.) focused on a single linear epitope in the third hypervariable region of the viral envelope glycoprotein gp120 known as the V3 loop. Antibodies to this loop are suggested to neutralize by inhibiting fusion of viral and cell membranes. However there is sequence variability within the loop and neutralizing antibodies are sensitive to sequence variations outside the loop (Albert J. et al., (1990) AIDS 4, 107-112). Hence anti-V3 loop antibodies are often strain-specific and mutations in the loop in vivo may provide a mechanism for viral escape from antibody neutralization. There is some indication that not all neutralizing antibodies act by blocking the attachment of virus, since a number of mouse monoclonal antibodies inhibiting CD4 binding to gp120 are either non-neutralizing (Lasky L A, et al., (1987) Cell 50:975-985.) or only weakly neutralizing (Sun N., et al., (1989) J. Virol. 63, 3579-3585).

It is widely accepted that such a vaccine will require both T-cell mediated immunity as well as the elicitation of a broadly neutralizing antibody (bNAb) response. (Barouch, D. H. Nature 455, 613-619 (2008); Walker, B. D. & Burton, D. R. Science 320, 760-764 (2008); Johnston, M. I. & Fauci, A. S. N Engl J Med 356, 2073-2081 (2007)). All of the known bNAbs provide protection in the best available primate models (Veazey, R. S., et al. Nat Med 9, 343-346 (2003); Hessell, A. J., et al. PLoS Pathog 5, e1000433 (2009); Parren, P. W., et al. J Virol 75, 8340-8347 (2001); Mascola, J. R. Vaccine 20, 1922-1925 (2002); Mascola, J. R., et al. Nat Med 6, 207-210 (2000); Mascola, J. R., et al. J Virol 73, 4009-4018 (1999)). Therefore, broadly neutralizing antibodies (bNAbs) are considered to be the types of antibodies that should be elicited by a vaccine. Unfortunately, existing immunogens, often designed based on these bNAbs, have failed to elicit NAb responses of the required breadth and potency. Therefore, it is of high priority to identify new bNAbs that bind to epitopes that may be more amenable to incorporation into immunogens for elicitation of NAb responses.

The present invention provides a novel method for isolating novel broad and potent neutralizing monoclonal antibodies against HIV. The method involves selection of a PBMC donor with high neutralization titer of antibodies in the plasma. B cells are screened for neutralization activity prior to rescue of antibodies. Novel broadly neutralizing antibodies are obtained by emphasizing neutralization as the initial screen.

The invention relates to potent, broadly neutralizing antibody (bNAb) wherein the antibody neutralizes HIV-1 species belonging to two or more clades, and further wherein the potency of neutralization of at least one member of each clade is determined by an IC50 value of less than 0.2 µg/mL. In some aspects, the clades are selected from Clade A, Clade B, Clade C, Clade D and Clade AE. In some aspects, the HIV-1 belonging two or more clades are non-Clade B viruses. In some aspects, the broadly neutralizing antibody neutralizes at least 60% of the HIV-1 strains listed in FIGS. 32A-F. In some embodiments, at least 70%, or at least 80%, or at least 90% of the HIV-1 strains listed in FIGS. 32A-F are neutralized.

The invention relates to potent, broadly neutralizing antibody (bNAb) wherein the antibody neutralizes HIV-1 species with a potency of neutralization of at least a plurality of HIV-1 species with an IC50 value of less than 0.2 µg/mL. In some embodiments the potency of neutralization of the HIV-1 species has an IC50 value of less than 0.15 µg/mL, or less than 0.10 µg/mL, or less than 0.05 µg/mL. In some aspects, a potent, broadly neutralizing antibody is defined as a bNAb that displays a potency of neutralization of at least a plurality of HIV-1 species with an IC90 value of less than 2.0 µg/mL. In some embodiments the potency of neutralization of the HIV-1 species has an IC90 value of less than 1.0 µg/mL, or less than 0.5 µg/mL.

An exemplary method is illustrated in the schematic shown in FIG. 4. Peripheral Blood Mononuclear Cells (PBMCs) were obtained from an HIV-infected donor selected for HIV-1 neutralizing activity in the plasma. Memory B cells were isolated and B cell culture supernatants were subjected to a primary screen of neutralization assay in a high throughput format. Optionally, HIV antigen binding assays using ELISA or like methods were also used as a screen. B cell lysates corresponding to supernatants exhibiting neutralizing activity were selected for rescue of monoclonal antibodies by standard recombinant methods.

In one embodiment, the recombinant rescue of the monoclonal antibodies involves use of a B cell culture system as described in Weitcamp J-H et al., J. Immunol. 171:4680-4688 (2003). Any other method for rescue of single B cells clones known in the art also may be employed such as EBV immortalization of B cells (Traggiai E., et al., Nat. Med. 10(8):871-875 (2004)), electrofusion (Buchacher, A., et al., 1994. AIDS Res. Hum. Retroviruses 10:359-369), and B cell hybridoma (Karpas A. et al., Proc. Natl. Acad. Sci. USA 98:1799-1804 (2001).

In some embodiments, monoclonal antibodies were rescued from the B cell cultures using variable chain gene-specific RT-PCR, and transfectant with combinations of H and L chain clones were screened again for neutralization and HIV antigen binding activities. mAbs with neutralization properties were selected for further characterization.

A novel high-throughput strategy was used to screen IgG-containing culture screening supernatants from approximately 30,000 activated memory B cells from a clade A infected donor for recombinant, monomeric gp120JR-CSF and gp41HxB2 (Env) binding as well as neutralization activity against HIV-1JR-CSF and HIV-1SF162 (See Table 1).

TABLE 1

| Memory B cell Screening. | |
|---|---|
| Total number of wells screened | 23,328 |
| Number of sIgG+ memory B cells screened | 30,300 |
| gp120 ELISA hits | 411 (1.36%) |
| gp41 ELISA hits | 167 (0.55%) |
| SF162 neutralization hits | 401 (1.32%) |
| JR-CSF neutralization hits | 401 (1.32%) |

Figure 3A:
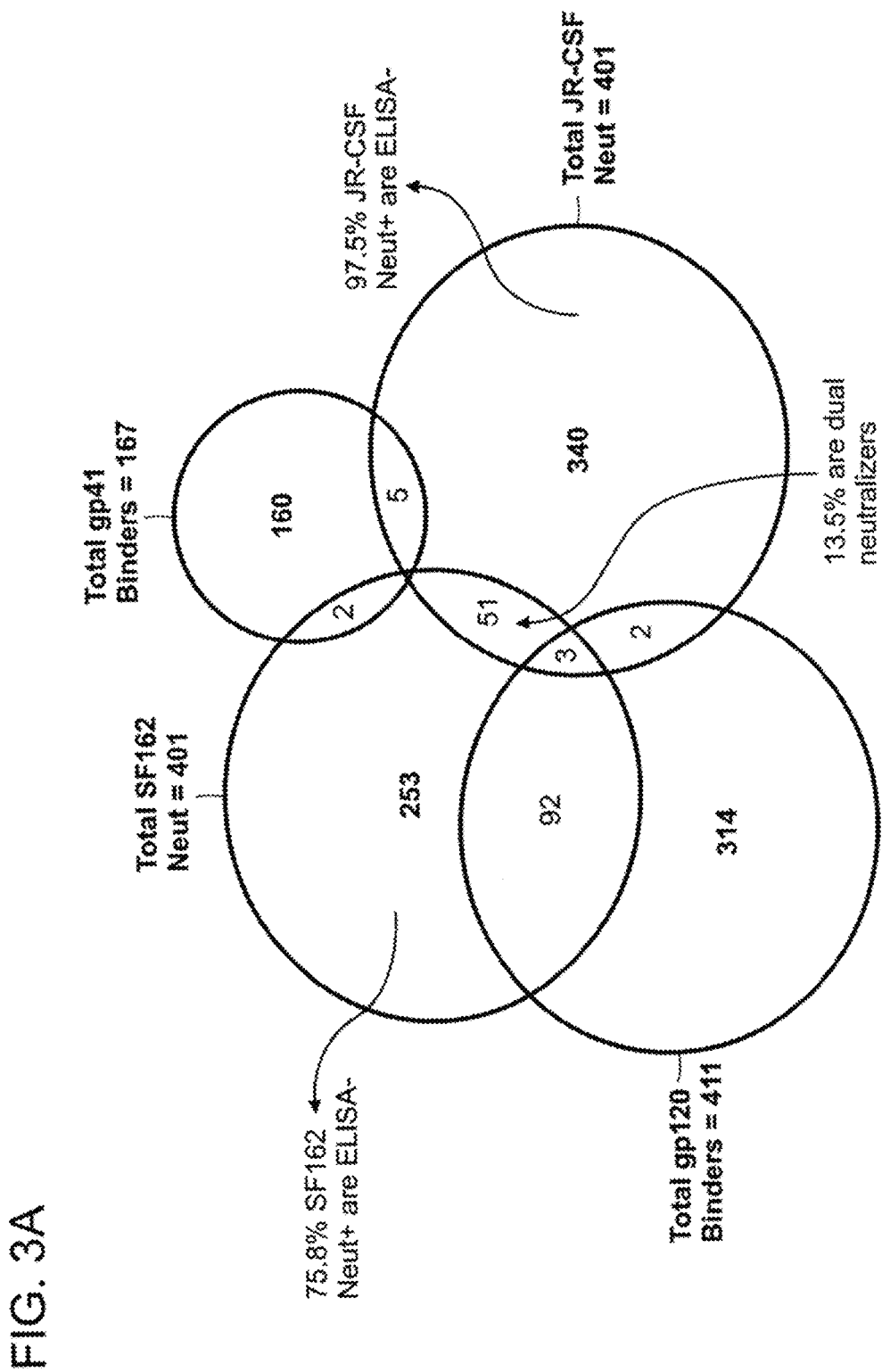
FIG. 3A is a schematic diagram that summarizes the screening results for neutralization and HIV-env protein (gp120 and gp41) binding assays from which B cell cultures were selected for antibody rescue and the monoclonal antibodies 1496_C09 (PG9), 1443_C16 (PG16), 1456_P20 (PG20), 1460_G14 (PGG14), and 1495_C14 (PGC14) were derived. A neutralization index value 0f 1.5 was used as a cut-off.
Figure 3B:
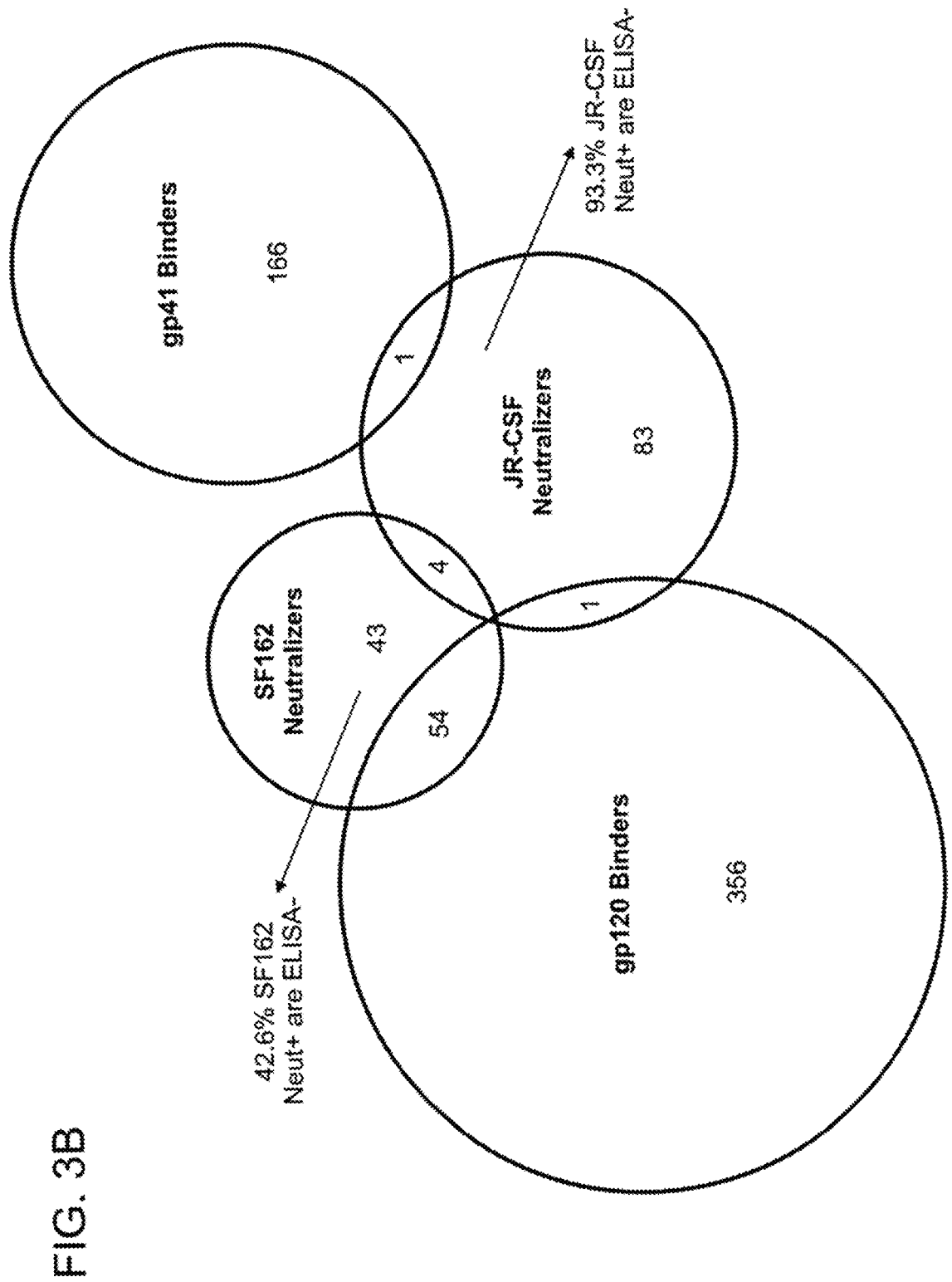
FIG. 3B is a schematic diagram that summaries the neutralizing activity and HIV-env protein (gp120 and gp41) binding activities of the monoclonal antibodies 1496_C09 (PG9), 1443_C16 (PG16), 1456_P20 (PG20), 1460_G14 (PGG14), and 1495_C14 (PGC14) as determined by ELISA assays among the B cell supernatants using a neutralization index cut-off value of 2.0. The neutralization index was expressed as the ratio of normalized relative luminescence units (RLU) of SIVmac239 to that of test viral strain derived from the same test B cell culture supernatant. The cut-off values used to distinguish neutralizing hits were determined by the neutralization index of a large number of negative control wells containing B cell culture supernatants derived from healthy donors.

Unexpectedly, a large proportion of the B cell supernatants that neutralized HIV-1JR-CSF did not bind monomeric gp120JR-CSF or gp41HxB2, and there were only a limited number of cultures that neutralized both viruses (FIG. 3B). Antibody genes were rescued from five B cell cultures selected for differing functional profiles; one bound to gp120 and only neutralized HIV-1SF162, two bound to gp120 and weakly neutralized both viruses, and two potently neutralized HIV-1JR-CSF, failed to neutralize HIV-1SF162, and did not bind to monomeric gp120 or gp41. Five antibodies identified according to these methods are disclosed herein. The antibodies were isolated from a human sample obtained through International AIDS Vaccine Initiative's (IAVI's) Protocol G, and are produced by the B cell cultures referred to as 1443_C16, 1456_P20, 1460_G14, 1495_C14 or 1496_C09. Antibodies referred to as 1443_C16 (PG16), 1456_P20 (PG20), 1460_G14 (PGG14), 1495_C14 (PGC14) or 1496_C09 (PG9), were isolated from the corresponding B cell cultures. These antibodies have been shown to neutralize HIV in vitro. Analysis of the antibody variable genes revealed that two antibody pairs were related by somatic hypermutation and that two of the somatic variants contained unusually long CDRH3 loops (Table 2). Long CDRH3 loops have previously been associated with polyreactivity. (Ichiyoshi, Y. & Casali, P. J Exp Med 180, 885-895 (1994)). The antibodies were tested against a panel of antigens and the antibodies were confirmed to be not polyreactive.

TABLE 2

Sequence Analysis of mAb Variable Genes

| Clone | Germline IGVL[a] | Germline IGVH[a] | CDRL3[b] | SEQ ID NO: | CDRH3[b] | SEQ ID NO: |
|---|---|---|---|---|---|---|
| PG16 | VL2-14*01 | VH3-33*05 | SSLTDRSHRIF | 1 | EAGGPIWHDDVKYYDFNDGYYNYHYMDV | 6 |
| PG9 | VL2-14*01 | VH3-33*05 | KSLTSTRRRVF | 2 | EAGGPDYRNGYNYYDFYDGYYNYHYMDV | 7 |
| PGG14 | VK1-39*01 | VH1-69*12 | SYSTPRTF | 3 | DRRVVPMATDNWLDP | 8 |
| PG20 | VK2-14*01 | VH1-69*12 | SFSTPRTF | 4 | DRRAVPIATDNWLDP | 9 |
| PGC14 | VL3-1*01 | VH1-24*01 | AWETTTTTFVFF | 5 | GAVGADSGSWFDP | 10 |

[a]Germ line gene sequences were determined using the IMGT database, which is publicly available at imgt.cines.fr.
"L" and "K" refer to lamda and kappa chains, respectively,
[b]Bolded amino acids denote differences between somatic variants.

TABLE 3A

Heavy Chain Gene Usage Summary

| mAb ID | mAb Specificity | V-Gene & allele | V-Gene identity | J-Gene & allele | J-Gene identity | CDR3 |
|---|---|---|---|---|---|---|
| 1443_C16 | ELISA-negative | IGHV3-33*05 | 85.07% (245/288 nt) | IGHJ6*03 | 85.48% (53/62 nt) | AREAGGPIWHDDVKYYDFNDGYYNYHYMDV (SEQ ID NO: 46) |
| 1456_P20 | gp120 | IGHV1-69*11 or IGHV1-69*12 | 85.07% (245/288 nt) | IGHJ5*02 | 88.24% (45/51 nt) | ARDRRAVPIATDNWLDP (SEQ ID NO: 47) |
| 1460_G14 | gp120 | IGHV1-69*11 or IGHV1-69*12 | 86.11% (248/288 nt) | IGHJ5*02 | 86.27% (44/51 nt) | TRDRRVVPMATDNWLDP (SEQ ID NO: 48) |

TABLE 3A-continued

Heavy Chain Gene Usage Summary

| mAb ID | mAb Specificity | V-Gene & allele | V-Gene identity | J-Gene & allele | J-Gene identity | CDR3 |
|---|---|---|---|---|---|---|
| 1495_C14 | gp120 | IGHV1-f*01 | 88.89% (256/288 nt) | IGHJ5*02 | 84.31% (43/51 nt) | AAGAVGADSGSWFDP (SEQ ID NO: 49) |
| 1496_C09 | ELISA-negative | IGHV3-33*05 | 85.07% (245/288 nt) | IGHJ6*03 | 83.87% (52/62 nt) | VREAGGPDYRNGYNYYDFYDGYYNYHYMDV (SEQ ID NO: 50) |

TABLE 3B

Light Chain Gene Usage Summary

| mAb ID | mAb Specificity | V-Gene and allele | V-gene identity | J-GENE and allele | J-Gene identity | CDR3 | SEQ ID NO: |
|---|---|---|---|---|---|---|---|
| 1443_C16 | ELISA-negative | IGLV2-14*01 | 88.19% (254/288 nt) | IGLJ2*01. or IGLJ3*01 or IGLJ3*02 | 83.33% (30/36 nt) | SSLTDRSHRI | 41 |
| 1456_P20 | gp120 | IGKV1-39*01, or IGKV1D-39*01 | 92.11% (257/279 nt) | IGKJ5*01 | 92.11% (35/38 nt) | QQSFSTPRT | 42 |
| 1460_G14 | gp120 | IGKV1-39*01, or IGKV1D-39*01 | 92.11% (257/279 nt) | IGKJ5*01 | 89.47% (34/38 nt) | QQSYSTPRT | 43 |
| 1495_C14 | gp120 | IGLV3-1*01 | 88.89% (248/279 nt) | IGLJ2*01. or IGLJ3*01 | 86.84% (33/38 nt) | QAWETTTTFVF | 44 |
| 1496_C09 | ELISA-negative | IGLV2-14*01 | 91.32% (263/288 nt) | IGLJ3*02 | 86.11% (31/36 nt) | KSLTSTRRRV | 45 |

The broadly neutralizing antibodies from 1443_C16 (PG16) and 1496_C09 (PG9) clones obtained by this method did not exhibit soluble gp120 or gp41 binding at levels that correlate with neutralization activity. The method of the invention therefore allows identification of novel antibodies with broad cross-clade neutralization properties regardless of binding activities in an ELISA screen. Further characterization of PG16 and PG9 is disclosed herein.

All five antibodies were first tested for neutralization activity against a multi-clade 16-pseudovirus panel (FIG. 22). Two of the antibodies that bound to monomeric gp120 in the initial screen (PGG14 and PG20) did not show substantial neutralization breadth or potency against any of the viruses tested, and the third antibody that bound to gp120 (PGC14) neutralized 4/16 viruses with varying degrees of potency. In contrast, the two antibodies that failed to bind recombinant Env in the initial screen (PG9 and PG16) neutralized a large proportion of the viruses at sub-microgram per ml concentrations. PG9 and PG16 neutralized non-clade B viruses with greater breadth than three out of the four existing bNAbs. This is significant considering that the majority of HIV-1 infected individuals worldwide are infected with non-clade B viruses.

FIG. 31A shows neutralization profiles (IC50 values) of monoclonal antibodies 1443_C16 (PG16), 1456_P20 (PG20), 1460_G14 (PGG14), 1495_C14 (PGC14) and 1496_C09 (PG9) and the known cross-clade neutralizing antibodies b12, 2G12, 2F5 and 4E10 on a diverse panel of 16 HIV pseudoviruses from different clades. 1443_C16 (PG16) and 1496_C09 (PG9) neutralize HIV-1 species from Clades A, B, C, D and CRF01_AE with better potency for most viral strains tested than known and generally accepted broad and potent neutralizing antibodies. However, neutralization profiles of individual species of HIV-1 belonging to these clades vary between 1443_C16 (PG16) and 1496_C09 (PG9) and the known cross-clade neutralizing antibodies b12, 2G12, 2F5 and 4E10. 1495_C14 (PGC14) neutralizes fewer HIV-1 species from Clades A, B and C comparable to other neutralizing antibodies. FIG. 31B shows IC90 values of the monoclonal antibodies 1443_C16 (PG16) and 1496_C09 (PG9) and the known cross-clade neutralizing antibodies b12, 2G12, 2F5 and 4E10 on the same panel of pseudoviruses. FIG. 4 shows neutralization activities of monoclonal antibodies 1443_C16 (PG16) and 1496_C09

(PG9) to six other HIV pseudoviruses (YU2, Bal, ADA, DU172, DU422, and ZM197) for clades B and C not included in FIGS. 31A-B.

PG9, PG16, and PGC14 were next evaluated on a large multi-clade pseudovirus panel consisting of 162 viruses to further assess the neutralization breadth and potency of these three antibodies (FIGS. 23A-B, FIGS. 32A-F and FIGS. 33A-B). The bNAbs b12, 2G12, 2F5, and 4E10, as well as the donor's serum, were also included in the panel for comparison. Overall, PG9 neutralized 127 out of 162 and PG16 neutralized 119 out of 162 viruses with a potency that frequently considerably exceeded that noted for the four control bNAbs.

The median IC50 and IC90 values for neutralized viruses across all clades were an order of magnitude lower for PG9 and PG16 than any of the four existing bNAbs (FIG. 23A, FIGS. 32A-F and FIGS. 33A-B). Both mAbs showed overall greater neutralization breadth than b12, 2G12, and 2F5 (FIG. 23B, FIGS. 32A-F and FIGS. 33A-B). At low antibody concentrations, PG9 and PG16 also demonstrated greater neutralization breadth than 4E10 (FIG. 23B). Furthermore, both mAbs potently neutralized one virus (IAVI-C18) that exhibits resistance to all four existing bNAbs (FIGS. 32A-F). The mAb neutralization curves reveal that, whereas the PG9 neutralization curves usually exhibit sharp slopes, the neutralization curves for PG16 sometimes exhibit gradual slopes or plateaus at less than 100% neutralization. Although neutralization curves with similar profiles have been reported previously (W. J. Honnen et al., J Virol 81, 1424 (February, 2007), A. Pinter et al., J Virol 79, 6909 (June, 2005)), the mechanism for this is not well understood.

Comparison of the neutralization profile of the serum with the neutralization profile of PG9, PG16 and PGC14 revealed that these three antibodies could recapitulate the breadth of the serum neutralization in most cases (FIGS. 32A-F). For example, almost all of the viruses that were neutralized by the serum with an IC50>1:500 were neutralized by PG9 and/or PG16 at <0.05 µg/mL. The one case where this did not occur was against HIV-1SF162, but this virus was potently neutralized by PGC14. Despite the fact that PG9 and PG16 are somatic variants, they exhibited different degrees of potency against a number of the viruses tested. For instance, PG9 neutralized HIV-16535.30 approximately 185 times more potently than PG16, and PG16 neutralized HIV-1MGRM-AG-001 approximately 440 times more potently than PG9. In some cases, the two antibodies also differed in neutralization breadth; PG9 neutralized nine viruses that were not affected by PG16, and PG16 neutralized two viruses that were not affected by PG9. Based on these results, it is postulated that broad serum neutralization might be mediated by somatic antibody variants that recognize slightly different epitopes and display varying degrees of neutralization breadth and potency against any given virus. In the face of an evolving viral response, it seems reasonable that the immune system might select for these types of antibodies.

Comparison of the neutralization profile of the serum with the neutralization profile of PG9, PG16 and PGC14 revealed that these three antibodies could recapitulate the breadth of the serum neutralization in most cases. For example, almost all of the viruses that were neutralized by the serum with an IC50>1:1000 were neutralized by PG9 and/or PG16 at <0.005 µg/mL. The one case where this did not occur was against HIV-1SF162, but this virus was potently neutralized by PGC14. FIGS. 23A-B show the neutralization activities—breadth and potency, respectively—of PG9, PG16, and PGC14 as well as four control bNAbs as measured by IC50 values. FIGS. 33A-B show results of the same analysis using IC90 values.

Despite the fact that PG9 and PG16 are somatic variants, they exhibited different degrees of potency against a number of the viruses tested. For instance, PG9 neutralized the virus 6535.30 about 100 times more potently than PG16, and PG16 neutralized the virus MGRM-AG-001 about 3000 times more potently than PG9. In some cases, the two antibodies also differed in neutralization breadth; PG9 neutralized seven viruses that were not neutralized by PG16, and PG16 neutralized three viruses that were not neutralized by PG9. Without being bound by theory, it appears that broad serum neutralization might be mediated by somatic variants that recognize slightly different epitopes and display varying degrees of neutralization breadth and potency against any given virus. In the face of an evolving viral response, the immune system likely selects for these types of antibodies.

Figure 5:
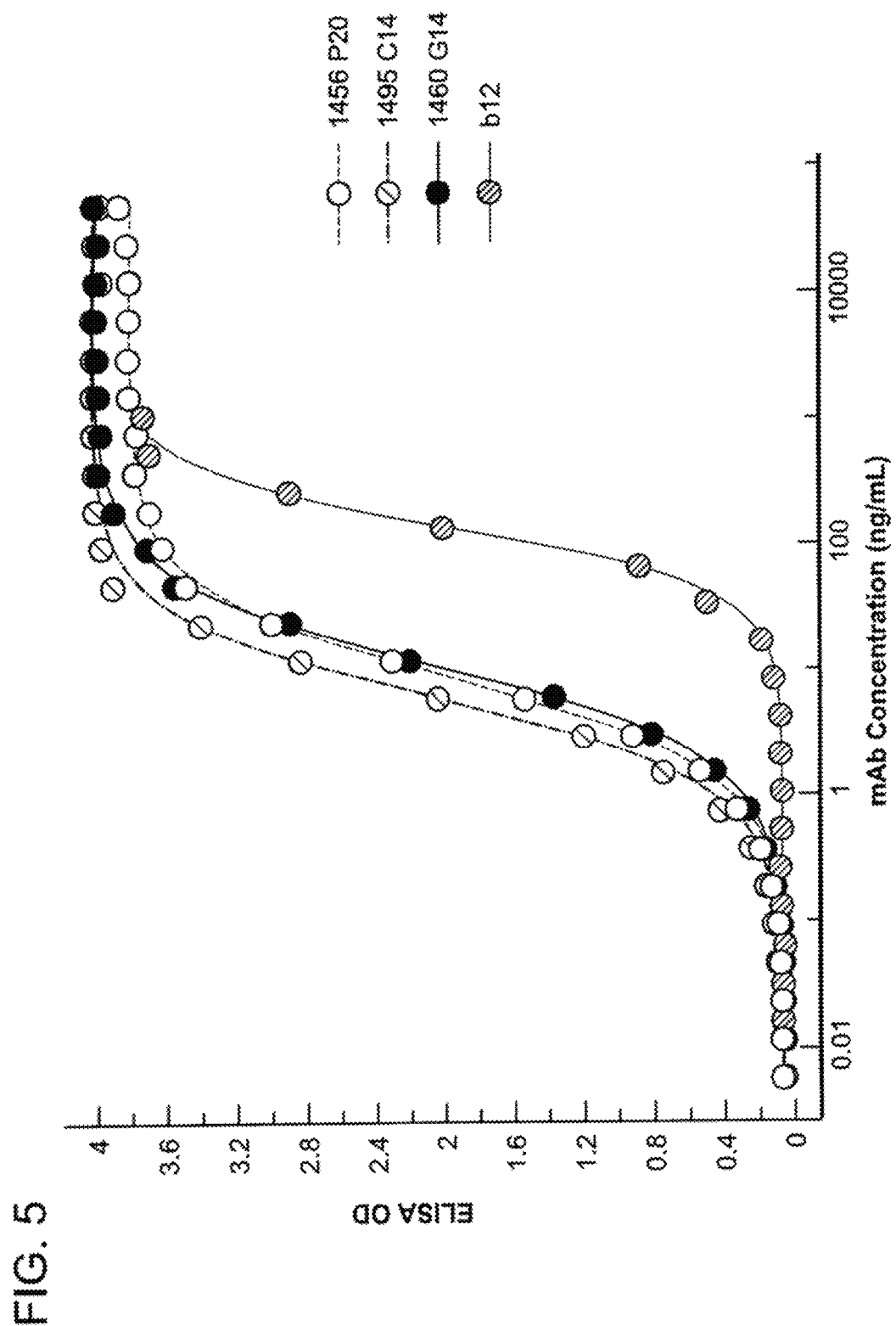
FIG. 5 is a graph depicting the dose response curves of 1456_P20 (PG20), 1495_C14 (PGC14) and 1460_G14 (PGG14) binding to recombinant gp120 in ELISA as compared to control anti-gp120 (b12). Data is presented as average OD values of triplicate ELISA wells obtained on the same plate.
Figure 6A:
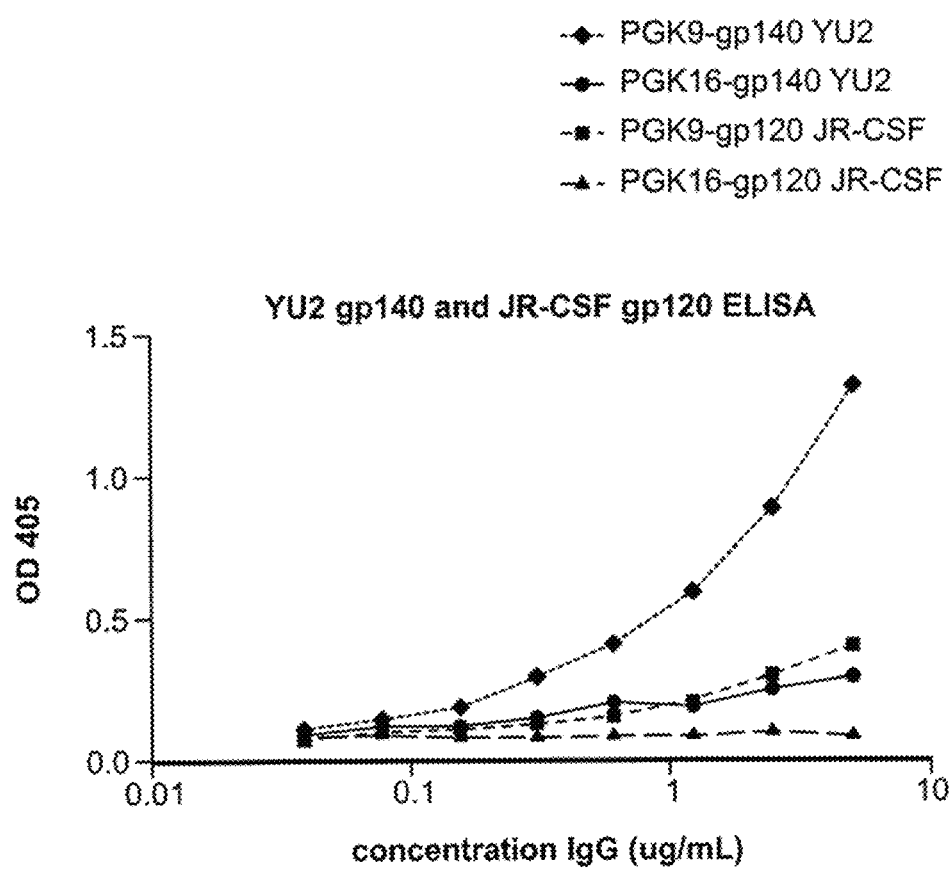

The antibodies were also tested for ability to bind soluble recombinant HIV envelope proteins. FIG. 5 shows dose response curves of 1456_P20 (PG20), 1495_C14 (PGC14) and 1460_G14 (PGG14) binding to recombinant gp120 in ELISA as compared to control anti-gp120 (b12). FIG. 6 shows ELISA binding assays of monoclonal antibodies 1443_C16 (PG16) and 1496_C09 (PG9) to HIV-1 strain YU2 gp140 and JR-CSF gp120, the membrane proximal region (MPER) of HIV-1 envelope glycoprotein gp41, and the V3 polypeptide. PG-9 binds to YU2 gp140 (IC50-20-40 nM), YU2 gp120 and weakly binds to JR-CSF gp120. However, PG16 weakly binds Yu2 gp120, but not the soluble form of HIV-1 envelope glycoprotein, gp120 JR-CSF. Neither mAb binds to JR-FL gp120, JR-FL gp140, MPER peptide of gp41 or V3 peptide.

Figure 7:
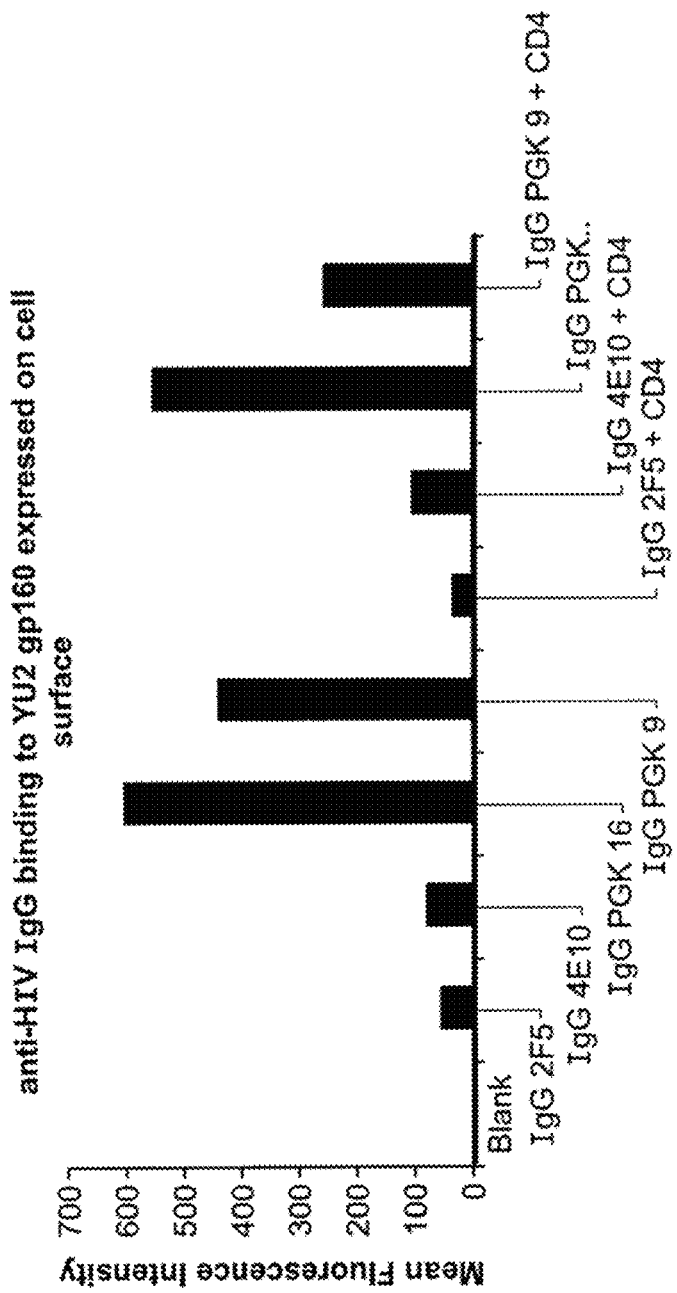
FIG. 7 is a graph depicting the results of a binding assay using monoclonal antibodies 1443_C16 (PG16) and 1496_C09 (PG9) to HIV-1 YU2 gp160 expressed on the cell surface in the presence and absence of soluble CD4 (sCD4).

FIG. 7 shows binding of monoclonal antibodies 1443_C16 (PG16) and 1496_C09 (PG9) to HIV-1 YU2 gp160 expressed on the cell surface in the presence and absence of sCD4. Competitive inhibition of the binding by sCD4 indicates that the binding of monoclonal antibody 1496_C09 to HIV-1 envelope protein gp160 expressed on the cell surface is presumably affected due to the conformational changes induced by sCD4. The data further suggest that 1443_C16 (PG16) and 1496_C09 (PG9) exhibit relatively stronger binding to trimeric forms of the HIV-1 Env (gp160 and gp140) than to the monomeric gp120.

FIG. 8 shows binding of monoclonal antibodies 1443_C16 (PG16) and 1496_C09 (PG9) to HIV-1 transfected cells. PG9 and PG16 do not bind untransfected cells. PG9 and PG16 bind JR-CSF, ADA, and YU2 gp160 transfected cells. PG9 and PG16 do not bind JR-FL gp160 transfected cells (cleaved or uncleaved). PG9 and PG16 do not bind ADA ΔV1/ΔV2 transfected cells. PG9 and PG16 binding to JR-CSF gp160 transfected cells is inhibited by sCD4.

Figure 9:
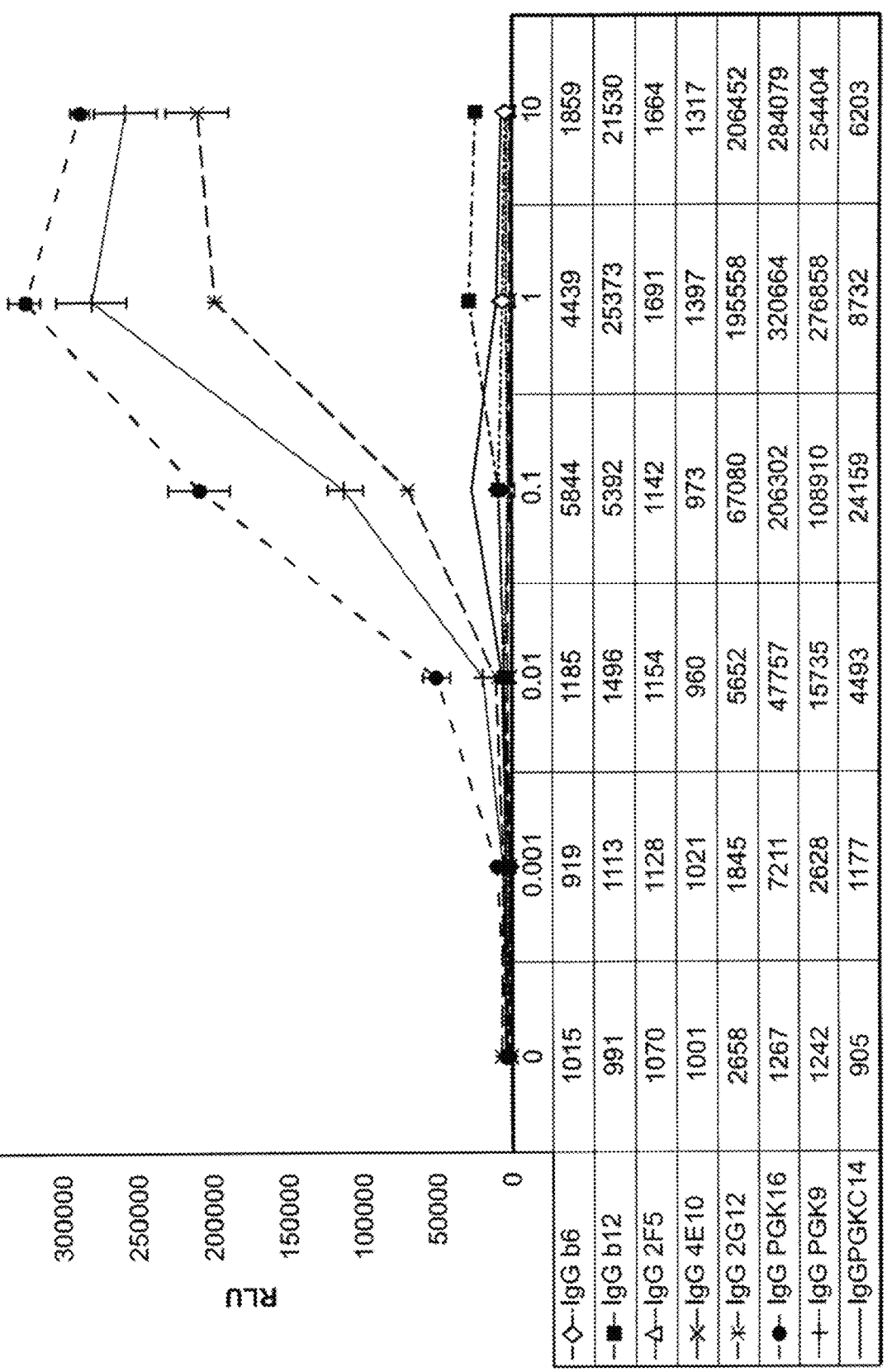
FIG. 9 is a series of graphs depicting the results of a capture assay. The data describe capturing of entry-competent JRCSF pseudovirus by neutralizing monoclonal antibodies 1443_C16 (PG16) and 1496_C09 (PG9) in a dose-dependent manner.

FIG. 9 shows the capturing of entry-competent JR-CSF pseudovirus by neutralizing monoclonal antibodies 1443_C16 (PG16) and 1496_C09 (PG9) in a dose-dependent manner. The ability of both antibodies to capture JR-CSF pseudovirus is higher than IgG b12 but comparable to IgG 2G12. It is postulated that the capture may be mediated by the binding of the mAbs to the HIV-1 Env on the virions.

Figure 10A:
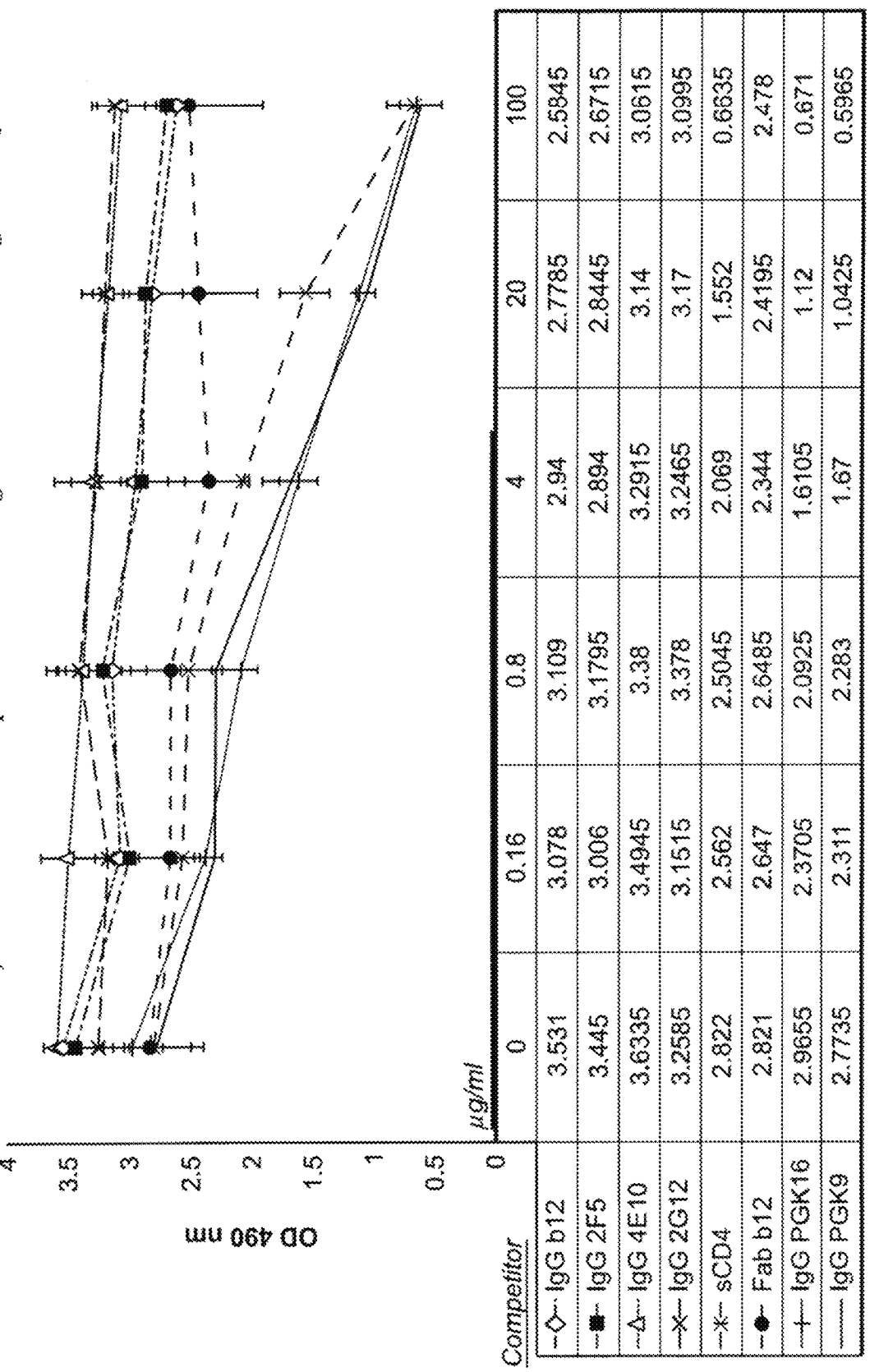
FIG. 10A is a graph depicting the results of a competitive binding assay using monoclonal antibodies sCD4, PG16 and PG9, wherein the claimed antibodies compete for the binding of monoclonal antibody 1443_C16 (PG16) to pseudovirus but control antibodies b12, 2G12, 2F5 and 4E10 do not competitively bind to the pseudovirus.

FIG. 10A shows that sCD4, PG16 and PG9 compete for the binding of monoclonal antibody 1443_C16 (PG16) to JR-CSF pseudovirus but b12, 2G12, 2F5 and 4E10 do not. FIG. 10B shows sCD4, PG16 and PG9 compete for the binding of monoclonal antibody 1496_C09 (PG9) to JR- CSF pseudovirus but b12, 2G12, 2F5 and 4E10 do not. This suggests that the PG16 and PG9 mAbs bind gp120 at a site different from those bound by b12 and 2G12. PG9 and PG16 binding to HIV-1 envelope protein is competitively inhibited by sCD4. Given that the MAbs are not inhibited by the CD4 binding site MAb b12, this suggests that PG9 and PG16 are binding to an epitope that is unavailable for sCD4 binding to gp120 as a result of conformational changes. The inability of PG9 and PG16 to bind monomeric gp120JR-CSF or gp41HxB2 in the initial screen while potently neutralizing HIV-1JR-CSF suggests that the epitope targeted by these antibodies is preferentially expressed on trimeric HIV envelope protein. The ability of PG9 and PG16 to bind monomeric gp120 from several different strains, artificially trimerized gp140 constructs, and trimeric Env expressed on the surface of transfected cells respectively, was compared. Although both antibodies bound with high affinity to cell surface Env, PG16 did not bind to any of the soluble gp120 or gp140 constructs and PG9 bound only weakly to monomeric gp120 and trimerized gp140 from certain strains (FIG. 11). It has been previously shown that a substantial fraction of cell surface Env is comprised of uncleaved gp160 molecules. (Pancera, M. & Wyatt, R. Virology 332, 145-156 (2005)). That PG9 and PG16 do not exhibit exclusive specificity for native HIV-1 trimers was confirmed by the fact that both antibodies bound with high affinity to cleavage-defective HIV-1YU2 trimers expressed on the surface of transfected cells (FIG. 12).

Figure 13A:
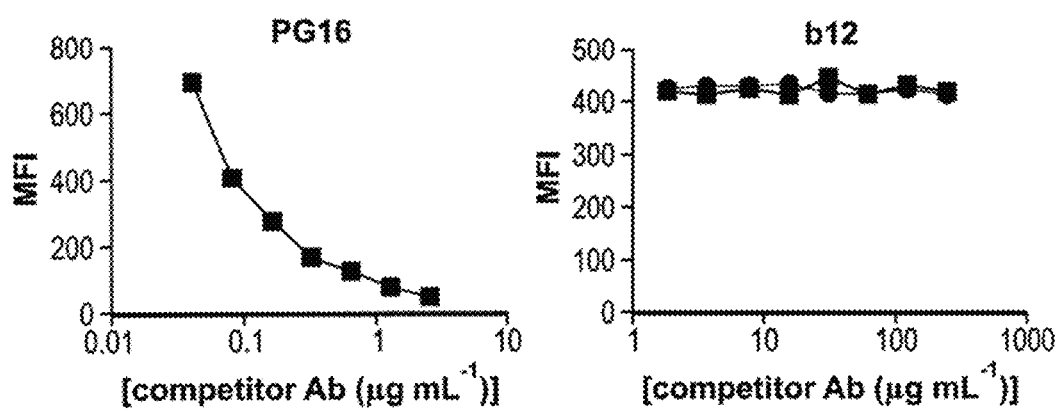
Figure 13B:
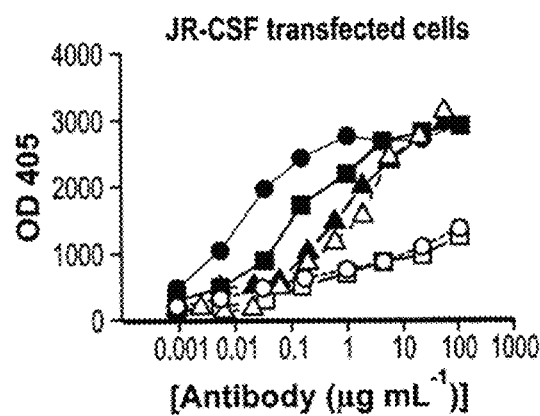
Figure 13C:
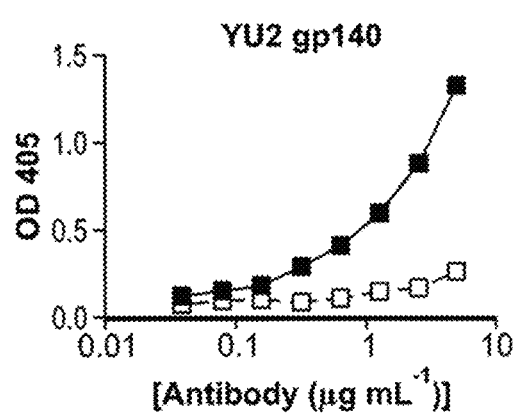

The epitopes recognized by PG9 and PG16 were investigated. Since the PG9 and PG16 antibodies are somatic variants, they recognize the same or overlapping epitopes. Both antibodies cross-competed for binding to HIV-1JR-CSF transfected cells (FIG. 13A). Ligation of monomeric gp120 or cell surface Env with soluble CD4 diminished binding of both PG9 and PG16, although neither antibody competed with CD4-binding site antibodies for trimer binding (FIG. 13A-13C). This result suggests that CD4-induced conformational changes cause a loss of the epitope targeted by the antibodies.

Since PG9 bound well enough to gp120 from certain isolates to generate ELISA binding curves, competition ELISAs were performed with PG9 using a panel of neutralizing and non-neutralizing antibodies. These data revealed that PG9 cross-competed with anti-V2, anti-V3, and to a lesser extent, CD4i antibodies for gp120. (FIGS. 13D and 14). Neither PG9 nor PG16 bound to V1/V2 or V3 deleted HIV-1JR-CSF variants expressed on the surface of transfected cells, further suggesting contributions of variable loops in forming their epitopes (FIG. 13E).

To dissect the fine specificity of PG9 and PG16, alanine scanning was performed using a large panel of HIV-1JR-CSF Env alanine mutants that have been described previously (Pantophlet, R., et al. J Virol 77, 642-658 (2003); Pantophlet, R., et al. J Virol 83, 1649-1659 (2009); Darbha, R., et al. Biochemistry 43, 1410-1417 (2004); Scanlan, C. N., et al. J Virol 76, 7306-7321 (2002)) as well as several new alanine mutants. Pseudoviruses incorporating single Env alanine mutations were generated, and PG9 and PG16 were tested for neutralization activity against each mutant pseudovirus. Mutations that resulted in viral escape from PG9 and PG16 neutralization were considered important for formation of the PG9 and PG16 epitopes (Tables 12 and 13).

Based on this criteria, and consistent with the competition experiments, residues that form the epitopes recognized by PG9 and PG16 appear to be located in conserved regions of the V2 and V3 loops of gp120. Certain co-receptor binding site mutations also had an effect on PG9 and PG16 neutralization, albeit to a lesser extent. Generally, PG9 and PG16 were dependent on the same residues, although PG16 was more sensitive to mutations located in the tip of the V3 loop than PG9. Interestingly, although neither antibody bound to wild-type HIV-1JR-FL transfected cells, a D to K mutation at position 168 in the V2 loop of HIV-1JR-FL generated high-affinity PG9 and PG16 recognition (FIGS. 32A-F). N156 and N160, sites of V2 N-glycosylation, also appear to be critical in forming the epitope since substitutions at these positions resulted in escape from PG9 and PG16 neutralization. Deglycosylation of gp120 abolished binding of PG9 (FIG. 16), confirming that certain glycans may be important in forming the epitope.

Figure 17:
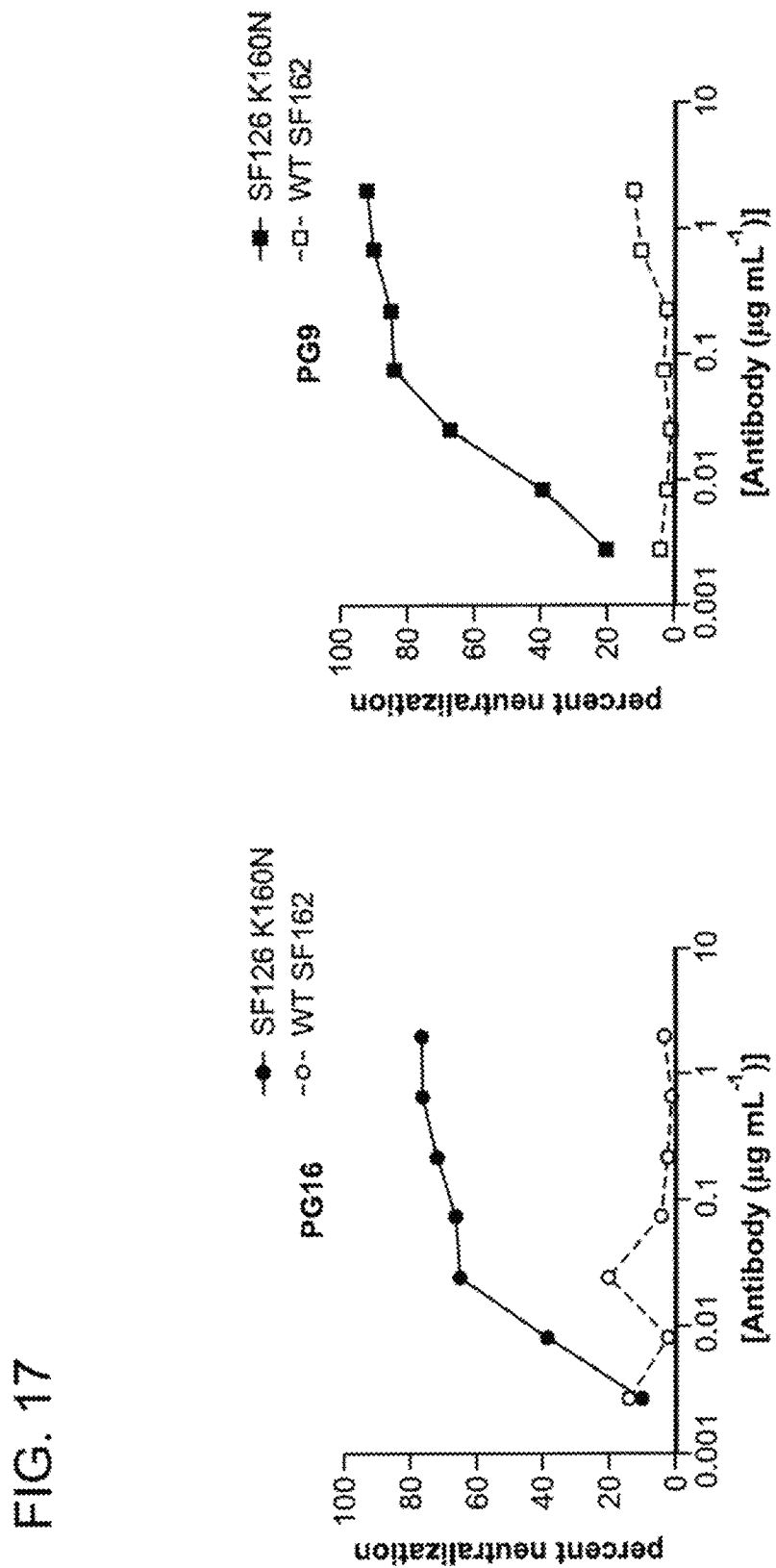
FIG. 17 is a series of graphs depicting the neutralization activity of PG9 and PG16 against HIV-1SF162 and HIV-1SF162 K160N, which was determined using a single-round replication luciferase reporter assay of pseudotyped virus.

HIV-1 SF162 contains a rare N to K polymorphism at position 160, and mutation of this residue to an Asn renders this isolate sensitive to PG9 and PG16 (FIG. 17).

Figure 18:
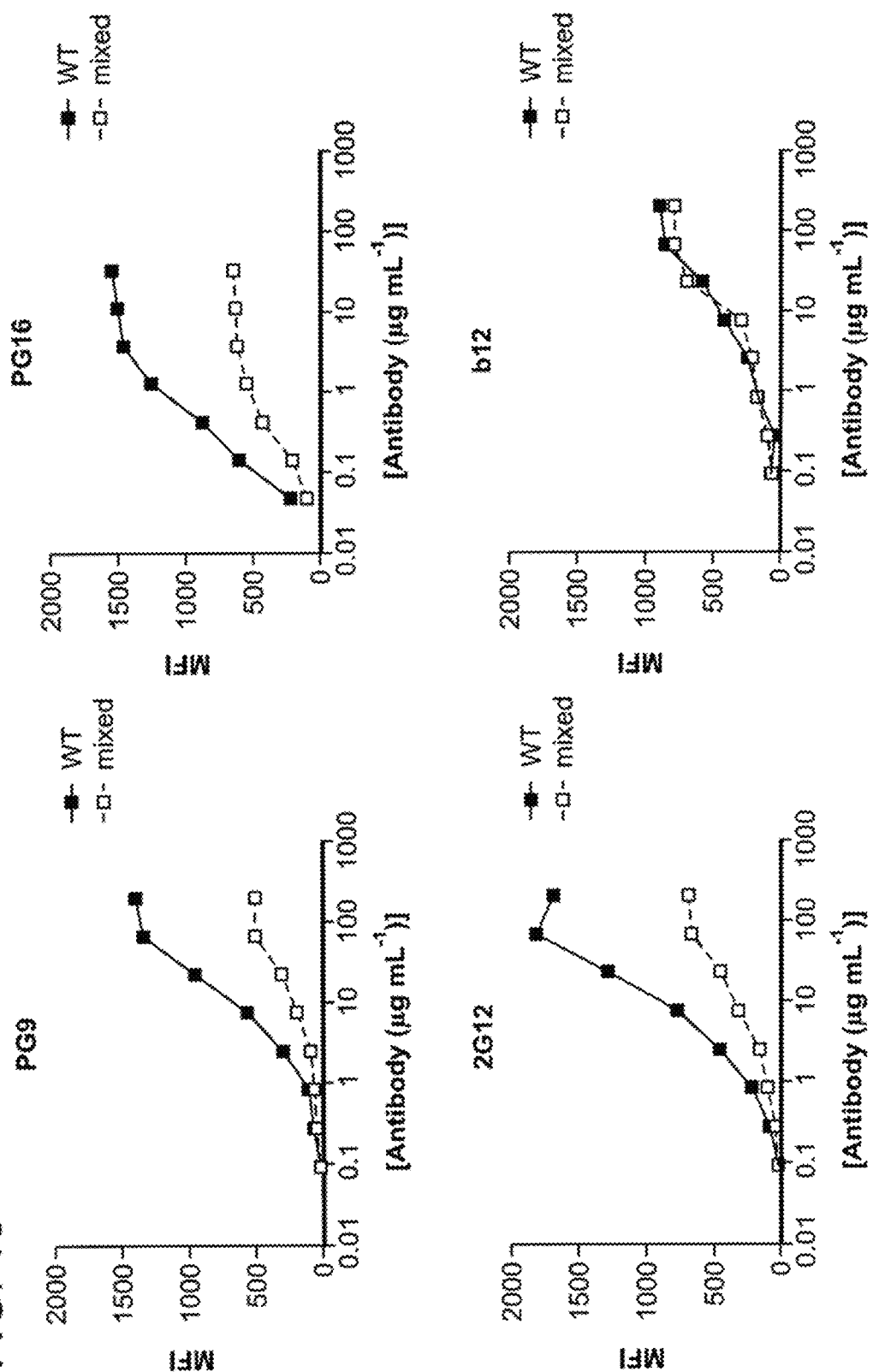
FIG. 18 is a series of graphs depicting the binding of PG9 and PG16 to mixed trimers. Alanine substitutions at positions 160 and 299 were introduced into HIV-1YU2 Env to abolish binding of PG9 and PG16. An alanine substitution at position 295 was also introduced into the same construct to abrogate binding of 2G12. Co-transfection of 293T cells with WT and mutant plasmids in a 1:2 ratio resulted in the expression of 29% mutant homotrimers, 44% heterotrimers with two mutant subunits, 23% heterotrimers with one mutant subunit, and 4% wild-type homotrimers.
Figure 19:
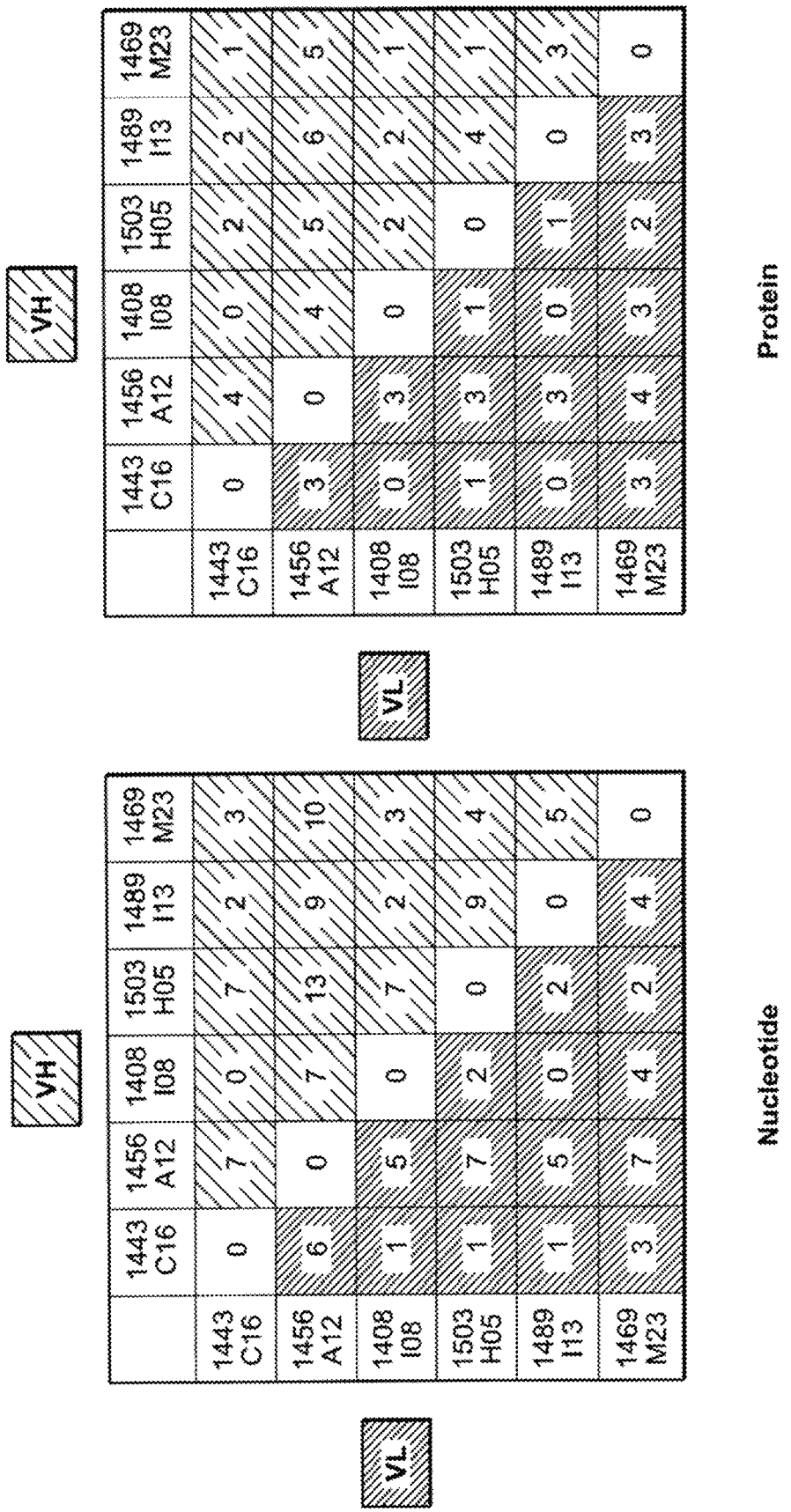
FIG. 19 is a series of graphical depictions of the number of nucleotide or amino acid differences in the heavy chain sequences of sister clones of 1443_C16 (PG16) among each other. Note that the single nucleotide difference of 1408 I08 translates into an identical protein sequence of 1443_C16. The nucleotide sequence of the 1408 I08 light chain is identical to the nucleotide sequence of the light chain of 1443_C16.
Figure 20A:
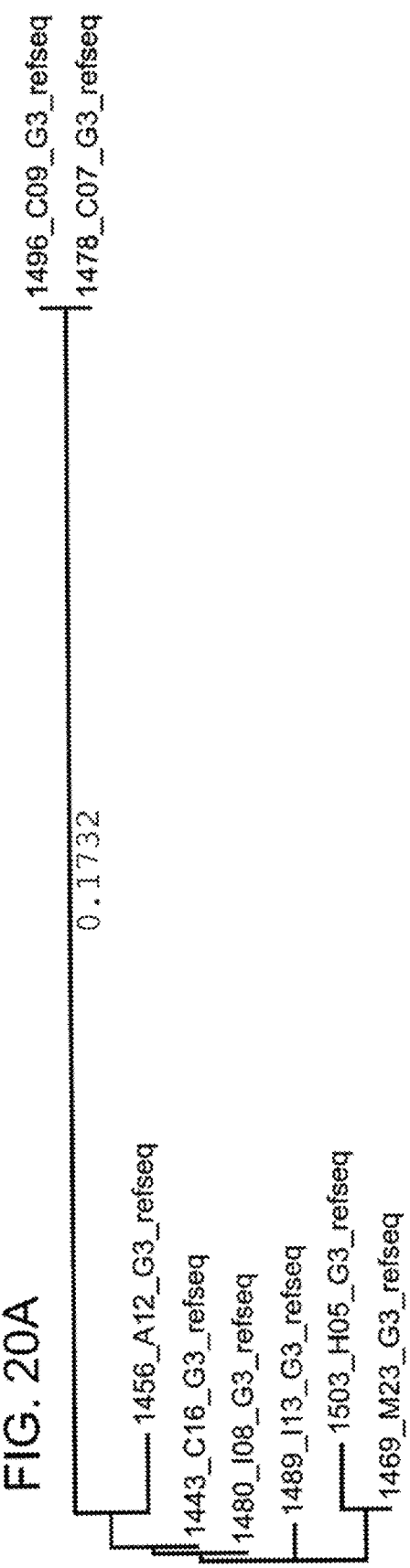
FIG. 20A is a tree diagram illustrating the correlation of the heavy chain of 1443_C16 sister clones to the heavy chain of 1496_C09 at the nucleotide level.
Figure 20B:
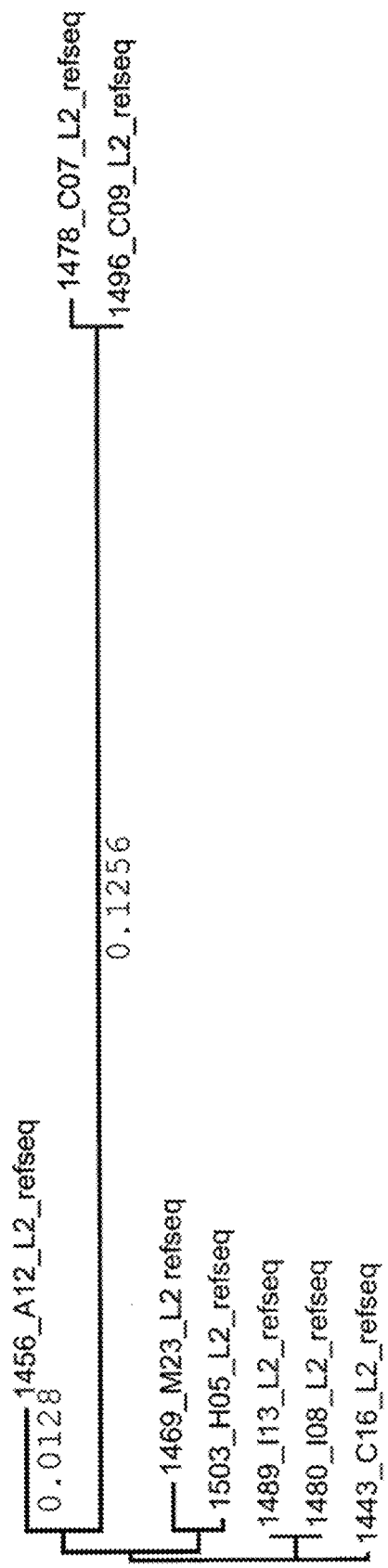
FIG. 20B is a tree diagram illustrating the correlation of the light chain of 1443_C16 sister clones to the light chain of 1496_C09 at the nucleotide level.
Figure 21A:
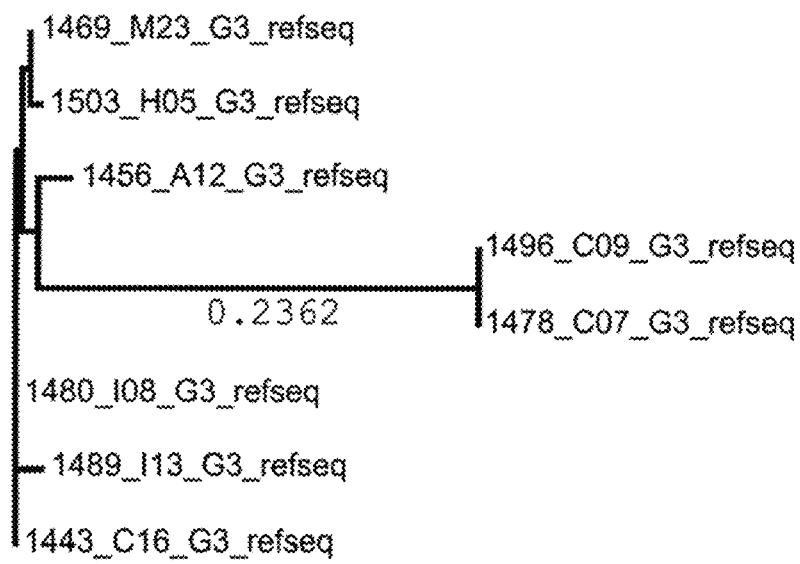
FIG. 21A is a tree diagram illustrating the correlation of the heavy chain of 1443_C16 sister clones to the heavy chain of 1496_C09 at the protein level.
Figure 21B:
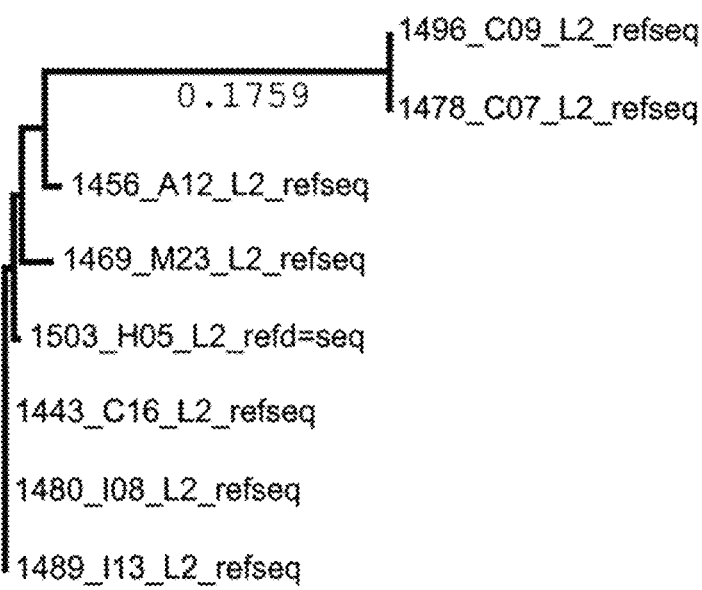
FIG. 21B is a tree diagram illustrating the correlation of the light chain of 1443_C16 sister clones to the light chain of 1496_C09 at the protein level.
Figure 24A:
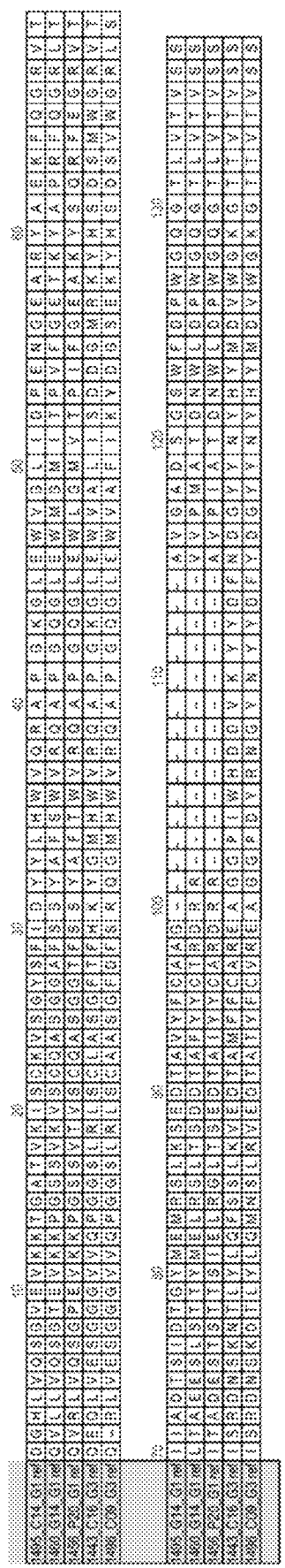
FIG. 24A depicts the Heavy Chain Variable Region Protein Alignment
Figure 24B:
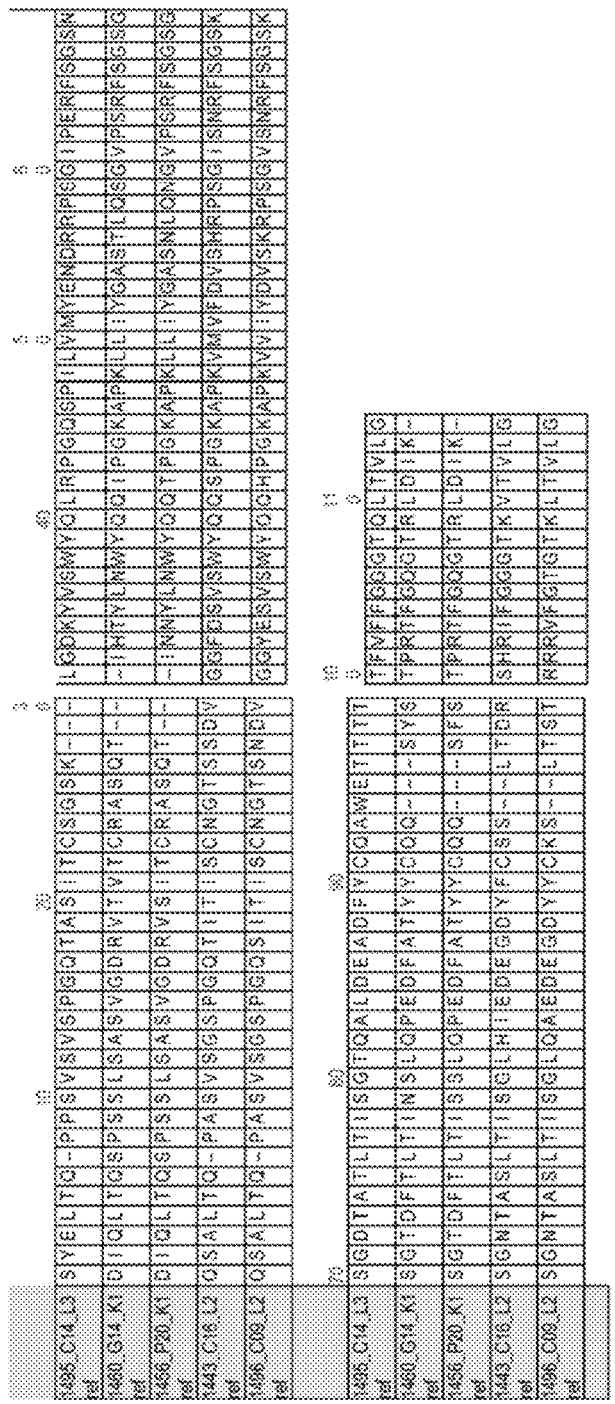
FIG. 24B depicts the Light Heavy Chain Variable Region Protein Alignment
Figure 25A:
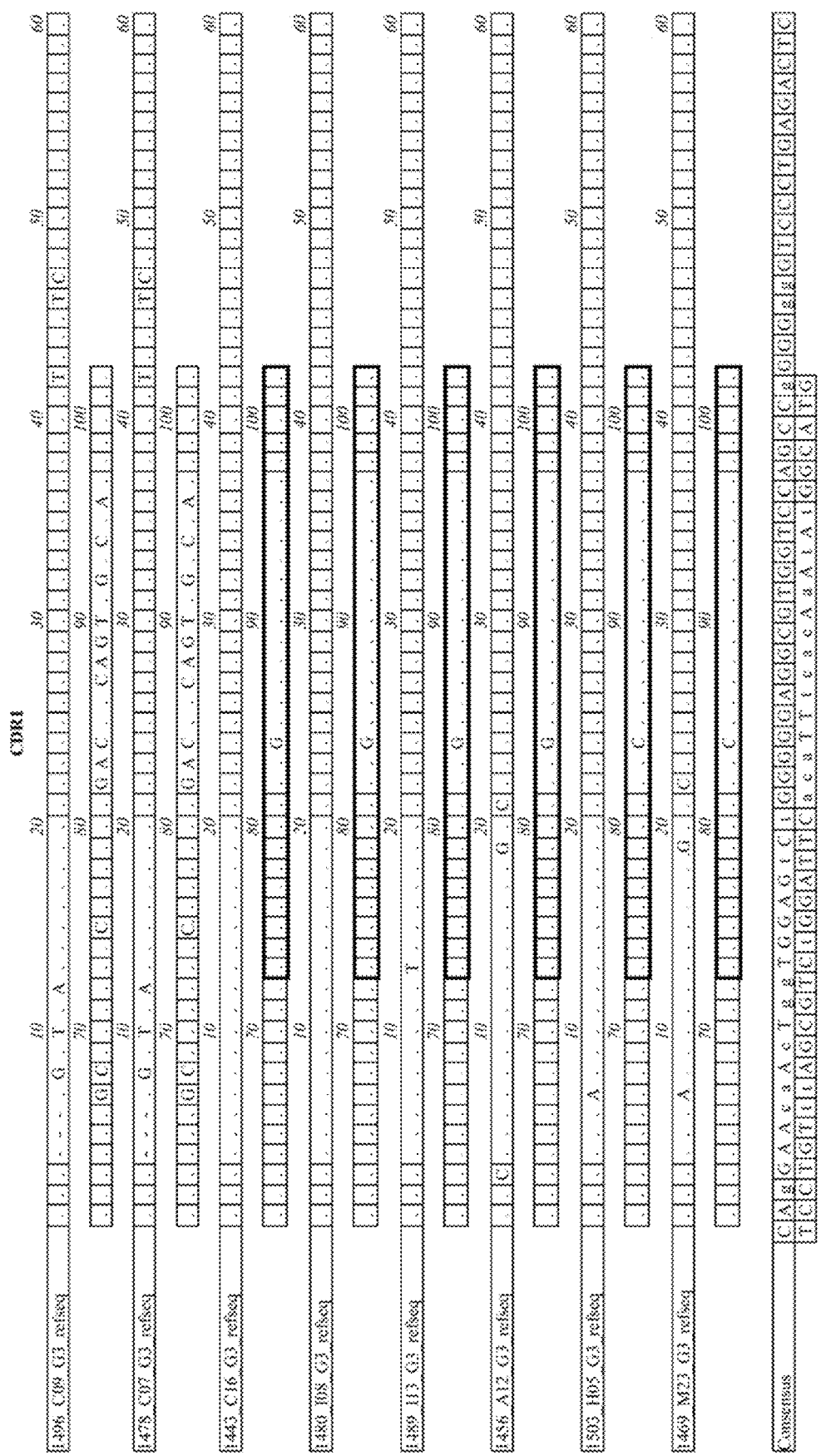
Figure 25C:
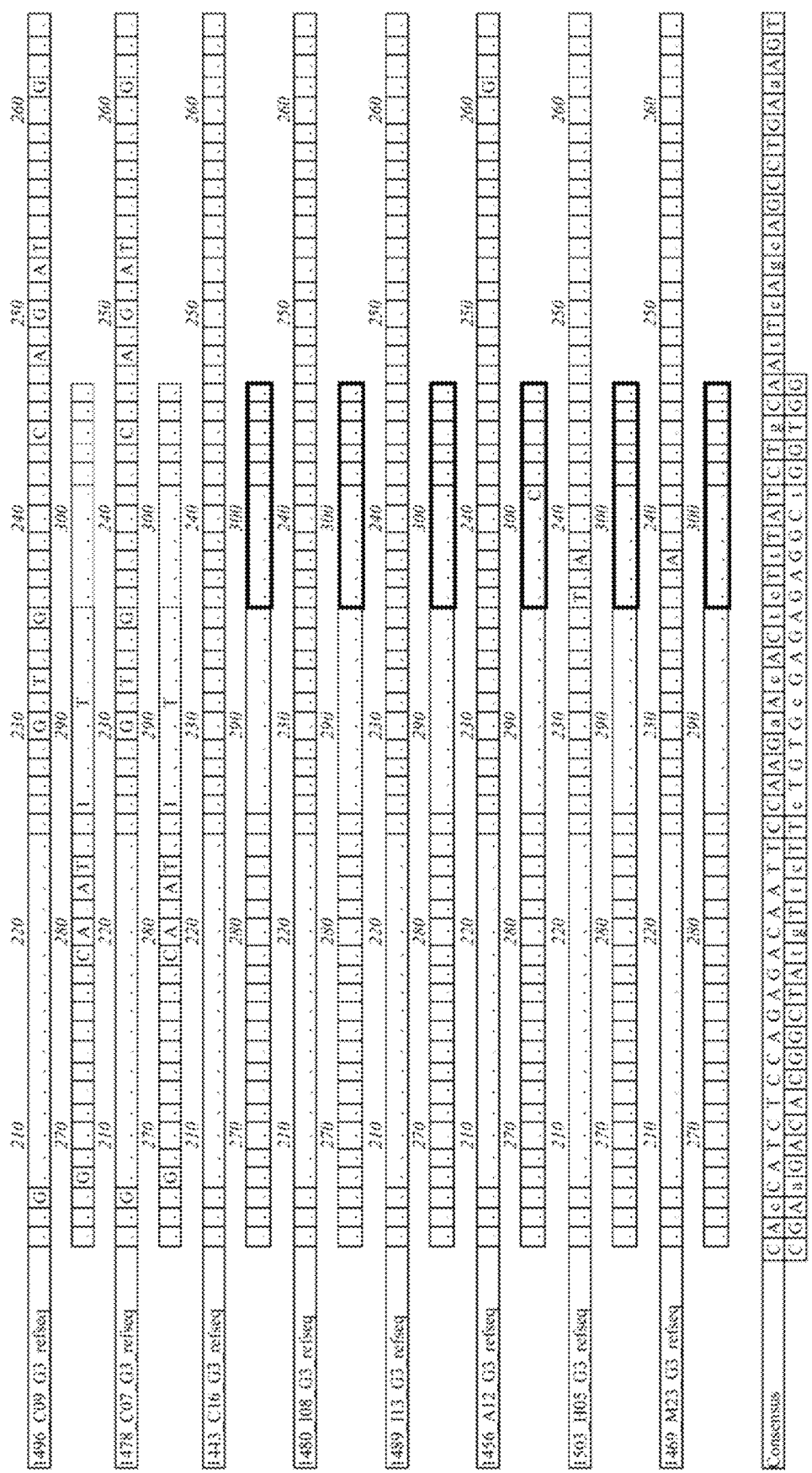
Figure 25D:
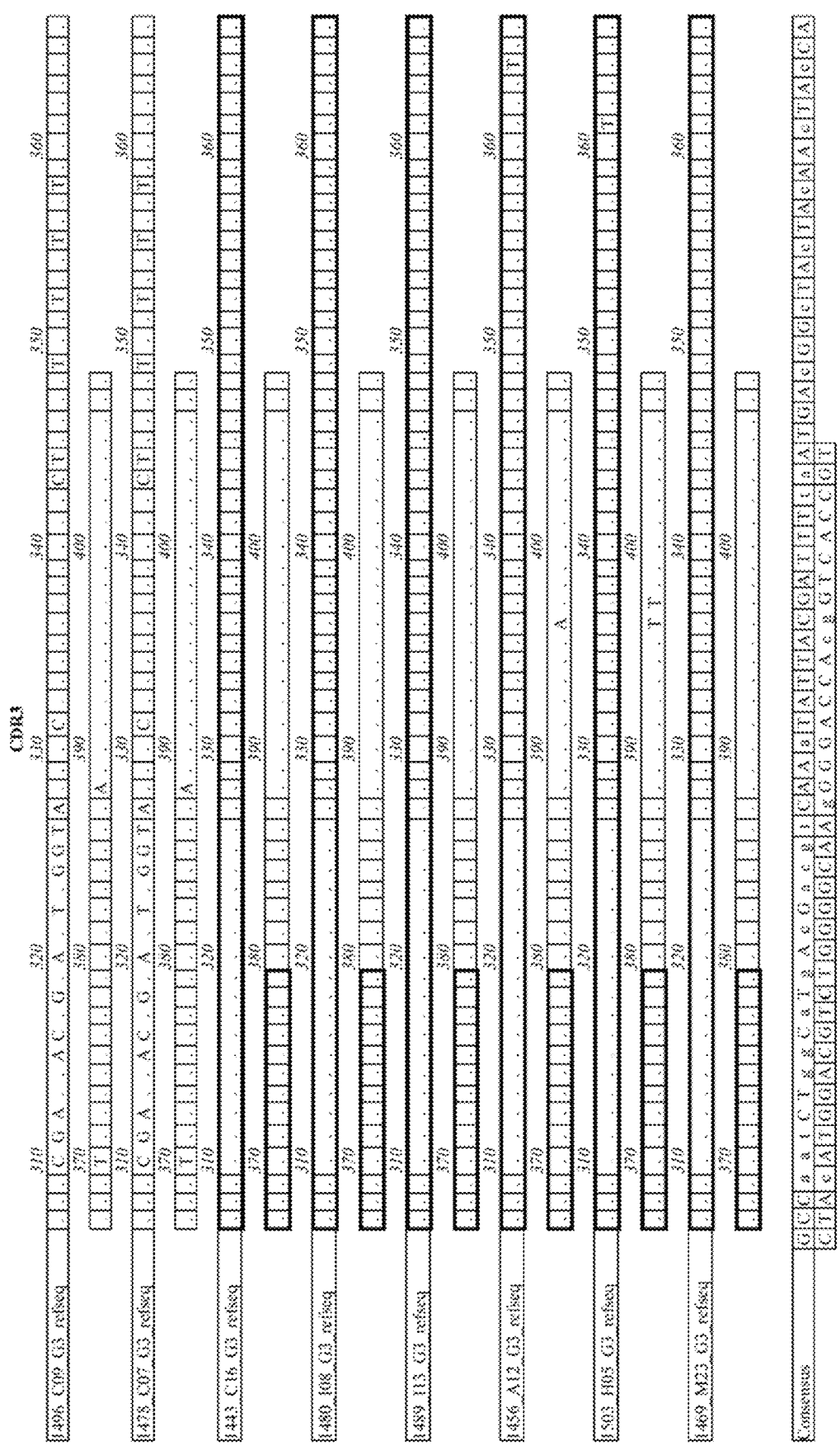
Figure 26A:
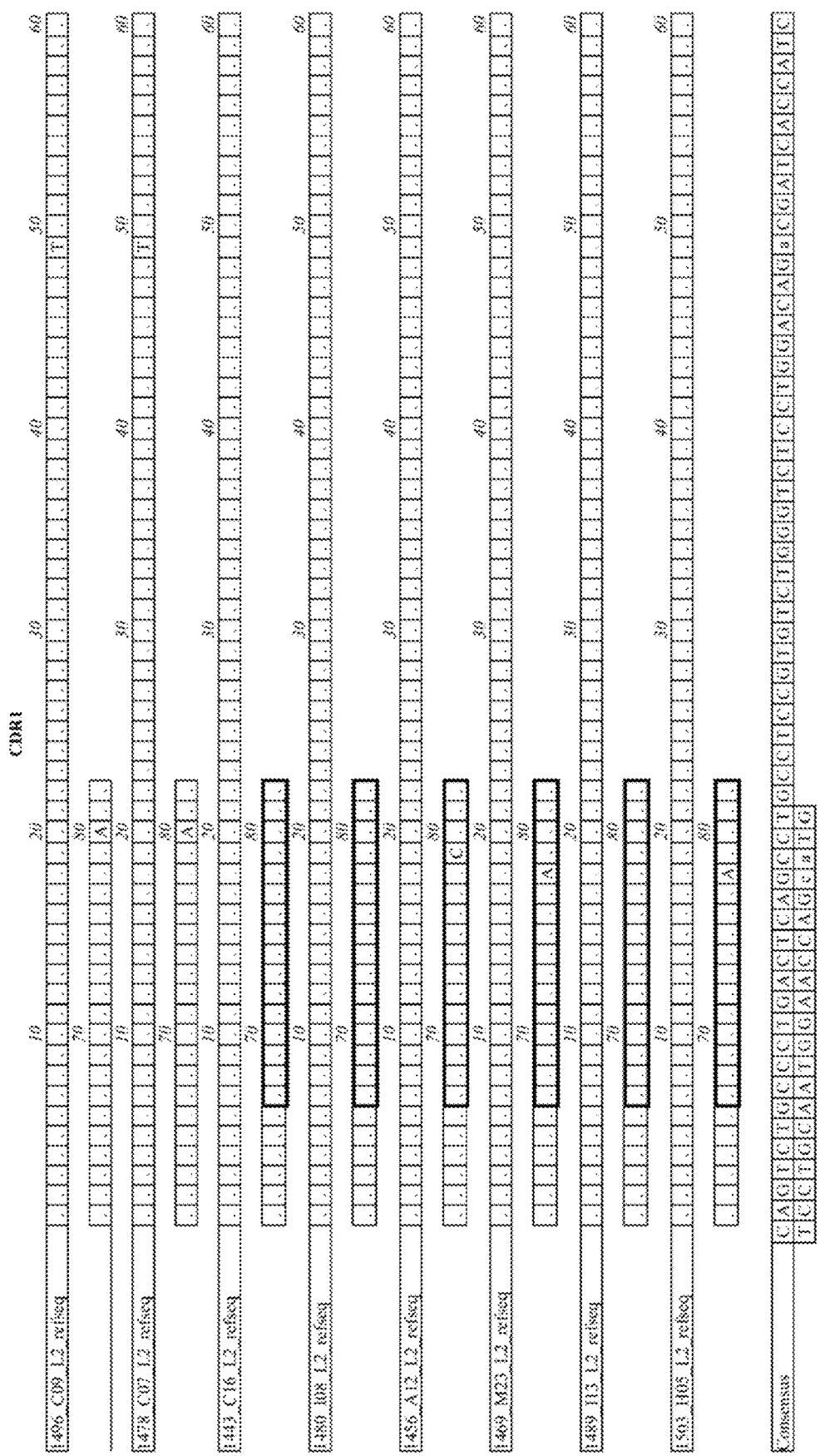
FIGS. 26A-26D depicts the alignment of light chain coding sequences of the variable domain of 1443_C16 sister clones to 1443_C16 and 1496_C09. Kabat CDR sequences for the PG16 sister clones are highlighted in boxes.
Figure 26B:
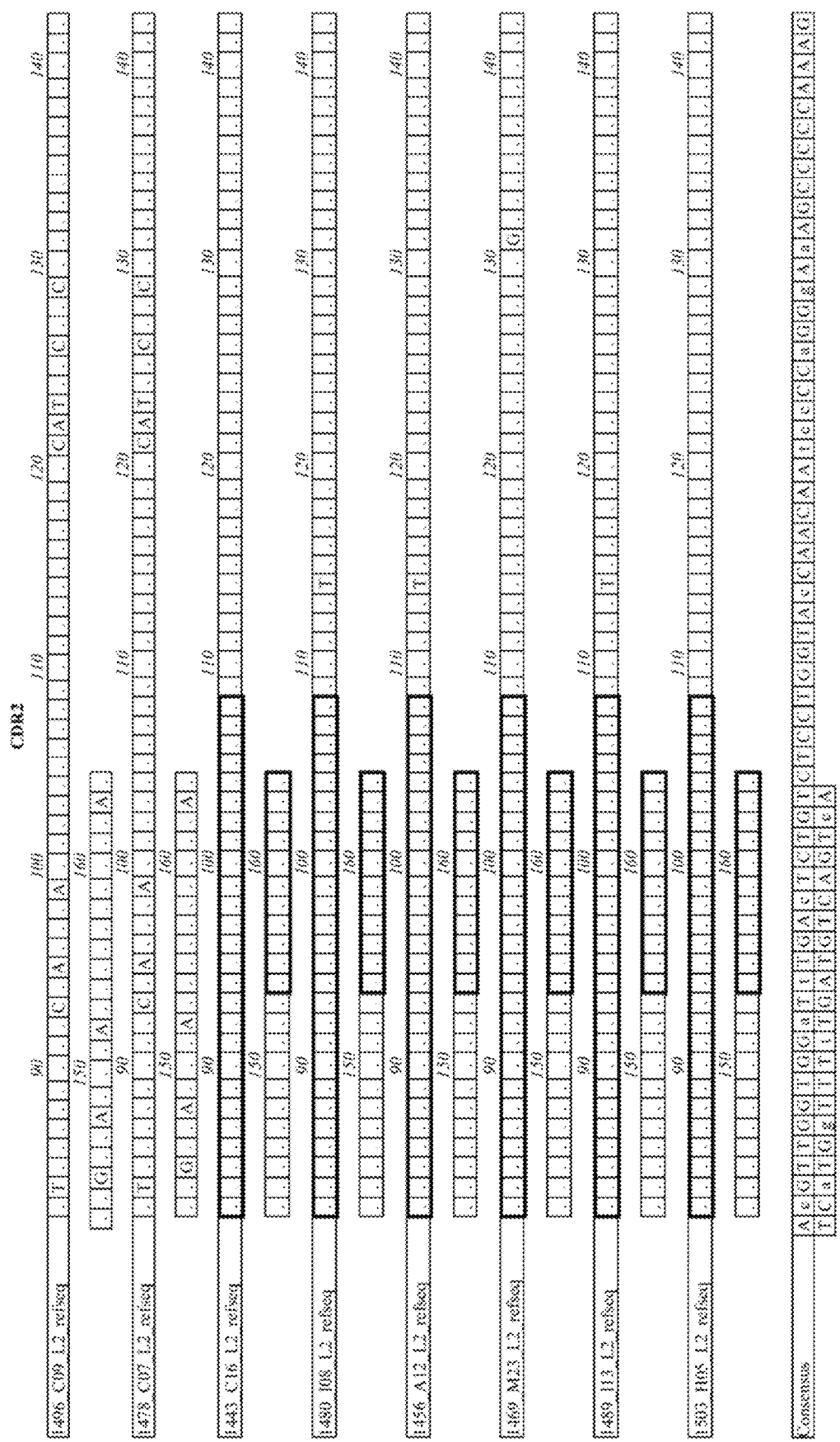
Figure 26C:
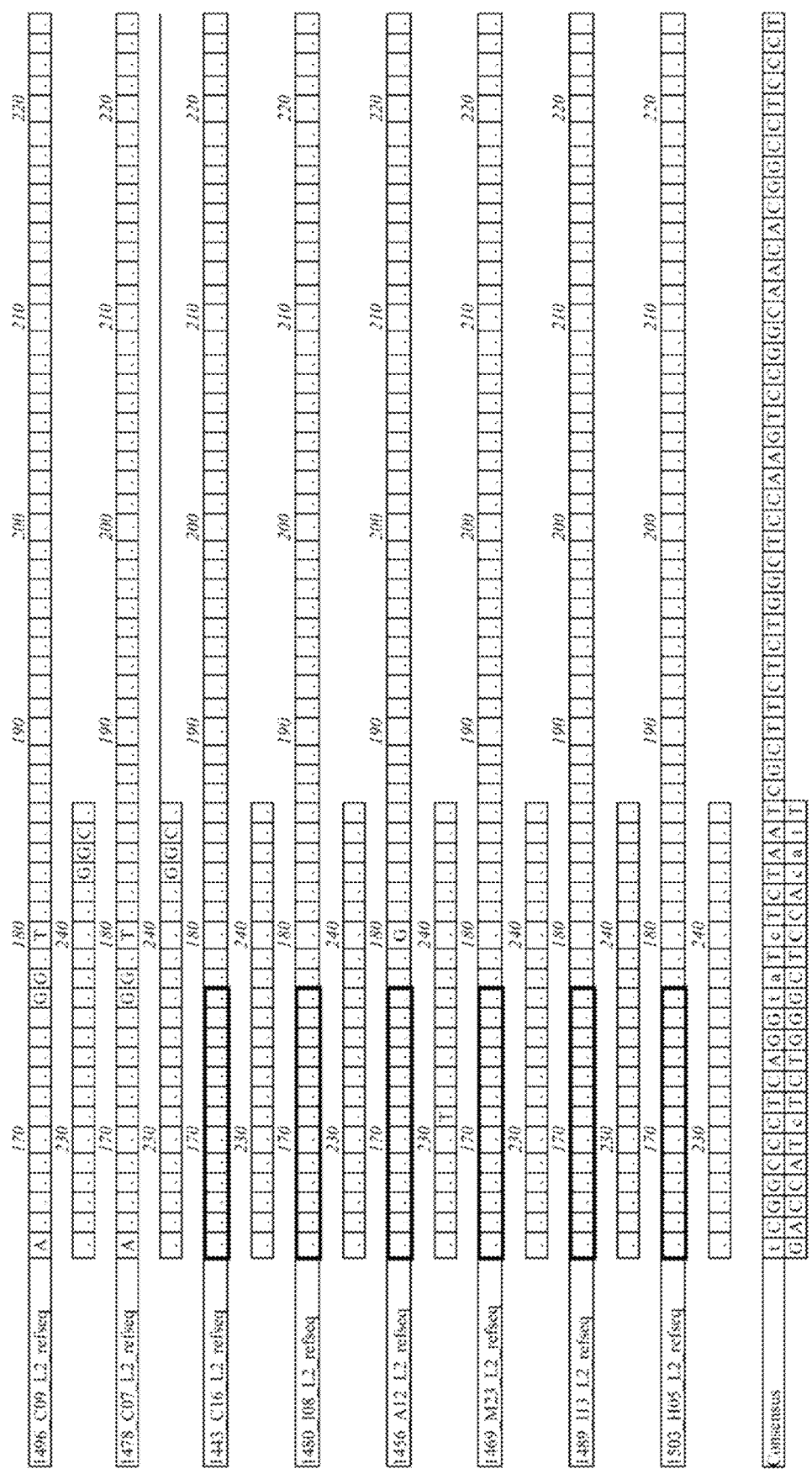
Figure 26D:
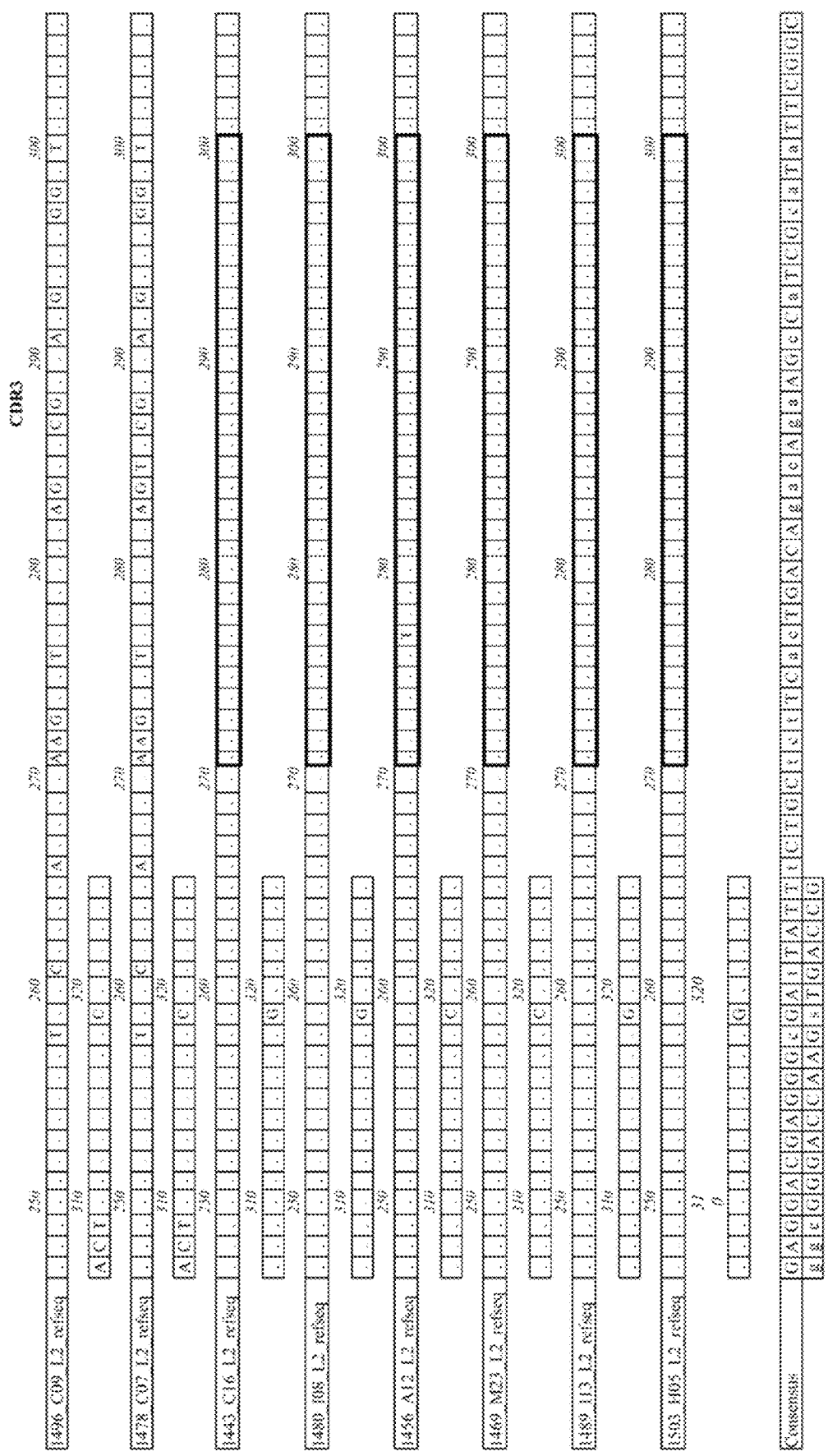
Figure 27:
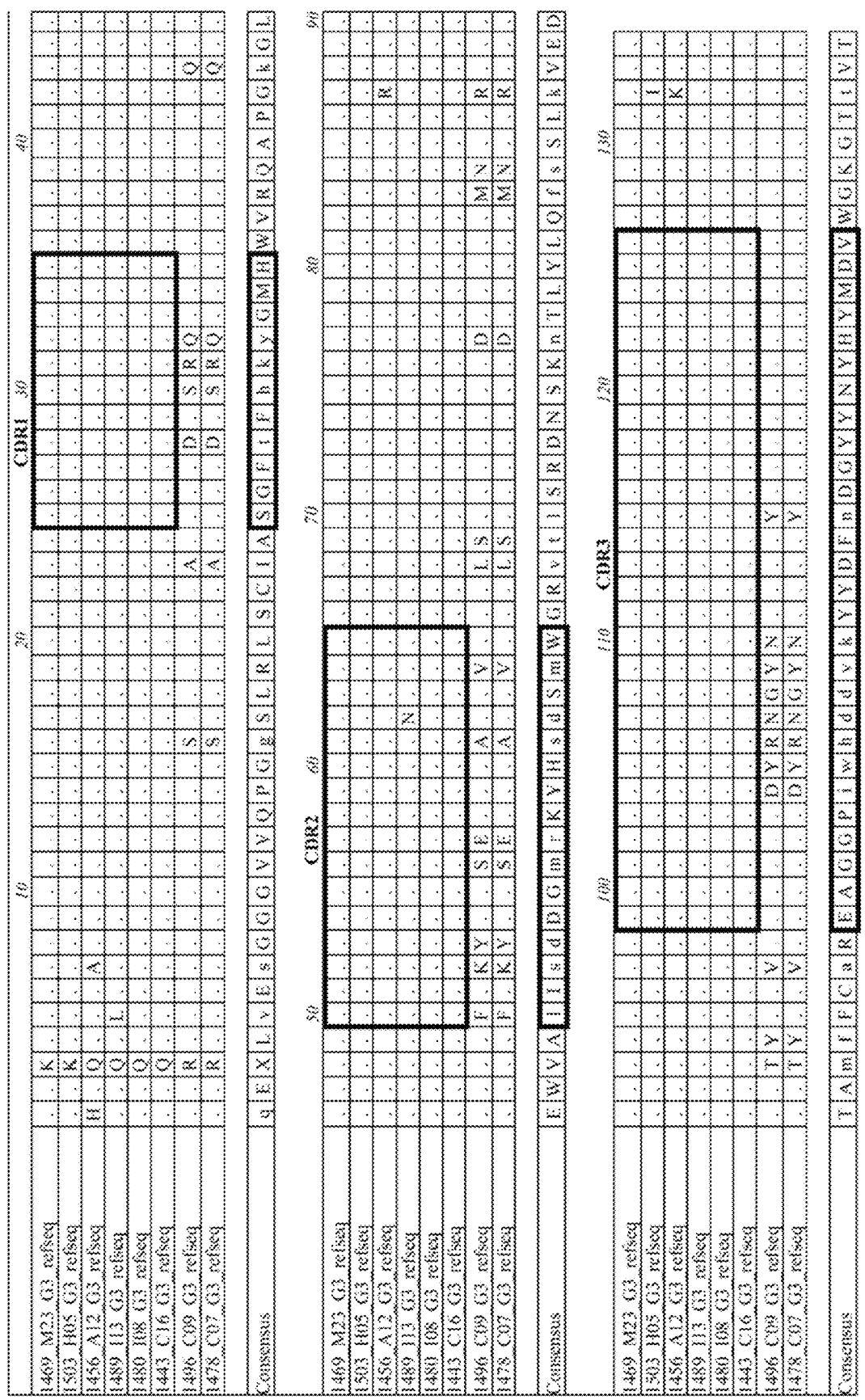
FIG. 27 depicts the alignment of heavy chain protein sequences of the variable domain of 1443_C16 sister clones to 1443_C16 and 1496_C09. Kabat CDR sequences for the PG16 sister clones are highlighted in boxes.
Figure 28:
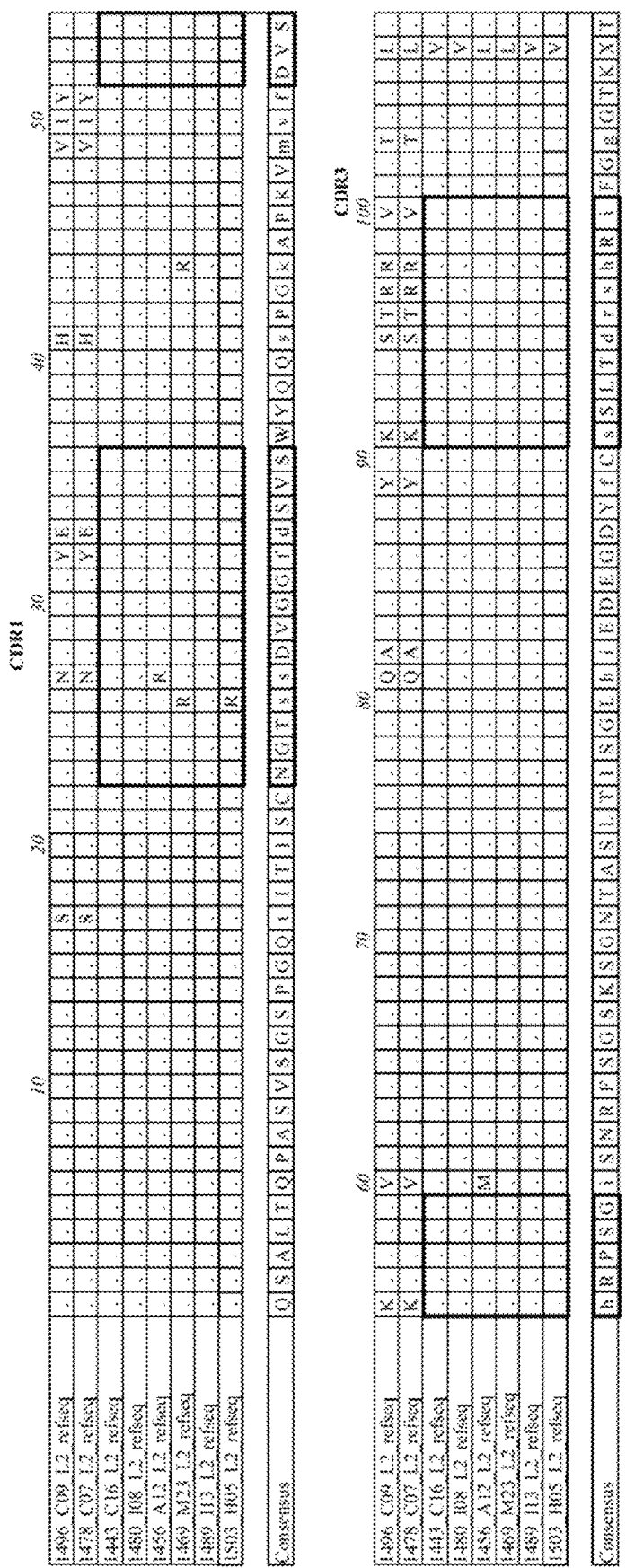
FIG. 28 depicts the alignment of light chain protein sequences of the variable domain of 1443_C16 sister clones to 1443_C16 and 1496_C09. Kabat CDR sequences for the PG16 sister clones are highlighted in black boxes.

The preferential binding of PG9 and PG16 to native trimers could either be a consequence of gp120 subunit cross-linking or recognition of a preferred oligomeric gp120 conformation. To address this question, the binding profiles of PG9 and PG16 to mixed HIV-1YU2 trimers were examined, in which two gp120 subunits containing point mutations abolished binding of the two antibodies. A third substitution that abrogates binding of 2G12, which binds with high affinity to both monomeric gp120 and trimeric Env, was also introduced into the same construct as an internal control. Cell surface binding analysis revealed that all three antibodies bound to the mixed trimers with similar apparent affinity as to wild-type trimers and all saturated at a similar lower level (FIG. 18). This result suggests that the preference of PG9 and PG16 for trimeric Env is due to gp120 subunit presentation in the context of the trimeric spike rather than gp120 cross-linking.

It has been shown that NAbs that bind to epitopes encompassing parts of the V2 or both the V2 and V3 domains can exhibit potency comparable to that of PG9 and PG16, although these antibodies have thus far displayed strong strain-specificity. (Honnen, W. J., et al. J Virol 81, 1424-1432 (2007); Gorny, M. K., et al. J Virol 79, 5232-5237 (2005)). Importantly, the epitopes recognized by these antibodies have been shown to differ from that of the clade B consensus sequence only by single amino acid substitutions, which suggested the existence of a relatively conserved structure within the V2 domain. (Honnen, W. J., et al. J Virol 81, 1424-1432 (2007)). The results observed with PG9 and PG16 confirm that this region serves as a potent neutralization target and demonstrates that antibodies that recognize conserved parts of V2 and V3 can possess broad reactivity.

The invention is based on novel monoclonal antibodies and antibody fragments that broadly and potently neutralize HIV infection. In some embodiments, these monoclonal antibodies and antibody fragments have a particularly high potency in neutralizing HIV infection in vitro across multiple clades or across a large number of different HIV species. Such antibodies are desirable, as only low concentrations are required to neutralize a given amount of virus. This facilitates higher levels of protection while administering lower amounts of antibody. Human monoclonal antibodies and the immortalized B cell clones that secrete such antibodies are included within the scope of the invention.

The invention provides methods for using high throughput functional screening to select neutralizing antibodies with unprecedented breadth and potency. The invention relates to other potent, and broadly neutralizing antibodies that can be developed using the same methods. In particular, the invention relates to potent, broadly neutralizing antibodies against different strains of HIV, wherein the bNAbs bind poorly to recombinant forms of Env. The invention provides two neutralizing antibodies, PG9 and PG16, with broad neutralizing activities particularly against non-clade B isolates. The invention provides vaccine-induced antibodies of high specificity that provide protection against a diverse range of the most prevalent isolates of HIV circulating worldwide. The invention provides antibodies with very high and broad neutralization potency, such as that exhibited by PG9 and PG16 in vitro, which provides protection at relatively modest serum concentrations, and are generated by vaccination unlike the broad NAbs known in the art. The invention provides immunogens that can be designed that focus the immune response on conserved regions of variable loops in the context of the trimeric spike of the gp120 subunit of the Env protein.

The invention also relates to the characterization of the epitope to which the antibodies bind and the use of that epitope in raising an immune response.

The invention also relates to various methods and uses involving the antibodies of the invention and the epitopes to which they bind. For example, monoclonal antibodies according to the invention can be used as therapeutics. In some aspects, the monoclonal antibodies are used for adjuvant therapy. Adjuvant therapy refers to treatment with the therapeutic monoclonal antibodies, wherein the adjuvant therapy is administered after the primary treatment to increase the chances of a cure or reduce the statistical risk of relapse.

The invention provides novel monoclonal or recombinant antibodies having particularly high potency in neutralizing HIV. The invention also provides fragments of these recombinant or monoclonal antibodies, particularly fragments that retain the antigen-binding activity of the antibodies, for example which retain at least one complementarity determining region (CDR) specific for HIV proteins. In this specification, by "high potency in neutralizing HIV" is meant that an antibody molecule of the invention neutralizes HIV in a standard assay at a concentration lower than antibodies known in the art.

Preferably, the antibody molecule of the present invention can neutralize at a concentration of 0.16 µg/ml or lower (i.e. 0.15, 0.125, 0.1, 0.075, 0.05, 0.025, 0.02, 0.016, 0.015, 0.0125, 0.01, 0.0075, 0.005, 0.004 or lower), preferably 0.016 µg/ml or lower (an antibody concentration of $10^{-8}$ or lower, preferably $10^{-9}$M or lower, preferably $10^{-10}$ M or lower, i.e. $10^{-11}$ $10^{-12}$ M, $10^{-13}$M or lower). This means that only very low concentrations of antibody are required for 50% neutralization of a clinical isolate of HIV in vitro. Potency can be measured using a standard neutralization assay as described in the art.

The antibodies of the invention are able to neutralize HIV. Monoclonal antibodies can be produced by known procedures, e.g., as described by R. Kennet et al. in "Monoclonal Antibodies and Functional Cell Lines; Progress and Applications". Plenum Press (New York), 1984. Further materials and methods applied are based on known procedures, e.g., such as described in J. Virol. 67:6642-6647, 1993.

These antibodies can be used as prophylactic or therapeutic agents upon appropriate formulation, or as a diagnostic tool.

A "neutralizing antibody" is one that can neutralize the ability of that pathogen to initiate and/or perpetuate an infection in a host and/or in target cells in vitro. The invention provides a neutralizing monoclonal human antibody, wherein the antibody recognizes an antigen from HIV.

Preferably an antibody according to the invention is a novel monoclonal antibody referred to herein as 1496_C09 (PG9), 1443_C16 (PG16), 1456_P20 (PG20), 1460_G14 (PGG14), and 1495_C14 (PGC14). These antibodies were initially isolated from human samples and are produced by the B cell cultures referred to as 1443_C16, 1456_P20, 1460_G14, 1495_C14 or 1496_C09. These antibodies have been shown to neutralize HIV in vitro. PG9 and PG16 have been shown to have broad, potent HIV neutralizing activity.

The CDRs of the antibody heavy chains are referred to as CDRH1, CDRH2 and CDRH3, respectively. Similarly, the CDRs of the antibody light chains are referred to as CDRL1, CDRL2 and CDRL3, respectively. The position of the CDR amino acids are defined according to the IMGT numbering system as: CDR1-IMGT positions 27 to 38, CDR2-IMGT positions 56 to 65 and CDR3-IMGT positions 105 to 117. (Lefranc, M P. et al. 2003 IMGT unique numbering for immunoglobulin and T cell receptor variable regions and Ig superfamily V-like domains. Dev Comp Immunol. 27(1): 55-77; Lefranc, M P. 1997. Unique database numbering system for immunogenetic analysis. Immunology Today, 18:509; Lefranc, M P. 1999. The IMGT unique numbering for Immunoglobulins, T cell receptors and Ig-like domains. The Immunologist, 7:132-136.)

The amino acid sequences of the CDR3 regions of the light and heavy chains of the antibodies are shown in Tables 3A and 3B.

A phylogram is a branching diagram (tree) assumed to be an estimate of phylogeny, branch lengths are proportional to the amount of inferred evolutionary change. Tree diagrams of the five heavy chains and the five light chains were prepared using ClustalW (Larkin M. A., Blackshields G., Brown N. P., Chenna R., McGettigan P. A., McWilliam H., Valentin F., Wallace I. M., Wilm A., Lopez R., Thompson J. D., Gibson T. J. and Higgins D. G. Bioinformatics 23(21): 2947-2948 (2007); Higgins D G et al. Nucleic Acids Research 22: 4673-4680. (1994)) and are shown in FIGS. 1A and 1B respectively.

The sequences of the antibodies were determined, including the sequences of the variable regions of the Gamma heavy and Kappa or Lambda light chains of the antibodies designated 1496_C09 (PG9), 1443_C16 (PG16), 1456_P20 (PG20), 1460_G14 (PGG14), and 1495_C14 (PGC14). In addition, the sequence of each of the polynucleotides encoding the antibody sequences was determined. Shown below are the polypeptide and polynucleotide sequences of the gamma heavy chains and kappa light chains, with the signal peptides at the N-terminus (or 5' end) and the constant regions at the C-terminus (or 3' end) of the variable regions, which are shown in bolded text.

1443_C16 (PG16) gamma heavy chain nucleotide sequence: 1443 C16 γ3 coding sequence (variable region in bold)

(SEQ ID NO: 11)

```
ATGGAGTTTGGGCTGAGCTGGGTTTTCCTCGCAACTCTGTTAAGAGTTGTGAAGTGTCAGGAACAACTGG
TGGAGTCTGGGGGAGGCGTGGTCCAGCCGGGGGGGTCCCTGAGACTCTCCTGTTTAGCGTCTGGATTCAC
GTTTCACAAATATGGCATGCACTGGGTCCGCCAGGCTCCAGGCAAGGGCCTGGAGTGGGTGGCACTCATC
TCAGATGACGGAATGAGGAAATATCATTCAGACTCCATGTGGGGCCGAGTCACCATCTCCAGAGACAATT
CCAAGAACACTCTTTATCTGCAATTCAGCAGCCTGAAAGTCGAAGACACGGCTATGTTCTTCTGTGCGAG
```

-continued

```
AGAGGCTGGTGGGCCAATCTGGCATGACGACGTCAAATATTACGATTTTAATGACGGCTACTACAACTAC
CACTACATGGACGTCTGGGGCAAGGGGACCACGGTCACCGTCTCGAGCGCCTCCACCAAGGGCCCATCGG
TCTTCCCCCTGGCACCCTCCTCCAAGAGCACCTCTGGGGGCACAGCGGCCCTGGGCTGCCTGGTCAAGGA
CTACTTCCCCGAACCGGTGACGGTGTCGTGGAACTCAGGCGCCCTGACCAGCGGCGTGCACACCTTCCCG
GCTGTCCTACAGTCCTCAGGACTCTACTCCCTCAGCAGCGTGGTGACCGTGCCCTCCAGCAGCTTGGGCA
CCCAGACCTACATCTGCAACGTGAATCACAAGCCCAGCAACACCAAGGTGGACAAGAGAGTTGAGCCCAA
ATCTTGTGACAAAACTCACACATGCCCACCGTGCCCAGCACCTGAACTCCTGGGGGGACCGTCAGTCTTC
CTCTTCCCCCCAAAACCCAAGGACACCCTCATGATCTCCCGGACCCCTGAGGTCACATGCGTGGTGGTGG
ACGTGAGCCACGAAGACCCTGAGGTCAAGTTCAACTGGTACGTGGACGGCGTGGAGGTGCATAATGCCAA
GACAAAGCCGCGGGAGGAGCAGTACAACAGCACGTACCGTGTGGTCAGCGTCCTCACCGTCCTGCACCAG
GACTGGCTGAATGGCAAGGAGTACAAGTGCAAGGTCTCCAACAAAGCCCTCCCAGCCCCCATCGAGAAAA
CCATCTCCAAAGCCAAAGGGCAGCCCCGAGAACCACAGGTGTACACCCTGCCCCCATCCCGGGAGGAGAT
GACCAAGAACCAGGTCAGCCTGACCTGCCTGGTCAAAGGCTTCTATCCCAGCGACATCGCCGTGGAGTGG
GAGAGCAATGGGCAGCCGGAGAACAACTACAAGACCACGCCTCCCGTGCTGGACTCCGACGGCTCCTTCT
TCCTCTATAGCAAGCTCACCGTGGACAAGAGCAGGTGGCAGCAGGGGAACGTCTTCTCATGCTCCGTGAT
GCATGAGGCTCTGCACAACCACTACACGCAGAAGAGCCTCTCCCTGTCTCCGGGTAAATGA
```

1443_C16 (PG16) gamma heavy chain variable region nucleotide sequence:

(SEQ ID NO: 99)
```
CAGGAACAACTGGTGGAGTCTGGGGGAGGCGTGGTCCAGCCGGGGGGGTCCCTGAGACTCTCCTGTTTAG
CGTCTGGATTCACGTTTCACAAATATGGCATGCACTGGGTCCGCCAGGCTCCAGGCAAGGGCCTGGAGTG
GGTGGCACTCATCTCAGATGACGGAATGAGGAAATATCATTCAGACTCCATGTGGGGCCGAGTCACCATC
TCCAGAGACAATTCCAAGAACACTCTTTATCTGCAATTCAGCAGCCTGAAAGTCGAAGACACGGCTATGT
TCTTCTGTGCGAGAGAGGCTGGTGGGCCAATCTGGCATGACGACGTCAAATATTACGATTTTAATGACGG
CTACTACAACTACCACTACATGGACGTCTGGGGCAAGGGGACCACGGTCACCGTCTCGAGC
```

1443_C16 (PG16) gamma heavy chain amino acid sequence: expressed protein with variable region in bold.

(SEQ ID NO: 12)

QEQLVESGGGVVQPGGSLRLSCLASGFTFHKYGMHWVRQAPGKGLEWVALISDDGMRKYHSDSM
WGRVTISRDNSKNTLYLQFSSLKVEDTAMFFCAREAGGPIWHDDVKYYDFNDGYYNYHYMDVWGK
GTTVTVSSASTKGPSVFPLAPSSKSTSGGTAALGCLVKDYFPEPVTVSWNSGALTSGVHTFPAVLQSSGLYS
LSSVVTVPSSSLGTQTYICNVNHKPSNTKVDKRVEPKSCDKTHTCPPCPAPELLGGPSVFLFPPKPKDTLMIS
RTPEVTCVVVDVSHEDPEVKFNWYVDGVEVHNAKTKPREEQYNSTYRVVSVLTVLHQDWLNGKEYKCK
VSNKALPAPIEKTISKAKGQPREPQVYTLPPSREEMTKNQVSLTCLVKGFYPSDIAVEWESNGQPENNYKTT
PPVLDSDGSFFLYSKLTVDKSRWQQGNVFSCSVMHEALHNHYTQKSLSLSPGK

1443_C16 (PG16) gamma heavy chain variable region amino acid sequence: (Kabat CDRs underlined, Chothia CDRs in bold italics)

(SEQ ID NO: 31)

QEQLVESGGGVVQPGGSLRLSCLA*SGFTFHKYGMH*WVRQAPGKGLEWVA*LISDDGMRKYHSDSMW*GRV
TISRDNSKNTLYLQFSSLKVEDTAMFFCAR*EAGGPIWHDDVKYYDFNDGYYNYHYMDV*WGKGTTVTVSS

1443_C16 (PG16) gamma heavy chain Kabat CDRs:
CDR 1: SGFTFHKYGMH (SEQ ID NO: 88)

CDR 2: LISDDGIVIRKYHSDSMW (SEQ ID NO: 89)

CDR 3: EAGGPIWHDDVKYYDFNDGYYNYHYMDV (SEQ ID NO: 6)

1443_C16 (PG16) gamma heavy chain Chothia CDRs:
CDR 1: SGFTFHKYGMH (SEQ ID NO: 88)

CDR 2: LISDDGIVIRKYHSDSMW (SEQ ID NO: 89)

CDR 3: EAGGPIWHDDVKYYDFNDGYYNYHYMDV (SEQ ID NO: 6)

1443_C16 (PG16) lambda light chain nucleotide sequence: 1443_C16 λ2 coding sequence (variable region in bold)

(SEQ ID NO: 13)
ATGGCCTGGGCTCTGCTATTCCTCACCCTCTTCACTCAGGGCACAGGGTCCTGGGGCCAGTCTGCCCTGACTCAGCC
TGCCTCCGTGTCTGGGTCTCCTGGACAGACGATCACCATCCTGCAATGGAACCAGCAGTGACGTTGGTGGATTTG
ACTCTGTCTCCTGGTACCAACAATCCCCAGGGAAAGCCCCCAAAGTCATGGTTTTTGATGTCAGTCATCGGCCCTCA
GGTATCTCTAATCGCTTCTCTGGCTCCAAGTCCGGCAACACGGCCTCCCTGACCATCTCTGGGCTCCACATTGAGGA
CGAGGGCGATTATTTCTGCTCTTCACTGACAGACAGAAGCCATCGGCGGCGGGACCAAGGTGACCGTTC
TAGGTCAGCCCAAGGCTGCCCCCTCGGTCACTCTGTTCCCGCCCTCCTCTGAGGAGCTTCAAGCCAACAAGGCCACA
CTGGTGTGTCTCATAAGTGACTTCTACCCGGGAGCCGTGACAGTGGCCTGGAAGGCAGATAGCAGCCCCGTCAAGGC
GGGAGTGGAGACCACCACACCCTCCAAACAAAGCAACAACAAGTACGCGGCCAGCAGCTACCTGAGCCTGACGCC
TGAGCAGTGGAAGTCCCACAAAAGCTACAGCTGCCAGGTCACGCATGAAGGGAGCACCGTGGAGAAGACAGTGGCCC
CTACAGAATGTTCATAG

1443_C16 (PG16) lambda light chain variable region nucleotide sequence:

(SEQ ID NO: 100)
CAGTCTGCCCTGACTCAGCCTGCCTCCGTGTCTGGGTCTCCTGGACAGACGATCACCATCCTGCAATGGAACCAG
CAGTGACGTTGGTGGATTTGACTCTGTCTCCTGGTACCAACAATCCCCAGGGAAAGCCCCCAAAGTCATGGTTTTTG
ATGTCAGTCATCGGCCCTCAGGTATCTCTAATCGCTTCTCTGGCTCCAAGTCCGGCAACACGGCCTCCCTGACCATC

```
TCTGGGCTCCACATTGAGGACGAGGGCGATTATTTCTGCTCTTCACTGACAGACAGAAGCCATCGCATATTCGGCGG
CGGGACCAAGGTGACCGTTCTA
```

1443_C16 (PG16) lambda light chain amino acid sequence: expressed protein with
variable region in bold.

(SEQ ID NO: 14)

```
QSALTQPASVSGSPGQTITISCNGTSSDVGGFDSVSWYQQSPGKAPKVMVFDVSHRPSGISNRFSGSKS
GNTASLTISGLHIEDEGDYFCSSLTDRSHRIFGGGTKVTVLGQPKAAPSVTLFPPSSEELQANKATLVCLI
SDFYPGAVTVAWKADSSPVKAGVETTTPSKQSNNKYAASSYLSLTPEQWKSHKSYSCQVTHEGSTVEKTV
APTECS
```

1443_C16 (PG16) lambda light chain variable region amino acid sequence: (Kabat CDRs
underlined, Chothia CDRs in bold italics)

(SEQ ID NO: 32)

```
QSALTQPASVSGSPGQTITISC*NGTSSDVGGFDSVS*WYQQSPGKAPKVMVF*DVSHRPSG*ISNRFSGSKSGNT
ASLTISGLHIEDEGDYFC*SSLTDRSHRI*FGGGTKVTVL
```

1443_C16 (PG16) lambda light chain Kabat CDRs:
CDR 1: NGTSSDVGGFDSVS (SEQ ID NO: 97)

CDR 2: DVSHRPSG (SEQ ID NO: 95)

CDR 3: SSLTDRSHRI (SEQ ID NO: 41)

1443_C16 (PG16) lambda light chain Chothia CDRs:
CDR 1: NGTSSDVGGFDSVS (SEQ ID NO: 97)

CDR 2: DVSHRPSG (SEQ ID NO: 95)

CDR 3: SSLTDRSHRI (SEQ ID NO: 41)

1456_P20 (PG20) gamma heavy chain nucleotide sequence: 1456_P20 γ1 coding
sequence (variable region in bold)

(SEQ ID NO: 15)

```
ATGGACTGGATTTGGAGGTTCCTCTTTGTGGTGGCAGCAGCTACAGGTGTCCAGTCCCAGGTCCGCCTGG
TACAGTCTGGGCCTGAGGTGAAGAAGCCTGGGTCCTCGGTGACGGTCTCCTGCCAGGCTTCTGGAGGCAC
CTTCAGCAGTTATGCTTTCACCTGGGTGCGCCAGGCCCCCGGACAAGGTCTTGAGTGGTTGGGCATGGTC
ACCCCAATCTTTGGTGAGGCCAAGTACTCACAAAGATTCGAGGGCAGAGTCACCATCACCGCGGACGAAT
CCACGAGCACAACCTCCATAGAATTGAGAGGCCTGACATCCGAAGACACGGCCATTTATTACTGTGCGCG
AGATCGGCGCGCGGTTCCAATTGCCACGGACAACTGGTTAGACCCCTGGGGCCAGGGGACCCTGGTCACC
GTCTCGAGCGCCTCCACCAAGGGCCCATCGGTCTTCCCCCTGGCACCCTCCTCCAAGAGCACCTCTGGGG
GCACAGCGGCCCTGGGCTGCCTGGTCAAGGACTACTTCCCCGAACCGGTGACGGTGTCGTGGAACTCAGG
CGCCCTGACCAGCGGCGTGCACACCTTCCCGGCTGTCCTACAGTCCTCAGGACTCTACTCCCTCAGCAGC
GTGGTGACCGTGCCCTCCAGCAGCTTGGGCACCCAGACCTACATCTGCAACGTGAATCACAAGCCCAGCA
ACACCAAGGTGGACAAGAGAGTTGAGCCCAAATCTTGTGACAAAACTCACACATGCCCACCGTGCCCAGC
ACCTGAACTCCTGGGGGGACCGTCAGTCTTCCTCTTCCCCCCAAAACCCAAGGACACCCTCATGATCTCC
CGGACCCCTGAGGTCACATGCGTGGTGGTGGACGTGAGCCACGAAGACCCTGAGGTCAAGTTCAACTGGT
ACGTGGACGGCGTGGAGGTGCATAATGCCAAGACAAAGCCGCGGGAGGAGCAGTACAACAGCACGTACCG
TGTGGTCAGCGTCCTCACCGTCCTGCACCAGGACTGGCTGAATGGCAAGGAGTACAAGTGCAAGGTCTCC
AACAAAGCCCTCCCAGCCCCCATCGAGAAAACCATCTCCAAAGCCAAAGGGCAGCCCCGAGAACCACAGG
TGTACACCCTGCCCCCATCCCGGGAGGAGATGACCAAGAACCAGGTCAGCCTGACCTGCCTGGTCAAAGG
CTTCTATCCCAGCGACATCGCCGTGGAGTGGGAGAGCAATGGGCAGCCGGAGAACAACTACAAGACCACG
CCTCCCGTGCTGGACTCCGACGGCTCCTTCTTCCTCTATAGCAAGCTCACCGTGGACAAGAGCAGGTGGC
AGCAGGGGAACGTCTTCTCATGCTCCGTGATGCATGAGGCTCTGCACAACCACTACACGCAGAAGAGCCT
CTCCCTGTCTCCGGGTAAATGA
```

1456_P20 (PG20) gamma heavy chain variable region nucleotide sequence:

(SEQ ID NO: 101)

```
CAGGTCCGCCTGGTACAGTCTGGGCCTGAGGTGAAGAAGCCTGGGTCCTCGGTGACGGTCTCCTGCCAGG
CTTCTGGAGGCACCTTCAGCAGTTATGCTTTCACCTGGGTGCGCCAGGCCCCCGGACAAGGTCTTGAGTG
GTTGGGCATGGTCACCCCAATCTTTGGTGAGGCCAAGTACTCACAAAGATTCGAGGGCAGAGTCACCATC
ACCGCGGACGAATCCACGAGCACAACCTCCATAGAATTGAGAGGCCTGACATCCGAAGACACGGCCATTT
ATTACTGTGCGCGAGATCGGCGCGCGGTTCCAATTGCCACGGACAACTGGTTAGACCCCTGGGGCCAGGG
GACCCTGGTCACCGTCTCGAGC
```

1456_P20 (PG20) gamma heavy chain amino acid sequence: expressed protein with
variable region in bold.

(SEQ ID NO: 16)

```
QVRLVQSGPEVKKPGSSVTVSCQASGGTFSSYAFTWVRQAPGQGLEWLGMVTPIFGEAKYSQRFEG
RVTITADESTSTTSIELRGLTSEDTAIYYCARDRRAVPIATDNWLDPWGQGTLVTVSSASTKGPSVFPLA
PSSKSTSGGTAALGCLVKDYFPEPVTVSWNSGALTSGVHTFPAVLQSSGLYSLSSVVTVPSSSLGTQTYICN
VNHKPSNTKVDKRVEPKSCDKTHTCPPCPAPELLGGPSVFLFPPKPKDTLMISRTPEVTCVVVDVSHEDPEV
KFNWYVDGVEVHNAKTKPREEQYNSTYRVVSVLTVLHQDWLNGKEYKCKVSNKALPAPIEKTISKAKGQ
PREPQVYTLPPSREEMTKNQVSLTCLVKGFYPSDIAVEWESNGQPENNYKTTPPVLDSDGSFFLYSKLTVD
KSRWQQGNVFSCSVMHEALHNHYTQKSLSLSPGK
```

1456_P20 (PG20) gamma heavy chain variable region amino acid sequence: (Kabat CDRs underlined, Chothia CDRs in bold italics)

(SEQ ID NO: 33)

QVRLVQSGPEVKKPGSSVTVSCQA*SGGTFSSYAFT*WVRQAPGQGLEWLQ*MVTPIFGEAKYSQRFE*GRVTI
TADESTSTTSIELRGLTSEDTAIYYCARD*RRAVPIATDNWLDP*WGQGTLVTVSS

1456_P20 (PG20) gamma heavy chain Kabat CDRs:
CDR 1: SGGTFSSYAFT (SEQ ID NO: 104)

CDR 2: MVTPIFGEAKYSQRFE (SEQ ID NO: 105)

CDR 3: RAVPIATDNWLDP (SEQ ID NO: 102)

1456_P20 (PG20) gamma heavy chain Chothia CDRs:
CDR 1: SGGTFSSYAFT (SEQ ID NO: 104)

CDR 2: MVTPIFGEAKYSQRFE (SEQ ID NO: 105)

CDR 3: RRAVPIATDNWLDP (SEQ ID NO: 103)

1456_P20 (PG20) kappa light chain nucleotide sequence: 1456_P20 κ1 coding sequence (variable region in bold)

(SEQ ID NO: 17)

ATGGACATGAGGGTCCCCGCTCAGCTCCTGGGGCTCCTGCTACTCTGGCTCCGAGGTGCCAGATGT**GACA
TCCAGTTGACCCAGTCTCCATCCTCCCTGTCTGCATCTGTTGGCGACAGAGTCTCCATCACTTGCCGGGC
GAGTCAGACCATTAACAACTACTTAAATTGGTATCAACAGACACCCGGGAAAGCCCCTAAACTCCTGATC
TATGGTGCCTCCAATTTGCAAAATGGGGTCCCATCAAGGTTCAGCGGCAGTGGCTCTGGGACAGACTTCA
CTCTCACCATCAGCAGTCTGCAACCTGAGGATTTTGCAACTTACTACTGTCAACAGAGTTTCAGTACTCC
GAGGACCTTCGGCCAAGGGACACGACTGGATATTAAA**CGTACGGTGGCTGCACCATCTGTCTTCATCTTC
CCGCCATCTGATGAGCAGTTGAAATCTGGAACTGCCTCTGTTGTGTGCCTGCTGAATAACTTCTATCCCA
GAGAGGCCAAAGTACAGTGGAAGGTGGATAACGCCCTCCAATCGGGTAACTCCCAGGAGAGTGTCACAGA
GCAGGACAGCAAGGACAGCACCTACAGCCTCAGCAGCACCCTGACGCTGAGCAAAGCAGACTACGAGAAA
CACAAAGTCTACGCCTGCGAAGTCACCCATCAGGGCCTGAGCTCGCCCGTCACAAAGAGCTTCAACAGGG
GAGAGTGTTAG

1456_P20 (PG20) kappa light chain variable region nucleotide sequence:

(SEQ ID NO: 106)

GACATCCAGTTGACCCAGTCTCCATCCTCCCTGTCTGCATCTGTTGGCGACAGAGTCTCCATCACTTGCC
GGGCGAGTCAGACCATTAACAACTACTTAAATTGGTATCAACAGACACCCGGGAAAGCCCCTAAACTCCT
GATCTATGGTGCCTCCAATTTGCAAAATGGGGTCCCATCAAGGTTCAGCGGCAGTGGCTCTGGGACAGAC
TTCACTCTCACCATCAGCAGTCTGCAACCTGAGGATTTTGCAACTTACTACTGTCAACAGAGTTTCAGTA
CTCCGAGGACCTTCGGCCAAGGGACACGACTGGATATTAAA

1456_P20 (PG20) kappa light chain amino acid sequence: expressed protein with variable region in bold.

(SEQ ID NO: 18)

**DIQLTQSPSSLSASVGDRVSITCRASQTINNYLNWYQQTPGKAPKWYGASNLQNGVPSRFSGSGSGT
DFTLTISSLQPEDFATYYCQQSFSTPRTFGQGTRLDIK**RTVAAPSVFIFPPSDEQLKSGTASVVCLLNNFY
PREAKVQWKVDNALQSGNSQESVTEQDSKDSTYSLSSTLTLSKADYEKHKVYACEVTHQGLSSPVTKSFN
RGEC

1456_P20 (PG20) kappa light chain variable region amino acid sequence: (Kabat CDRs underlined, Chothia CDRs in bold italics)

(SEQ ID NO: 34)

DIQLTQSPSSLSASVGDRVSITC*RASQTINNYLN*WYQQTPGKAPKLLIY*GASNLQNG*VPSRFSGSGSGTDFTL
TISSLQPEDFATYYC*QQSFSTPRT*FGQGTRLDIK

1456_P20 (PG20) kappa light chain Kabat CDRs:
CDR 1: RASQTINNYLN (SEQ ID NO: 107)

CDR 2: GASNLQNG (SEQ ID NO: 108)

CDR 3: QQSFSTPRT (SEQ ID NO: 42)

1456_P20 (PG20) kappa light chain Chothia CDRs:
CDR 1: RASQTINNYLN (SEQ ID NO: 107)

CDR 2: GASNLQNG (SEQ ID NO: 108)

CDR 3: QQSFSTPRT (SEQ ID NO: 42)

1460_G14 (PGG14) gamma heavy chain nucleotide sequence: 1460_G14 γ1 coding sequence (variable region in bold)

(SEQ ID NO: 19)

ATGGACTGGATTTGGAGGTTCCTCTTGGTGGTGGCAGCAGCTACAGGTGTCCAGTCC**CAGGTCCTGCTGG
TGCAGTCTGGGACTGAGGTGAAGAAGCCTGGGTCCTCGGTGAAGGTCTCCTGTCAGGCTTCTGGAGGCGC
CTTCAGTAGTTATGCTTTCAGCTGGGTGCGACAGGCCCCTGGACAGGGGCTTGAATGGATGGGCATGATC
ACCCCTGTCTTTGGTGAGACTAAATATGCACCGAGGTTCCAGGGCAGACTCACACTTACCGCGGAAGAAT**

-continued

CCTTGAGCACCACCTACATGGAATTGAGAAGCCTGACATCTGATGACACGGCCTTTTATTATTGTACGAG
AGATCGGCGCGTAGTTCCAATGGCCACAGACAACTGGTTAGACCCCTGGGGCCAGGGGACGCTGGTCACC
GTCTCGAGCGCCTCCACCAAGGGCCCATCGGTCTTCCCCCTGGCACCCTCCTCCAAGAGCACCTCTGGGG
GCACAGCGGCCCTGGGCTGCCTGGTCAAGGACTACTTCCCCGAACCGGTGACGGTGTCGTGGAACTCAGG
CGCCCTGACCAGCGGCGTGCACACCTTCCCGGCTGTCCTACAGTCCTCAGGACTCTACTCCCTCAGCAGC
GTGGTGACCGTGCCCTCCAGCAGCTTGGGCACCCAGACCTACATCTGCAACGTGAATCACAAGCCCAGCA
ACACCAAGGTGGACAAGAGAGTTGAGCCCAAATCTTGTGACAAAACTCACACATGCCCACCGTGCCCAGC
ACCTGAACTCCTGGGGGGACCGTCAGTCTTCCTCTTCCCCCCAAAACCCAAGGACACCCTCATGATCTCC
CGGACCCCTGAGGTCACATGCGTGGTGGTGGACGTGAGCCACGAAGACCCTGAGGTCAAGTTCAACTGGT
ACGTGGACGGCGTGGAGGTGCATAATGCCAAGACAAAGCCGCGGGAGGAGCAGTACAACAGCACGTACCG
TGTGGTCAGCGTCCTCACCGTCCTGCACCAGGACTGGCTGAATGGCAAGGAGTACAAGTGCAAGGTCTCC
AACAAAGCCCTCCCAGCCCCCATCGAGAAAACCATCTCCAAAGCCAAAGGGCAGCCCCGAGAACCACAGG
TGTACACCCTGCCCCCATCCCGGGAGGAGATGACCAAGAACCAGGTCAGCCTGACCTGCCTGGTCAAAGG
CTTCTATCCCAGCGACATCGCCGTGGAGTGGGAGAGCAATGGGCAGCCGGAGAACAACTACAAGACCACG
CCTCCCGTGCTGGACTCCGACGGCTCCTTCTTCCTCTATAGCAAGCTCACCGTGGACAAGAGCAGGTGGC
AGCAGGGGAACGTCTTCTCATGCTCCGTGATGCATGAGGCTCTGCACAACCACTACACGCAGAAGAGCCT
CTCCCTGTCTCCGGGTAAATGA

1460_G14 (PGG14) gamma heavy chain variable region nucleotide sequence:
(SEQ ID NO: 109)
CAGGTCCTGCTGGTGCAGTCTGGGACTGAGGTGAAGAAGCCTGGGTCCTCGGTGAAGGTCTCCTGTCAGG
CTTCTGGAGGCGCCTTCAGTAGTTATGCTTTCAGCTGGGTGCGACAGGCCCCTGGACAGGGGCTTGAATG
GATGGGCATGATCACCCCTGTCTTTGGTGAGACTAAATATGCACCGAGGTTCCAGGGCAGACTCACACTT
ACCGCGGAAGAATCCTTGAGCACCACCTACATGGAATTGAGAAGCCTGACATCTGATGACACGGCCTTTT
ATTATTGTACGAGAGATCGGCGCGTAGTTCCAATGGCCACAGACAACTGGTTAGACCCCTGGGGCCAGGG
GACGCTGGTCACCGTCTCGAGC 1460_G14 gamma heavy chain amino acid sequence: expressed protein with variable
region in bold.
**QVLLVQSGTEVKKPGSSVKVSCQASGGAFSSYAFSWVRQAPGQGLEWMGMITPVFGETKYAPRFQG
RLTLTAEESLSTTYMELRSLTSDDTAFYYCTRDRRVVPMATDNWLDPWGQGTLVTVSS**ASTKGPSVF
PLAPSSKSTSGGTAALGCLVKDYFPEPVTVSWNSGALTSGVHTFPAVLQSSGLYSLSSVVTVPSSSLGTQTYI
CNVNHKPSNTKVDKRVEPKSCDKTHTCPPCPAPELLGGPSVFLFPPKPKDTLMISRTPEVTCVVVDVSHEDP
EVKFNWYVDGVEVHNAKTKPREEQYNSTYRVVSVLTVLHQDWLNGKEYKCKVSNKALPAPIEKTISKAK
GQPREPQVYTLPPSREEMTKNQVSLTCLVKGFYPSDIAVEWESNGQPENNYKTTPPVLDSDGSFFLYSKLT
VDKSRWQQGNVFSCSVMHEALHNHYTQKSLSLSPG (SEQ ID NO: 20)

1460_G14 gamma heavy chain variable region amino acid sequence: (Kabat CDRs
underlined, Chothia CDRs in bold italics)
(SEQ ID NO: 35)
QVLLVQSGILVKKPGSSVKVSCQA*SGGAFSSYAFS*WVRQAPGQGLEWMG*MITPVFGETKYAPRFQ*GRLT
LTAEESLSTTYMELRSLTSDDTAFYYCTRD*RVVPMATDNWLDP*WGQGTLVTVSS 1460_G14 gamma heavy chain Kabat CDRs:
CDR 1: SGGAFSSYAFS (SEQ ID NO: 110)

CDR 2: MITPVFGETKYAPRFQ (SEQ ID NO: 111)

CDR 3: RVVPMATDNWLDP (SEQ ID NO: 102)

1460_G14 gamma heavy chain Chothia CDRs:
CDR 1: SGGAFSSYAFS (SEQ ID NO: 110)

CDR 2: MITPVFGETKYAPRFQ (SEQ ID NO: 111)

CDR 3: RRVVPMATDNWLDP (SEQ ID NO: 103)

1460_G14 (PGG14) kappa light chain nucleotide sequence: 1460_G14 κ1 coding
sequence (variable region in bold)
(SEQ ID NO: 21)
ATGGACATGAGGGTCCCCGCTCAGCTCCTGGGGCTCCTGCTCCTCTGGCTCCGAGGTGCCACATGT**GACA
TCCAGTTGACCCAGTCTCCATCCTCCCTGTCTGCATCTGTAGGAGACAGGGTCACCGTCACTTGCCGGGC
GAGTCAGACCATACACACCTATTTAAATTGGTATCAGCAAATTCCAGGAAAAGCCCCTAAGCTCCTGATC
TATGGTGCCTCCACCTTGCAAAGTGGGGTCCCGTCAAGGTTCAGTGGCAGTGGATCTGGGACAGATTTCA
CTCTCACCATCAACAGTCTCCAACCTGAGGACTTTGCAACTTACTACTGTCAACAGAGTTACAGTACCCC
AAGGACCTTCGGCCAAGGGACACGACTGGATATTAAA**CGTACGGTGGCTGCACCATCTGTCTTCATCTTC
CCGCCATCTGATGAGCAGTTGAAATCTGGAACTGCCTCTGTTGTGTGCCTGCTGAATAACTTCTATCCCA
GAGAGGCCAAAGTACAGTGGAAGGTGGATAACGCCCTCCAATCGGGTAACTCCCAGGAGAGTGTCACAGA
GCAGGACAGCAAGGACAGCACCTACAGCCTCAGCAGCACCCTGACGCTGAGCAAAGCAGACTACGAGAAA
CACAAAGTCTACGCCTGCGAAGTCACCCATCAGGGCCTGAGCTCGCCCGTCACAAAGAGCTTCAACAGGG
GAGAGTGTTAG 1460_G14 (PGG14) kappa light chain variable region nucleotide sequence:
(SEQ ID NO: 112)
GACATCCAGTTGACCCAGTCTCCATCCTCCCTGTCTGCATCTGTAGGAGACAGGGTCACCGTCACTTGCC
GGGCGAGTCAGACCATACACACCTATTTAAATTGGTATCAGCAAATTCCAGGAAAAGCCCCTAAGCTCCT
GATCTATGGTGCCTCCACCTTGCAAAGTGGGGTCCCGTCAAGGTTCAGTGGCAGTGGATCTGGGACAGAT
TTCACTCTCACCATCAACAGTCTCCAACCTGAGGACTTTGCAACTTACTACTGTCAACAGAGTTACAGTA
CCCCAAGGACCTTCGGCCAAGGGACACGACTGGATATTAAA 1460_G14 kappa light chain amino acid sequence: expressed protein with variable region
in bold.
(SEQ ID NO: 22)

**DIQLTQSPSSLSASVGDRVTVTCRASQTIHTYLNWYQQIPGKAPKWYGASTLQSGVPSRFSGSGSGT
DFTLTINSLQPEDFATYYCQQSYSTPRTFGQGTRLDIK**RTVAAPSVFIFPPSDEQLKSGTASVVCLLNNFY
PREAKVQWKVDNALQSGNSQESVTEQDSKDSTYSLSSTLTLSKADYEKHKVYACEVTHQGLSSPVTKSFN
RGEC

1460_G14 kappa light chain variable region amino acid sequence: (Kabat CDRs
underlined, Chothia CDRs in bold italics)
(SEQ ID NO: 36)
DIQLTQSPSSLSASVGDRVTVTC*RASQTIHTYLN*WYQQIPGKAPKLLIY*GASTLQSG*VPSRFSGSGSGTDFTL
TINSLQPEDFATYYC*QQSYSTPRT*FGQGTRLDIK 1460_G14 kappa light chain Kabat CDRs:
CDR 1: RASQTIHTYL (SEQ ID NO: 113)

CDR 2: GASTLQSG (SEQ ID NO: 114)

CDR 3: QQSYSTPRT (SEQ ID NO: 43)

1460_G14 kappa light chain Chothia CDRs:
CDR 1: RASQTIHTYL (SEQ ID NO: 113)

CDR 2: GASTLQSG (SEQ ID NO: 114)

CDR 3: QQSYSTPRT (SEQ ID NO: 43)

1495_C14 (PGC14) gamma heavy chain nucleotide sequence: 1495_C14 γ1 coding
sequence (variable region in bold)
(SEQ ID NO: 23)
ATGGACTGGATTTGGAGGATCCTCCTCTTGGTGGCAGCAGCTACAGGCACCCTCGCC**GACGGCCACCTGG
TTCAGTCTGGGGTTGAGGTGAAGAAGACTGGGGCTACAGTCAAAATCTCCTGCAAGGTTTCTGGATACAG
CTTCATCGACTACTACCTTCATTGGGTGCAACGGGCCCCTGGAAAAGGCCTTGAGTGGGTGGGACTTATT
GATCCTGAAAATGGTGAGGCTCGATATGCAGAGAAGTTCCAGGGCAGAGTCACCATAATCGCGGACACGT
CTATAGATACAGGCTACATGGAAATGAGGAGCCTGAAATCTGAGGACACGGCCGTGTATTTCTGTGCAGC
AGGTGCCGTGGGGGCTGATTCCGGGAGCTGGTTCGACCCCTGGGGCCAGGGAACTCTGGTCACCGTCTCG
AGC**GCCTCCACCAAGGGCCCATCGGTCTTCCCCCTGGCACCCTCCTCCAAGAGCACCTCTGGGGGCACAG
CGGCCCTGGGCTGCCTGGTCAAGGACTACTTCCCCGAACCGGTGACGGTGTCGTGGAACTCAGGCGCCCT
GACCAGCGGCGTGCACACCTTCCCGGCTGTCCTACAGTCCTCAGGACTCTACTCCCTCAGCAGCGTGGTG
ACCGTGCCCTCCAGCAGCTTGGGCACCCAGACCTACATCTGCAACGTGAATCACAAGCCCAGCAACACCA
AGGTGGACAAGAGAGTTGAGCCCAAATCTTGTGACAAAACTCACACATGCCCACCGTGCCCAGCACCTGA
ACTCCTGGGGGGACCGTCAGTCTTCCTCTTCCCCCCAAAACCCAAGGACACCCTCATGATCTCCCGGACC
CCTGAGGTCACATGCGTGGTGGTGGACGTGAGCCACGAAGACCCTGAGGTCAAGTTCAACTGGTACGTGG
ACGGCGTGGAGGTGCATAATGCCAAGACAAAGCCGCGGGAGGAGCAGTACAACAGCACGTACCGTGTGGT
CAGCGTCCTCACCGTCCTGCACCAGGACTGGCTGAATGGCAAGGAGTACAAGTGCAAGGTCTCCAACAAA
GCCCTCCCAGCCCCCATCGAGAAAACCATCTCCAAAGCCAAAGGGCAGCCCCGAGAACCACAGGTGTACA
CCCTGCCCCCATCCCGGGAGGAGATGACCAAGAACCAGGTCAGCCTGACCTGCCTGGTCAAAGGCTTCTA
TCCCAGCGACATCGCCGTGGAGTGGGAGAGCAATGGGCAGCCGGAGAACAACTACAAGACCACGCCTCCC
GTGCTGGACTCCGACGGCTCCTTCTTCCTCTATAGCAAGCTCACCGTGGACAAGAGCAGGTGGCAGCAGG
GGAACGTCTTCTCATGCTCCGTGATGCATGAGGCTCTGCACAACCACTACACGCAGAAGAGCCTCTCCCT
GTCTCCGGGTAAATGA 1495_C14 (PGC14) gamma heavy chain variable region nucleotide sequence:
(SEQ ID NO: 115)
GACGGCCACCTGGTTCAGTCTGGGGTTGAGGTGAAGAAGACTGGGGCTACAGTCAAAATCTCCTGCAAGG
TTTCTGGATACAGCTTCATCGACTACTACCTTCATTGGGTGCAACGGGCCCCTGGAAAAGGCCTTGAGTG
GGTGGGACTTATTGATCCTGAAAATGGTGAGGCTCGATATGCAGAGAAGTTCCAGGGCAGAGTCACCATA
ATCGCGGACACGTCTATAGATACAGGCTACATGGAAATGAGGAGCCTGAAATCTGAGGACACGGCCGTGT
ATTTCTGTGCAGCAGGTGCCGTGGGGGCTGATTCCGGGAGCTGGTTCGACCCCTGGGGCCAGGGAACTCT
GGTCACCGTCTCGAGC 1495_C14 (PGC14) gamma heavy chain amino acid sequence: expressed protein with
variable region in bold.
(SEQ ID NO: 24)
**DGHLVQSGVEVKKTGATVKISCKVSGYSFIDYYLHWVQRAPGKGLEWVGLIDPENGEARYAEKFQG
RVTIIADTSIDTGYMEMRSLKSEDTAVYFCAAGAVGADSGSWFDPWGQGTLVTVSS**ASTKGPSVFPLA
PSSKSTSGGTAALGCLVKDYFPEPVTVSWNSGALTSGVHTFPAVLQSSGLYSLSSVVTVPSSSLGTQTYICN
VNHKPSNTKVDKRVEPKSCDKTHTCPPCPAPELLGGPSVFLFPPKPKDTLMISRTPEVTCVVVDVSHEDPEV
KFNWYVDGVEVHNAKTKPREEQYNSTYRVVSVLTVLHQDWLNGKEYKCKVSNKALPAPIEKTISKAKGQ
PREPQVYTLPPSREEMTKNQVSLTCLVKGFYPSDIAVEWESNGQPENNYKTTPPVLDSDGSFFLYSKLTVD
KSRWQQGNVFSCSVMHEALHNHYTQKSLSLSPGK 1495_C14 (PGC14) gamma heavy chain variable region amino acid sequence: (Kabat
CDRs underlined, Chothia CDRs in bold italics)
(SEQ ID NO: 37)
DGHLVQSGVEVKKTGATVKISCKV*SGYSFIDYYLH*WVQRAPGKGLEWVG*LIDPENGEARYAEKFQ*GRVTI
IADTSIDTGYMEMRSLKSEDTAVYFCAAG*AVGADSGSWFDP*WGQGTLVTVSS

```
1495_C14 gamma heavy chain Kabat CDRs:
CDR 1: SGYSFIDYYLH (SEQ ID NO: 116)

CDR 2: LIDPENGEARYAEKFQ (SEQ ID NO: 117)

CDR 3: AVGADSGSWFDP (SEQ ID NO: 118)

1495_C14 gamma heavy chain Chothia CDRs:
CDR 1: SGYSFIDYYLH (SEQ ID NO: 116)

CDR 2: LIDPENGEARYAEKFQ (SEQ ID NO: 117)

CDR 3: AVGADSGSWFDP (SEQ ID NO: 118)

1495_C14 (PGC14) lambda light chain nucleotide sequence: 1495_C14 λ3 coding
sequence (variable region in bold)
                                                              (SEQ ID NO: 25)
ATGGCCTGGATCCCTCTCTTCCTCGGCGTCCTTGCTTACTGCACAGATTCCGTAGTCTCCTATGAACTGA
CTCAGCCACCCTCAGTGTCCGTGTCCCCAGGACAGACAGCCAGCATCACCTGTTCTGGATCTAAATTGGG
GGATAAATATGTTTCCTGGTATCAACTGAGGCCAGGCCAGTCCCCCATACTGGTCATGTATGAAAATGAC
AGGCGGCCCTCCGGGATCCCTGAGCGATTCTCCGGTTCCAATTCTGGCGACACTGCCACTCTGACCATCA
GCGGGACCCAGGCTTTGGATGAGGCTGACTTCTACTGTCAGGCGTGGGAGACCACCACCACCACTTTTGT
TTTCTTCGGCGGAGGGACCCAGCTGACCGTTCTAGGTCAGCCCAAGGCTGCCCCCTCGGTCACTCTGTTC
CCGCCCTCCTCTGAGGAGCTTCAAGCCAACAAGGCCACACTGGTGTGTCTCATAAGTGACTTCTACCCGG
GAGCCGTGACAGTGGCCTGGAAGGCAGATAGCAGCCCCGTCAAGGCGGACCAGGCCAGTCCCCCATACTG
CAAACAAAGCAACAACAAGTACGCGGCCAGCAGCTACCTGAGCCTGACGCCTGAGCAGTGGAAGTCCCAC
AAAAGCTACAGCTGCCAGGTCACGCATGAAGGGAGCACCGTGGAGAAGACAGTGGCCCCTACAGAATGTT
CATAG 1495_C14 (PGC14) lambda light chain variable region nucleotide sequence:
                                                              (SEQ ID NO: 119)
TCCTATGAACTGACTCAGCCACCCTCAGTGTCCGTGTCCCCAGGACAGACAGCCAGCATCACCTGTTCTG
GATCTAAATTGGGGGATAAATATGTTTCCTGGTATCAACTGAGGCCAGGCCAGTCCCCCATACTGGTCAT
GTATGAAAATGACAGGCGGCCCTCCGGGATCCCTGAGCGATTCTCCGGTTCCAATTCTGGCGACACTGCC
ACTCTGACCATCAGCGGGACCCAGGCTTTGGATGAGGCTGACTTCTACTGTCAGGCGTGGGAGACCACCA
CCACCACTTTTGTTTTCTTCGGCGGAGGGACCCAGCTGACCGTTCTA 1495_C14 (PGC14) lambda light chain amino acid sequence: expressed protein with
variable region in bold.
                                                              (SEQ ID NO: 26)
**SYELTQPPSYSVSPGQTASITCSGSKLGDKYVSWYQLRPGQSPILVMYENDRRPSGIPERFSGSNSGDT
ATLTISGTQALDEADFYCQAWETTTTTFVFFGGGTQLTVL**GQPKAAPSVTLFPPSSEELQANKATLVCLI
SDFYPGAVTVAWKADSSPVKAGVETTTPSKQSNNKYAASSYLSLTPEQWKSHKSYSCQVTHEGSTVEKTV
APTECS 1495_C14 (PGC14) lambda light chain variable region amino acid sequence: (Kabat
CDRs underlined, Chothia CDRs in bold italics)
                                                              (SEQ ID NO: 38)
SYELTQPPSVSVSPGQTASITC***SGSKLGDKYVS***WYQLRPGQSPILVMY***ENDRRPSG***IPERFSGSNSGDTATLTI
SGTQALDEADFYC*QAWETTTTTFVF*FGGGTQLTVL 1495_C14 (PGC14) lambda light chain Kabat CDRs:
CDR 1: SGSKLGDKYVS (SEQ ID NO: 120)

CDR 2: ENDRRPSG (SEQ ID NO: 121)

CDR 3: QAWETTTTTFVF (SEQ ID NO: 44)

1495_C14 (PGC14) lambda light chain Chothia CDRs:
CDR 1: SGSKLGDKYVS (SEQ ID NO: 120)

CDR 2: ENDRRPSG (SEQ ID NO: 121)

CDR 3: QAWETTTTTFVF (SEQ ID NO: 44)

1496_C09 (PG9) gamma heavy chain nucleotide sequence: 1496_C09 γ3 coding
sequence (variable region in bold)
                                                              (SEQ ID NO: 27)
ATGGAGTTTGGGCTGAGCTGGGTTTTCCTCGTTGCTTTCTTAAGAGGTGTCCAGTGT**CAGCGATTAGTGG
AGTCTGGGGGAGGCGTGGTCCAGCCTGGGTCGTCCCTGAGACTCTCCTGTGCAGCGTCCGGATTCGACTT
CAGTAGACAAGGCATGCACTGGGTCCGCCAGGCTCCAGGCCAGGGGCTGGAGTGGGTGGCATTTATTAAA
TATGATGGAAGTGAGAAATATATCATGCTGACTCCGTATGGGGCAGTCAGCATCTCCAGAGACAATTCCA
AGGATACGCTTTATCTCCAAATGAATAGCCTGAGAGTCGAGGACACGGCTACATATTTTTGTGTGAGAGA
GGCTGGTGGGCCCGACTACCGTAATGGGTACAACTATTACGATTTCTATGATGGTTATTATAACTACCAC
TATATGGACGTCTGGGGCAAAGGGACCACGGTCACCGTCTCGAGC**GCCTCCACCAAGGGCCCATCGGTCT
TCCCCCTGGCACCCTCCTCCAAGAGCACCTCTGGGGGCACAGCGGCCCTGGGCTGCCTGGTCAAGGACTA
CTTCCCCGAACCGGTGACGGTGTCGTGGAACTCAGGCGCCCTGACCAGCGGCGTGCACACCTTCCCGGCT
GTCCTACAGTCCTCAGGACTCTACTCCCTCAGCAGCGTGGTGACCGTGCCCTCCAGCAGCTTGGGCACCC
```

-continued

```
AGACCTACATCTGCAACGTGAATCACAAGCCCAGCAACACCAAGGTGGACAAGAGAGTTGAGCCCAAATC
TTGTGACAAAACTCACACATGCCCACCGTGCCCAGCACCTGAACTCCTGGGGGGACCGTCAGTCTTCCTC
TTCCCCCCAAAACCCAAGGACACCCTCATGATCTCCCGGACCCCTGAGGTCACATGCGTGGTGGTGGACG
TGAGCCACGAAGACCCTGAGGTCAAGTTCAACTGGTACGTGGACGGCGTGGAGGTGCATAATGCCAAGAC
AAAGCCGCGGGAGGAGCAGTACAACAGCACGTACCGTGTGGTCAGCGTCCTCACCGTCCTGCACCAGGAC
TGGCTGAATGGCAAGGAGTACAAGTGCAAGGTCTCCAACAAAGCCCTCCCAGCCCCCATCGAGAAAACCA
TCTCCAAAGCCAAAGGGCAGCCCCGAGAACCACAGGTGTACACCCTGCCCCCATCCCGGGAGGAGATGAC
CAAGAACCAGGTCAGCCTGACCTGCCTGGTCAAAGGCTTCTATCCCAGCGACATCGCCGTGAGTGGGAG
AGCAATGGGCAGCCGGAGAACAACTACAAGACCACGCCTCCCGTGCTGGACTCCGACGGCTCCTTCTTCC
TCTATAGCAAGCTCACCGTGGACAAGAGCAGGTGGCAGCAGGGGAACGTCTTCTCATGCTCCGTGATGCA
TGAGGCTCTGCACAACCACTACACGCAGAAGAGCCTCTCCCTGTCTCCGGGTAAATGA
```

1496_C09 (PG9) gamma heavy chain variable region nucleotide sequence:
(SEQ ID NO: 122)

```
CAGCGATTAGTGGAGTCTGGGGGAGGCGTGGTCCAGCCTGGGTCGTCCCTGAGACTCTCCTGTGCAGCGTCCGGATT
CGACTTCAGTAGACAAGGCATGCACTGGGTCCGCCAGGCTCCAGGCCAGGGGCTGGAGTGGGTGGCATTTATTAAAT
ATGATGGAAGTGAGAAATATCATGCTGACTCCGTATGGGGCCGACTCAGCATCTCCAGAGACAATTCCAAGGATACG
CTTTATCTCCAAATGAATAGCCTGAGAGTCGAGGACACGGCTACATATTTTTGTGTGAGAGAGGCTGGTGGGCCCGA
CTACCGTAATGGGTACAACTATTACGATTTCTATGATGGTTATTATAACTACCACTATATGGACGTCTGGGGCAAAG
GGACCACGGTCACCGTCTCGAGC
```

1496_C09 (PG9) gamma heavy chain amino acid sequence: expressed protein with variable region in bold.
(SEQ ID NO: 28)

**QRLVESGGGVVQPGSSLRLSCAASGFDFSRQGMHWVRQAPGQGLEWVAFIKYDGSEKYHADSVWG
RLSISRDNSKDTLYLQMNSLRVEDTATYFCVREAGGPDYRNGYNYYDFYDGYYNYHYMDVWGKGT
TVTVSS**ASTKGPSVFPLAPSSKSTSGGTAALGCLVKDYFPEPVTVSWNSGALTSGVHTFPAVLQSSGLYSLS
SVVTVPSSSLGTQTYICNVNHKPSNTKVDKRVEPKSCDKTHTCPPCPAPELLGGPSVFLFPPKPKDTLMISRT
PEVTCVVVDVSHEDPEVKFNWYVDGVEVHNAKTKPREEQYNSTYRVVSVLTVLHQDWLNGKEYKCKVS
NKALPAPIEKTISKAKGQPREPQVYTLPPSREEMTKNQVSLTCLVKGFYPSDIAVEWESNGQPENNYKTTPP
VLDSDGSFFLYSKLTVDKSRWQQGNVFSCSVMHEALHNHYTQKSLSLSPGK

1496_C09 (PG9) gamma heavy chain variable region amino acid sequence: (Kabat CDRs underlined, Chothia CDRs in bold italics)
(SEQ ID NO: 39)

QRLVESGGGVVQPGSSLRLSCAA*SGFDFSRQGMH*WVRQAPGQGLEWVA*FIKYDGSEKYHADSVW*GRLSI
SRDNSKDTLYLQMNSLRVEDTATYFCVR*EAGGPDYRNGYNYYDFYDGYYNYHYMDV*WGKGTTVTVSS

1496_C09 (PG9) gamma heavy chain Kabat CDRs:
CDR 1: SGFDFSRQGMH (SEQ ID NO: 123)

CDR 2: FIKYDGSEKYHADSVW (SEQ ID NO: 124)

CDR 3: EAGGPDYRNGYNYYDFYDGYYNYHYMDV (SEQ ID NO: 7)

1496_C09 (PG9) gamma heavy chain Chothia CDRs:
CDR 1: SGFDFSRQGMH (SEQ ID NO: 123)

CDR 2: FIKYDGSEKYHADSVW (SEQ ID NO: 124)

CDR 3: EAGGPDYRNGYNYYDFYDGYYNYHYMDV (SEQ ID NO: 7)

1496_C09 (PG9) lambda light chain nucleotide sequence: 1496_C09 λ2 coding sequence (variable region in bold)
(SEQ ID NO: 29)

ATGGCCTGGGCTCTGCTTTTCCTCACCCTCCTCACTCAGGGCACAGGGTCCTGGGCC**CAGTCTGCCCTGA
CTCAGCCTGCCTCCGTGTCTGGGTCTCCTGGACAGTCGATCACCATCTCCTGCAATGGAACCAGCAATGA
TGTTGGTGGCTATGAATCTGTCTCCTGGTACCAACAACATCCCGGCAAAGCCCCCAAAGTCGTGATTTAT
GATGTCAGTAAACGGCCCTCAGGGGTTTCTAATCGCTTCTCTGGCTCCAAGTCCGGCAACACGGCCTCCC
TGACCATCTCTGGGCTCCAGGCTGAGGACGAGGGTGACTATTACTGCAAGTCTCTGACAAGCACGAGACG
TCGGGTTTTCGGCACTGGGACCAAGCTGACCGTTCTA**GGTCAGCCCAAGGCTGCCCCCTCGGTCACTCTG
TTCCCGCCCTCCTCTGAGGAGCTTCAAGCCAACAAGGCCACACTGGTGTGTCTCATAAGTGACTTCTACC
CGGGAGCCGTGACAGTGGCCTGGAAGGCAGATAGCAGCCCCGTCAAGGCGGGAGTGGAGACCACCACACC
CTCCAAACAAAGCAACAACAAGTACGCGGCCAGCAGCTACCTGAGCCTGACGCCTGAGCAGTGGAAGTCC
CACAAAAGCTACAGCTGCCAGGTCACGCATGAAGGGAGCACCGTGGAGAAGACAGTGGCCCCTACAGAAT
GTTCATAG

1496_C09 (PG9) lambda light chain variable region nucleotide sequence:
(SEQ ID NO: 125)

CAGTCTGCCCTGACTCAGCCTGCCTCCGTGTCTGGGTCTCCTGGACAGTCGATCACCATCTCCTGCAATG
GAACCAGCAATGATGTTGGTGGCTATGAATCTGTCTCCTGGTACCAACAACATCCCGGCAAAGCCCCCAA
AGTCGTGATTTATGATGTCAGTAAACGGCCCTCAGGGGTTTCTAATCGCTTCTCTGGCTCCAAGTCCGGC
AACACGGCCTCCCTGACCATCTCTGGGCTCCAGGCTGAGGACGAGGGTGACTATTACTGCAAGTCTCTGA
CAAGCACGAGACGTCGGGTTTTCGGCACTGGGACCAAGCTGACCGTTCTA

```
1496_C09 (PG9) lambda light chain amino acid sequence: expressed protein with
variable region in bold.
                                                                    (SEQ ID NO: 30)
QSALTQPASVSGSPGQSITISCNGTSNDVGGYESVSWYQQHPGKAPKVVIYDVSKRPSGVSNRFSGSKS
GNTASLTISGLQAEDEGDYYCKSLTSTRRRVFGTGTKLTVLGQPKAAPSVTLFPPSSEELQANKATLVC
LISDFYPGAVTVAWKADSSPVKAGVETTTPSKQSNNKYAASSYLSLTPEQWKSHKSYSCQVTHEGSTVEKT
VAPTECS 1496_C09 (PG9) lambda light chain variable region amino acid sequence: (Kabat CDRs
underlined, Chothia CDRs in bold italics)
                                                                    (SEQ ID NO: 40)
QSALTQPASVSGSPGQSITISCNGTSNDVGGYESVSWYQQHPGKAPKVVIYDVSKRPSGVSNRFSGSKSGNT
ASLTISGLQAEDEGDYYCKSLTSTRRRVFGTGTKLTVL 1496_C09 (PG9) lambda light chain Kabat CDRs:
CDR 1: NGTSNDVGGYESVS (SEQ ID NO: 126)

CDR 2: DVSKRPSG (SEQ ID NO: 127)

CDR 3: KSLTSTRRRV (SEQ ID NO: 45)

1496_C09 (PG9) lambda light chain Chothia CDRs:
CDR 1: NGTSNDVGGYESVS (SEQ ID NO: 126)

CDR 2: DVSKRPSG (SEQ ID NO: 127)

CDR 3: KSLTSTRRRV (SEQ ID NO: 45)
```

The PG16 antibody includes a heavy chain variable region (SEQ ID NO: 31), encoded by the nucleic acid sequence shown in SEQ ID NO: 99, and a light chain variable region (SEQ ID NO: 32) encoded by the nucleic acid sequence shown in SEQ ID NO: 100.

The heavy chain CDRs of the PG16 antibody have the following sequences per Kabat and Chothia definitions: SGFTFHKYGMH (SEQ ID NO: 88), LISDDGMRKYHSDSMW (SEQ ID NO: 89), and EAGGPIWHDDVKYYDFNDGYYNYHYMDV (SEQ ID NO: 6). The light chain CDRs of the PG16 antibody have the following sequences per Kabat and Chothia definitions: NGTSSDVGGFDSVS (SEQ ID NO: 97), DVSHRPSG (SEQ ID NO: 95), and SSLTDRSHRI (SEQ ID NO: 41).

The PG20 antibody includes a heavy chain variable region (SEQ ID NO: 33), encoded by the nucleic acid sequence shown in SEQ ID NO: 101, and a light chain variable region (SEQ ID NO: 34) encoded by the nucleic acid sequence shown in SEQ ID NO: 106.

The heavy chain CDRs of the PG20 antibody have the following sequences per Kabat definition: SGGTFSSYAFT (SEQ ID NO: 104), MVTPIFGEAKYSQRFE (SEQ ID NO: 105), and RAVPIATDNWLDP (SEQ ID NO: 102). The light chain CDRs of the PG20 antibody have the following sequences per Kabat definition: RASQTINNYLN (SEQ ID NO: 107), GASNLQNG (SEQ ID NO: 108), and QQSFSTPRT (SEQ ID NO: 42).

The heavy chain CDRs of the PG20 antibody have the following sequences per Chothia definition: SGGTFSSYAFT (SEQ ID NO: 104), MVTPIFGEAKYSQRFE (SEQ ID NO: 105), and RRAVPIATDNWLDP (SEQ ID NO: 103). The light chain CDRs of the PG20 antibody have the following sequences per Chothia definition: RASQTINNYLN (SEQ ID NO: 107), GASNLQNG (SEQ ID NO: 108), and QQSFSTPRT (SEQ ID NO: 42).

The PGG14 antibody includes a heavy chain variable region (SEQ ID NO: 35), encoded by the nucleic acid sequence shown in SEQ ID NO: 109, and a light chain variable region (SEQ ID NO: 36) encoded by the nucleic acid sequence shown in SEQ ID NO: 112.

The heavy chain CDRs of the PGG14 antibody have the following sequences per Kabat definition: SGGAFSSYAFS (SEQ ID NO: 110), MITPVFGETKYAPRFQ (SEQ ID NO: 111), and RVVPMATDNWLDP (SEQ ID NO: 102). The light chain CDRs of the PGG14 antibody have the following sequences per Kabat definition: RASQTIHTYL (SEQ ID NO: 113), GASTLQSG (SEQ ID NO: 114), and QQSYSTPRT (SEQ ID NO: 43).

The heavy chain CDRs of the PGG14 antibody have the following sequences per Chothia definition: SGGAFSSYAFS (SEQ ID NO: 110), MITPVFGETKYAPRFQ (SEQ ID NO: 111), RRVVPMATDNWLDP (SEQ ID NO: 103). The light chain CDRs of the PGG14 antibody have the following sequences per Chothia definition: RASQTIHTYL (SEQ ID NO: 113), GASTLQSG (SEQ ID NO: 114), and QQSYSTPRT (SEQ ID NO: 43).

The PGC14 antibody includes a heavy chain variable region (SEQ ID NO: 37), encoded by the nucleic acid sequence shown in SEQ ID NO: 115, and a light chain variable region (SEQ ID NO: 38) encoded by the nucleic acid sequence shown in SEQ ID NO: 119.

The heavy chain CDRs of the PGC14 antibody have the following sequences per Kabat and Chothia definitions: SGYSFIDYYLH (SEQ ID NO: 116), LIDPENGEARYAEKFQ (SEQ ID NO: 117), and AVGADSGSWFDP (SEQ ID NO: 118). The light chain CDRs of the PGC14 antibody have the following sequences per Kabat and Chothia definitions: SGSKLGDKYVS (SEQ ID NO: 120), ENDRRPSG (SEQ ID NO: 121), and QAWETTTTTFVF (SEQ ID NO: 44).

The PG9 antibody includes a heavy chain variable region (SEQ ID NO: 39), encoded by the nucleic acid sequence shown in SEQ ID NO: 122, and a light chain variable region (SEQ ID NO: 40) encoded by the nucleic acid sequence shown in SEQ ID NO: 125.

The heavy chain CDRs of the PG9 antibody have the following sequences per Kabat and Chothia definitions: SGFDFSRQGMH (SEQ ID NO: 123), FIKYDGSEKY- HADSVW (SEQ ID NO: 124), and EAGGPDYRNGY-NYYDFYDGYYNYHYMDV (SEQ ID NO: 7). The light chain CDRs of the PG9 antibody have the following sequences per Kabat and Chothia definitions: NGTSNDVG-GYESVS (SEQ ID NO: 126), DVSKRPSG (SEQ ID NO: 127), and KSLTSTRRRV (SEQ ID NO: 45).

The sequences of sister clones to human monoclonal antibody 1443_C16 (PG16) were determined, including the sequences of the variable regions of the Gamma heavy and Kappa or Lambda light chains. In addition, the sequence of each of the polynucleotides encoding the antibody sequences was determined. Shown below are the polypeptide and polynucleotide sequences of the gamma heavy chains and kappa light chains, with the signal peptides at the N-terminus (or 5' end) and the constant regions at the C-terminus (or 3' end) of the variable regions, which are shown in bolded text.

```
1469_M23 gamma heavy chain nucleotide sequence:
1469_M23 γ3 coding sequence (variable region in bold)
                                                    (SEQ ID NO: 138)
ATGGAGTTTGGGCTGAGCTGGGTTTTCCTCGCAACTCTGTTAAGAGTTGTGAAGTGTCAGGAAAAACTGG

TGGAGTCTGGGGGAGGCGTGGTCCAGCCGGGGGGGTCCCTGAGACTCTCCTGTTTAGCGTCTGGATTCAC

CTTTCACAAATATGGCATGCACTGGGTCCGCCAGGCTCCAGGCAAGGGCCTGGAGTGGGTGGCACTCATC

TCAGATGACGGAATGAGGAAATATCATTCAGACTCCATGTGGGGCCGAGTCACCATCTCCAGAGACAATT

CCAAGAACACTCTATATCTGCAATTCaGCAGCCTGAAAGTCGAAGACACGGCTATGTTCTTCTGTGCGAG

AGAGGCTGGTGGGCCAATCTGGCATGACGACGTCAAATATTACGATTTTAATGACGGCTACTACAACTAC

CACTACATGGACGTCTGGGGCAAGGGGACCACGGTCACCGTCTCCTCAGCGTCGACCAAGGGCCCATCGG

TCTTCCCTCTGGCACCATCATCCAAGTCGACCTCTGGGGGCACAGCGGCCCTGGGCTGCCTGGTCAAGGA

CTACTTCCCCGAACCGGTGACGGTGTCGTGGAACTCAGGCGCCCTGACCAGCGGCGTGCACACCTTCCCG

GCTGTCCTACAGTCCTCAGGACTCTACTCCCTCAGCAGCGTGGTGACCGTGCCCTCCAGCAGCTTGGGCA

CCCAGACCTACATCTGCAACGTGAATCACAAGCCCAGCAACACCAAGGTGGACAAGAGAGTTGAGCCCAA

ATCTTGTGACAAAACTCACACATGCCCACCGTGCCCAGCACCTGAACTCCTGGGGGGACCGTCAGTCTTC

CTCTTCCCCCCAAAACCCAAGGACACCCTCATGATCTCCCGGACCCCTGAGGTCACATGCGTGGTGGTGG

ACGTGAGCCACGAAGACCCTGAGGTCAAGTTCAACTGGTACGTGGACGGCGTGGAGGTGCATAATGCCAA

GACAAAGCCGCGGGAGGAGCAGTACAACAGCACGTACCGTGTGGTCAGCGTCCTCACCGTCCTGCACCAG

GACTGGCTGAATGGCAAGGAGTACAAGTGCAAGGTCTCCAACAAAGCCCTCCCAGCCCCCATCGAGAAAA

CCATCTCCAAAGCCAAAGGGCAGCCCCGAGAACCACAGGTGTACACCCTGCCCCCATCCCGGGAGGAGAT

GACCAAGAACCAGGTCAGCCTGACCTGCCTGGTCAAAGGCTTCTATCCCAGCGACATCGCCGTGGAGTGG

GAGAGCAATGGGCAGCCGGAGAACAACTACAAGACCACGCCTCCCGTGCTGGACTCCGACGGCTCCTTCT

TCCTCTATAGCAAGCTCACCGTGGACAAGAGCAGGTGGCAGCAGGGGAACGTCTTCTCATGCTCCGTGAT

GCATGAGGCTCTGCACAACCACTACACGCAGAAGAGCCTCTCCCTGTCTCCGGGTAAATGA

1469_M23 gamma heavy chain variable region nucleotide sequence:
                                                    (SEQ ID NO: 128)
CAGGAAAAACTGGTGGAGTCTGGGGGAGGCGTGGTCCAGCCGGGGGGGTCCCTGAGACTCTCCTGTTTAG

CGTCTGGATTCACCTTTCACAAATATGGCATGCACTGGGTCCGCCAGGCTCCAGGCAAGGGCCTGGAGTG

GGTGGCACTCATCTCAGATGACGGAATGAGGAAATATCATTCAGACTCCATGTGGGGCCGAGTCACCATC

TCCAGAGACAATTCCAAGAACACTCTATATCTGCAATTCaGCAGCCTGAAAGTCGAAGACACGGCTATGT

TCTTCTGTGCGAGAGAGGCTGGTGGGCCAATCTGGCATGACGACGTCAAATATTACGATTTTAATGACGG

CTACTACAACTACCACTACATGGACGTCTGGGGCAAGGGGACCACGGTCACCGtCTCCTCA

1469_M23 gamma heavy chain amino acid sequence:
expressed protein with variable region in bold.
                                                    (SEQ ID NO: 139)
QEKLVESGGGVVQPGGSLRLSCLASGFTFHKYGMHWVRQAPGKGLEWVALISDDGMRKY

HSDSMWGRVTISRDNSKNTLYLQFSSLKVEDTAMFFCAREAGGPIWHDDVKYYDFNDGYY

NYHYMDVYVGKGTTVTVSSASTKGPSVFPLAPSSKSTSGGTAALGCLVKDYFPEPVTVSWNSGA

LTSGVHTFPAVLQSSGLYSLSSVVTVPSSSLGTQTYICNVNHKPSNTKVDKRVEPKSCDKTHTCPP
```

```
CPAPELLGGPSVFLFPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKGQPREPQVYTLPPSRE

EMTKNQVSLTCLVKGFYPSDIAVEWESNGQPENNYKTTPPVLDSDGSFFLYSKLTVDKSRWQQG

NVFSCSVMHEALHNHYTQKSLSLSPGK
```

1469_M23 gamma heavy chain variable region amino acid sequence:
(Kabat CDRs underlined, Chothia CDRs in bold italics)

(SEQ ID NO: 140)
```
QEKLVESGGGVVQPGGSLRLSCLASGFTFHKYGMHWVRQAPGKGLEWVALISDDGMRKYHSD

SMWGRVTISRDNSKNTLYLQFSSLKVEDTAMFFCAREAGGPIWHDDVKYYDFNDGYYNYHYMD

VWGKGTTVTVSS
```

1469_M23 gamma heavy chain Kabat CDRs:
CDR 1:

(SEQ ID NO: 88)
```
SGFTFHKYGMH
```

CDR 2:

(SEQ ID NO: 89)
```
LISDDGMRKYHSDSMW
```

CDR 3:

(SEQ ID NO: 6)
```
EAGGPIWHDDVKYYDFNDGYYNYHYMDV
```

1469_M23 gamma heavy chain Chothia CDRs:
CDR 1:

(SEQ ID NO: 88)
```
SGFTFHKYGMH
```

CDR 2:

(SEQ ID NO: 89)
```
LISDDGMRKYHSDSMW
```

CDR 3:

(SEQ ID NO: 6)
```
EAGGPIWHDDVKYYDFNDGYYNYHYMDV
```

1469_M23 lambda light chain nucleotide sequence:
1469_M23 λ2 coding sequence (variable region in bold)

(SEQ ID NO: 141)
```
ATGGCCTGGGCTCTGCTATTCCTCACCCTCTTCACTCAGGGCACAGGGTCCTGGGGCCAGTCTGCCCTGA

CTCAGCCTGCCTCCGTGTCTGGGTCTCCTGGACAGACGATCACCATCTCCTGCAATGGAACCAGAAGTGA

CGTTGGTGGATTTGACTCTGTCTCCTGGTACCAACAATCCCCAGGGAGAGCCCCCAAAGTCATGGTTTTT

GATGTCAGTCATCGGCCCTCAGGTATCTCTAATCGCTTCTCTGGCTCCAAGTCCGGCAACACGGCCTCCC

TGACCATCTCTGGGCTCCACATTGAGGACGAGGGCGATTATTTCTGCTCTTCACTGACAGACAGAAGCCA

TCGCATATTCGGCGGCGGGACCAAGCTGACCGTTCTAGGTCAGCCCAAGGCTGCCCCCTCGGTCACTCTG

TTCCCGCCCTCCTCTGAGGAGCTTCAAGCCAACAAGGCCACACTGGTGTGTCTCATAAGTGACTTCTACC

CGGGAGCCGTGACAGTGGCCTGGAAGGCAGATAGCAGCCCCGTCAAGGCGGGAGTGGAGACCACCACACC

CTCCAAACAAAGCAACAACAAGTACGCGGCCAGCAGCTACCTGAGCCTGACGCCTGAGCAGTGGAAGTCC

CACAAAAGCTACAGCTGCCAGGTCACGCATGAAGGGAGCACCGTGGAGAAGACAGTGGCCCCTACAGAAT

GTTCATAG
```

1469_M23 lambda light chain variable region nucleotide sequence:

(SEQ ID NO: 129)
```
CAGTCTGCCCTGACTCAGCCTGCCTCCGTGTCTGGGTCTCCTGGACAGACGATCACCATCTCCTGCAATG

GAACCAGAAGTGACGTTGGTGGATTTGACTCTGTCTCCTGGTACCAACAATCCCCAGGGAGAGCCCCCAA

AGTCATGGTTTTTGATGTCAGTCATCGGCCCTCAGGTATCTCTAATCGCTTCTCTGGCTCCAAGTCCGGC

AACACGGCCTCCCTGACCATCTCTGGGCTCCACATTGAGGACGAGGGCGATTATTTCTGCTCTTCACTGA

CAGACAGAAGCCATCGCATATTCGGCGGCGGGACCAAGCTGACCGTTCTA
```

-continued

1469_M23 lambda light chain amino acid sequence:
expressed protein with variable region in bold.
(SEQ ID NO: 142)

QSALTQPASVSGSPCQTITISCNCTRSDYGGFDSVSWYQQSPGRAPKVMVFDVSHRPSGISN

RFSGSKSGNTASLTISGLHIEDEGDYFCSSLTDRSHRIFGGGTKLTVLGQPKAAPSVTLFPPSS

EELQANKATLVCLISDFYPGAVTVAWKADSSPVKAGVETTTPSKQSNNKYAASSYLSLTPEQWK

SHKSYSCQVTHEGSTVEKTVAPTECS

1469_M23 lambda light chain variable region amino acid sequence:
(Kabat CDRs underlined, Chothia CDRs in bold italics)
(SEQ ID NO: 96)
QSALTQPASVSGSPGQTITISC*__NGTRSDVGGFDSVS__*WYQQSPGRAPKVMVF*__DVSHRPSG__*ISNRFS

GSKSGNTASLTISGLHIEDEGDYFC*__SSLTDRSHRI__*FGGGTKLTVL

1469_M23 lambda light chain Kabat CDRs:
CDR 1:
(SEQ ID NO: 92)
NGTRSDVGGFDSVS

CDR 2:
(SEQ ID NO: 95)
DVSHRPSG

CDR 3:
(SEQ ID NO: 41)
SSLTDRSHRI

1469_M23 lambda light chain Chothia CDRs:
CDR 1:
(SEQ ID NO: 92)
NGTRSDVGGFDSVS

CDR 2:
(SEQ ID NO: 95)
DVSHRPSG

CDR 3:
(SEQ ID NO: 41)
SSLTDRSHRI

1456_A12 gamma heavy chain nucleotide sequence:
1456 A12 γ3 coding sequence (variable region in bold)
(SEQ ID NO: 46)
ATGGAGTTTGGGCTGAGCTGGGTTTTCCTCGCAACTCTGTTAAGAGTTGTGAAGTGTCACGAACAACTGG

TGGAGGCCGGGGGAGGCGTGGTCCAGCCGGGGGGGTCCCTGAGACTCTCCTGTTTAGCGTCTGGATTCAC

GTTTCACAAATATGGCATGCACTGGGTCCGCCAGGCTCCAGGCAAGGGCCTGGAGTGGGTGGCACTCATC

TCAGATGACGGAATGAGGAAATATCATTCAGACTCCATGTGGGGCCGAGTCACCATCTCCAGAGACAATT

CCAAGAACACTCTTTATCTGCAATTCAGCAGCCTGAGAGTCGAAGACACGGCTATGTTCTTCTGTGCGAG

AGAGGCCGGTGGGCCAATCTGGCATGACGACGTCAAATATTACGATTTTAATGACGGCTACTACAACTAT

CACTACATGGACGTCTGGGGCAAGGGGACCAAGGTCACCGTCTCCTCAGCGTCGACCAAGGGCCCATCGG

TCTTCCCTCTGGCACCATCATCCAAGTCGACCTCTGGGGGCACAGCGGCCCTGGGCTGCCTGGTCAAGGA

CTACTTCCCCGAACCGGTGACGGTGTCGTGGAACTCAGGCGCCCTGACCAGCGGCGTGCACACCTTCCCG

GCTGTCCTACAGTCCTCAGGACTCTACTCCCTCAGCAGCGTGGTGACCGTGCCCTCCAGCAGCTTGGGCA

CCCAGACCTACATCTGCAACGTGAATCACAAGCCCAGCAACACCAAGGTGGACAAGAGAGTTGAGCCCAA

ATCTTGTGACAAAACTCACACATGCCCACCGTGCCCAGCACCTGAACTCCTGGGGGGACCGTCAGTCTTC

CTCTTCCCCCCAAAACCCAAGGACACCCTCATGATCTCCCGGACCCCTGAGGTCACATGCGTGGTGGTGG

ACGTGAGCCACGAAGACCCTGAGGTCAAGTTCAACTGGTACGTGGACGGCGTGGAGGTGCATAATGCCAA

GACAAAGCCGCGGGAGGAGCAGTACAACAGCACGTACCGTGTGGTCAGCGTCCTCACCGTCCTGCACCAG

GACTGGCTGAATGGCAAGGAGTACAAGTGCAAGGTCTCCAACAAAGCCCTCCCAGCCCCCATCGAGAAAA

CCATCTCCAAAGCCAAAGGGCAGCCCCGAGAACCACAGGTGTACACCCTGCCCCCATCCCGGGAGGAGAT

-continued

```
GACCAAGAACCAGGTCAGCCTGACCTGCCTGGTCAAAGGCTTCTATCCCAGCGACATCGCCGTGGAGTGG

GAGAGCAATGGGCAGCCGGAGAACAACTACAAGACCACGCCTCCCGTGCTGGACTCCGACGGCTCCTTCT

TCCTCTATAGCAAGCTCACCGTGGACAAGAGCAGGTGGCAGCAGGGGAACGTCTTCTCATGCTCCGTGAT

GCATGAGGCTCTGCACAACCACTACACGCAGAAGAGCCTCTCCCTGTCTCCGGGTAAATGA
```

1456_A12 gamma heavy chain variable region nucleotide sequence:
(SEQ ID NO: 130)

```
CACGAACAACTGGTGGAGGCCGGGGGAGGCGTGGTCCAGCCGGGGGGGTCCCTGAGACTCTCCTGTTTAG

CGTCTGGATTCACGTTTCACAAATATGGCATGCACTGGGTCCGCCAGGCTCCAGGCAAGGGCCTGGAGTG

GGTGGCACTCATCTCAGATGACGGAATGAGGAAATATCATTCAGACTCCATGTGGGGCCGAGTCACCATC

TCCAGAGACAATTCCAAGAACACTCTTTATCTGCAATTCAGCAGCCTGAGAGTCGAAGACACGGCTATGT

TCTTCTGTGCGAGAGAGGCCGGTGGGCCAATCTGGCATGACGACGTCAAATATTACGATTTTAATGACGG

CTACTACAACTATCACTACATGGACGTCTGGGGCAAGGGGACCAAGGTCACCGTCTCCTCA
```

1456_A12 gamma heavy chain amino acid sequence:
expressed protein with variable region in bold.
(SEQ ID NO: 47)

HEQLVEAGGGVVQPGGSLRLSCLASGFTFHKYGMHWVRQAPGKGLEWVALISDDGMRK

YHSDSMWGRVTISRDNSKNTLYLQFSSLRVEDTAMFFCAREAGGPIVVHDDVKYYDFNDGY

YNYHYMDVYVGKGTKVTVSSASTKGPSVFPLAPSSKSTSGGTAALGCLVKDYFPEPVTVSWNS

GALTSGVHTFPAVLQSSGLYSLSSVVTVPSSSLGTQTYICNVNHKPSNTKVDKRVEPKSCDKTHT

CPPCPAPELLGGPSVFLFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKT1SKAKGQPREPQVYTLPP

SREEMTKNQVSLTCLVKGFYPSDIAVEWESNGQPENNYKTTPPVLDSDGSFFLYSKLTVDKSRW

QQGNVFSCSVMHEALHNHYTQKSLSLSPGK

1456_A12 gamma heavy chain variable region amino acid sequence:
(Kabat CDRs underlined, Chothia CDRs in bold italics)
(SEQ ID NO: 48)

HEQLVEAGGGVVQPGGSLRLSCLA*SGFTFHKYGMH*WVRQAPGKGLEWVA*LISDDGMRKYHSD*

*SMW*GRVTISRDNSKNTLYLQFSSLRVEDTAMFFCAR*EAGGPIWHDDVKYYDFNDGYYNYHYMD*

*V*WGKGTKVTVSS

1456_A12 gamma heavy chain Kabat CDRs:
CDR 1:
(SEQ ID NO: 88)
SGFTFHKYGMH

CDR 2:
(SEQ ID NO: 89)
LISDDGIVIRKYHSDSMW

CDR 3:
(SEQ ID NO: 6)
EAGGPIWHDDVKYYDFNDGYYNYHYMDV

1456_A12 gamma heavy chain Chothia CDRs:
CDR 1:
(SEQ ID NO: 88)
SGFTFHKYGMH

CDR 2:
(SEQ ID NO: 89)
LISDDGIVIRKYHSDSMW

CDR 3:
(SEQ ID NO: 6)
EAGGPIWHDDVKYYDFNDGYYNYHYMDV

-continued

1456_A12 lambda light chain nucleotide sequence:
1456 A12 λ2 coding sequence (variable region in bold)
(SEQ ID NO: 49)
ATGGCCTGGGCTTGCTATTCCTCACCCTCTTCACTCAGGGCACAGGGTCCTGGGGCCAGTCTGCCCTGAC

TCAGCCTGCCTCCGTGTCTGGGTCTCCTGGACAGACGATCACCATCTCCTGCAATGGAACCAGCCGTGAC

GTTGGTGGATTTGACTCTGTCTCCTGGTATCAACAATCCCCAGGGAAAGCCCCCAAAGTCATGGTTTTTG

ATGTCAGTCATCGGCCCTCAGGTATGTCTAATCGCTTCTCTGGCTCCAAGTCCGGCAACACGGCCTCCCT

GACCATTTCTGGGCTCCACATTGAGGACGAGGGCGATTATTTCTGCTCTTCATTGACAGACAGAAGCCAT

CGCATATTCGGCGGCGGGACCAAGCTGACCGTTCTAGGTCAGCCCAAGGCTGCCCCCTCGGTCACTCTGT

TCCCGCCCTCCTCTGAGGAGCTTCAAGCCAACAAGGCCACACTGGTGTGTCTCATAAGTGACTTCTACCC

GGGAGCCGTGACAGTGGCCTGGAAGGCAGATAGCAGCCCCGTCAAGGCGGGAGTGGAGACCACCACACCC

TCCAAACAAAGCAACAACAAGTACGCGGCCAGCAGCTACCTGAGCCTGACGCCTGAGCAGTGGAAGTCCC

ACAAAAGCTACAGCTGCCAGGTCACGCATGAAGGGAGCACCGTGGAGAAGACAGTGGCCCCTACAGAATG

TTCATAG

1456_A12 lambda light chain variable region nucleotide sequence:
(SEQ ID NO: 131)
CAGTCTGCCCTGACTCAGCCTGCCTCCGTGTCTGGGTCTCCTGGACAGACGATCACCATCTCCTGCAATG

GAACCAGCCGTGACGTTGGTGGATTTGACTCTGTCTCCTGGTATCAACAATCCCCAGGGAAAGCCCCCAA

AGTCATGGTTTTTGATGTCAGTCATCGGCCCTCAGGTATGTCTAATCGCTTCTCTGGCTCCAAGTCCGGC

AACACGGCCTCCCTGACCATTTCTGGGCTCCACATTGAGGACGAGGGCGATTATTTCTGCTCTTCATTGA

CAGACAGAAGCCATCGCATATTCGGCGGCGGGACCAAGCTGACCGTTCTA

1456_A12 lambda light chain amino acid sequence:
expressed protein with variable region in bold.
(SEQ ID NO: 50)
QSALTQPASVSGSPGQTITISCNGTSRDVGGFDSVSWYQQSPGKAPKVMVFDVSHRPSGMS

NRFSGSKSGNTASLTISGLHIEDEGDYFCSSLTDRSHRIFGGGTKLTVLGQPKAAPSVTLFPPS

SEELQANKATLVCLISDFYPGAVTVAWKADSSPVKAGVETTTPSKQSNNKYAASSYLSLTPEQW

KSHKSYSCQVTHEGSTVEKTVAPTECS

1456_A12 lambda light chain variable region amino acid sequence:
(Kabat CDRs underlined, Chothia CDRs in bold italics)
(SEQ ID NO: 51)
QSALTQPASVSGSPGQTITISC*NGTSRDVGGFDSVS*WYQQSPGKAPKVMVF*DVSHRPSG*MSNRFS

GSKSGNTASLTISGLHIEDEGDYFC*SSLTDRSHRI*FGGGTKLTVL

1456_A12 lambda light chain Kabat CDRs:
CDR 1:
(SEQ ID NO: 93)
NGTSRDVGGFDSVS

CDR 2:
(SEQ ID NO: 95)
DVSHRPSG

CDR 3:
(SEQ ID NO: 41)
SSLTDRSHRI

1456_A12 lambda light chain Chothia CDRs:
CDR 1:
(SEQ ID NO: 93)
NGTSRDVGGFDSVS
CDR 2:
(SEQ ID NO: 95)
DVSHRPSG
CDR 3:
(SEQ ID NO 41)
SSLTDRSHRI 1503_H05 gamma heavy chain nucleotide sequence:
1503_H05 γ3 coding sequence (variable region in bold)

(SEQ ID NO: 52)

ATGGAGTTTGGCTGAGCTGGGTTTTCCTCGCAACTCTGTTAAGAGTTGTGAAGTGTCAGGAAAAACTGGT

GGAGTCTGGGGGAGGCGTGGTCCAGCCGGGGGGGTCCCTGAGACTCTCCTGTTTAGCGTCTGGATTCACC

TTTCACAAATATGGCATGCACTGGGTCCGCCAGGCTCCAGGCAAGGGCCTGGAGTGGGTGGCACTCATCT

CAGATGACGGAATGAGGAAATATCATTCAGACTCCATGTGGGGCCGAGTCACCATCTCCAGAGACAATTC

CAAGAACACTTTATATCTGCAATTCAGCAGCCTGAAAGTCGAAGACACGGCTATGTTCTTCTGTGCGAGA

GAGGCTGGTGGGCCAATCTGGCATGACGACGTCAAATATTACGATTTTAATGACGGCTACTACAATTACC

ACTACATGGACGTCTGGGGCAAGGGGACCATTGTCACCGTCTCCTCAGCGTCGACCAAGGGCCCATCGGT

CTTCCCTCTGGCACCATCATCCAAGTCGACCTCTGGGGGCACAGCGGCCCTGGGCTGCCTGGTCAAGGAC

TACTTCCCCGAACCGGTGACGGTGTCGTGGAACTCAGGCGCCCTGACCAGCGGCGTGCACACCTTCCCGG

CTGTCCTACAGTCCTCAGGACTCTACTCCCTCAGCAGCGTGGTGACCGTGCCCTCCAGCAGCTTGGGCAC

CCAGACCTACATCTGCAACGTGAATCACAAGCCCAGCAACACCAAGGTGGACAAGAGAGTTGAGCCCAAA

TCTTGTGACAAAACTCACACATGCCCACCGTGCCCAGCACCTGAACTCCTGGGGGGACCGTCAGTCTTCC

TCTTCCCCCCAAAACCCAAGGACACCCTCATGATCTCCCGGACCCCTGAGGTCACATGCGTGGTGGTGGA

CGTGAGCCACGAAGACCCTGAGGTCAAGTTCAACTGGTACGTGGACGGCGTGGAGGTGCATAATGCCAAG

ACAAAGCCGCGGGAGGAGCAGTACAACAGCACGTACCGTGTGGTCAGCGTCCTCACCGTCCTGCACCAGG

ACTGGCTGAATGGCAAGGAGTACAAGTGCAAGGTCTCCAACAAAGCCCTCCCAGCCCCCATCGAGAAAAC

CATCTCCAAAGCCAAAGGGCAGCCCCGAGAACCACAGGTGTACACCCTGCCCCCATCCCGGGAGGAGATG

ACCAAGAACCAGGTCAGCCTGACCTGCCTGGTCAAAGGCTTCTATCCCAGCGACATCGCCGTGGAGTGGG

AGAGCAATGGGCAGCCGGAGAACAACTACAAGACCACGCCTCCCGTGCTGGACTCCGACGGCTCCTTCTT

CCTCTATAGCAAGCTCACCGTGGACAAGAGCAGGTGGCAGCAGGGGAACGTCTTCTCATGCTCCGTGATG

CATGAGGCTCTGCACAACCACTACACGCAGAAGAGCCTCTCCCTGTCTCCGGGTAAATGA

1503_H05 gamma heavy chain variable region nucleotide sequence:

(SEQ ID NO: 132)

CAGGAAAAACTGGTGGAGTCTGGGGGAGGCGTGGTCCAGCCGGGGGGGTCCCTGAGACTCTCCTGTTTAG

CGTCTGGATTCACCTTTCACAAATATGGCATGCACTGGGTCCGCCAGGCTCCAGGCAAGGGCCTGGAGTG

GGTGGCACTCATCTCAGATGACGGAATGAGGAAATATCATTCAGACTCCATGTGGGGCCGAGTCACCATC

TCCAGAGACAATTCCAAGAACACTTTATATCTGCAATTCAGCAGCCTGAAAGTCGAAGACACGGCTATGT

TCTTCTGTGCGAGAGAGGCTGGTGGGCCAATCTGGCATGACGACGTCAAATATTACGATTTTAATGACGG

CTACTACAATTACCACTACATGGACGTCTGGGGCAAGGGGACCATTGTCACCGTCTCCTCA

1503_H05 gamma heavy chain amino acid sequence:
expressed protein with variable region in bold.

(SEQ ID NO: 53)

QEKLVESGGGVVQPGGSLRLSCLASGFTFHKYGMHWVRQAPGKGLEWVALISDDGMRKY

HSDSMWGRVTISRDNSKNTLYLQFSSLKVEDTAMFFCAREAGGPIWHDDVKYYDFNDGYY

NYHYMDVWGKGTIVTVSSASTKGPSVFPLAPSSKSTSGGTAALGCLVKDYFPEPVTVSWNSGA

LTSGVHTFPAVLQSSGLYSLSSVVTVPSSSLGTQTYICNVNHKPSNTKVDKRVEPKSCDKTHTCPP

CPAPELLGGPSVFLFPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKGQPREPQVYTLPPSRE

EMTKNQVSLTCLVKGFYPSDIAVEWESNGQPENNYKTTPPVLDSDGSFFLYSKLTVDKSRWQQG

NVFSCSVMHEALHNHYTQKSLSLSPGK.

gamma heavy chain variable region amino acid sequence: (Kabat CDRs underlined, Chothia CDRs in bold italics)

(SEQ ID NO: 54)
QEKLVESGGGVVQPGGSLRLSCLA*SGFTFHKYGMH*WVRQAPGKGLEWVA*LISDDGMRKYHSD*

*SMW*GRVTISRDNSKNTLYLQFSSLKVEDTAMFFCAR*EAGGPIWHDDVKYYDFNDGYYNYHYMD*

*V*WGKGTIVTVSS

1503_H05 gamma heavy chain Kabat CDRs:
CDR 1:
(SEQ ID NO: 88)
SGFTFHKYGMEI

CDR 2:
(SEQ ID NO: 89)
LISDDGIVIRKYHSDSMW

CDR 3:
(SEQ ID NO: 6)
EAGGPIWHDDVKYYDFNDGYYNYHYMDV

1503_H05 gamma heavy chain Chothia CDRs:
CDR 1:
(SEQ ID NO: 88)
SGFTFHKYGMEI

CDR 2:
(SEQ ID NO: 89)
LISDDGIVIRKYHSDSMW

CDR 3:
(SEQ ID NO: 6)
EAGGPIWHDDVKYYDFNDGYYNYHYMDV

1503_H05 lambda light chain nucleotide sequence:
1503_H05 λ2 coding sequence (variable region in bold)
(SEQ ID NO: 55)
ATGGCCTGGGCTTGCTATTCCTCACCCTCTTCACTCAGGGCACAGGGTCCTGGGGCCAGTCTGCCCTGAC

TCAGCCTGCCTCCGTGTCTGGGTCTCCTGGACAGACGATCACCATCTCCTGCAATGGAACCAGAAGTGAC

GTTGGTGGATTTGACTCTGTCTCCTGGTACCAACAATCCCCAGGGAAAGCCCCCAAAGTCATGGTTTTTG

ATGTCAGTCATCGGCCCTCAGGTATCTCTAATCGCTTCTCTGGCTCCAAGTCCGGCAACACGGCCTCCCT

GACCATCTCTGGGCTCCACATTGAGGACGAGGGCGATTATTTCTGCTCTTCACTGACAGACAGAAGCCAT

CGCATATTCGGCGGCGGGACCAAGGTGACCGTTCTAGGTCAGCCCAAGGCTGCCCCCTCGGTCACTCTGT

TCCCGCCCTCCTCTGAGGAGCTTCAAGCCAACAAGGCCACACTGGTGTGTCTCATAAGTGACTTCTACCC

GGGAGCCGTGACAGTGGCCTGGAAGGCAGATAGCAGCCCCGTCAAGGCGGGAGTGGAGACCACCACACCC

TCCAAACAAAGCAACAACAAGTACGCGGCCAGCAGCTACCTGAGCCTGACGCCTGAGCAGTGGAAGTCCC

ACAAAAGCTACAGCTGCCAGGTCACGCATGAAGGGAGCACCGTGGAGAAGACAGTGGCCCCTACAGAATG

TTCATAG

1503_H05 lambda light chain variable region nucleotide sequence:
(SEQ ID NO: 133)
CAGTCTGCCCTGACTCAGCCTGCCTCCGTGTCTGGGTCTCCTGGACAGACGATCACCATCTCCTGCAATG

GAACCAGAAGTGACGTTGGTGGATTTGACTCTGTCTCCTGGTACCAACAATCCCCAGGGAAAGCCCCCAA

AGTCATGGTTTTTGATGTCAGTCATCGGCCCTCAGGTATCTCTAATCGCTTCTCTGGCTCCAAGTCCGGC

AACACGGCCTCCCTGACCATCTCTGGGCTCCACATTGAGGACGAGGGCGATTATTTCTGCTCTTCACTGA

CAGACAGAAGCCATCGCATATTCGGCGGCGGGACCAAGGTGACCGTTCTA

1503_H05 lambda light chain amino acid sequence:
expressed protein with variable region in bold.
(SEQ ID NO: 56)
QSALTQPASVSGSPGQTITISCNGTRSDVGGFDSVSWYQQSPGKAPKVMVFDVSHRPSGISN

RFSGSKSGNTASLTISGLHIEDEGDYFCSSLTDRSHRIFGGGTKVTVLGQPKAAPSVTLFPPSS

EELQANKATLVCLISDFYPGAVTVAWKADSSPVKAGVETTTPSKQSNNKYAASSYLSLTPEQWK

SHKSYSCQVTHEGSTVEKTVAPTECS

1503_H05 lambda light chain variable region amino acid sequence:
(Kabat CDRs underlined, Chothia CDRs in bold italics)
(SEQ ID NO: 57)
QSALTQPASVSGSPGQTITISC*NGTRSDVGGFDSVS*WYQQSPGKAPKVMVE*DVSHRPSG*ISNRFS

GSKSGNTASLTISGLHIEDEGDYFC*SSLTDRSHRI*FGGGTKVTVL

1503_H05 lambda light chain Kabat CDRs:
CDR 1:
(SEQ ID NO: 92)
NGTRSDVGGFDSVS

CDR 2:
(SEQ ID NO: 95)
DVSHRPSG

CDR 3:
(SEQ ID NO: 41)
SSLTDRSHRI

1503_H05 lambda light chain Chothia CDRs:

CDR 1:
(SEQ ID NO: 92)
NGTRSDVGGFDSVS

CDR 2:
(SEQ ID NO: 95)
DVSHRPSG
CDR 3:
(SEQ ID NO: 41)
SSLTDRSHRI

1489_I13 gamma heavy chain nucleotide sequence:
1489_I13 γ3 coding sequence (variable region in bold)
(SEQ ID NO: 58)
ATGGAGTTTGGGCTGAGCTGGGTTTTCCTCGCAACTCTGTTAAGAGTTGTGAAGTGTCAGGAACAACTGT

TGGAGTCTGGGGGAGGCGTGGTCCAGCCGGGGGGGTCCCTGAGACTCTCCTGTTTAGCGTCTGGATTCAC

GTTTCACAAATATGGCATGCACTGGGTCCGCCAGGCTCCAGGCAAGGGCCTGGAGTGGGTGGCACTCATC

TCAGATGACGGAATGAGGAAATATCATTCAAACTCCATGTGGGGCCGAGTCACCATCTCCAGAGACAATT

CCAAGAACACTCTTTATCTGCAATTCAGCAGCCTGAAAGTCGAAGACACGGCTATGTTCTTCTGTGCGAG

AGAGGCTGGTGGGCCAATCTGGCATGACGACGTCAAATATTACGATTTTAATGACGGCTACTACAACTAC

CACTACATGGACGTCTGGGGCAAGGGGACCACGGTCACCGTCTCCTCAGCGTCGACCAAGGGCCCATCGG

TCTTCCCTCTGGCACCATCATCCAAGTCGACCTCTGGGGGCACAGCGGCCCTGGGCTGCCTGGTCAAGGA

CTACTTCCCCGAACCGGTGACGGTGTCGTGGAACTCAGGCGCCCTGACCAGCGGCGTGCACACCTTCCCG

GCTGTCCTACAGTCCTCAGGACTCTACTCCCTCAGCAGCGTGGTGACCGTGCCCTCCAGCAGCTTGGGCA

CCCAGACCTACATCTGCAACGTGAATCACAAGCCCAGCAACACCAAGGTGGACAAGAGAGTTGAGCCCAA

ATCTTGTGACAAAACTCACACATGCCCACCGTGCCCAGCACCTGAACTCCTGGGGGGACCGTCAGTCTTC

CTCTTCCCCCCAAAACCCAAGGACACCCTCATGATCTCCCGGACCCCTGAGGTCACATGCGTGGTGGTGG

ACGTGAGCCACGAAGACCCTGAGGTCAAGTTCAACTGGTACGTGGACGGCGTGGAGGTGCATAATGCCAA

GACAAAGCCGCGGGAGGAGCAGTACAACAGCACGTACCGTGTGGTCAGCGTCCTCACCGTCCTGCACCAG

GACTGGCTGAATGGCAAGGAGTACAAGTGCAAGGTCTCCAACAAAGCCCTCCCAGCCCCCATCGAGAAAA

CCATCTCCAAAGCCAAAGGGCAGCCCCGAGAACCACAGGTGTACACCCTGCCCCCATCCCGGGAGGAGAT

GACCAAGAACCAGGTCAGCCTGACCTGCCTGGTCAAAGGCTTCTATCCCAGCGACATCGCCGTGGAGTGG

GAGAGCAATGGGCAGCCGGAGAACAACTACAAGACCACGCCTCCCGTGCTGGACTCCGACGGCTCCTTCT

TCCTCTATAGCAAGCTCACCGTGGACAAGAGCAGGTGGCAGCAGGGGAACGTCTTCTCATGCTCCGTGAT

GCATGAGGCTCTGCACAACCACTACACGCAGAAGAGCCTCTCCCTGTCTCCGGGTAAATGA

1489_I13 gamma heavy chain variable region nucleotide sequence:
(SEQ ID NO: 134)
CAGGAACAACTGTTGGAGTCTGGGGGAGGCGTGGTCCAGCCGGGGGGGTCCCTGAGACTCTCCTGTTTAG

CGTCTGGATTCACGTTTCACAAATATGGCATGCACTGGGTCCGCCAGGCTCCAGGCAAGGGCCTGGAGTG

GGTGGCACTCATCTCAGATGACGGAATGAGGAAATATCATTCAAACTCCATGTGGGGCCGAGTCACCATC

TCCAGAGACAATTCCAAGAACACTCTTTATCTGCAATTCAGCAGCCTGAAAGTCGAAGACACGGCTATGT

TCTTCTGTGCGAGAGAGGCTGGTGGGCCAATCTGGCATGACGACGTCAAATATTACGATTTTAATGACGG

CTACTACAACTACCACTACATGGACGTCTGGGGCAAGGGGACCACGGTCACCGTCTCCTCA

1489_I13 gamma heavy chain amino acid sequence:
expressed protein with variable region in bold.
(SEQ ID NO: 59)
QEQLLESGGGVVQPGGSLRLSCLASGFTFHKYGMHWVRQAPGKGLEWVALISDDGMRKY

HSNSMWGRVTISRDNSKNTLYLQFSSLKVEDTAMFFCAREAGGPIWHDDVKYYDFNDGYY

NYHYMDVWGKGTTVTVSSASTKGPSVFPLAPSSKSTSGGTAALGCLVKDYFPEPVTVSWNSGA

LTSGVHTFPAVLQSSGLYSLSSVVTVPSSSLGTQTYICNVNHKPSNTKVDKRVEPKSCDKTHTCPP

CPAPELLGGPSVFLFPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKGQPREPQVYTLPPSRE

EMTKNQVSLTCLVKGFYPSDIAVEWESNGQPENNYKTTPPVLDSDGSFFLYSKLTVDKSRWQQG

NVFSCSVMHEALHNHYTQKSLSLSPGK

1489_I13 gamma heavy chain variable region amino acid sequence:
(Kabat CDRs underlined, Chothia CDRs in bold italics)
(SEQ ID NO: 60)
QEQLLESGGGVVQPGGSLRLSCLA*SGFTFHKYGMH*WVRQAPGKGLEWVA*LISDDGMRKYHSD*

*SMW*GRVTISRDNSKNTLYLQFSSLKVEDTAMFFCAR*EAGGPIWHDDVKYYDFNDGYYNYHYMD*

*V*WGKGTTVTVSS

1489_I13 gamma heavy chain Kabat CDRs:
CDR 1:
(SEQ ID NO: 88)
SGFTFHKYGMH

CDR 2:
(SEQ ID NO: 98)
LISDDGIVIRKYHSNSMW

CDR 3:
(SEQ ID NO: 6)
EAGGPIWHDDVKYYDFNDGYYNYHYMDV

1489_I13 gamma heavy chain Chothia CDRs:
CDR 1:
(SEQ ID NO: 88)
SGFTFHKYGMH

CDR 2:
(SEQ ID NO: 98)
LISDDGIVIRKYHSNSMW

CDR 3:
(SEQ ID NO: 6)
EAGGPIWHDDVKYYDFNDGYYNYHYMDV

1489_I13 lambda light chain nucleotide sequence:
1489_I13 λ2 coding sequence (variable region in bold)
(SEQ ID NO: 61)
ATGGCCTGGGCTCTGCTATTCCTCACCCTCTTCACTCAGGGCACAGGGTCCCGGGGCCAGTCTGCCCTGA

CTCAGCCTGCCTCCGTGTCTGGGTCTCCTGGACAGACGATCACCATCTCCTGCAATGGAACCAGCAGTGA

-continued

```
CGTTGGTGGATTTGACTCTGTCTCCTGGTATCAACAATCCCCAGGGAAAGCCCCCAAAGTCATGGTTTTT

GATGTCAGTCATCGGCCCTCAGGTATCTCTAATCGCTTCTCTGGCTCCAAGTCCGGCAACACGGCCTCCC

TGACCATCTCTGGGCTCCACATTGAGGACGAGGGCGATTATTTCTGCTCTTCACTGACAGACAGAAGCCA

TCGCATATTCGGCGGCGGGACCAAGGTGACCGTTCTAGGTCAGCCCAAGGCTGCCCCCTCGGTCACTCTG

TTCCCGCCCTCCTCTGAGGAGCTTCAAGCCAACAAGGCCACACTGGTGTGTCTCATAAGTGACTTCTACC

CGGGAGCCGTGACAGTGGCCTGGAAGGCAGATAGCAGCCCCGTCAAGGCGGGAGTGGAGACCACCACACC

CTCCAAACAAAGCAACAACAAGTACGCGGCCAGCAGCTACCTGAGCCTGACGCCTGAGCAGTGGAAGTCC

CACAAAAGCTACAGCTGCCAGGTCACGCATGAAGGGAGCACCGTGGAGAAGACAGTGGCCCCTACAGAAT

GTTCATAG
```

1489_I13 lambda light chain variable region nucleotide sequence:
(SEQ ID NO: 135)
```
CAGTCTGCCCTGACTCAGCCTGCCTCCGTGTCTGGGTCTCCTGGACAGACGATCACCATCTCCTGCAATG

GAACCAGCAGTGACGTTGGTGGATTTGACTCTGTCTCCTGGTATCAACAATCCCCAGGGAAAGCCCCCAA

AGTCATGGTTTTTGATGTCAGTCATCGGCCCTCAGGTATCTCTAATCGCTTCTCTGGCTCCAAGTCCGGC

AACACGGCCTCCCTGACCATCTCTGGGCTCCACATTGAGGACGAGGGCGATTATTTCTGCTCTTCACTGA

CAGACAGAAGCCATCGCATATTCGGCGGCGGGACCAAGGTGACCGTTCTA
```

1489_I13 lambda light chain amino acid sequence:
expressed protein with variable region in bold.
(SEQ ID NO: 14)
QSALTQPASVSGSPGQTITISCNGTSSDVGGFDSVSWYQQSPGKAPKVMVFDVSHRPSGISN

RFSGSKSGNTASLTISGLHIEDEGDYFCSSLTDRSHRIFGGGTKVTVLGQPKAAPSVTLFPPSS

EELQANKATLVCLISDFYPGAVTVAWKADSSPVKAGVETTTPSKQSNNKYAASSYLSLTPEQWK

SHKSYSCQVTHEGSTVEKTVAPTECS

1489_I13 lambda light chain variable region amino acid sequence:
(Kabat CDRs underlined, Chothia CDRs in bold italics).
(SEQ ID NO: 32)
QSALTQPASVSGSPGQTITISC*NGTSSDVGGFDSVS*WYQQSPGKAPKVMVF*DVSHRPSG*ISNRFS

GSKSGNTASLTISGLHIEDEGDYFC*SSLTDRSHRI*FGGGTKVTVL

1489_I13 lambda light chain Kabat CDRs:
CDR 1:
(SEQ ID NO: 97)
NGTSSDVGGFDSVS

CDR 2:
(SEQ ID NO: 95)
DVSHRPSG

CDR 3:
(SEQ ID NO: 41)
SSLTDRSHRI

1489_I13 lambda light chain Chothia CDRs:
CDR 1:
(SEQ ID NO: 97)
NGTSSDVGGFDSVS

CDR 2:
(SEQ ID NO: 95)
DVSHRPSG

CDR 3:
(SEQ ID NO: 41)
SSLTDRSHRI

1480_I08 gamma heavy chain nucleotide sequence:
1480_I08 γ3 coding sequence (variable region in bold)
(SEQ ID NO: 64)
ATGGAGTTTGGCTGAGCTGGGTTTTCCTCGCAACTCTGTTAAGAGTTGTGAAGTGTCAGGAACAACTGGT

GGAGTCTGGGGGAGGCGTGGTCCAGCCGGGGGGGTCCCTGAGACTCTCCTGTTTAGCGTCTGGATTCACG

```
TTTCACAAATATGGCATGCACTGGGTCCGCCAGGCTCCAGGCAAGGGCCTGGAGTGGGTGGCACTCATCT

CAGATGACGGAATGAGGAAATATCATTCAGACTCCATGTGGGGCCGAGTCACCATCTCCAGAGACAATTC

CAAGAACACTCTTTATCTGCAATTCAGCAGCCTGAAAGTCGAAGACACGGCTATGTTCTTCTGTGCGAGA

GAGGCTGGTGGGCCAATCTGGCATGACGACGTCAAATATTACGATTTTAATGACGGCTACTACAACTACC

ACTACATGGACGTCTGGGGCAAGGGGACCACGGTCACCGTCTCCTCAGCGTCGACCAAGGGCCCATCGGT

CTTCCCTCTGGCACCATCATCCAAGTCGACCTCTGGGGGCACAGCGGCCCTGGGCTGCCTGGTCAAGGAC

TACTTCCCCGAACCGGTGACGGTGTCGTGGAACTCAGGCGCCCTGACCAGCGGCGTGCACACCTTCCCGG

CTGTCCTACAGTCCTCAGGACTCTACTCCCTCAGCAGCGTGGTGACCGTGCCCTCCAGCAGCTTGGGCAC

CCAGACCTACATCTGCAACGTGAATCACAAGCCCAGCAACACCAAGGTGGACAAGAGAGTTGAGCCCAAA

TCTTGTGACAAAACTCACACATGCCCACCGTGCCCAGCACCTGAACTCCTGGGGGGACCGTCAGTCTTCC

TCTTCCCCCCAAAACCCAAGGACACCCTCATGATCTCCCGGACCCCTGAGGTCACATGCGTGGTGGTGGA

CGTGAGCCACGAAGACCCTGAGGTCAAGTTCAACTGGTACGTGGACGGCGTGGAGGTGCATAATGCCAAG

ACAAAGCCGCGGGAGGAGCAGTACAACAGCACGTACCGTGTGGTCAGCGTCCTCACCGTCCTGCACCAGG

ACTGGCTGAATGGCAAGGAGTACAAGTGCAAGGTCTCCAACAAAGCCCTCCCAGCCCCCATCGAGAAAAC

CATCTCCAAAGCCAAAGGGCAGCCCCGAGAACCACAGGTGTACACCCTGCCCCCATCCCGGGAGGAGATG

ACCAAGAACCAGGTCAGCCTGACCTGCCTGGTCAAAGGCTTCTATCCCAGCGACATCGCCGTGGAGTGGG

AGAGCAATGGGCAGCCGGAGAACAACTACAAGACCACGCCTCCCGTGCTGGACTCCGACGGCTCCTTCTT

CCTCTATAGCAAGCTCACCGTGGACAAGAGCAGGTGGCAGCAGGGGAACGTCTTCTCATGCTCCGTGATG

CATGAGGCTCTGCACAACCACTACACGCAGAAGAGCCTCTCCCTGTCTCCGGGTAAATGA
```

1480_I08 gamma heavy chain variable region nucleotide sequence:
(SEQ ID NO: 136)

```
CAGGAACAACTGGTGGAGTCTGGGGGAGGCGTGGTCCAGCCGGGGGGGTCCCTGAGACTCTCCTGTTTAG

CGTCTGGATTCACGTTTCACAAATATGGCATGCACTGGGTCCGCCAGGCTCCAGGCAAGGGCCTGGAGTG

GGTGGCACTCATCTCAGATGACGGAATGAGGAAATATCATTCAGACTCCATGTGGGGCCGAGTCACCATC

TCCAGAGACAATTCCAAGAACACTCTTTATCTGCAATTCAGCAGCCTGAAAGTCGAAGACACGGCTATGT

TCTTCTGTGCGAGAGAGGCTGGTGGGCCAATCTGGCATGACGACGTCAAATATTACGATTTTAATGACGG

CTACTACAACTACCACTACATGGACGTCTGGGGCAAGGGGACCACGGTCACCGTCTCCTCA
```

1480_I08 gamma heavy chain amino acid sequence:
expressed protein with variable region in bold.
(SEQ ID NO: 65)

QEQLVESGGGVVQPGGSLRLSCLASGFTFHKYGMHWVRQAPGKGLEWVALISDDGMRKY

HSDSMYVGRVTISRDNSKNTLYLQFSSLKVEDTAMFFCAREAGGPIWHDDYKYYDFNDGYY

NYHYMDVYVGKGTTVTVSSASTKGPSVFPLAPSSKSTSGGTAALGCLVKDYFPEPVTVSWNSGA

LTSGVHTFPAVLQSSGLYSLSSVVTVPSSSLGTQTYICNVNHKPSNTKVDKRVEPKSCDKTHTCPP

CPAPELLGGPSVFLFPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKGQPREPQVYTLPPSRE

EMTKNQVSLTCLVKGFYPSDIAVEWESNGQPENNYKTTPPVLDSDGSFFLYSKLTVDKSRWQQG

NVFSCSVMHEALHNHYTQKSLSLSPGK

1480_I08 gamma heavy chain variable region amino acid sequence:
(Kabat CDRs underlined, Chothia CDRs in bold italics)
(SEQ ID NO: 31)
QEQLVESGGGVVQPGGSLRLSCLA*SGFTFHKYGMH*WVRQAPGKGLEWVA*LISDDGMRKYHSD*

*SMW*GRVTISRDNSKNTLYLQFSSLKVEDTAMFFCAR*EAGGPIWHDDVKYYDFNDGYYNYHYMD*

*V*WGKGTTVTVSS

1480_I08 gamma heavy chain Kabat CDRs:
CDR 1:
(SEQ ID NO: 88)
SGFTFHKYGMH

CDR 2:
(SEQ ID NO: 89)
LISDDGIVIRKYHSDSMW

CDR 3:
(SEQ ID NO: 6)
EAGGPIWHDDVKYYDFNDGYYNYHYMDV

1480_I08 gamma heavy chain Chothia CDRs:
CDR 1:
(SEQ ID NO: 88)
SGFTFHKYGMH

CDR 2:
(SEQ ID NO: 89)
LISDDGIVIRKYHSDSMW

CDR 3:
(SEQ ID NO: 6)
EAGGPIWHDDVKYYDFNDGYYNYHYMDV

1480_I08 lambda light chain nucleotide sequence:
1480_I08 λ2 coding sequence (variable region in bold)
(SEQ ID NO: 67)
ATGGCCTGGGCTCTGCTATTCGTCACCCTCCTCACTCAGGGCACAGGGTCCTGGGGCCAGTCTGCCCTGA

CTCAGCCTGCCTCCGTGTCTGGGTCTCCTGGACAGACGATCACCATCTCCTGCAATGGAACCAGCAGTGA

CGTTGGTGGATTTGACTCTGTCTCCTGGTATCAACAATCCCCAGGGAAAGCCCCCAAAGTCATGGTTTTT

GATGTCAGTCATCGGCCCTCAGGTATCTCTAATCGCTTCTCTGGCTCCAAGTCCGGCAACACGGCCTCCC

TGACCATCTCTGGGCTCCACATTGAGGACGAGGGCGATTATTTCTGCTCTTCACTGACAGACAGAAGCCA

TCGCATATTCGGCGGCGGGACCAAGGTGACCGTTCTAGGTCAGCCCAAGGCTGCCCCCTCGGTCACTCTG

TTCCCGCCCTCCTCTGAGGAGCTTCAAGCCAACAAGGCCACACTGGTGTGTCTCATAAGTGACTTCTACC

CGGGAGCCGTGACAGTGGCCTGGAAGGCAGATAGCAGCCCCGTCAAGGCGGGAGTGGAGACCACCACACC

CTCCAAACAAAGCAACAACAAGTACGCGGCCAGCAGCTACCTGAGCCTGACGCCTGAGCAGTGGAAGTCC

CACAAAAGCTACAGCTGCCAGGTCACGCATGAAGGGAGCACCGTGGAGAAGACAGTGGCCCCTACAGAAT

GTTCATAG

1480_I08 lambda light chain variable region nucleotide sequence:
(SEQ ID NO: 137)
CAGTCTGCCCTGACTCAGCCTGCCTCCGTGTCTGGGTCTCCTGGACAGACGATCACCATCTCCTGCAATG

GAACCAGCAGTGACGTTGGTGGATTTGACTCTGTCTCCTGGTATCAACAATCCCCAGGGAAAGCCCCCAA

AGTCATGGTTTTTGATGTCAGTCATCGGCCCTCAGGTATCTCTAATCGCTTCTCTGGCTCCAAGTCCGGC

AACACGGCCTCCCTGACCATCTCTGGGCTCCACATTGAGGACGAGGGCGATTATTTCTGCTCTTCACTGA

CAGACAGAAGCCATCGCATATTCGGCGGCGGGACCAAGGTGACCGTTCTA

1480_I08 lambda light chain amino acid sequence:
expressed protein with variable region in bold.
(SEQ ID NO: 14)
QSALTQPASVSGSPGQTITISCNCTSSDVGCFDSVSWYQQSPCKAPKVMVFDVSHRPSGISN

RFSGSKSGNTASLTISGLHIEDEGDYFCSSLTDRSHRIFGGGTKVTVLGQPKAAPSVTLFPPSS

EELQANKATLVCLISDFYPGAVTVAWKADSSPVKAGVETITPSKQSNNKYAASSYLSLTPEQWK

SHKSYSCQVTHEGSTVEKTVAPTECS

1480_I08 lambda light chain variable region amino acid sequence:
(Kabat CDRs underlined, Chothia CDRs in bold italics)
(SEQ ID NO: 32)
QSALTQPASVSGSPGQTITISC<u>*NGTSSDVGGFDSVS*</u>WYQQSPGKAPKVMVF*<u>DVSHRPSG</u>*ISNRFS GSKSGNTASLTISGLHIEDEGDYFC*<u>SSLTDRSHRI</u>*FGGGTKVTVL

```
1480_I08 lambda light chain Kabat CDRs:
CDR 1:
                                                           (SEQ ID NO: 97)
NGTSSDVGGFDSVS CDR 2:
                                                           (SEQ ID NO: 95)
DVSHRPSG CDR 3:
                                                           (SEQ ID NO: 41)
SSLTDRSHRI 1480_I08 lambda light chain Chothia CDRs:
CDR 1:
                                                           (SEQ ID NO: 97)
NGTSSDVGGFDSVS CDR 2:
                                                           (SEQ ID NO: 95)
DVSHRPSG CDR 3:
                                                           (SEQ ID NO: 41)
SSLTDRSHRI
```

The 1469_M23 (PG16) antibody includes a heavy chain variable region (SEQ ID NO: 139), encoded by the nucleic acid sequence shown in SEQ ID NO: 128, and a light chain variable region (SEQ ID NO: 142) encoded by the nucleic acid sequence shown in SEQ ID NO: 129.

The heavy chain CDRs of the 1469_M23 (PG16) antibody have the following sequences per Kabat and Chothia definitions: SGFTFHKYGMH (SEQ ID NO: 88), LISDDGMRKYHSDSMW (SEQ ID NO: 89), and EAGGPIWHDDVKYYDFNDGYYNYHYMDV (SEQ ID NO: 6). The light chain CDRs of the 1469 M23 (PG16) antibody have the following sequences per Kabat and Chothia definitions: NGTRSDVGGFDSVS (SEQ ID NO: 92), DVSHRPSG (SEQ ID NO: 95), and SSLTDRSHRI (SEQ ID NO: 41).

The 1456_A12 (PG16) antibody includes a heavy chain variable region (SEQ ID NO: 47), encoded by the nucleic acid sequence shown in SEQ ID NO: 130, and a light chain variable region (SEQ ID NO: 50) encoded by the nucleic acid sequence shown in SEQ ID NO: 131.

The heavy chain CDRs of the 1456_A12 (PG16) antibody have the following sequences per Kabat and Chothia definitions: SGFTFHKYGMH (SEQ ID NO: 88), LISDDGMRKYHSDSMW (SEQ ID NO: 89), and EAGGPIWHDDVKYYDFNDGYYNYHYMDV (SEQ ID NO: 6). The light chain CDRs of the 1456_A12 (PG16) antibody have the following sequences per Kabat and Chothia definitions: NGTSRDVGGFDSVS (SEQ ID NO: 93), DVSHRPSG (SEQ ID NO: 95), and SSLTDRSHRI (SEQ ID NO: 41).

The 1503_H05 (PG16) antibody includes a heavy chain variable region (SEQ ID NO: 53), encoded by the nucleic acid sequence shown in SEQ ID NO: 132, and a light chain variable region (SEQ ID NO: 56) encoded by the nucleic acid sequence shown in SEQ ID NO: 133.

The heavy chain CDRs of the 1503_H05 (PG16) antibody have the following sequences per Kabat and Chothia definitions: SGFTFHKYGMH (SEQ ID NO: 88), LISDDGMRKYHSDSMW (SEQ ID NO: 89), and EAGGPIWHDDVKYYDFNDGYYNYHYMDV (SEQ ID NO: 6). The light chain CDRs of the 1503_H05 (PG16) antibody have the following sequences per Kabat and Chothia definitions: NGTRSDVGGFDSVS (SEQ ID NO: 92), DVSHRPSG (SEQ ID NO: 95), and SSLTDRSHRI (SEQ ID NO: 41).

The 1489_I13 (PG16) antibody includes a heavy chain variable region (SEQ ID NO: 59), encoded by the nucleic acid sequence shown in SEQ ID NO: 134, and a light chain variable region (SEQ ID NO: 14) encoded by the nucleic acid sequence shown in SEQ ID NO: 135.

The heavy chain CDRs of the 1489_I13 (PG16) antibody have the following sequences per Kabat and Chothia definitions: SGFTFHKYGMH (SEQ ID NO: 88), LISDDGMRKYHSNSMW (SEQ ID NO: 98), and EAGGPIWHDDVKYYDFNDGYYNYHYMDV (SEQ ID NO: 6). The light chain CDRs of the 1489 113 (PG16) antibody have the following sequences per Kabat and Chothia definitions: NGTSSDVGGFDSVS (SEQ ID NO: 97), DVSHRPSG (SEQ ID NO: 95), and SSLTDRSHRI (SEQ ID NO: 41).

The 1480_I08 (PG16) antibody includes a heavy chain variable region (SEQ ID NO: 65), encoded by the nucleic acid sequence shown in SEQ ID NO: 136, and a light chain variable region (SEQ ID NO: 14) encoded by the nucleic acid sequence shown in SEQ ID NO: 137.

The heavy chain CDRs of the 1480_I08 (PG16) antibody have the following sequences per Kabat and Chothia definitions: SGFTFHKYGMH (SEQ ID NO: 88), LISDDGMRKYHSDSMW (SEQ ID NO: 89), and EAGGPIWHDDVKYYDFNDGYYNYHYMDV (SEQ ID NO: 6). The light chain CDRs of the 1480_I08 (PG16) antibody have the following sequences per Kabat and Chothia definitions: NGTSSDVGGFDSVS (SEQ ID NO: 97), DVSHRPSG (SEQ ID NO: 95), and SSLTDRSHRI (SEQ ID NO: 41).

In one aspect, an antibody according to the invention contains a heavy chain having the amino acid sequence of SEQ ID NOs: 12, 16, 20, 24, 28, 139, 47, 53, 59, or 65 and a light chain having the amino acid sequence of SEQ ID NOs: 14, 18, 22, 26, 30, 142, 50, or 56. Alternatively, an antibody according to the invention contains a heavy chain variable region having the amino acid sequence of SEQ ID NOs: 31, 33, 35, 37, 39, 140, 48, 54, or 60 and a light chain variable region having the amino acid sequence of SEQ ID NOs: 32, 34, 36, 38, 40, 96, 51, or 57.

In another aspect, an antibody according to the invention contains a heavy chain having the amino acid sequence encoded by the nucleic acid sequence of SEQ ID NOs: 11, 15, 19, 23, 27, 138, 46, 52, 58, or 64 and a light chain having the amino acid sequence encoded by the nucleic acid sequence of SEQ ID NOs: 13, 17, 21, 25, 29, 141, 49, 55, 61, or 67. Alternatively, an antibody according to the invention contains a heavy chain variable region having the amino acid sequence encoded by the nucleic acid sequence of SEQ ID NOs: 99, 101, 109, 115, 122, 128, 130, 132, 134, or 136 and a light chain variable region having the amino acid sequence encoded by the nucleic acid sequence of SEQ ID NOs: 100, 106, 112, 119, 125, 129, 131, 133, 135, or 137. Furthermore, an antibody according to the invention contains a heavy chain having the amino acid sequence encoded by a nucleic acid sequence of SEQ ID NOs: 11, 15, 19, 23, 27, 138, 46, 52, 58, or 64, which contains a silent or degenerate mutation, and a light chain having the amino acid sequence encoded by the nucleic acid sequence of SEQ ID NOs: 13, 17, 21, 25, 29, 141, 49, 55, 61, or 67, which contains a silent or degenerate mutation. Silent and degenerate mutations alter the nucleic acid sequence, but do not alter the resultant amino acid sequence.

Preferably the three heavy chain CDRs include an amino acid sequence of at least 90%, 92%, 95%, 97%, 98%, 99%, or more identical to the amino acid sequence of SGFTFHKYGMH (SEQ ID NO: 88), LISDDGMRKYHSDSMW (SEQ ID NO: 89), EAGGPIWHDDVKYYDFNDGYYNYHYMDV (SEQ ID NO: 6), SGGTFSSYAFT (SEQ ID NO: 104), MVTPIFGEAKYSQRFE (SEQ ID NO: 105), RAVPIATDNWLDP (SEQ ID NO: 102), SGGAFSSYAFS (SEQ ID NO: 110), MITPVFGETKYAPRFQ (SEQ ID NO: 111), SGYSFIDYYLH (SEQ ID NO: 116), LIDPENGEARYAEKFQ (SEQ ID NO: 117), AVGADSGSWFDP (SEQ ID NO: 118), SGFDFSRQGMH (SEQ ID NO: 123), FIKYDGSEKYHADSVW (SEQ ID NO: 124), EAGGPDYRNGYNYYDFYDGYYNYHYMDV (SEQ ID NO: 7), LISDDGMRKYHSNSMW (SEQ ID NO: 98) (as determined by the Kabat method) or SGFTFHKYGMH (SEQ ID NO: 88), LISDDGMRKYHSDSMW (SEQ ID NO: 89), EAGGPIWHDDVKYYDFNDGYYNYHYMDV (SEQ ID NO: 6), SGGTFSSYAFT (SEQ ID NO: 104), MVTPIFGEAKYSQRFE (SEQ ID NO: 105), RRAVPIATDNWLDP (SEQ ID NO: 103), SGGAFSSYAFS (SEQ ID NO: 110), MITPVFGETKYAPRFQ (SEQ ID NO: 111), SGYSFIDYYLH (SEQ ID NO: 116), LIDPENGEARYAEKFQ (SEQ ID NO: 117), AVGADSGSWFDP (SEQ ID NO: 118), SGFDFSRQGMH (SEQ ID NO: 123), FIKYDGSEKYHADSVW (SEQ ID NO: 124), EAGGPDYRNGYNYYDFYDGYYNYHYMDV (SEQ ID NO: 7), LISDDGMRKYHSNSMW (SEQ ID NO: 98) (as determined by the Chothia method) and a light chain with three CDRs that include an amino acid sequence of at least 90%, 92%, 95%, 97%, 98%, 99%, or more identical to the amino acid sequence of NGTSSDVGGFDSVS (SEQ ID NO: 97), DVSHRPSG (SEQ ID NO: 95), SSLTDRSHRI (SEQ ID NO: 41), RASQTINNYLN (SEQ ID NO: 107), GASNLQNG (SEQ ID NO: 108), QQSFSTPRT (SEQ ID NO: 42), RASQTIHTYL (SEQ ID NO: 113), GASTLQSG (SEQ ID NO: 114), QQSYSTPRT (SEQ ID NO: 43), SGSKLGDKYVS (SEQ ID NO: 120), ENDRRPSG (SEQ ID NO: 121), QAWETTTTTFVF (SEQ ID NO: 44), NGTSNDVGGYESVS (SEQ ID NO: 126), DVSKRPSG (SEQ ID NO: 127), KSLTSTRRRV (SEQ ID NO: 45), NGTRSDVGGFDSVS (SEQ ID NO: 92), NGTSRDVGGFDSVS (SEQ ID NO: 93) (as determined by the Kabat method) or NGTSSDVGGFDSVS (SEQ ID NO: 97), DVSHRPSG (SEQ ID NO: 95), SSLTDRSHRI (SEQ ID NO: 41), RASQTINNYLN (SEQ ID NO: 107), GASNLQNG (SEQ ID NO: 108), QQSFSTPRT (SEQ ID NO: 42), RASQTIHTYL (SEQ ID NO: 113), GASTLQSG (SEQ ID NO: 114), QQSYSTPRT (SEQ ID NO: 43), SGSKLGDKYVS (SEQ ID NO: 120), ENDRRPSG (SEQ ID NO: 121), QAWETTTTTFVF (SEQ ID NO: 44), NGTSNDVGGYESVS (SEQ ID NO: 126), DVSKRPSG (SEQ ID NO: 127), KSLTSTRRRV (SEQ ID NO: 45), NGTRSDVGGFDSVS (SEQ ID NO: 92), NGTSRDVGGFDSVS (SEQ ID NO: 93) (as determined by the Chothia method).

The heavy chain of the anti-HIV monoclonal antibody is derived from a germ line variable (V) gene such as, for example, the IGHV1 or IGHV3 germline gene.

The anti-HIV antibodies of the invention include a variable heavy chain ($V_H$) region encoded by a human IGHV1 or IGHV3 germline gene sequence. IGHV1 germline gene sequences are shown, e.g., in Accession numbers L22582, X27506, X92340, M83132, X67905, L22583, Z29978, Z14309, Z14307, Z14300, Z14296, and Z14301. IGHV3 germline gene sequences are shown, e.g., in Accession numbers AB019439, M99665, M77305, M77335, and M77334. The anti-HIV antibodies of the invention include a $V_H$ region that is encoded by a nucleic acid sequence that is at least 80% homologous to the IGHV1 or IGHV3 germline gene sequence. Preferably, the nucleic acid sequence is at least 90%, 95%, 96%, 97% homologous to the IGHV1 or IGHV3 germline gene sequence, and more preferably, at least 98%, 99% homologous to the IGHV1 or IGHV3 germline gene sequence. The $V_H$ region of the anti-HIV antibody is at least 80% homologous to the amino acid sequence of the $V_H$ region encoded by the IGHV1 or IGHV3 $V_H$ germline gene sequence. Preferably, the amino acid sequence of $V_H$ region of the anti-HIV antibody is at least 90%, 95%, 96%, 97% homologous to the amino acid sequence encoded by the IGHV1 or IGHV3 germline gene sequence, and more preferably, at least 98%, 99% homologous to the sequence encoded by the IGHV1 or IGHV3 germline gene sequence.

The light chain of the anti-HIV monoclonal antibody is derived from a germ line variable (V) gene such as, for example, the IGLV2, IGLV3 or IGKV1 germline gene.

The anti-HIV antibodies of the invention also include a variable light chain ($V_L$) region encoded by a human IGLV2, IGLV3 or IGKV1 germline gene sequence. A human IGLV2 $V_L$ germline gene sequence is shown, e.g., Accession numbers Z73664, L27822, Y12412, and Y12413. A human IGLV3 $V_L$ germline gene sequence is shown, e.g., Accession number X57826.

A human IGKV1 $V_L$ germline gene sequence is shown, e.g., Accession numbers AF306358, AF490911, L12062, L12064, L12065, L12066, L12068, L12072, L12075, L12076, L12079, L12080, L12081, L12082, L12083, L12084, L12085, L12086, :12088, L12091, L12093, L12101, L12106, L12108, L12110, L12112, M95721, M95722, M95723, X73855, X73860, X98972, X98973, Z15073, Z15074, Z15075, Z15077, Z15079, Z15081. Alternatively, the anti-HIV antibodies include a $V_L$ region that is encoded by a nucleic acid sequence that is at least 80% homologous to the IGLV2, IGLV3 or IGKV1 germline gene sequence. Preferably, the nucleic acid sequence is at least 90%, 95%, 96%, 97% homologous to the IGLV2, IGLV3 or IGKV1 germline gene sequence, and more preferably, at least 98%, 99% homologous to the IGLV2, IGLV3 or IGKV1 germline gene sequence. The $V_L$ region of the anti-CMV antibody is at least 80% homologous to the amino acid sequence of the $V_L$ region encoded the IGLV2, IGLV3 or IGKV1 germline gene sequence. Preferably, the amino acid sequence of $V_L$ region of the anti-HIV antibody is at least 90%, 95%, 96%, 97% homologous to the amino acid sequence encoded by the IGLV2, IGLV3 or IGKV1 germline gene sequence, and more preferably, at least 98%, 99% homologous to the sequence encoded by the IGLV2, IGLV3 or IGKV1 germline gene sequence.

TABLE 11

Consensus nucleotide sequences of Kabat CDRs of heavy chains of 1443 PG16 sister clones.

CDR1:

| | |
|---|---|
| 1443 C16 | TCTGGATTCACGTTTCACAAATATGGCATGCAC (SEQ ID NO: 68) |
| 1469 M23 | TCTGGATTCACCTTTCACAAATATGGCATGCAC (SEQ ID NO: 69) |
| 1456 A12 | TCTGGATTCACGTTTCACAAATATGGCATGCAC (SEQ ID NO: 68) |
| 1503 H05 | TCTGGATTCACCTTTCACAAATATGGCATGCAC (SEQ ID NO: 70) |
| 1489 I13 | TCTGGATTCACGTTTCACAAATATGGCATGCAC (SEQ ID NO: 68) |
| 1480 I08 | TCTGGATTCACGTTTCACAAATATGGCATGCAC (SEQ ID NO: 68) |
| Consensus* | TCTGGATTCACXTTTCACAAATATGGCATGCAC (SEQ ID NO: 71) |
| Variation1 | TCTGGATTCACGTTTCACAAATATGGCATGCAC (SEQ ID NO: 68) |
| Variation2 | TCTGGATTCACCTTTCACAAATATGGCATGCAC (SEQ ID NO: 70) |

* Wherein X is C or G.

CDR2:

| | |
|---|---|
| 1443 C16 | CTCATCTCAGATGACGGAATGAGGAAATATCATTCAGACTCCATGTGG (SEQ ID NO: 72) |
| 1469 M23 | CTCATCTCAGATGACGGAATGAGGAAATATCATTCAGACTCCATGTGG (SEQ ID NO: 72) |
| 1456 A12 | CTCATCTCAGATGACGGAATGAGGAAATATCATTCAGACTCCATGTGG (SEQ ID NO: 72) |
| 1503 H05 | CTCATCTCAGATGACGGAATGAGGAAATATCATTCAGACTCCATGTGG (SEQ ID NO: 72) |
| 1489 I13 | CTCATCTCAGATGACGGAATGAGGAAATATCATTCAAACTCCATGTGG (SEQ ID NO: 73) |
| 1480 I08 | CTCATCTCAGATGACGGAATGAGGAAATATCATTCAGACTCCATGTGG (SEQ ID NO: 72) |
| Consensus* | CTCATCTCAGATGACGGAATGAGGAAATATCATTCAXACTCCATGTGG (SEQ ID NO: 74) |
| Variation1 | CTCATCTCAGATGACGGAATGAGGAAATATCATTCAGACTCCATGTGG (SEQ ID NO: 72) |
| Variation2 | CTCATCTCAGATGACGGAATGAGGAAATATCATTCAAACTCCATGTGG (SEQ ID NO: 73) |

* Wherein X is A or G.

CDR3:

1443 C16 (SEQ ID NO: 75)
GAGGCTGGTGGGCCAATCTGGCATGACGACGTCAAATATTACGATTTTAATGACGGCTACTACAACTACCACTACATGGACGTC
1469 M23 (SEQ ID NO: 75)
GAGGCTGGTGGGCCAATCTGGCATGACGACGTCAAATATTACGATTTTAATGACGGCTACTACAACTACCACTACATGGACGTC
1456 A12 (SEQ ID NO: 77)
GAGGCCGGTGGGCCAATCTGGCATGACGACGTCAAATATTACGATTTTAATGACGGCTACTACAACTATCACTACATGGACGTC
1503_H05 (SEQ ID NO:79)
GAGGCTGGTGGGCCAATCTGGCATGACGACGTCAAATATTACGATTTTAATGACGGCTACTACAATTACCACTACATGGACGTC
1489 I13 (SEQ ID NO: 75)
GAGGCTGGTGGGCCAATCTGGCATGACGACGTCAAATATTACGATTTTAATGACGGCTACTACAACTACCACTACATGGACGTC
1480 I08 (SEQ ID NO: 75)
GAGGCTGGTGGGCCAATCTGGCATGACGACGTCAAATATTACGATTTTAATGACGGCTACTACAACTACCACTACATGGACGTC
Consensus (SEQ ID NO: 76)

TABLE 11 -continued

Consensus nucleotide sequences of Kabat CDRs of heavy chains of 1443 PG16 sister clones.

GAGGCXGGTGGGCCAATCTGGCATGACGACGTCAAATATTACGATTTTAATGACGGCTACTACAACTATCACTACATGGACGTC
Variation1 (SEQ ID NO: 78)
GAGGCGGGTGGGCCAATCTGGCATGACGACGTCAAATATTACGATTTTAATGACGGCTACTACAACTATCACTACATGGACGTC
Variation2 (SEQ ID NO: 77)
GAGGCCGGTGGGCCAATCTGGCATGACGACGTCAAATATTACGATTTTAATGACGGCTACTACAACTATCACTACATGGACGTC

* Wherein X is T, C or G.

TABLE 12

Consensus nucleotide sequences of Kabat CDRs of light chains of 1443 PG16 sister clones.

CDR1:

| | |
|---|---|
| 1443 C16 | AATGGAACCAGCCGTGACGTTGGTGGATTTGACTCTGTCTCC (SEQ ID NO: 80) |
| 1469 M23 | AATGGAACCAGAAGTGACGTTGGTGGATTTGACTCTGTCTCC (SEQ ID NO: 82) |
| 1456 A12 | AATGGAACCAGCCGTGACGTTGGTGGATTTGACTCTGTCTCC (SEQ ID NO: 82) |
| 1503 H05 | AATGGAACCAGAAGTGACGTTGGTGGATTTGACTCTGTCTCC (SEQ ID NO: 83) |
| 1489 I13 | AATGGAACCAGCCGTGACGTTGGTGGATTTGACTCTGTCTCC (SEQ ID NO: 80) |
| 1480 I08 | AATGGAACCAGCCGTGACGTTGGTGGATTTGACTCTGTCTCC (SEQ ID NO: 80) |
| Consensus* | AATGGAACCAGX₁X₂GTGACGTTGGTGGATTTGACTCTGTCTCC (SEQ ID NO: 81) |
| Variation1 | AATGGAACCAGCCGTGACGTTGGTGGATTTGACTCTGTCTCC (SEQ ID NO: 80) |
| Variation2 | AATGGAACCAGAAGTGACGTTGGTGGATTTGACTCTGTCTCC (SEQ ID NO: 82) |
| Variation2 | AATGGAACCAGCCGTGACGTTGGTGGATTTGACTCTGTCTCC (SEQ ID NO: 83) |

*Wherein $X_1$ is C or A. Wherein $X_2$ is C or A.

CDR2:

| | |
|---|---|
| 1443 C16 | GATGTCAGTCATCGGCCCTCAGGT (SEQ ID NO: 84) |
| 1469 M23 | GATGTCAGTCATCGGCCCTCAGGT (SEQ ID NO: 84) |
| 1456 A12 | GATGTCAGTCATCGGCCCTCAGGT (SEQ ID NO: 84) |
| 1503 H05 | GATGTCAGTCATCGGCCCTCAGGT (SEQ ID NO: 84) |
| 1489 I13 | GATGTCAGTCATCGGCCCTCAGGT (SEQ ID NO: 84) |
| 1480 I08 | GATGTCAGTCATCGGCCCTCAGGT (SEQ ID NO: 84) |
| Consensus | GATGTCAGTCATCGGCCCTCAGGT (SEQ ID NO: 84) |

CDR3:

| | |
|---|---|
| 1443 C16 | TCTTCACTGACAGACAGAAGCCATCGCATA (SEQ ID NO: 85) |
| 1469 M23 | TCTTCACTGACAGACAGAAGCCATCGCATA (SEQ ID NO: 85) |
| 1456 A12 | TCTTCATTGACAGACAGAAGCCATCGCATA (SEQ ID NO: 86) |
| 1503 H05 | TCTTCACTGACAGACAGAAGCCATCGCATA (SEQ ID NO: 85) |
| 1489 I13 | TCTTCACTGACAGACAGAAGCCATCGCATA (SEQ ID NO: 85) |
| 1480 I08 | TCTTCACTGACAGACAGAAGCCATCGCATA (SEQ ID NO: 85) |
| Consensus* | TCTTCAXTGACAGACAGAAGCCATCGCATA (SEQ ID NO: 87) |
| Variation1 | TCTTCACTGACAGACAGAAGCCATCGCATA (SEQ ID NO: 85) |

TABLE 12 -continued

Consensus nucleotide sequences of Kabat CDRs of light chains of 1443 PG16 sister clones.

Variation2   TCTTCATTGACAGACAGAAGCCATCGCATA
             (SEQ ID NO: 86)
*Wherein X₁ is C or T. Wherein X₂ is C or T.

TABLE 13

Consensus protein sequences of Kabat CDRs of Heavy chains of 1443 PG16 sister clones.

CDR1:

| | | |
|---|---|---|
| 1443 C16 | SGFTFHKYGMH | (SEQ ID NO: 88) |
| 1469 M23 | SGFTFHKYGMH | (SEQ ID NO: 88) |
| 1456 A12 | SGFTFHKYGMH | (SEQ ID NO: 88) |
| 1503 H05 | SGFTFHKYGMH | (SEQ ID NO: 88) |
| 1489 I13 | SGFTFHKYGMH | (SEQ ID NO: 88) |
| 1480 I08 | SGFTFHKYGMH | (SEQ ID NO: 88) |
| Consensus | SGFTFHKYGMH | (SEQ ID NO: 88) |

CDR2:

| | | |
|---|---|---|
| 1443 C16 | LISDDGMRKYHSDSMW | (SEQ ID NO: 89) |
| 1469 M23 | LISDDGMRKYHSDSMW | (SEQ ID NO: 89) |
| 1456 A12 | LISDDGMRKYHSDSMW | (SEQ ID NO: 89) |
| 1503 H05 | LISDDGMRKYHSDSMW | (SEQ ID NO: 89) |
| 1489 I13 | LISDDGMRKYHSNSMW | (SEQ ID NO: 98) |
| 1480 I08 | LISDDGMRKYHSDSMW | (SEQ ID NO: 89) |
| Consensus* | LISDDGMRKYHSXSMW | (SEQ ID NO: 91) |
| Variation1 | LISDDGMRKYHSDSMW | (SEQ ID NO: 89) |
| Variation2 | LISDDGMRKYHSNSMW | (SEQ ID NO: 98) |

*Wherein X is D or N, or wherein X is an amino acid with similar physical properties to either D or N.

CDR3:

| | | |
|---|---|---|
| 1443 C16 | EAGGPIWHDDVKYYDFNDGYYNYHYMDV | (SEQ ID NO: 6) |
| 1469 M23 | EAGGPIWHDDVKYYDFNDGYYNYHYMDV | (SEQ ID NO: 6) |
| 1456 A12 | EAGGPIWHDDVKYYDFNDGYYNYHYMDV | (SEQ ID NO: 6) |
| 1503 H05 | EAGGPIWHDDVKYYDFNDGYYNYHYMDV | (SEQ ID NO: 6) |
| 1489 I13 | EAGGPIWHDDVKYYDFNDGYYNYHYMDV | (SEQ ID NO: 6) |
| 1480 I08 | EAGGPIWHDDVKYYDFNDGYYNYHYMDV | (SEQ ID NO: 6) |
| Consensus | EAGGPIWHDDVKYYDFNDGYYNYHYMDV | (SEQ ID NO: 6) |

TABLE 14

Consensus protein sequences of Kabat CDRs of light chains of 1443 PG16 sister clones.

CDR1:

| | | |
|---|---|---|
| 1443 C16 | NGTSSDVGGFDSVS | (SEQ ID NO: 97) |
| 1469 M23 | NGTRSDVGGFDSVS | (SEQ ID NO: 92) |
| 1456 A12 | NGTSRDVGGFDSVS | (SEQ ID NO: 93) |
| 1503 H05 | NGTRSDVGGFDSVS | (SEQ ID NO: 92) |
| 1489 I13 | NGTSSDVGGFDSVS | (SEQ ID NO: 97) |
| 1480 I08 | NGTSSDVGGFDSVS | (SEQ ID NO: 97) |
| Consensus* | NGTX₁X₂DVGGEDSVS | (SEQ ID NO: 94) |
| Variation1 | NGTSSDVGGFDSVS | (SEQ ID NO: 97) |

TABLE 14 -continued

Consensus protein sequences of Kabat CDRs of light chains of 1443 PG16 sister clones.

| | | |
|---|---|---|
| Variation2 | NGTRSDVGGFDSVS | (SEQ ID NO: 92) |
| Variation3 | NGTSRDVGGFDSVS | (SEQ ID NO: 93) |

* Wherein X₁ is S or R, or wherein X₁ is an amino acid with similar physical properties to either S or R. Wherein X₂ is S or R, or wherein X₂ is an amino acid with similar physical properties to either S or R.

CDR2:

| | | |
|---|---|---|
| 1443 C16 | DVSHRPSG | (SEQ ID NO: 95) |
| 1469 M23 | DVSHRPSG | (SEQ ID NO: 95) |
| 1456 A12 | DVSHRPSG | (SEQ ID NO: 95) |
| 1503 H05 | DVSHRPSG | (SEQ ID NO: 95) |
| 1489 I13 | DVSHRPSG | (SEQ ID NO: 95) |
| 1408 I08 | DVSHRPSG | (SEQ ID NO: 95) |
| Consensus | DVSHRPSG | (SEQ ID NO: 95) |

CDR3:

| | | |
|---|---|---|
| 1443 C16 | SSLTDRSHRI | (SEQ ID NO: 41) |
| 1469 M23 | SSLTDRSHRI | (SEQ ID NO: 41) |
| 1456 A12 | SSLTDRSHRI | (SEQ ID NO: 41) |
| 1503 H05 | SSLTDRSHRI | (SEQ ID NO: 41) |
| 1489 I13 | SSLTDRSHRI | (SEQ ID NO: 41) |
| 1480 I08 | SSLTDRSHRI | (SEQ ID NO: 41) |
| Consensus | SSLTDRSHRI | (SEQ ID NO: 41) |

Monoclonal and recombinant antibodies are particularly useful in identification and purification of the individual polypeptides or other antigens against which they are directed. The antibodies of the invention have additional utility in that they may be employed as reagents in immunoassays, radioimmunoassays (MA) or enzyme-linked immunosorbent assays (ELISA). In these applications, the antibodies can be labeled with an analytically-detectable reagent such as a radioisotope, a fluorescent molecule or an enzyme. The antibodies may also be used for the molecular identification and characterization (epitope mapping) of antigens.

As mentioned above, the antibodies of the invention can be used to map the epitopes to which they bind. Applicants have discovered that the antibodies 1496_C09 (PG9), 1443_C16 (PG16), 1456_P20 (PG20), 1460_G14 (PGG14), 1495_C14 (PGC14), 1469_M23 (PG16), 1456_A12 (PG16), 1503_H05 (PG16), 1489_I13 (PG16), and 1080_I08 (PG16) neutralize HIV. Although the Applicant does not wish to be bound by this theory, it is postulated that the antibodies 1496_C09 (PG9), 1443_C16 (PG16), 1456_P20 (PG20), 1460_G14 (PGG14), 1495_C14 (PGC14), 1469_M23 (PG16), 1456_A12 (PG16), 1503_H05 (PG16), 1489_I13 (PG16), and/or 1080_I08 (PG16) bind to one or more conformational epitopes formed by HIV1-encoded proteins.

Neutralization activity of human monoclonal antibodies was tested against HIV-1 strains SF162 and JR-CSF. HIV-1 strains SF162 and JR-CSF both belong to HIV clade B. Each clonal monoclonal antibody was screened for neutralization activity and for anti-gp120, anti-gp41 and total IgG in quantitative ELISA. For the monoclonal antibodies 1456_P20, 1495_C14, and 1460_G14 anti-gp120 antigen-specific binding was detected. Neutralizing activity against SF162, but not JR-CSF was detected for 1456_P20 (PG20), 1495_C14 (PGC14), and 1460_G14 (PGG14). For the two monoclonal antibody preparations that did not show binding to gp120 in the ELISA assay, 1443_C16 (PG16) and 1496_C09 (PG9), high quantities of human IgG were determined to be present in the assay. However, 1443_C16 (PG16) and 1496_C09 (PG9) both were found to exhibit neutralizing activity against HIV-1 strain JR-CSF, but not against strain SF162. 1443_C16 (PG16) and 1496_C09 (PG9) also were found to lack gp41 binding activity in the ELISA assay.

The epitopes recognized by these antibodies may have a number of uses. The epitopes and mimotopes in purified or synthetic form can be used to raise immune responses (i.e. as a vaccine, or for the production of antibodies for other uses) or for screening patient serum for antibodies that immunoreact with the epitopes or mimotopes. Preferably, such an epitope or mimotope, or antigen comprising such an epitope or mimotope is used as a vaccine for raising an immune response. The antibodies of the invention can also be used in a method to monitor the quality of vaccines in particular to check that the antigen in a vaccine contains the correct immunogenic epitope in the correct conformation.

The epitopes may also be useful in screening for ligands that bind to said epitopes. Such ligands preferably block the epitopes and thus prevent infection. Such ligands are encompassed within the scope of the invention.

Standard techniques of molecular biology may be used to prepare DNA sequences coding for the antibodies or fragments of the antibodies of the present invention. Desired DNA sequences may be synthesized completely or in part using oligonucleotide synthesis techniques. Site-directed mutagenesis and polymerase chain reaction (PCR) techniques may be used as appropriate.

Any suitable host cell/vector system may be used for expression of the DNA sequences encoding the antibody molecules of the present invention or fragments thereof. Bacterial, for example E. coli, and other microbial systems may be used, in part, for expression of antibody fragments such as Fab and F(ab')$_2$ fragments, and especially Fv fragments and single chain antibody fragments, for example, single chain Fvs. Eukaryotic, e.g. mammalian, host cell expression systems may be used for production of larger antibody molecules, including complete antibody molecules. Suitable mammalian host cells include CHO, HEK293T, PER.C6, myeloma or hybridoma cells.

The present invention also provides a process for the production of an antibody molecule according to the present invention comprising culturing a host cell comprising a vector of the present invention under conditions suitable for leading to expression of protein from DNA encoding the antibody molecule of the present invention, and isolating the antibody molecule. The antibody molecule may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

Alternatively, antibodies according to the invention may be produced by i) expressing a nucleic acid sequence according to the invention in a cell, and ii) isolating the expressed antibody product. Additionally, the method may include iii) purifying the antibody. Transformed B cells are screened for those producing antibodies of the desired antigen specificity, and individual B cell clones can then be produced from the positive cells. The screening step may be carried out by ELISA, by staining of tissues or cells (including transfected cells), a neutralization assay or one of a number of other methods known in the art for identifying desired antigen specificity. The assay may select on the basis of simple antigen recognition, or may select on the additional basis of a desired function e.g. to select neutralizing antibodies rather than just antigen-binding antibodies, to select antibodies that can change characteristics of targeted cells, such as their signaling cascades, their shape, their growth rate, their capability of influencing other cells, their response to the influence by other cells or by other reagents or by a change in conditions, their differentiation status, etc.

The cloning step for separating individual clones from the mixture of positive cells may be carried out using limiting dilution, micromanipulation, single cell deposition by cell sorting or another method known in the art. Preferably the cloning is carried out using limiting dilution.

The immortalized B cell clones of the invention can be used in various ways e.g. as a source of monoclonal antibodies, as a source of nucleic acid (DNA or mRNA) encoding a monoclonal antibody of interest, for research, etc.

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., Sambrook, et al. Molecular Cloning: A Laboratory Manual (2nd Edition, 1989); Maniatis et al. Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984). The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

The following definitions are useful in understanding the present invention: The term "antibody" (Ab) as used herein includes monoclonal antibodies, polyclonal antibodies, multispecific antibodies (e.g., bispecific antibodies), and antibody fragments, as long as they exhibit the desired biological activity. The term "immunoglobulin" (Ig) is used interchangeably with "antibody" herein.

A "neutralizing antibody" may inhibit the entry of HIV-1 virus for example SF162 and/or JR-CSF with a neutralization index >1.5 or >2.0. (Kostrikis L G et al. J Virol. 1996; 70(1): 445-458.) By "broad and potent neutralizing antibodies" are meant antibodies that neutralize more than one HIV-1 virus species (from diverse clades and different strains within a clade) in a neutralization assay. A broad neutralizing antibody may neutralize at least 2, 3, 4, 5, 6, 7, 8, 9 or more different strains of HIV-1, the strains belonging to the same or different clades. A broad neutralizing antibody may neutralize multiple HIV-1 species belonging to at least 2, 3, 4, 5, or 6 different clades. The inhibitory concentration of the monoclonal antibody may be less than about 25 mg/ml to neutralize about 50% of the input virus in the neutralization assay.

An "isolated antibody" is one that has been separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, the antibody is purified: (1) to greater than 95% by weight of antibody as determined by the Lowry method, and most preferably more than 99% by weight; (2) to a degree sufficient to obtain at least 15 residues of N-terminal or internal amino acid sequence by use of a spinning cup sequenator; or (3) to homogeneity by SDS-PAGE under reducing or non-reducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The basic four-chain antibody unit is a heterotetrameric glycoprotein composed of two identical light (L) chains and two identical heavy (H) chains. An IgM antibody consists of 5 basic heterotetramer units along with an additional polypeptide called J chain, and therefore contain 10 antigen binding sites, while secreted IgA antibodies can polymerize to form polyvalent assemblages comprising 2-5 of the basic 4-chain units along with J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable region ($V_H$) followed by three constant domains ($C_H$) for each of the α and γ chains and four $C_H$ domains for μ and ε isotypes. Each L chain has at the N-terminus, a variable region ($V_L$) followed by a constant domain ($C_L$) at its other end. The $V_L$ is aligned with the $V_H$ and the $C_L$ is aligned with the first constant domain of the heavy chain ($C_H1$). Particular amino acid residues are believed to form an interface between the light chain and heavy chain variable regions. The pairing of a $V_H$ and $V_L$ together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, Conn., 1994, page 71, and Chapter 6.

The L chain from any vertebrate species can be assigned to one of two clearly distinct types, called kappa (κ) and lambda (λ), based on the amino acid sequences of their constant domains ($C_L$). Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated alpha (α), delta (δ)☐, epsilon (ε), gamma (γ☐) and mu (μ)☐, respectively. The γ and α classes are further divided into subclasses on the basis of relatively minor differences in $C_H$ sequence and function, e.g., humans express the following subclasses: IgG1, IgG2, IgG3, IgG4, IgA1, and IgA2.

The term "variable" refers to the fact that certain segments of the V domains differ extensively in sequence among antibodies. The V domain mediates antigen binding and defines specificity of a particular antibody for its particular antigen. However, the variability is not evenly distributed across the 110-amino acid span of the variable regions. Instead, the V regions consist of relatively invariant stretches called framework regions (FRs) of 15-30 amino acids separated by shorter regions of extreme variability called "hypervariable regions" that are each 9-12 amino acids long. The variable regions of native heavy and light chains each comprise four FRs, largely adopting a β-sheet configuration, connected by three hypervariable regions, which form loops connecting, and in some cases forming part of, the ☐β-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody that are responsible for antigen binding. The hypervariable region generally comprises amino acid residues from a "complementarity determining region" or "CDR" (e.g., around about residues 24-34 (L1), 50-56 (L2) and 89-97 (L3) in the $V_L$, and around about 31-35 (H1), 50-65 (H2) and 95-102 (H3) in the $V_H$ when numbered in accordance with the Kabat numbering system; Kabat et al., Sequences of Proteins of Immunological Interest, 5th Ed. Public Health Service, National Institutes of Health, Bethesda, Md. (1991)); and/or those residues from a "hypervariable loop" (e.g., residues 24-34 (L1), 50-56 (L2) and 89-97 (L3) in the $V_L$, and 26-32 (H1), 52-56 (H2) and 95-101 (H3) in the $V_H$ when numbered in accordance with the Chothia numbering system; Chothia and Lesk, J. Mol. Biol. 196:901-917 (1987)); and/or those residues from a "hypervariable loop"/CDR (e.g., residues 27-38 (L1), 56-65 (L2) and 105-120 (L3) in the $V_L$, and 27-38 (H1), 56-65 (H2) and 105-120 (H3) in the $V_H$ when numbered in accordance with the IMGT numbering system; Lefranc, M. P. et al. Nucl. Acids Res. 27:209-212 (1999), Ruiz, M. e al. Nucl. Acids Res. 28:219-221 (2000)). Optionally the antibody has symmetrical insertions at one or more of the following points 28, 36 (L1), 63, 74-75 (L2) and 123 (L3) in the $V_L$, and 28, 36 (H1), 63, 74-75 (H2) and 123 (H3) in the $V_H$ when numbered in accordance with AHo; Honneger, A. and Plunkthun, A. J. Mol. Biol. 309:657-670 (2001)).

By "germline nucleic acid residue" is meant the nucleic acid residue that naturally occurs in a germline gene encoding a constant or variable region. "Germline gene" is the DNA found in a germ cell (i.e., a cell destined to become an egg or in the sperm). A "germline mutation" refers to a heritable change in a particular DNA that has occurred in a germ cell or the zygote at the single-cell stage, and when transmitted to offspring, such a mutation is incorporated in every cell of the body. A germline mutation is in contrast to a somatic mutation which is acquired in a single body cell. In some cases, nucleotides in a germline DNA sequence encoding for a variable region are mutated (i.e., a somatic mutation) and replaced with a different nucleotide.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222: 581-597 (1991), for example.

In some aspects, the alternative EBV immortalization method described in WO2004/076677 is used. Using this method, B-cells producing the antibody of the invention can be transformed with EBV in the presence of a polyclonal B cell activator. Transformation with EBV is a standard technique and can easily be adapted to include polyclonal B cell activators. Additional stimulants of cellular growth and differentiation may be added during the transformation step to further enhance the efficiency. These stimulants may be cytokines such as IL-2 and IL-15. In a particularly preferred aspect, IL-2 is added during the immortalization step to further improve the efficiency of immortalization, but its use is not essential.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81:6851-6855 (1984)). The present invention provides variable region antigen-binding sequences derived from human antibodies. Accordingly, chimeric antibodies of primary interest herein include antibodies having one or more human antigen binding sequences (e.g., CDRs) and containing one or more sequences derived from a non-human antibody, e.g., an FR or C region sequence. In addition, chimeric antibodies of primary interest herein include those comprising a human variable region antigen binding sequence of one antibody class or subclass and another sequence, e.g., FR or C region sequence, derived from another antibody class or subclass. Chimeric antibodies of interest herein also include those containing variable region antigen-binding sequences related to those described herein or derived from a different species, such as a non-human primate (e.g., Old World Monkey, Ape, etc). Chimeric antibodies also include primatized and humanized antibodies.

Furthermore, chimeric antibodies may comprise residues that are not found in the recipient antibody or in the donor antibody. These modifications are made to further refine antibody performance. For further details, see Jones et al., Nature 321:522-525 (1986); Riechmann et al., Nature 332: 323-329 (1988); and Presta, Curr. Op. Struct. Biol. 2:593-596 (1992).

A "humanized antibody" is generally considered to be a human antibody that has one or more amino acid residues introduced into it from a source that is non-human. These non-human amino acid residues are often referred to as "import" residues, which are typically taken from an "import" variable region. Humanization is traditionally performed following the method of Winter and co-workers (Jones et al., Nature, 321:522-525 (1986); Reichmann et al., Nature, 332:323-327 (1988); Verhoeyen et al., Science, 239:1534-1536 (1988)), by substituting import hypervariable region sequences for the corresponding sequences of a human antibody. Accordingly, such "humanized" antibodies are chimeric antibodies (U.S. Pat. No. 4,816,567) wherein substantially less than an intact human variable region has been substituted by the corresponding sequence from a non-human species.

A "human antibody" is an antibody containing only sequences present in an antibody naturally produced by a human. However, as used herein, human antibodies may comprise residues or modifications not found in a naturally occurring human antibody, including those modifications and variant sequences described herein. These are typically made to further refine or enhance antibody performance.

An "intact" antibody is one that comprises an antigen-binding site as well as a $C_L$ and at least heavy chain constant domains, $C_H1$, $C_H2$ and $C_H3$. The constant domains may be native sequence constant domains (e.g., human native sequence constant domains) or amino acid sequence variant thereof. Preferably, the intact antibody has one or more effector functions.

An "antibody fragment" comprises a portion of an intact antibody, preferably the antigen binding or variable region of the intact antibody. Examples of antibody fragments include Fab, Fab', F(ab')$_2$, and Fv fragments; diabodies; linear antibodies (see U.S. Pat. No. 5,641,870; Zapata et al., Protein Eng. 8(10): 1057-1062 [1995]); single-chain antibody molecules; and multispecific antibodies formed from antibody fragments.

The phrase "functional fragment or analog" of an antibody is a compound having qualitative biological activity in common with a full-length antibody. For example, a functional fragment or analog of an anti-IgE antibody is one that can bind to an IgE immunoglobulin in such a manner so as to prevent or substantially reduce the ability of such molecule from having the ability to bind to the high affinity receptor, Fc$_\varepsilon$RT.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')2 fragment that roughly corresponds to two disulfide linked Fab fragments having divalent antigen-binding activity and is still capable of cross-linking antigen. Fab' fragments differ from Fab fragments by having additional few residues at the carboxy terminus of the $C_H1$ domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments that have hinge cysteines between them. Other chemical couplings of antibody fragments are also known.

The "Fc" fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment that contains a complete antigen-recognition and -binding site. This fragment consists of a dimer of one heavy- and one light-chain variable region domain in tight, non-covalent association. From the folding of these two domains emanate six hypervariable loops (three loops each from the H and L chain) that contribute the amino acid residues for antigen binding and confer antigen binding specificity to the antibody. However, even a single variable region (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains that enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the $V_H$ and $V_L$ domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993).

Domain antibodies (dAbs), which can be produced in fully human form, are the smallest known antigen-binding fragments of antibodies, ranging from 11 kDa to 15 kDa. dAbs are the robust variable regions of the heavy and light chains of immunoglobulins ($V_H$ and $V_L$ respectively). They are highly expressed in microbial cell culture, show favourable biophysical properties including solubility and temperature stability, and are well suited to selection and affinity maturation by in vitro selection systems such as phage display. dAbs are bioactive as monomers and, owing to their small size and inherent stability, can be formatted into larger molecules to create drugs with prolonged serum half-lives or other pharmacological activities. Examples of this technology have been described in WO9425591 for antibodies derived from Camelidae heavy chain Ig, as well as in US20030130496 describing the isolation of single domain fully human antibodies from phage libraries.

As used herein, an antibody that "internalizes" is one that is taken up by (i.e., enters) the cell upon binding to an antigen on a mammalian cell (e.g., a cell surface polypeptide or receptor). The internalizing antibody will of course include antibody fragments, human or chimeric antibody, and antibody conjugates. For certain therapeutic applications, internalization in vivo is contemplated. The number of antibody molecules internalized will be sufficient or adequate to kill a cell or inhibit its growth, especially an infected cell. Depending on the potency of the antibody or antibody conjugate, in some instances, the uptake of a single antibody molecule into the cell is sufficient to kill the target cell to which the antibody binds. For example, certain toxins are highly potent in killing such that internalization of one molecule of the toxin conjugated to the antibody is sufficient to kill the infected cell.

As used herein, an antibody is said to be "immunospecific," "specific for" or to "specifically bind" an antigen if it reacts at a detectable level with the antigen, preferably with an affinity constant, $K_a$, of greater than or equal to about $10^4$ $M^{-1}$, or greater than or equal to about $10^5$ $M^{-1}$, greater than or equal to about $10^6$ $M^{-1}$, greater than or equal to about $10^7$ $M^{-1}$, or greater than or equal to $10^8$ $M^{-1}$. Affinity of an antibody for its cognate antigen is also commonly expressed as a dissociation constant $K_D$, and in certain embodiments, HIV1 antibody specifically binds to an HIV1 polypeptide if it binds with a $K_D$ of less than or equal to $10^{-4}$ M, less than or equal to about $10^{-5}$ M, less than or equal to about $10^{-6}$ M, less than or equal to $10^{-7}$ M, or less than or equal to $10^{-8}$ M. Affinities of antibodies can be readily determined using conventional techniques, for example, those described by Scatchard et al. (Ann. N.Y. Acad. Sci. USA 51:660 (1949)).

Binding properties of an antibody to antigens, cells or tissues thereof may generally be determined and assessed using immunodetection methods including, for example, immunofluorescence-based assays, such as immuno-histo-chemistry (IHC) and/or fluorescence-activated cell sorting (FACS).

An antibody having a "biological characteristic" of a designated antibody is one that possesses one or more of the biological characteristics of that antibody which distinguish it from other antibodies. For example, in certain embodiments, an antibody with a biological characteristic of a designated antibody will bind the same epitope as that bound by the designated antibody and/or have a common effector function as the designated antibody.

The term "antagonist" antibody is used in the broadest sense, and includes an antibody that partially or fully blocks, inhibits, or neutralizes a biological activity of an epitope, polypeptide, or cell that it specifically binds. Methods for identifying antagonist antibodies may comprise contacting a polypeptide or cell specifically bound by a candidate antagonist antibody with the candidate antagonist antibody and measuring a detectable change in one or more biological activities normally associated with the polypeptide or cell.

An "antibody that inhibits the growth of infected cells" or a "growth inhibitory" antibody is one that binds to and results in measurable growth inhibition of infected cells expressing or capable of expressing an HIV1 epitope bound by an antibody. Preferred growth inhibitory antibodies inhibit growth of infected cells by greater than 20%, preferably from about 20% to about 50%, and even more preferably, by greater than 50% (e.g., from about 50% to about 100%) as compared to the appropriate control, the control typically being infected cells not treated with the antibody being tested. Growth inhibition can be measured at an antibody concentration of about 0.1 to 30 µg/ml or about 0.5 nM to 200 nM in cell culture, where the growth inhibition is determined 1-10 days after exposure of the infected cells to the antibody. Growth inhibition of infected cells in vivo can be determined in various ways known in the art.

The antibody is growth inhibitory in vivo if administration of the antibody at about 1 µg/kg to about 100 mg/kg body weight results in reduction the percent of infected cells or total number of infected cells within about 5 days to 3 months from the first administration of the antibody, preferably within about 5 to 30 days.

An antibody that "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). Preferably the cell is an infected cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody that induces apoptosis is one that results in about 2 to 50 fold, preferably about 5 to 50 fold, and most preferably about 10 to 50 fold, induction of annexin binding relative to untreated cell in an annexin binding assay.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

"Antibody-dependent cell-mediated cytotoxicity" or "ADCC" refers to a form of cytotoxicity in which secreted Ig bound to Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are required for such killing. The primary cells for mediating ADCC, NK cells, express FcγRIII only, whereas monocytes express FcγRI, FcγRII and FcγRIII. FcR expression on hematopoietic cells is summarized in FIG. 22 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al., *Proc. Natl. Acad. Sci.* (USA) 95:652-656 (1998).

"Fc receptor" or "FcR" describes a receptor that binds to the Fc region of an antibody. In certain embodiments, the FcR is a native sequence human FcR. Moreover, a preferred FcR is one that binds an IgG antibody (a gamma receptor) and includes receptors of the FcγRI, FcγRII, and FcγRIII subclasses, including allelic variants and alternatively spliced forms of these receptors. FCγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daeron, Annu. Rev. Immunol. 15:203-234 (1997)). FcRs are reviewed in Ravetch and Kinet, Annu. Rev. Immunol 9:457-92 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976) and Kim et al., J. Immunol. 24:249 (1994)).

"Human effector cells" are leukocytes that express one or more FcRs and perform effector functions. Preferably, the cells express at least FcγRIII and perform ADCC effector function. Examples of human leukocytes that mediate ADCC include PBMC, NK cells, monocytes, cytotoxic T cells and neutrophils; with PBMCs and NK cells being preferred. The effector cells may be isolated from a native source, e.g., from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) that are bound to their cognate antigen. To assess complement activation, a CDC assay, e.g., as described in Gazzano-Santoro et al., J. Immunol. Methods 202:163 (1996), may be performed.

A "mammal" for purposes of treating an infection, refers to any mammal, including humans, domestic and farm animals, and zoo, sports, or pet animals, such as dogs, cats, cattle, horses, sheep, pigs, goats, rabbits, etc. Preferably, the mammal is human.

"Treating" or "treatment" or "alleviation" refers to both therapeutic treatment and prophylactic or preventative measures; wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for an infection if, after receiving a therapeutic amount of an antibody according to the methods of the present invention, the patient shows observable and/or measurable reduction in or absence of one or more of the following: reduction in the number of infected cells or absence of the infected cells; reduction in the percent of total cells that are infected; and/or relief to some extent, one or more of the symptoms associated with the specific infection; reduced morbidity and mortality, and improvement in quality of life issues. The above parameters for assessing successful treatment and improvement in the disease are readily measurable by routine procedures familiar to a physician.

The term "therapeutically effective amount" refers to an amount of an antibody or a drug effective to "treat" a disease or disorder in a subject or mammal. See preceding definition of "treating."

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

Administration "in combination with" one or more further therapeutic agents includes simultaneous (concurrent) and consecutive administration in any order.

"Carriers" as used herein include pharmaceutically acceptable carriers, excipients, or stabilizers that are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ polyethylene glycol (PEG), and PLURONICS™.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below.

A "growth inhibitory agent" when used herein refers to a compound or composition which inhibits growth of a cell, either in vitro or in vivo. Examples of growth inhibitory agents include agents that block cell cycle progression, such as agents that induce G1 arrest and M-phase arrest. Classical M-phase blockers include the vinca alkaloids (vincristine, vinorelbine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (W B Saunders: Philadelphia, 1995), especially p. 13. The taxanes (paclitaxel and docetaxel) are anticancer drugs both derived from the yew tree. Docetaxel (TAXOTERE™, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Label" as used herein refers to a detectable compound or composition that is conjugated directly or indirectly to the antibody so as to generate a "labeled" antibody. The label may be detectable by itself (e.g., radioisotope labels or fluorescent labels) or, in the case of an enzymatic label, may catalyze chemical alteration of a substrate compound or composition that is detectable.

The term "epitope tagged" as used herein refers to a chimeric polypeptide comprising a polypeptide fused to a "tag polypeptide." The tag polypeptide has enough residues to provide an epitope against which an antibody can be made, yet is short enough such that it does not interfere with activity of the polypeptide to which it is fused. The tag polypeptide is also preferably fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

A "small molecule" is defined herein to have a molecular weight below about 500 Daltons.

The terms "nucleic acid" and "polynucleotide" are used interchangeably herein to refer to single- or double-stranded RNA, DNA, or mixed polymers. Polynucleotides may include genomic sequences, extra-genomic and plasmid sequences, and smaller engineered gene segments that express, or may be adapted to express polypeptides.

An "isolated nucleic acid" is a nucleic acid that is substantially separated from other genome DNA sequences as well as proteins or complexes such as ribosomes and polymerases, which naturally accompany a native sequence. The term embraces a nucleic acid sequence that has been removed from its naturally occurring environment, and includes recombinant or cloned DNA isolates and chemically synthesized analogues or analogues biologically synthesized by heterologous systems. A substantially pure nucleic acid includes isolated forms of the nucleic acid. Of course, this refers to the nucleic acid as originally isolated and does not exclude genes or sequences later added to the isolated nucleic acid by the hand of man.

The term "polypeptide" is used in its conventional meaning, i.e., as a sequence of amino acids. The polypeptides are not limited to a specific length of the product. Peptides, oligopeptides, and proteins are included within the definition of polypeptide, and such terms may be used interchangeably herein unless specifically indicated otherwise. This term also does not refer to or exclude post-expression modifications of the polypeptide, for example, glycosylations, acetylations, phosphorylations and the like, as well as other modifications known in the art, both naturally occurring and non-naturally occurring. A polypeptide may be an entire protein, or a subsequence thereof. Particular polypeptides of interest in the context of this invention are amino acid subsequences comprising CDRs and being capable of binding an antigen or HIV-infected cell.

An "isolated polypeptide" is one that has been identified and separated and/or recovered from a component of its natural environment. In preferred embodiments, the isolated polypeptide will be purified (1) to greater than 95% by weight of polypeptide as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or, preferably, silver stain. Isolated polypeptide includes the polypeptide in situ within recombinant cells since at least one component of the polypeptide's natural environment will not be present. Ordinarily, however, isolated polypeptide will be prepared by at least one purification step.

A "native sequence" polynucleotide is one that has the same nucleotide sequence as a polynucleotide derived from nature. A "native sequence" polypeptide is one that has the same amino acid sequence as a polypeptide (e.g., antibody)

derived from nature (e.g., from any species). Such native sequence polynucleotides and polypeptides can be isolated from nature or can be produced by recombinant or synthetic means.

A polynucleotide "variant," as the term is used herein, is a polynucleotide that typically differs from a polynucleotide specifically disclosed herein in one or more substitutions, deletions, additions and/or insertions. Such variants may be naturally occurring or may be synthetically generated, for example, by modifying one or more of the polynucleotide sequences of the invention and evaluating one or more biological activities of the encoded polypeptide as described herein and/or using any of a number of techniques well known in the art.

A polypeptide "variant," as the term is used herein, is a polypeptide that typically differs from a polypeptide specifically disclosed herein in one or more substitutions, deletions, additions and/or insertions. Such variants may be naturally occurring or may be synthetically generated, for example, by modifying one or more of the above polypeptide sequences of the invention and evaluating one or more biological activities of the polypeptide as described herein and/or using any of a number of techniques well known in the art.

Modifications may be made in the structure of the polynucleotides and polypeptides of the present invention and still obtain a functional molecule that encodes a variant or derivative polypeptide with desirable characteristics. When it is desired to alter the amino acid sequence of a polypeptide to create an equivalent, or even an improved, variant or portion of a polypeptide of the invention, one skilled in the art will typically change one or more of the codons of the encoding DNA sequence.

For example, certain amino acids may be substituted for other amino acids in a protein structure without appreciable loss of its ability to bind other polypeptides (e.g., antigens) or cells. Since it is the binding capacity and nature of a protein that defines that protein's biological functional activity, certain amino acid sequence substitutions can be made in a protein sequence, and, of course, it's underlying DNA coding sequence, and nevertheless obtain a protein with like properties. It is thus contemplated that various changes may be made in the peptide sequences of the disclosed compositions, or corresponding DNA sequences that encode said peptides without appreciable loss of their biological utility or activity.

In many instances, a polypeptide variant will contain one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity. U.S. Pat. No. 4,554,101 states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

Polypeptides may comprise a signal (or leader) sequence at the N-terminal end of the protein, which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

When comparing polynucleotide and polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogenes pp. 626-645 *Methods in Enzymology* vol. 183, Academic Press, Inc., San Diego, Calif.; Higgins, D. G. and Sharp, P. M. (1989) CABIOS 5:151-153; Myers, E. W. and Muller W. (1988) CABIOS 4:11-17; Robinson, E. D. (1971) *Comb. Theor* 11:105; Santou, N. Nes, M. (1987) *Mol. Biol. Evol.* 4:406-425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) *Proc. Natl. Acad., Sci.* USA 80:726-730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J Mol. Biol.* 48:443, by the search for similarity methods of Pearson and Lipman (1988) *Proc. Natl. Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al. (1977) *Nucl. Acids Res.* 25:3389-3402 and Altschul et al. (1990) *J Mol. Biol.* 215:403-410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information.

In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) Proc. Natl. Acad. Sci. USA 89:10915) alignments, (B) of 50, expectation (E) of 10, M=5, N=−4 and a comparison of both strands.

For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one approach, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residues occur in both sequences to yield the number of matched positions, dividing the number of matched positions by the total number of positions in the reference sequence (i.e., the window size) and multiplying the results by 100 to yield the percentage of sequence identity.

"Homology" refers to the percentage of residues in the polynucleotide or polypeptide sequence variant that are identical to the non-variant sequence after aligning the sequences and introducing gaps, if necessary, to achieve the maximum percent homology. In particular embodiments, polynucleotide and polypeptide variants have at least 70%, at least 75%, at least 80%, at least 90%, at least 95%, at least 98%, or at least 99% polynucleotide or polypeptide homology with a polynucleotide or polypeptide described herein.

"Vector" includes shuttle and expression vectors. Typically, the plasmid construct will also include an origin of replication (e.g., the ColE1 origin of replication) and a selectable marker (e.g., ampicillin or tetracycline resistance), for replication and selection, respectively, of the plasmids in bacteria. An "expression vector" refers to a vector that contains the necessary control sequences or regulatory elements for expression of the antibodies including antibody fragment of the invention, in bacterial or eukaryotic cells. Suitable vectors are disclosed below. As used in this specification and the appended claims, the singular forms "a," "an" and "the" include plural references unless the content clearly dictates otherwise.

The invention also includes nucleic acid sequences encoding part or all of the light and heavy chains and CDRs of the present invention. Due to redundancy of the genetic code, variants of these sequences will exist that encode the same amino acid sequences.

Variant antibodies are also included within the scope of the invention. Thus, variants of the sequences recited in the application are also included within the scope of the invention. Further variants of the antibody sequences having improved affinity may be obtained using methods known in the art and are included within the scope of the invention. For example, amino acid substitutions may be used to obtain antibodies with further improved affinity. Alternatively, codon optimization of the nucleotide sequence may be used to improve the efficiency of translation in expression systems for the production of the antibody.

Preferably, such variant antibody sequences will share 70% or more (i.e. 80, 85, 90, 95, 97, 98, 99% or more) sequence identity with the sequences recited in the application. Preferably such sequence identity is calculated with regard to the full length of the reference sequence (i.e. the sequence recited in the application). Preferably, percentage identity, as referred to herein, is as determined using BLAST version 2.1.3 using the default parameters specified by the NCBI [Blosum 62 matrix; gap open penalty=11 and gap extension penalty=1].

Further included within the scope of the invention are vectors such as expression vectors, comprising a nucleic acid sequence according to the invention. Cells transformed with such vectors are also included within the scope of the invention.

As will be understood by the skilled artisan, general description of antibodies herein and methods of preparing and using the same also apply to individual antibody polypeptide constituents and antibody fragments.

The antibodies of the present invention may be polyclonal or monoclonal antibodies. However, in preferred embodiments, they are monoclonal. In particular embodiments, antibodies of the present invention are human antibodies. Methods of producing polyclonal and monoclonal antibodies are known in the art and described generally, e.g., in U.S. Pat. No. 6,824,780.

Typically, the antibodies of the present invention are produced recombinantly, using vectors and methods available in the art, as described further below. Human antibodies may also be generated by in vitro activated B cells (see U.S. Pat. Nos. 5,567,610 and 5,229,275).

Human antibodies may also be produced in transgenic animals (e.g., mice) that are capable of producing a full repertoire of human antibodies in the absence of endogenous immunoglobulin production. For example, it has been described that the homozygous deletion of the antibody heavy-chain joining region (JO gene in chimeric and germline mutant mice results in complete inhibition of endogenous antibody production. Transfer of the human germ-line immunoglobulin gene array into such germ-line mutant mice results in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggemann et al., Year in Immuno., 7:33 (1993); U.S. Pat. Nos. 5,545,806, 5,569,825, 5,591,669 (all of GenPharm); U.S. Pat. No. 5,545,807; and WO 97/17852. Such animals may be genetically engineered to produce human antibodies comprising a polypeptide of the present invention.

In certain embodiments, antibodies of the present invention are chimeric antibodies that comprise sequences derived from both human and non-human sources. In particular embodiments, these chimeric antibodies are humanized or Primatized™. In practice, humanized antibodies are typically human antibodies in which some hypervariable region residues and possibly some FR residues are substituted by residues from analogous sites in rodent antibodies.

In the context of the present invention, chimeric antibodies also include human antibodies wherein the human hypervariable region or one or more CDRs are retained, but one or more other regions of sequence have been replaced by corresponding sequences from a non-human animal.

The choice of non-human sequences, both light and heavy, to be used in making the chimeric antibodies is important to reduce antigenicity and human anti-non-human antibody responses when the antibody is intended for human therapeutic use. It is further important that chimeric antibodies retain high binding affinity for the antigen and other favorable biological properties. To achieve this goal, according to a preferred method, chimeric antibodies are prepared by a process of analysis of the parental sequences and various conceptual chimeric products using three-dimensional models of the parental human and non-human sequences. Three-dimensional immunoglobulin models are commonly available and are familiar to those skilled in the art. Computer programs are available which illustrate and display probable three-dimensional conformational structures of selected candidate immunoglobulin sequences.

Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

As noted above, antibodies (or immunoglobulins) can be divided into five different classes, based on differences in the amino acid sequences in the constant region of the heavy chains. All immunoglobulins within a given class have very similar heavy chain constant regions. These differences can be detected by sequence studies or more commonly by serological means (i.e. by the use of antibodies directed to these differences). Antibodies, or fragments thereof, of the present invention may be any class, and may, therefore, have a gamma, mu, alpha, delta, or epsilon heavy chain. A gamma chain may be gamma 1, gamma 2, gamma 3, or gamma 4; and an alpha chain may be alpha 1 or alpha 2.

In a preferred embodiment, an antibody of the present invention, or fragment thereof, is an IgG. IgG is considered the most versatile immunoglobulin, because it is capable of carrying out all of the functions of immunoglobulin molecules. IgG is the major Ig in serum, and the only class of Ig that crosses the placenta. IgG also fixes complement, although the IgG4 subclass does not. Macrophages, monocytes, PMN's and some lymphocytes have Fc receptors for the Fc region of IgG. Not all subclasses bind equally well; IgG2 and IgG4 do not bind to Fc receptors. A consequence of binding to the Fc receptors on PMN's, monocytes and macrophages is that the cell can now internalize the antigen better. IgG is an opsonin that enhances phagocytosis. Binding of IgG to Fc receptors on other types of cells results in the activation of other functions. Antibodies of the present invention may be of any IgG subclass.

In another preferred embodiment, an antibody, or fragment thereof, of the present invention is an IgE. IgE is the least common serum Ig since it binds very tightly to Fc receptors on basophils and mast cells even before interacting with antigen. As a consequence of its binding to basophils and mast cells, IgE is involved in allergic reactions. Binding of the allergen to the IgE on the cells results in the release of various pharmacological mediators that result in allergic symptoms. IgE also plays a role in parasitic helminth diseases. Eosinophils have Fc receptors for IgE and binding of eosinophils to IgE-coated helminths results in killing of the parasite. IgE does not fix complement.

In various embodiments, antibodies of the present invention, and fragments thereof, comprise a variable light chain that is either kappa or lambda. The lamba chain may be any of subtype, including, e.g., lambda 1, lambda 2, lambda 3, and lambda 4.

As noted above, the present invention further provides antibody fragments comprising a polypeptide of the present invention. In certain circumstances there are advantages of using antibody fragments, rather than whole antibodies. For example, the smaller size of the fragments allows for rapid clearance, and may lead to improved access to certain tissues, such as solid tumors. Examples of antibody fragments include: Fab, Fab', F(ab')2 and Fv fragments; diabodies; linear antibodies; single-chain antibodies; and multispecific antibodies formed from antibody fragments.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from E. coli, thus allowing the facile production of large amounts of these fragments. Fab'-SH fragments can be directly recovered from E. coli and chemically coupled to form F(ab')2 fragments (Carter et al., Bio/Technology 10:163-167 (1992)). According to another approach, F(ab')2 fragments can be isolated directly from recombinant host cell culture. Fab and F(ab')2 fragment with increased in vivo half-life comprising a salvage receptor binding epitope residues are described in U.S. Pat. No. 5,869,046. Other techniques for the production of antibody fragments will be apparent to the skilled practitioner.

In other embodiments, the antibody of choice is a single chain Fv fragment (scFv). See WO 93/16185; U.S. Pat. Nos. 5,571,894; and 5,587,458. Fv and sFv are the only species with intact combining sites that are devoid of constant regions. Thus, they are suitable for reduced nonspecific binding during in vivo use. sFv fusion proteins may be constructed to yield fusion of an effector protein at either the amino or the carboxy terminus of an sFv. See Antibody Engineering, ed. Borrebaeck, supra. The antibody fragment may also be a "linear antibody", e.g., as described in U.S. Pat. No. 5,641,870 for example. Such linear antibody fragments may be monospecific or bispecific.

In certain embodiments, antibodies of the present invention are bispecific or multispecific. Bispecific antibodies are antibodies that have binding specificities for at least two different epitopes. Exemplary bispecific antibodies may bind to two different epitopes of a single antigen. Other such antibodies may combine a first antigen binding site with a binding site for a second antigen. Alternatively, an anti-HIV1 arm may be combined with an arm that binds to a triggering molecule on a leukocyte, such as a T-cell receptor molecule (e.g., CD3), or Fc receptors for IgG (FcγR), such as FcγRI (CD64), FcγRII (CD32) and FcγRIII (CD16), so as to focus and localize cellular defense mechanisms to the infected cell. Bispecific antibodies may also be used to localize cytotoxic agents to infected cells. These antibodies possess an HIV1-binding arm and an arm that binds the cytotoxic agent (e.g., saporin, anti-interferon-α, vinca alkaloid, ricin A chain, methotrexate or radioactive isotope hapten). Bispecific antibodies can be prepared as full length antibodies or antibody fragments (e.g., F(ab')2 bispecific antibodies). WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcα antibody is shown in WO98/02463. U.S. Pat. No. 5,821,337 teaches a bispecific anti-ErbB2/anti-CD3 antibody.

Methods for making bispecific antibodies are known in the art. Traditional production of full length bispecific antibodies is based on the co-expression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of ten different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J 10:3655-3659 (1991).

According to a different approach, antibody variable regions with the desired binding specificities (antibody-antigen combining sites) are fused to immunoglobulin constant domain sequences. Preferably, the fusion is with an Ig heavy chain constant domain, comprising at least part of the hinge, $C_H2$, and $C_H3$ regions. It is preferred to have the first heavy-chain constant region ($C_H1$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121:210 (1986).

According to another approach described in U.S. Pat. No. 5,731,168, the interface between a pair of antibody molecules can be engineered to maximize the percentage of heterodimers that are recovered from recombinant cell culture. The preferred interface comprises at least a part of the $C_H3$ domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine).

This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229: 81 (1985) describe a procedure wherein intact antibodies are proteolytically cleaved to generate F(ab')2 fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from E. coli, which can be chemically coupled to form bispecific antibodies. Shalaby et al., J. Exp. Med., 175: 217-225 (1992) describe the production of a humanized bispecific antibody F(ab')2 molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol., 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90:6444-6448 (1993) has provided an alternative mechanism for making bispecific antibody fragments. The fragments comprise a $V_H$ connected to a $V_L$ by a linker that is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., J. Immunol., 152:5368 (1994).

Antibodies with more than two valencies are contemplated. For example, trispecific antibodies can be prepared. Tutt et al., J. Immunol. 147: 60 (1991). A multivalent antibody may be internalized (and/or catabolized) faster than a bivalent antibody by a cell expressing an antigen to which the antibodies bind. The antibodies of the present invention can be multivalent antibodies with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable regions. For instance, the polypeptide chain(s) may comprise VD1-$(X1)_n$-VD2-$(X2)_n$-Fc, wherein VD1 is a first variable region, VD2 is a second variable region, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable region polypeptides. The multivalent antibody herein may, for instance, comprise from about two to about eight light chain variable region polypeptides. The light chain variable region polypeptides contemplated here comprise a light chain variable region and, optionally, further comprise a $C_L$ domain.

Antibodies of the invention further include single chain antibodies. In particular embodiments, antibodies of the invention are internalizing antibodies.

Amino acid sequence modification(s) of the antibodies described herein are contemplated. For example, it may be desirable to improve the binding affinity and/or other biological properties of the antibody. Amino acid sequence variants of the antibody may be prepared by introducing appropriate nucleotide changes into a polynucleotide that encodes the antibody, or a chain thereof, or by peptide synthesis. Such modifications include, for example, deletions from, and/or insertions into and/or substitutions of, residues within the amino acid sequences of the antibody. Any combination of deletion, insertion, and substitution may be made to arrive at the final antibody, provided that the final construct possesses the desired characteristics. The amino acid changes also may alter post-translational processes of the antibody, such as changing the number or position of glycosylation sites. Any of the variations and modifications described above for polypeptides of the present invention may be included in antibodies of the present invention.

A useful method for identification of certain residues or regions of an antibody that are preferred locations for mutagenesis is called "alanine scanning mutagenesis" as described by Cunningham and Wells in Science, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with PSCA antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed anti-antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of an antibody include the fusion to the N- or C-terminus of the antibody to an enzyme (e.g., for ADEPT) or a polypeptide that increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative and non-conservative substitutions are contemplated.

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

One type of substitutional variant involves substituting one or more hypervariable region residues of a parent antibody. Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and an antigen or infected cell. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

The antibody of the invention is modified with respect to effector function, e.g., so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med. 176:1191-1195 (1992) and Shopes, B. J. Immunol. 148:2918-2922 (1992). Homodimeric antibodies with enhanced anti-infection activity may also be prepared using heterobifunctional cross-linkers as described in Wolff et al., Cancer Research 53:2560-2565 (1993). Alternatively, an antibody can be engineered which has dual Fc regions and may thereby have enhanced complement lysis and ADCC capabilities. See Stevenson et al., Anti-Cancer Drug Design 3:219-230 (1989). To increase the serum half-life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule.

Antibodies of the present invention may also be modified to include an epitope tag or label, e.g., for use in purification or diagnostic applications. The invention also pertains to therapy with immunoconjugates comprising an antibody conjugated to an anti-cancer agent such as a cytotoxic agent or a growth inhibitory agent. Chemotherapeutic agents useful in the generation of such immunoconjugates have been described above.

Conjugates of an antibody and one or more small molecule toxins, such as a calicheamicin, maytansinoids, a trichothene, and CC1065, and the derivatives of these toxins that have toxin activity, are also contemplated herein.

In one preferred embodiment, an antibody (full length or fragments) of the invention is conjugated to one or more maytansinoid molecules. Maytansinoids are mitototic inhibitors that act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

In an attempt to improve their therapeutic index, maytansine and maytansinoids have been conjugated to antibodies specifically binding to tumor cell antigens. Immunoconjugates containing maytansinoids and their therapeutic use are disclosed, for example, in U.S. Pat. Nos. 5,208,020, 5,416,064 and European Patent EP 0 425 235 B1. Liu et al., Proc. Natl. Acad. Sci. USA 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay.

Antibody-maytansinoid conjugates are prepared by chemically linking an antibody to a maytansinoid molecule without significantly diminishing the biological activity of either the antibody or the maytansinoid molecule. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody conjugates, including, for example, those disclosed in U.S. Pat. No. 5,208,020 or EP Patent 0 425 235 B1, and Chari et al., Cancer Research 52: 127-131 (1992). The linking groups include disufide groups, thioether groups, acid labile groups, photolabile groups, peptidase labile groups, or esterase labile groups, as disclosed in the above-identified patents, disulfide and thioether groups being preferred.

Immunoconjugates may be made using a variety of bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio)propionate (SPDP) (Carlsson et al., Biochem. J. 173:723-737 [1978]) and N-succinimidyl-4-(2-pyridylthio)pentanoate (SPP) to provide for a disulfide linkage. For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, Cancer Research 52: 127-131 (1992); U.S. Pat. No. 5,208,020) may be used.

Another immunoconjugate of interest comprises an antibody conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714, 586, 5,739,116, 5,767,285, 5,770,701, 5,770,710, 5,773,001, 5,877,296 (all to American Cyanamid Company). Another drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Examples of other agents that can be conjugated to the antibodies of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof that can be used include, e.g., diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes. See, for example, WO 93/21232.

The present invention further includes an immunoconjugate formed between an antibody and a compound with nucleolytic activity (e.g., a ribonuclease or a DNA endonuclease such as a deoxyribonuclease; DNase).

For selective destruction of infected cells, the antibody includes a highly radioactive atom. A variety of radioactive isotopes are available for the production of radioconjugated anti-PSCA antibodies. Examples include $At^{211}$, $I^{131}$, $I^{125}$, $Y^{90}$, $Re^{186}$, $Rc^{188}$, $Sm^{153}$, $Bi^{212}$, $P^{32}$, $Pb^{212}$ and radioactive isotopes of Lu. When the conjugate is used for diagnosis, it may comprise a radioactive atom for scintigraphic studies, for example $tc^{99m}$ or $I^{123}$, or a spin label for nuclear magnetic resonance (NMR) imaging (also known as magnetic resonance imaging, mri), such as iodine-123, iodine-131, indium-111, fluorine-19, carbon-13, nitrogen-15, oxygen-17, gadolinium, manganese or iron.

The radio- or other label is incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al. (1978) Biochem. Biophys. Res. Commun. 80: 49-57 can be used to incorporate iodine-123. "Monoclonal Antibodies in Immunoscintigraphy" (Chatal, CRC Press 1989) describes other methods in detail.

Alternatively, a fusion protein comprising the antibody and cytotoxic agent is made, e.g., by recombinant techniques or peptide synthesis. The length of DNA may comprise respective regions encoding the two portions of the conjugate either adjacent one another or separated by a region encoding a linker peptide which does not destroy the desired properties of the conjugate. The antibodies of the present invention are also used in antibody dependent enzyme mediated prodrug therapy (ADET) by conjugating the antibody to a prodrug-activating enzyme which converts a prodrug (e.g., a peptidyl chemotherapeutic agent, see WO81/01145) to an active anti-cancer drug (see, e.g., WO 88/07378 and U.S. Pat. No. 4,975,278).

The enzyme component of the immunoconjugate useful for ADEPT includes any enzyme capable of acting on a prodrug in such a way so as to covert it into its more active, cytotoxic form. Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as *serratia* protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, Nature 328: 457-458 (1987)). Antibody-abzyme conjugates can be prepared as described herein for delivery of the abzyme to a infected cell population.

The enzymes of this invention can be covalently bound to the antibodies by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., Nature, 312: 604-608 (1984).

Other modifications of the antibody are contemplated herein. For example, the antibody may be linked to one of a variety of nonproteinaceous polymers, e.g., polyethylene glycol, polypropylene glycol, polyoxyalkylenes, or copolymers of polyethylene glycol and polypropylene glycol. The antibody also may be entrapped in microcapsules prepared, for example, by coacervation techniques or by interfacial polymerization (for example, hydroxymethylcellulose or gelatin-microcapsules and poly-(methylmethacylate)microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, 16th edition, Oslo, A., Ed., (1980).

The antibodies disclosed herein are also formulated as immunoliposomes. A "liposome" is a small vesicle composed of various types of lipids, phospholipids and/or surfactant that is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al., Proc. Natl. Acad. Sci. USA, 82:3688 (1985); Hwang et al., Proc. Natl Acad. Sci. USA, 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired a diameter. Fab' fragments of the antibody of the present invention can be conjugated to the liposomes as described in Martin et al., J. Biol. Chem. 257: 286-288 (1982) via a disulfide interchange reaction. A chemotherapeutic agent is optionally contained within the liposome. See Gabizon et al., J. National Cancer Inst. 81(19)1484 (1989). Antibodies of the present invention, or fragments thereof, may possess any of a variety of biological or functional characteristics. In certain embodiments, these antibodies are HIV1 protein specific antibodies, indicating that they specifically bind to or preferentially bind to HIV1 as compared to a normal control cell.

In particular embodiments, an antibody of the present invention is an antagonist antibody, which partially or fully blocks or inhibits a biological activity of a polypeptide or cell to which it specifically or preferentially binds. In other embodiments, an antibody of the present invention is a growth inhibitory antibody, which partially or fully blocks or inhibits the growth of an infected cell to which it binds. In another embodiment, an antibody of the present invention induces apoptosis. In yet another embodiment, an antibody of the present invention induces or promotes antibody-dependent cell-mediated cytotoxicity or complement dependent cytotoxicity.

HIV1-expressing cells or virus described above are used to screen the biological sample obtained from a patient infected with HIV1 for the presence of antibodies that preferentially bind to the cell expressing HIV1 polypeptides using standard biological techniques. For example, in certain embodiments, the antibodies may be labeled, and the presence of label associated with the cell detected, e.g., using FMAT or FACs analysis. In particular embodiments, the biological sample is blood, serum, plasma, bronchial lavage, or saliva. Methods of the present invention may be practiced using high throughput techniques.

Identified human antibodies may then be characterized further. For example the particular conformational epitopes with in the HIV1 polypeptides that are necessary or sufficient for binding of the antibody may be determined, e.g., using site-directed mutagenesis of expressed HIV1 polypeptides. These methods may be readily adapted to identify human antibodies that bind any protein expressed on a cell surface. Furthermore, these methods may be adapted to determine binding of the antibody to the virus itself, as opposed to a cell expressing recombinant HIV1 or infected with the virus.

Polynucleotide sequences encoding the antibodies, variable regions thereof, or antigen-binding fragments thereof may be subcloned into expression vectors for the recombinant production of human anti-HIV1 antibodies. In one embodiment, this is accomplished by obtaining mononuclear cells from the patient from the serum containing the identified HIV1 antibody was obtained; producing B cell clones from the mononuclear cells; inducing the B cells to become antibody-producing plasma cells; and screening the supernatants produced by the plasma cells to determine if it contains the HIV1 antibody. Once a B cell clone that produces an HIV1 antibody is identified, reverse-transcription polymerase chain reaction (RT-PCR) is performed to clone the DNAs encoding the variable regions or portions thereof of the HIV1 antibody. These sequences are then subcloned into expression vectors suitable for the recombinant production of human HIV1 antibodies. The binding specificity may be confirmed by determining the recombinant antibody's ability to bind cells expressing HIV1 polypeptide.

In particular embodiments of the methods described herein, B cells isolated from peripheral blood or lymph nodes are sorted, e.g., based on their being CD19 positive, and plated, e.g., as low as a single cell specificity per well, e.g., in 96, 384, or 1536 well configurations. The cells are induced to differentiate into antibody-producing cells, e.g., plasma cells, and the culture supernatants are harvested and tested for binding to cells expressing the infectious agent polypeptide on their surface using, e.g., FMAT or FACS analysis. Positive wells are then subjected to whole well RT-PCR to amplify heavy and light chain variable regions of the IgG molecule expressed by the clonal daughter plasma cells. The resulting PCR products encoding the heavy and light chain variable regions, or portions thereof, are subcloned into human antibody expression vectors for recombinant expression. The resulting recombinant antibodies are then tested to confirm their original binding specificity and may be further tested for pan-specificity across various strains of isolates of the infectious agent.

Thus, in one embodiment, a method of identifying HIV1 antibodies is practiced as follows. First, full length or approximately full length HIV1 cDNAs are transfected into a cell line for expression of HIV1 polypeptides. Secondly, individual human plasma or sera samples are tested for antibodies that bind the cell-expressed HIV1 polypeptides. And lastly, MAbs derived from plasma- or serum-positive individuals are characterized for binding to the same cell-expressed HIV1 polypeptides. Further definition of the fine specificities of the MAbs can be performed at this point.

Polynucleotides that encode the HIV1 antibodies or portions thereof of the present invention may be isolated from cells expressing HIV1 antibodies, according to methods available in the art and described herein, including amplification by polymerase chain reaction using primers specific for conserved regions of human antibody polypeptides. For example, light chain and heavy chain variable regions may be cloned from the B cell according to molecular biology techniques described in WO 92/02551; U.S. Pat. No. 5,627,052; or Babcook et al., Proc. Natl. Acad. Sci. USA 93:7843-48 (1996). In certain embodiments, polynucleotides encoding all or a region of both the heavy and light chain variable regions of the IgG molecule expressed by the clonal daughter plasma cells expressing the HIV1 antibody are subcloned and sequenced. The sequence of the encoded polypeptide may be readily determined from the polynucleotide sequence.

Isolated polynucleotides encoding a polypeptide of the present invention may be subcloned into an expression vector to recombinantly produce antibodies and polypeptides of the present invention, using procedures known in the art and described herein.

Binding properties of an antibody (or fragment thereof) to HIV1 polypeptides or HIv1 infected cells or tissues may generally be determined and assessed using immunodetection methods including, for example, immunofluorescence-based assays, such as immuno-histochemistry (IHC) and/or fluorescence-activated cell sorting (FACS). Immunoassay methods may include controls and procedures to determine whether antibodies bind specifically to HIV1 polypeptides from one or more specific clades or strains of HIV, and do not recognize or cross-react with normal control cells.

Following pre-screening of serum to identify patients that produce antibodies to an infectious agent or polypeptide thereof, e.g., HIV1, the methods of the present invention typically include the isolation or purification of B cells from a biological sample previously obtained from a patient or subject. The patient or subject may be currently or previously diagnosed with or suspect or having a particular disease or infection, or the patient or subject may be considered free or a particular disease or infection. Typically, the patient or subject is a mammal and, in particular embodiments, a human. The biological sample may be any sample that contains B cells, including but not limited to, lymph node or lymph node tissue, pleural effusions, peripheral blood, ascites, tumor tissue, or cerebrospinal fluid (CSF). In various embodiments, B cells are isolated from different types of biological samples, such as a biological sample affected by a particular disease or infection. However, it is understood that any biological sample comprising B cells may be used for any of the embodiments of the present invention.

Once isolated, the B cells are induced to produce antibodies, e.g., by culturing the B cells under conditions that support B cell proliferation or development into a plasmacyte, plasmablast, or plasma cell. The antibodies are then screened, typically using high throughput techniques, to identify an antibody that specifically binds to a target antigen, e.g., a particular tissue, cell, infectious agent, or polypeptide. In certain embodiments, the specific antigen, e.g., cell surface polypeptide bound by the antibody is not known, while in other embodiments, the antigen specifically bound by the antibody is known.

According to the present invention, B cells may be isolated from a biological sample, e.g., a tumor, tissue, peripheral blood or lymph node sample, by any means known and available in the art. B cells are typically sorted by FACS based on the presence on their surface of a B cell-specific marker, e.g., CD19, CD138, and/or surface IgG. However, other methods known in the art may be employed, such as, e.g., column purification using CD19 magnetic beads or IgG-specific magnetic beads, followed by elution from the column. However, magnetic isolation of B cells utilizing any marker may result in loss of certain B cells. Therefore, in certain embodiments, the isolated cells are not sorted but, instead, phicol-purified mononuclear cells isolated from tumor are directly plated to the appropriate or desired number of specificities per well.

In order to identify B cells that produce an infectious agent-specific antibody, the B cells are typically plated at low density (e.g., a single cell specificity per well, 1-10 cells per well, 10-100 cells per well, 1-100 cells per well, less than 10 cells per well, or less than 100 cells per well) in multi-well or microtiter plates, e.g., in 96, 384, or 1536 well configurations. When the B cells are initially plated at a density greater than one cell per well, then the methods of the present invention may include the step of subsequently diluting cells in a well identified as producing an antigen-specific antibody, until a single cell specificity per well is achieved, thereby facilitating the identification of the B cell that produces the antigen-specific antibody. Cell supernatants or a portion thereof and/or cells may be frozen and stored for future testing and later recovery of antibody polynucleotides.

In certain embodiments, the B cells are cultured under conditions that favor the production of antibodies by the B cells. For example, the B cells may be cultured under conditions favorable for B cell proliferation and differentiation to yield antibody-producing plasmablast, plasmacytes, or plasma cells. In particular embodiments, the B cells are cultured in the presence of a B cell mitogen, such as lipopolysaccharide (LPS) or CD40 ligand. In one specific embodiment, B cells are differentiated to antibody-producing cells by culturing them with feed cells and/or other B cell activators, such as CD40 ligand.

Cell culture supernatants or antibodies obtained therefrom may be tested for their ability to bind to a target antigen, using routine methods available in the art, including those described herein. In particular embodiments, culture supernatants are tested for the presence of antibodies that bind to a target antigen using high-throughput methods. For example, B cells may be cultured in multi-well microtiter dishes, such that robotic plate handlers may be used to simultaneously sample multiple cell supernatants and test for the presence of antibodies that bind to a target antigen. In particular embodiments, antigens are bound to beads, e.g., paramagnetic or latex beads) to facilitate the capture of antibody/antigen complexes. In other embodiments, antigens and antibodies are fluorescently labeled (with different labels) and FACS analysis is performed to identify the presence of antibodies that bind to target antigen. In one embodiment, antibody binding is determined using FMAT™ analysis and instrumentation (Applied Biosystems, Foster City, Calif.). FMAT™ is a fluorescence macro-confocal platform for high-throughput screening, which mix-and-read, non-radioactive assays using live cells or beads.

In the context of comparing the binding of an antibody to a particular target antigen (e.g., a biological sample such as infected tissue or cells, or infectious agents) as compared to a control sample (e.g., a biological sample such as uninfected cells, or a different infectious agent), in various embodiments, the antibody is considered to preferentially bind a particular target antigen if at least two-fold, at least three-fold, at least five-fold, or at least ten-fold more antibody binds to the particular target antigen as compared to the amount that binds a control sample.

Polynucleotides encoding antibody chains, variable regions thereof, or fragments thereof, may be isolated from cells utilizing any means available in the art. In one embodiment, polynucleotides are isolated using polymerase chain reaction (PCR), e.g., reverse transcription-PCR (RT-PCR) using oligonucleotide primers that specifically bind to heavy or light chain encoding polynucleotide sequences or complements thereof using routine procedures available in the art. In one embodiment, positive wells are subjected to whole well RT-PCR to amplify the heavy and light chain variable regions of the IgG molecule expressed by the clonal daughter plasma cells. These PCR products may be sequenced.

The resulting PCR products encoding the heavy and light chain variable regions or portions thereof are then subcloned into human antibody expression vectors and recombinantly expressed according to routine procedures in the art (see, e.g., U.S. Pat. No. 7,112,439). The nucleic acid molecules encoding a tumor-specific antibody or fragment thereof, as described herein, may be propagated and expressed according to any of a variety of well-known procedures for nucleic acid excision, ligation, transformation, and transfection. Thus, in certain embodiments expression of an antibody fragment may be preferred in a prokaryotic host cell, such as *Escherichia coli* (see, e.g., Pluckthun et al., Methods Enzymol. 178:497-515 (1989)). In certain other embodiments, expression of the antibody or an antigen-binding fragment thereof may be preferred in a eukaryotic host cell, including yeast (e.g., *Saccharomyces cerevisiae, Schizosaccharomyces pombe*, and *Pichia pastoris*); animal cells (including mammalian cells); or plant cells. Examples of suitable animal cells include, but are not limited to, myeloma, COS, CHO, or hybridoma cells. Examples of plant cells include tobacco, corn, soybean, and rice cells. By methods known to those having ordinary skill in the art and based on the present disclosure, a nucleic acid vector may be designed for expressing foreign sequences in a particular host system, and then polynucleotide sequences encoding the tumor-specific antibody (or fragment thereof) may be inserted. The regulatory elements will vary according to the particular host.

One or more replicable expression vectors containing a polynucleotide encoding a variable and/or constant region may be prepared and used to transform an appropriate cell line, for example, a non-producing myeloma cell line, such as a mouse NSO line or a bacterium, such as *E. coli*, in which production of the antibody will occur. In order to obtain efficient transcription and translation, the polynucleotide sequence in each vector should include appropriate regulatory sequences, particularly a promoter and leader sequence operatively linked to the variable region sequence. Particular methods for producing antibodies in this way are generally well known and routinely used. For example, molecular biology procedures are described by Sambrook et al. (*Molecular Cloning, A Laboratory Manual,* 2nd ed., Cold Spring Harbor Laboratory, New York, 1989; see also Sambrook et al., 3rd ed., Cold Spring Harbor Laboratory, New York, (2001)). While not required, in certain embodiments, regions of polynucleotides encoding the recombinant antibodies may be sequenced. DNA sequencing can be performed as described in Sanger et al. (*Proc. Natl. Acad. Sci. USA* 74:5463 (1977)) and the Amersham International plc sequencing handbook and including improvements thereto.

In particular embodiments, the resulting recombinant antibodies or fragments thereof are then tested to confirm their original specificity and may be further tested for pan-specificity, e.g., with related infectious agents. In particular embodiments, an antibody identified or produced according to methods described herein is tested for cell killing via antibody dependent cellular cytotoxicity (ADCC) or apoptosis, and/or well as its ability to internalize.

The present invention, in other aspects, provides polynucleotide compositions. In preferred embodiments, these polynucleotides encode a polypeptide of the invention, e.g., a region of a variable chain of an antibody that binds to HIV1. Polynucleotides of the invention are single-stranded (coding or antisense) or double-stranded DNA (genomic, cDNA or synthetic) or RNA molecules. RNA molecules include, but are not limited to, HnRNA molecules, which contain introns and correspond to a DNA molecule in a one-to-one manner, and mRNA molecules, which do not contain introns. Alternatively, or in addition, coding or non-coding sequences are present within a polynucleotide of the present invention. Also alternatively, or in addition, a polynucleotide is linked to other molecules and/or support materials of the invention. Polynucleotides of the invention are used, e.g., in hybridization assays to detect the presence of an HIV1 antibody in a biological sample, and in the recombinant production of polypeptides of the invention. Further, the invention includes all polynucleotides that encode any polypeptide of the present invention.

In other related embodiments, the invention provides polynucleotide variants having substantial identity to the sequences of 1443_C16, 1456_P20, 1460_G14, 1495_C14 or 1496_C09, for example those comprising at least 70% sequence identity, preferably at least 75%, 80%, 85%, 90%, 95%, 96%, 97%, 98%, or 99% or higher, sequence identity compared to a polynucleotide sequence of this invention, as determined using the methods described herein, (e.g., BLAST analysis using standard parameters). One skilled in this art will recognize that these values can be appropriately adjusted to determine corresponding identity of proteins encoded by two nucleotide sequences by taking into account codon degeneracy, amino acid similarity, reading frame positioning, and the like.

Typically, polynucleotide variants contain one or more substitutions, additions, deletions and/or insertions, preferably such that the immunogenic binding properties of the polypeptide encoded by the variant polynucleotide is not substantially diminished relative to a polypeptide encoded by a polynucleotide sequence specifically set forth herein.

In additional embodiments, the present invention provides polynucleotide fragments comprising various lengths of contiguous stretches of sequence identical to or complementary to one or more of the sequences disclosed herein. For example, polynucleotides are provided by this invention that comprise at least about 10, 15, 20, 30, 40, 50, 75, 100, 150, 200, 300, 400, 500 or 1000 or more contiguous nucleotides of one or more of the sequences disclosed herein as well as all intermediate lengths there between. As used herein, the term "intermediate lengths" is meant to describe any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200-500; 500-1,000, and the like.

In another embodiment of the invention, polynucleotide compositions are provided that are capable of hybridizing under moderate to high stringency conditions to a polynucleotide sequence provided herein, or a fragment thereof, or a complementary sequence thereof. Hybridization techniques are well known in the art of molecular biology. For purposes of illustration, suitable moderately stringent conditions for testing the hybridization of a polynucleotide of this invention with other polynucleotides include prewashing in a solution of 5×SSC, 0.5% SDS, 1.0 mM EDTA (pH 8.0); hybridizing at 50° C.–60° C., 5×SSC, overnight; followed by washing twice at 65° C. for 20 minutes with each of 2×, 0.5× and 0.2×SSC containing 0.1% SDS. One skilled in the art will understand that the stringency of hybridization can be readily manipulated, such as by altering the salt content of the hybridization solution and/or the temperature at which the hybridization is performed. For example, in another embodiment, suitable highly stringent hybridization conditions include those described above, with the exception that the temperature of hybridization is increased, e.g., to 60-65° C. or 65-70° C.

In preferred embodiments, the polypeptide encoded by the polynucleotide variant or fragment has the same binding specificity (i.e., specifically or preferentially binds to the same epitope or HIV strain) as the polypeptide encoded by the native polynucleotide. In certain preferred embodiments, the polynucleotides described above, e.g., polynucleotide variants, fragments and hybridizing sequences, encode polypeptides that have a level of binding activity of at least about 50%, preferably at least about 70%, and more preferably at least about 90% of that for a polypeptide sequence specifically set forth herein.

The polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. A nucleic acid fragment of almost any length is employed, with the total length preferably being limited by the ease of preparation and use in the intended recombinant DNA protocol. For example, illustrative polynucleotide segments with total lengths of about 10,000, about 5000, about 3000, about 2,000, about 1,000, about 500, about 200, about 100, about 50 base pairs in length, and the like, (including all intermediate lengths) are included in many implementations of this invention.

It will be appreciated by those of ordinary skill in the art that, as a result of the degeneracy of the genetic code, there are multiple nucleotide sequences that encode a polypeptide as described herein. Some of these polynucleotides bear minimal homology to the nucleotide sequence of any native gene. Nonetheless, polynucleotides that encode a polypeptide of the present invention but which vary due to differences in codon usage are specifically contemplated by the invention. Further, alleles of the genes including the polynucleotide sequences provided herein are within the scope of the invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

In certain embodiments of the present invention, mutagenesis of the disclosed polynucleotide sequences is performed in order to alter one or more properties of the encoded polypeptide, such as its binding specificity or binding strength. Techniques for mutagenesis are well-known in the art, and are widely used to create variants of both polypeptides and polynucleotides. A mutagenesis approach, such as site-specific mutagenesis, is employed for the preparation of variants and/or derivatives of the polypeptides described herein. By this approach, specific modifications in a polypeptide sequence are made through mutagenesis of the underlying polynucleotides that encode them. These techniques provides a straightforward approach to prepare and test sequence variants, for example, incorporating one or more of the foregoing considerations, by introducing one or more nucleotide sequence changes into the polynucleotide.

Site-specific mutagenesis allows the production of mutants through the use of specific oligonucleotide sequences include the nucleotide sequence of the desired mutation, as well as a sufficient number of adjacent nucleotides, to provide a primer sequence of sufficient size and sequence complexity to form a stable duplex on both sides of the deletion junction being traversed. Mutations are employed in a selected polynucleotide sequence to improve, alter, decrease, modify, or otherwise change the properties of the polynucleotide itself, and/or alter the properties, activity, composition, stability, or primary sequence of the encoded polypeptide.

In other embodiments of the present invention, the polynucleotide sequences provided herein are used as probes or primers for nucleic acid hybridization, e.g., as PCR primers. The ability of such nucleic acid probes to specifically hybridize to a sequence of interest enables them to detect the presence of complementary sequences in a given sample. However, other uses are also encompassed by the invention, such as the use of the sequence information for the preparation of mutant species primers, or primers for use in preparing other genetic constructions. As such, nucleic acid segments of the invention that include a sequence region of at least about a 15-nucleotide long contiguous sequence that has the same sequence as, or is complementary to, a 15 nucleotide long contiguous sequence disclosed herein is particularly useful. Longer contiguous identical or complementary sequences, e.g., those of about 20, 30, 40, 50, 100, 200, 500, 1000 (including all intermediate lengths) including full length sequences, and all lengths in between, are also used in certain embodiments.

Polynucleotide molecules having sequence regions consisting of contiguous nucleotide stretches of 10-14, 15-20, 30, 50, or even of 100-200 nucleotides or so (including intermediate lengths as well), identical or complementary to a polynucleotide sequence disclosed herein, are particularly contemplated as hybridization probes for use in, e.g., Southern and Northern blotting, and/or primers for use in, e.g., polymerase chain reaction (PCR). The total size of fragment, as well as the size of the complementary stretch (es), ultimately depends on the intended use or application of the particular nucleic acid segment. Smaller fragments are generally used in hybridization embodiments, wherein the length of the contiguous complementary region may be varied, such as between about 15 and about 100 nucleotides, but larger contiguous complementarity stretches may be used, according to the length complementary sequences one wishes to detect.

The use of a hybridization probe of about 15-25 nucleotides in length allows the formation of a duplex molecule that is both stable and selective. Molecules having contiguous complementary sequences over stretches greater than 12 bases in length are generally preferred, though, in order to increase stability and selectivity of the hybrid, and thereby improve the quality and degree of specific hybrid molecules obtained. Nucleic acid molecules having gene-complementary stretches of 15 to 25 contiguous nucleotides, or even longer where desired, are generally preferred.

Hybridization probes are selected from any portion of any of the sequences disclosed herein. All that is required is to review the sequences set forth herein, or to any continuous portion of the sequences, from about 15-25 nucleotides in length up to and including the full length sequence, that one wishes to utilize as a probe or primer. The choice of probe and primer sequences is governed by various factors. For example, one may wish to employ primers from towards the termini of the total sequence.

Polynucleotide of the present invention, or fragments or variants thereof, are readily prepared by, for example, directly synthesizing the fragment by chemical means, as is commonly practiced using an automated oligonucleotide synthesizer. Also, fragments are obtained by application of nucleic acid reproduction technology, such as the PCR™ technology of U.S. Pat. No. 4,683,202, by introducing selected sequences into recombinant vectors for recombinant production, and by other recombinant DNA techniques generally known to those of skill in the art of molecular biology.

The invention provides vectors and host cells comprising a nucleic acid of the present invention, as well as recombinant techniques for the production of a polypeptide of the present invention. Vectors of the invention include those capable of replication in any type of cell or organism, including, e.g., plasmids, phage, cosmids, and mini chromosomes. In various embodiments, vectors comprising a polynucleotide of the present invention are vectors suitable for propagation or replication of the polynucleotide, or vectors suitable for expressing a polypeptide of the present invention. Such vectors are known in the art and commercially available.

Polynucleotides of the present invention are synthesized, whole or in parts that are then combined, and inserted into a vector using routine molecular and cell biology techniques, including, e.g., subcloning the polynucleotide into a linearized vector using appropriate restriction sites and restriction enzymes. Polynucleotides of the present invention are amplified by polymerase chain reaction using oligonucleotide primers complementary to each strand of the polynucleotide. These primers also include restriction enzyme cleavage sites to facilitate subcloning into a vector. The replicable vector components generally include, but are not limited to, one or more of the following: a signal sequence, an origin of replication, and one or more marker or selectable genes.

In order to express a polypeptide of the present invention, the nucleotide sequences encoding the polypeptide, or functional equivalents, are inserted into an appropriate expression vector, i.e., a vector that contains the necessary elements for the transcription and translation of the inserted coding sequence. Methods well known to those skilled in the art are used to construct expression vectors containing sequences encoding a polypeptide of interest and appropriate transcriptional and translational control elements. These methods include in vitro recombinant DNA techniques, synthetic techniques, and in vivo genetic recombination. Such techniques are described, for example, in Sambrook, J., et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York. N.Y.

A variety of expression vector/host systems are utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

Within one embodiment, the variable regions of a gene expressing a monoclonal antibody of interest are amplified from a hybridoma cell using nucleotide primers. These primers are synthesized by one of ordinary skill in the art, or may be purchased from commercially available sources (see, e.g., Stratagene (La Jolla, Calif.), which sells primers for amplifying mouse and human variable regions. The primers are used to amplify heavy or light chain variable regions, which are then inserted into vectors such as ImmunoZAP™ H or ImmunoZAP™ L (Stratagene), respectively. These vectors are then introduced into E. coli, yeast, or mammalian-based systems for expression. Large amounts of a single-chain protein containing a fusion of the $V_H$ and $V_L$ domains are produced using these methods (see Bird et al., Science 242:423-426 (1988)).

The "control elements" or "regulatory sequences" present in an expression vector are those non-translated regions of the vector, e.g., enhancers, promoters, 5' and 3' untranslated regions, that interact with host cellular proteins to carry out transcription and translation. Such elements may vary in their strength and specificity. Depending on the vector system and host utilized, any number of suitable transcription and translation elements, including constitutive and inducible promoters, are used.

Examples of promoters suitable for use with prokaryotic hosts include the phoa promoter, β-lactamase and lactose promoter systems, alkaline phosphatase promoter, a tryptophan (trp) promoter system, and hybrid promoters such as the tac promoter. However, other known bacterial promoters are suitable. Promoters for use in bacterial systems also usually contain a Shine-Dalgarno sequence operably linked to the DNA encoding the polypeptide. Inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like are used.

A variety of promoter sequences are known for eukaryotes and any are used according to the present invention. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

In mammalian cell systems, promoters from mammalian genes or from mammalian viruses are generally preferred. Polypeptide expression from vectors in mammalian host cells are controlled, for example, by promoters obtained from the genomes of viruses such as polyoma virus, fowlpox virus, adenovirus (e.g., Adenovirus 2), bovine papilloma virus, avian sarcoma virus, cytomegalovirus (CMV), a retrovirus, hepatitis-B virus and most preferably Simian Virus 40 (SV40), from heterologous mammalian promoters, e.g., the actin promoter or an immunoglobulin promoter, and from heat-shock promoters, provided such promoters are compatible with the host cell systems. If it is necessary to generate a cell line that contains multiple copies of the sequence encoding a polypeptide, vectors based on SV40 or EBV may be advantageously used with an appropriate selectable marker. One example of a suitable expression vector is pcDNA-3.1 (Invitrogen, Carlsbad, Calif.), which includes a CMV promoter.

A number of viral-based expression systems are available for mammalian expression of polypeptides. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus that is capable of expressing the polypeptide in infected host cells (Logan, J. and Shenk, T. (1984) Proc. Natl. Acad. Sci. 81:3655-3659). In addition, transcription enhancers, such as the Rous sarcoma virus (RSV) enhancer, may be used to increase expression in mammalian host cells.

In bacterial systems, any of a number of expression vectors are selected depending upon the use intended for the expressed polypeptide. For example, when large quantities are desired, vectors that direct high level expression of fusion proteins that are readily purified are used. Such vectors include, but are not limited to, the multifunctional *E. coli* cloning and expression vectors such as BLUESCRIPT (Stratagene), in which the sequence encoding the polypeptide of interest may be ligated into the vector in frame with sequences for the amino-terminal Met and the subsequent 7 residues of β-galactosidase, so that a hybrid protein is produced; pIN vectors (Van Heeke, G. and S. M. Schuster (1989) J. Biol. Chem. 264:5503-5509); and the like. pGEX Vectors (Promega, Madison, Wis.) are also used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH are used. Examples of other suitable promoter sequences for use with yeast hosts include the promoters for 3-phosphoglycerate kinase or other glycolytic enzymes, such as enolase, glyceraldehyde-3-phosphate dehydrogcnase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. For reviews, see Ausubel et al. (supra) and Grant et al. (1987) Methods Enzymol. 153:516-544. Other yeast promoters that are inducible promoters having the additional advantage of transcription controlled by growth conditions include the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

In cases where plant expression vectors are used, the expression of sequences encoding polypeptides are driven by any of a number of promoters. For example, viral promoters such as the 35S and 19S promoters of CaMV are used alone or in combination with the omega leader sequence from TMV (Takamatsu, N. (1987) *EMBO J.* 6:307-311. Alternatively, plant promoters such as the small subunit of RUBISCO or heat shock promoters are used (Coruzzi, G. et al. (1984) EMBO J. 3:1671-1680; Broglie, R. et al. (1984) Science 224:838-843; and Winter, J., et al. (1991) Results Probl. Cell Differ. 17:85-105). These constructs can be introduced into plant cells by direct DNA transformation or pathogen-mediated transfection. Such techniques are described in a number of generally available reviews (see, e.g., Hobbs, S. or Murry, L. E. in McGraw Hill Yearbook of Science and Technology (1992) McGraw Hill, New York, N.Y.; pp. 191-196).

An insect system is also used to express a polypeptide of interest. For example, in one such system, *Autographa californica* nuclear polyhedrosis virus (AcNPV) is used as a vector to express foreign genes in *Spodoptera frugiperda* cells or in *Trichoplusia* larvae. The sequences encoding the polypeptide are cloned into a non-essential region of the virus, such as the polyhedrin gene, and placed under control of the polyhedrin promoter. Successful insertion of the polypeptide-encoding sequence renders the polyhedrin gene inactive and produce recombinant virus lacking coat protein. The recombinant viruses are then used to infect, for example, *S. frugiperda* cells or *Trichoplusia* larvae, in which the polypeptide of interest is expressed (Engelhard, E. K. et al. (1994) Proc. Natl. Acad. Sci. 91:3224-3227).

Specific initiation signals are also used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon are provided. Furthermore, the initiation codon is in the correct reading frame to ensure correct translation of the inserted polynucleotide. Exogenous translational elements and initiation codons are of various origins, both natural and synthetic.

Transcription of a DNA encoding a polypeptide of the invention is often increased by inserting an enhancer sequence into the vector. Many enhancer sequences are known, including, e.g., those identified in genes encoding globin, elastase, albumin, α-fetoprotein, and insulin. Typically, however, an enhancer from a eukaryotic cell virus is used. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer is spliced into the vector at a position 5' or 3' to the polypeptide-encoding sequence, but is preferably located at a site 5' from the promoter.

Expression vectors used in eukaryotic host cells (yeast, fungi, insect, plant, animal, human, or nucleated cells from other multicellular organisms) typically also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding anti-PSCA antibody. One useful transcription termination component is the bovine growth hormone polyadenylation region. See WO94/11026 and the expression vector disclosed therein.

Suitable host cells for cloning or expressing the DNA in the vectors herein are the prokaryote, yeast, plant or higher eukaryote cells described above. Examples of suitable prokaryotes for this purpose include eubacteria, such as Gram-negative or Gram-positive organisms, for example, Enterobacteriaceae such as *Escherichia*, e.g., *E. coli, Enterobacter, Envinia, Klebsiella, Proteus, Salmonella*, e.g., *Salmonella typhimurium, Serratia*, e.g., *Serratia marcescens*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

*Saccharomyces cerevisiae*, or common baker's yeast, is the most commonly used among lower eukaryotic host microorganisms. However, a number of other genera, species, and strains are commonly available and used herein, such as *Schizosaccharomyces pombe; Kluyveromyces* hosts such as, e.g., *K lactis, K. fragilis* (ATCC 12,424), *K. bulgaricus* (ATCC 16,045), K wickeramii (ATCC 24,178), *K. waltii* (ATCC 56,500), *K. drosophilarum* (ATCC 36,906), *K thermotolerans*, and *K. marxianus; yarrowia* (EP 402, 226); *Pichia pastoris*. (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

In certain embodiments, a host cell strain is chosen for its ability to modulate the expression of the inserted sequences or to process the expressed protein in the desired fashion. Such modifications of the polypeptide include, but are not limited to, acetylation, carboxylation. glycosylation, phosphorylation, lipidation, and acylation. Post-translational processing that cleaves a "prepro" form of the protein is also used to facilitate correct insertion, folding and/or function. Different host cells such as CHO, COS, HeLa, MDCK, HEK293, and WI38, which have specific cellular machinery and characteristic mechanisms for such post-translational activities, are chosen to ensure the correct modification and processing of the foreign protein.

Methods and reagents specifically adapted for the expression of antibodies or fragments thereof are also known and available in the art, including those described, e.g., in U.S. Pat. Nos. 4,816,567 and 6,331,415. In various embodiments, antibody heavy and light chains, or fragments thereof, are expressed from the same or separate expression vectors. In one embodiment, both chains are expressed in the same cell, thereby facilitating the formation of a functional antibody or fragment thereof.

Full length antibody, antibody fragments, and antibody fusion proteins are produced in bacteria, in particular when glycosylation and Fc effector function are not needed, such as when the therapeutic antibody is conjugated to a cytotoxic agent (e.g., a toxin) and the immunoconjugate by itself shows effectiveness in infected cell destruction. For expression of antibody fragments and polypeptides in bacteria, see, e.g., U.S. Pat. Nos. 5,648,237, 5,789,199, and 5,840,523, which describes translation initiation region (TIR) and signal sequences for optimizing expression and secretion. After expression, the antibody is isolated from the *E. coli* cell paste in a soluble fraction and can be purified through, e.g., a protein A or G column depending on the isotype. Final purification can be carried out using a process similar to that used for purifying antibody expressed e.g., in CHO cells.

Suitable host cells for the expression of glycosylated polypeptides and antibodies are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopicius* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses are used as the virus herein according to the present invention, particularly for transfection of *Spodoptera frugiperda* cells. Plant cell cultures of cotton, corn, potato, soybean, *petunia*, tomato, and tobacco are also utilized as hosts.

Methods of propagation of antibody polypeptides and fragments thereof in vertebrate cells in culture (tissue culture) are encompassed by the invention. Examples of mammalian host cell lines used in the methods of the invention are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors for polypeptide production and cultured in conventional nutrient media modified as appropriate for inducing promoters, selecting transformants, or amplifying the genes encoding the desired sequences.

For long-term, high-yield production of recombinant proteins, stable expression is generally preferred. For example, cell lines that stably express a polynucleotide of interest are transformed using expression vectors that contain viral origins of replication and/or endogenous expression elements and a selectable marker gene on the same or on a separate vector. Following the introduction of the vector, cells are allowed to grow for 1-2 days in an enriched media before they are switched to selective media. The purpose of the selectable marker is to confer resistance to selection, and its presence allows growth and recovery of cells that successfully express the introduced sequences. Resistant clones of stably transformed cells are proliferated using tissue culture techniques appropriate to the cell type.

A plurality of selection systems are used to recover transformed cell lines. These include, but are not limited to, the herpes simplex virus thymidine kinase (Wigler, M. et al. (1977) Cell 11:223-32) and adenine phosphoribosyltransferase (Lowy, I. et al. (1990) Cell 22:817-23) genes that are employed in tk$^-$ or aprt$^-$ cells, respectively. Also, antimetabolite, antibiotic or herbicide resistance is used as the basis for selection; for example, dhfr, which confers resistance to methotrexate (Wigler, M. et al. (1980) Proc. Natl. Acad. Sci. 77:3567-70); npt, which confers resistance to the aminoglycosides, neomycin and G-418 (Colbere-Garapin, F. et al. (1981) J. Mol. Biol. 150:1-14); and als or pat, which confer resistance to chlorsulfuron and phosphinotricin acetyltransferase, respectively (Murry, supra). Additional selectable genes have been described. For example, trpB allows cells to utilize indole in place of tryptophan, and hisD allows cells to utilize histinol in place of histidine (Hartman, S. C. and R. C. Mulligan (1988) Proc. Natl. Acad. Sci. 85:8047-51). The use of visible markers has gained popularity with such markers as anthocyanins, beta-glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121-131).

Although the presence/absence of marker gene expression suggests that the gene of interest is also present, its presence and expression is confirmed. For example, if the sequence encoding a polypeptide is inserted within a marker gene sequence, recombinant cells containing sequences are identified by the absence of marker gene function. Alternatively, a marker gene is placed in tandem with a polypeptide-encoding sequence under the control of a single promoter. Expression of the marker gene in response to induction or selection usually indicates expression of the tandem gene as well.

Alternatively, host cells that contain and express a desired polynucleotide sequence are identified by a variety of procedures known to those of skill in the art. These procedures include, but are not limited to, DNA-DNA or DNA-RNA hybridizations and protein bioassay or immunoassay techniques which include, for example, membrane, solution, or chip based technologies for the detection and/or quantification of nucleic acid or protein.

A variety of protocols for detecting and measuring the expression of polynucleotide-encoded products, using either polyclonal or monoclonal antibodies specific for the product are known in the art. Nonlimiting examples include enzyme-linked immunosorbent assay (ELISA), radioimmunoassay (MA), and fluorescence activated cell sorting (FACS). A two-site, monoclonal-based immunoassay utilizing monoclonal antibodies reactive to two non-interfering epitopes on a given polypeptide is preferred for some applications, but a competitive binding assay may also be employed. These and other assays are described, among other places, in Hampton, R. et al. (1990; Serological Methods, a Laboratory Manual, APS Press, St Paul. Minn.) and Maddox, D. E. et al. (1983; J. Exp. Med. 158:1211-1216).

Various labels and conjugation techniques are known by those skilled in the art and are used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof are cloned into a vector for the production of an mRNA probe. Such vectors are known in the art, are commercially available, and are used to synthesize RNA probes in vitro by addition of an appropriate RNA polymerase such as T7, T3, or SP6 and labeled nucleotides. These procedures are conducted using a variety of commercially available kits. Suitable reporter molecules or labels, which are used include, but are not limited to, radionucleotides, enzymes, fluorescent, chemiluminescent, or chromogenic agents as well as substrates, cofactors, inhibitors, magnetic particles, and the like.

The polypeptide produced by a recombinant cell is secreted or contained intracellularly depending on the sequence and/or the vector used. Expression vectors containing polynucleotides of the invention are designed to contain signal sequences that direct secretion of the encoded polypeptide through a prokaryotic or eukaryotic cell membrane.

In certain embodiments, a polypeptide of the invention is produced as a fusion polypeptide further including a polypeptide domain that facilitates purification of soluble proteins. Such purification-facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Amgen, Seattle, Wash.). The inclusion of cleavable linker sequences such as those specific for Factor XA or enterokinase (Invitrogen. San Diego, Calif.) between the purification domain and the encoded polypeptide are used to facilitate purification. An exemplary expression vector provides for expression of a fusion protein containing a polypeptide of interest and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, Prot. Exp. Purif. 3:263-281) while the enterokinase cleavage site provides a means for purifying the desired polypeptide from the fusion protein. A discussion of vectors used for producing fusion proteins is provided in Kroll, D. J. et al. (1993; DNA Cell Biol. 12:441-453).

In certain embodiments, a polypeptide of the present invention is fused with a heterologous polypeptide, which may be a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells, the signal sequence is selected, for example, from the group of the alkaline phosphatase, penicillinase, 1pp, or heat-stable enterotoxin II leaders. For yeast secretion, the signal sequence is selected from, e.g., the yeast invertase leader, a factor leader (including *Saccharomyces* and *Kluyveromyces* a factor leaders), or acid phosphatase leader, the *C. albicans* glucoamylase leader, or the signal described in WO 90/13646. In mammalian cell expression, mammalian signal sequences as well as viral secretory leaders, for example, the herpes simplex gD signal, are available.

When using recombinant techniques, the polypeptide or antibody is produced intracellularly, in the periplasmic space, or directly secreted into the medium. If the polypeptide or antibody is produced intracellularly, as a first step, the particulate debris, either host cells or lysed fragments, are removed, for example, by centrifugation or ultrafiltration. Carter et al., Bio/Technology 10:163-167 (1992) describe a procedure for isolating antibodies that are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris is removed by centrifugation. Where the polypeptide or antibody is secreted into the medium, supernatants from such expression systems are generally first concentrated using a commercially available protein concentration filter, for example, an Amicon or Millipore Pellicon ultrafiltration unit. Optionally, a protease inhibitor such as PMSF is included in any of the foregoing steps to inhibit proteolysis and antibiotics are included to prevent the growth of adventitious contaminants.

The polypeptide or antibody composition prepared from the cells are purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the polypeptide or antibody. Protein A is used to purify antibodies or fragments thereof that are based on human $\gamma_1$, $\gamma_2$, or $\gamma_4$ heavy chains (Lindmark et al., J. Immunol. Meth. 62:1-13 (1983)). Protein G is recommended for all mouse isotypes and for human $\gamma_3$ (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the polypeptide or antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the polypeptide or antibody to be recovered.

Following any preliminary purification step(s), the mixture comprising the polypeptide or antibody of interest and contaminants are subjected to low pH hydrophobic interaction chromatography using an elution buffer at a pH between about 2.5-4.5, preferably performed at low salt concentrations (e.g., from about 0-0.25M salt).

The invention further includes pharmaceutical formulations including a polypeptide, antibody, or modulator of the present invention, at a desired degree of purity, and a pharmaceutically acceptable carrier, excipient, or stabilizer (Remingion's Pharmaceutical Sciences 16th edition, Osol, A. Ed. (1980)). In certain embodiments, pharmaceutical formulations are prepared to enhance the stability of the polypeptide or antibody during storage, e.g., in the form of lyophilized formulations or aqueous solutions.

Acceptable carriers, excipients, or stabilizers are nontoxic to recipients at the dosages and concentrations employed, and include, e.g., buffers such as acetate, Tris, phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; metal complexes (e.g. Zn-protein complexes); and/or non-ionic surfactants such as TWEEN™, PLURONICS™ or polyethylene glycol (PEG). In certain embodiments, the therapeutic formulation preferably comprises the polypeptide or antibody at a concentration of between 5-200 mg/ml, preferably between 10-100 mg/ml.

The formulations herein also contain one or more additional therapeutic agents suitable for the treatment of the particular indication, e.g., infection being treated, or to prevent undesired side-effects. Preferably, the additional therapeutic agent has an activity complementary to the polypeptide or antibody of the resent invention, and the two do not adversely affect each other. For example, in addition to the polypeptide or antibody of the invention, an additional or second antibody, anti-viral agent, anti-infective agent and/or cardioprotectant is added to the formulation. Such molecules are suitably present in the pharmaceutical formulation in amounts that are effective for the purpose intended.

The active ingredients, e.g., polypeptides and antibodies of the invention and other therapeutic agents, are also entrapped in microcapsules prepared, for example, by coacervation techniques or by interfacial polymerization, for example, hydroxymethylcellulose or gelatin-microcapsules and polymethylmethacylate) microcapsules, respectively, in colloidal drug delivery systems (for example, liposomes, albumin microspheres, microemulsions, nano-particles and nanocapsules) or in macroemulsions. Such techniques are disclosed in Remingion's Pharmaceutical Sciences 16th edition, Osol, A. Ed. (1980).

Sustained-release preparations are prepared. Suitable examples of sustained-release preparations include, but are not limited to, semi-permeable matrices of solid hydrophobic polymers containing the antibody, which matrices are in the form of shaped articles, e.g., films, or microcapsules. Nonlimiting examples of sustained-release matrices include polyesters, hydrogels (for example, poly(2-hydroxyethylmethacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxyburyric acid.

Formulations to be used for in vivo administration are preferably sterile. This is readily accomplished by filtration through sterile filtration membranes.

Antibodies of the invention can be coupled to a drug for delivery to a treatment site or coupled to a detectable label to facilitate imaging of a site comprising cells of interest, such as cells infected with HIV. Methods for coupling antibodies to drugs and detectable labels are well known in the art, as are methods for imaging using detectable labels. Labeled antibodies may be employed in a wide variety of assays, employing a wide variety of labels. Detection of the formation of an antibody-antigen complex between an antibody of the invention and an epitope of interest (an HIV epitope) can be facilitated by attaching a detectable substance to the antibody. Suitable detection means include the use of labels such as radionucleotides, enzymes, coenzymes, fluorescers, chemiluminescers, chromogens, enzyme substrates or co-factors, enzyme inhibitors, prosthetic group complexes, free radicals, particles, dyes, and the like. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material is luminol; examples of bioluminescent materials include luciferase, luciferin, and aequorin; and examples of suitable radioactive material include $^{125}$I, $^{131}$I, $^{35}$S, or $^{3}$H. Such labeled reagents may be used in a variety of well-known assays, such as radioimmunoassays, enzyme immunoassays, e.g., ELISA, fluorescent immunoassays, and the like.

The antibodies are tagged with such labels by known methods. For instance, coupling agents such as aldehydes, carbodiimides, dimaleimide, imidates, succinimides, bid-diazotized benzadine and the like are used to tag the antibodies with the above-described fluorescent, chemiluminescent, and enzyme labels. An enzyme is typically combined with an antibody using bridging molecules such as carbodiimides, periodate, diisocyanates, glutaraldehyde and the like. Various labeling techniques are described in Morrison, Methods in Enzymology 32b, 103 (1974), Syvanen et al., J. Biol. Chem. 284, 3762 (1973) and Bolton and Hunter, *Biochem J.* 133, 529(1973).

An antibody according to the invention may be conjugated to a therapeutic moiety such as a cytotoxin, a therapeutic agent, or a radioactive metal ion or radioisotope. Examples of radioisotopes include, but are not limited to, I-131, I-123, I-125, Y-90, Re-188, Re-186, At-211, Cu-67, Bi-212, Bi-213, Pd-109, Tc-99, In-111, and the like. Such antibody conjugates can be used for modifying a given biological response; the drug moiety is not to be construed as limited to classical chemical therapeutic agents. For example, the drug moiety may be a protein or polypeptide possessing a desired biological activity. Such proteins may include, for example, a toxin such as abrin, ricin A, *pseudomonas* exotoxin, or diphtheria toxin.

Techniques for conjugating such therapeutic moiety to antibodies are well known. See, for example, Arnon et al. (1985) "Monoclonal Antibodies for Immunotargeting of Drugs in Cancer Therapy," in Monoclonal Antibodies and Cancer Therapy, ed. Reisfeld et al. (Alan R. Liss, Inc.), pp. 243-256; ed. Hellstrom et al. (1987) "Antibodies for Drug Delivery," in Controlled Drug Delivery, ed. Robinson et al. (2d ed; Marcel Dekker, Inc.), pp. 623-653; Thorpe (1985) "Antibody Carriers of Cytotoxic Agents in Cancer Therapy: A Review," in Monoclonal Antibodies '84: Biological and Clinical Applications, ed. Pinchera et al. pp. 475-506 (Editrice Kurtis, Milano, Italy, 1985); "Analysis, Results, and Future Prospective of the Therapeutic Use of Radiolabeled Antibody in Cancer Therapy," in Monoclonal Antibodies for Cancer Detection and Therapy, ed. Baldwin et al. (Academic Press, New York, 1985), pp. 303-316; and Thorpe et al. (1982) Immunol. Rev. 62:119-158.

Diagnostic methods generally involve contacting a biological sample obtained from a patient, such as, e.g., blood, serum, saliva, urine, sputum, a cell swab sample, or a tissue biopsy, with an HIV1 antibody and determining whether the antibody preferentially binds to the sample as compared to a control sample or predetermined cut-off value, thereby indicating the presence of infected cells. In particular embodiments, at least two-fold, three-fold, or five-fold more HIV1 antibody binds to an infected cell as compared to an appropriate control normal cell or tissue sample. A predetermined cut-off value is determined, e.g., by averaging the amount of HIV1 antibody that binds to several different appropriate control samples under the same conditions used to perform the diagnostic assay of the biological sample being tested.

Bound antibody is detected using procedures described herein and known in the art. In certain embodiments, diagnostic methods of the invention are practiced using HIV1 antibodies that are conjugated to a detectable label, e.g., a fluorophore, to facilitate detection of bound antibody. However, they are also practiced using methods of secondary detection of the HIV1 antibody. These include, for example, MA, ELISA, precipitation, agglutination, complement fixation and immuno-fluorescence.

HIV1 antibodies of the present invention are capable of differentiating between patients with and patients without an HIV infection, and determining whether or not a patient has an infection, using the representative assays provided herein. According to one method, a biological sample is obtained from a patient suspected of having or known to have HIV1 infection. In preferred embodiments, the biological sample includes cells from the patient. The sample is contacted with an HIV1 antibody, e.g., for a time and under conditions sufficient to allow the HIV1 antibody to bind to infected cells present in the sample. For instance, the sample is contacted with an HIV1 antibody for 10 seconds, 30 seconds, 1 minute, 5 minutes, 10 minutes, 30 minutes, 1 hour, 6 hours, 12 hours, 24 hours, 3 days or any point in between. The amount of bound HIV1 antibody is determined and compared to a control value, which may be, e.g., a predetermined value or a value determined from normal tissue sample. An increased amount of antibody bound to the patient sample as compared to the control sample is indicative of the presence of infected cells in the patient sample.

In a related method, a biological sample obtained from a patient is contacted with an HIV1 antibody for a time and under conditions sufficient to allow the antibody to bind to infected cells. Bound antibody is then detected, and the presence of bound antibody indicates that the sample contains infected cells. This embodiment is particularly useful when the HIV1 antibody does not bind normal cells at a detectable level.

Different HIV1 antibodies possess different binding and specificity characteristics. Depending upon these characteristics, particular HIV1 antibodies are used to detect the presence of one or more strains of HIV1. For example, certain antibodies bind specifically to only one or several strains of HIV1, whereas others bind to all or a majority of different strains of HIV1. Antibodies specific for only one strain of HIV1 are used to identify the strain of an infection.

In certain embodiments, antibodies that bind to an infected cell preferably generate a signal indicating the presence of an infection in at least about 20% of patients with the infection being detected, more preferably at least about 30% of patients. Alternatively, or in addition, the antibody generates a negative signal indicating the absence of the infection in at least about 90% of individuals without the infection being detected. Each antibody satisfies the above criteria; however, antibodies of the present invention are used in combination to improve sensitivity.

The present invention also includes kits useful in performing diagnostic and prognostic assays using the antibodies of the present invention. Kits of the invention include a suitable container comprising an HIV1 antibody of the invention in either labeled or unlabeled form. In addition, when the antibody is supplied in a labeled form suitable for an indirect binding assay, the kit further includes reagents for performing the appropriate indirect assay. For example, the kit includes one or more suitable containers including enzyme substrates or derivatizing agents, depending on the nature of the label. Control samples and/or instructions are also included.

Passive immunization has proven to be an effective and safe strategy for the prevention and treatment of viral diseases. (See Keller et al., Clin. Microbiol. Rev. 13:602-14 (2000); Casadevall, Nat. Biotechnol. 20:114 (2002); Shibata et al., Nat. Med. 5:204-10 (1999); and Igarashi et al., Nat. Med. 5:211-16 (1999), each of which are incorporated herein by reference)). Passive immunization using human monoclonal antibodies, provide an immediate treatment strategy for emergency prophylaxis and treatment of HIV1.

HIV1 antibodies and fragments thereof, and therapeutic compositions, of the invention specifically bind or preferentially bind to infected cells, as compared to normal control uninfected cells and tissue. Thus, these HIV1 antibodies are used to selectively target infected cells or tissues in a patient, biological sample, or cell population. In light of the infection-specific binding properties of these antibodies, the present invention provides methods of regulating (e.g., inhibiting) the growth of infected cells, methods of killing infected cells, and methods of inducing apoptosis of infected cells. These methods include contacting an infected cell with an HIV1 antibody of the invention. These methods are practiced in vitro, ex vivo, and in vivo.

In various embodiments, antibodies of the invention are intrinsically therapeutically active. Alternatively, or in addition, antibodies of the invention are conjugated to a cytotoxic agent or growth inhibitory agent, e.g., a radioisotope or toxin that is used in treating infected cells bound or contacted by the antibody.

Subjects at risk for HIV1-related diseases or disorders include patients who have come into contact with an infected person or who have been exposed to HIV1 in some other way. Administration of a prophylactic agent can occur prior to the manifestation of symptoms characteristic of HIV1-related disease or disorder, such that a disease or disorder is prevented or, alternatively, delayed in its progression.

Methods for preventing an increase in HIV1 virus titer, virus replication, virus proliferation or an amount of an HIV1 viral protein in a subject are further provided. In one embodiment, a method includes administering to the subject an amount of an HIV1 antibody effective to prevent an increase in HIV1 titer, virus replication or an amount of an HIV1 protein of one or more HIV strains or isolates in the subject.

For in vivo treatment of human and non-human patients, the patient is usually administered or provided a pharmaceutical formulation including an HIV1 antibody of the invention. When used for in vivo therapy, the antibodies of the invention are administered to the patient in therapeutically effective amounts (i.e., amounts that eliminate or reduce the patient's viral burden). The antibodies are administered to a human patient, in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. The antibodies may be administered parenterally, when possible, at the target cell site, or intravenously. Intravenous or subcutaneous administration of the antibody is preferred in certain embodiments. Therapeutic compositions of the invention are administered to a patient or subject systemically, parenterally, or locally.

For parenteral administration, the antibodies are formulated in a unit dosage injectable form (solution, suspension, emulsion) in association with a pharmaceutically acceptable, parenteral vehicle. Examples of such vehicles are water, saline, Ringer's solution, dextrose solution, and 5% human serum albumin. Nonaqueous vehicles such as fixed oils and ethyl oleate are also used. Liposomes are used as carriers. The vehicle contains minor amounts of additives such as substances that enhance isotonicity and chemical stability, e.g., buffers and preservatives. The antibodies are typically formulated in such vehicles at concentrations of about 1 mg/ml to 10 mg/ml.

The dose and dosage regimen depends upon a variety of factors readily determined by a physician, such as the nature of the infection and the characteristics of the particular cytotoxic agent or growth inhibitory agent conjugated to the antibody (when used), e.g., its therapeutic index, the patient, and the patient's history. Generally, a therapeutically effective amount of an antibody is administered to a patient. In particular embodiments, the amount of antibody administered is in the range of about 0.1 mg/kg to about 50 mg/kg of patient body weight. Depending on the type and severity of the infection, about 0.1 mg/kg to about 50 mg/kg body weight (e.g., about 0.1-15 mg/kg/dose) of antibody is an initial candidate dosage for administration to the patient, whether, for example, by one or more separate administrations, or by continuous infusion. The progress of this therapy is readily monitored by conventional methods and assays and based on criteria known to the physician or other persons of skill in the art.

In one particular embodiment, an immunoconjugate including the antibody conjugated with a cytotoxic agent is administered to the patient. Preferably, the immunoconjugate is internalized by the cell, resulting in increased therapeutic efficacy of the immunoconjugate in killing the cell to which it binds. In one embodiment, the cytotoxic agent targets or interferes with the nucleic acid in the infected cell. Examples of such cytotoxic agents are described above and include, but are not limited to, maytansinoids, calicheamicins, ribonucleases and DNA endonucleases.

Other therapeutic regimens are combined with the administration of the HIV1 antibody of the present invention. The combined administration includes co-administration, using separate formulations or a single pharmaceutical formulation, and consecutive administration in either order, wherein preferably there is a time period while both (or all) active agents simultaneously exert their biological activities. Preferably such combined therapy results in a synergistic therapeutic effect.

In certain embodiments, it is desirable to combine administration of an antibody of the invention with another antibody directed against another antigen associated with the infectious agent.

Aside from administration of the antibody protein to the patient, the invention provides methods of administration of the antibody by gene therapy. Such administration of nucleic acid encoding the antibody is encompassed by the expression "administering a therapeutically effective amount of an antibody". See, for example, PCT Patent Application Publication WO96/07321 concerning the use of gene therapy to generate intracellular antibodies.

In another embodiment, anti-HIV1 antibodies of the invention are used to determine the structure of bound antigen, e.g., conformational epitopes, the structure of which is then used to develop a vaccine having or mimicking this structure, e.g., through chemical modeling and SAR methods. Such a vaccine could then be used to prevent HIV1 infection.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1: Selection of Patient Sample

Serum from approximately 1,800 HIV-1 infected donors from Asia, Australia, Europe, North America and sub-Saharan African countries were screened for neutralization activity and donors who exhibit among the broadest and most potent neutralizing serum activity observed to date were identified. (Simek, M. D., *J Virol* (2009)). Monoclonal antibodies were generated from these donors using different approaches.

A patient was selected based upon the patient's eligibility for enrollment, which was defined as: male or female at least 18 years of age with documented HIV infection for at least three years, clinically asymptomatic at the time of enrollment, and not currently receiving antiretroviral therapy. (Simek, M. D., *J Virol* (2009 July) 83(14):7337-48). Selection of individuals for monoclonal antibody generation was based on a rank-order high throughput analytical screening algorithm. The volunteer was identified as an individual with broad neutralizing serum based on broad and potent neutralizing activity against a cross-clade pseudovirus panel.

A novel high-throughput strategy was used to screen IgG-containing culture supernatants from approximately 30,000 activated memory B cells from a clade A infected donor for recombinant, monomeric $gp120_{JR-CSF}$ and $gp41_{HxB2}$ (Env) binding as well as neutralization activity against HIV-1 JR-CSF and HIV-1 SF162 as shown in Table 1. The memory B cells were cultured at near clonal density such that the authentic antibody heavy and light chain pair could be reconstituted from each culture well.

Example 2: Generation of Monoclonal Antibodies

The human monoclonal antibody discovery platform utilized a short term B cell culture system to interrogate the memory B cell repertoire. 30,300 $CD19^+$ and surface IgG-expressing memory B cells were isolated from ten million peripheral blood mononuclear cells (PBMC) of the HIV-1 infected donor. $CD19^+/sIgG^+$ B cells were then seeded in 384-well microtiter plates at an average of 1.3 cells/well under conditions that promoted B cell activation, proliferation, terminal differentiation and antibody secretion. Culture supernatants were screened in a high throughput format for binding reactivity to recombinant gp120 and gp41 indirectly and directly immobilized on ELISA plates, respectively. In parallel, the culture supernatants were also screened for neutralization activity in a high throughput micro-neutralization assay.

Heavy and light variable regions were isolated from lysates of selected neutralizing hits by RT-PCR amplification using family-specific primer sets. From positive family-specific PCR reactions, pools of the $V_H$ or $V_L$-region clones were cloned into an expression vector upstream to human IgG1 constant domain sequence. Minipreps (QIAGEN, Valencia, Calif.) of these DNA pools, derived from suspension bacterial cultures, were combined in all possible heavy and light chain family-specific pairs and used to transiently transfect 293 cells. All transfectant supernatants containing secreted recombinant antibodies were screened in ELISA and neutralization assays. For B-cell wells that contained more than one B cell clone per culture well, multiple $V_H$ and $V_L$ domain sequences were isolated. ELISA (for B-cell wells positive for ELISA) and neutralization screens identified the heavy and light chain combination pools that reconstituted the binding and neutralizing activity as observed for the B-cell well. DNA sequences of the heavy and light chain variable regions for all neutralizing mAbs were confirmed by multiple sequencing reactions using purified DNA from maxipreps (QIAGEN).

Example 3: Screening of Monoclonal Antibodies for Binding to Recombinant gp120 and gp41 by ELISA Assay Recombinant gp120 with sequence derived from gp120 of primary HIV-1 isolate JR-CSF and expressed in insect cells was obtained from IAVI NAC repository. Recombinant gp41 generated with sequences derived from HxB2 clone of HIV-1 and expressed in *Pichia pastoris* was manufactured by Vybion, Inc., obtained from IAVI NAC repository Sheep anti-gp120 antibodies used as capturing agent to indirectly immobilize gp120 on ELISA plates was purchased from Aalto Bio Reagents (Dublin, Ireland). All ELISA assays were conducted at 25 μL/well on MaxiSorp plates from Nunc.

In anti-gp120 ELISA, recombinant gp120 (0.5 μg/ml) was captured on 384 well ELISA plates pre-coated (at 4° C. overnight) with goat anti-gp120 (5 μg/ml) in BSA-containing assay buffer (PBS with 0.05% Tween-20) for 1 hr at room temperature. After excess gp120 was removed and plates were washed thrice with assay buffer, B cell culture supernatants diluted 5-fold was added to incubate for 1 hr at room temperature. Following three washes in assay buffer, secondary HRP-conjugated goat anti-human Ig Fc in BSA-containing assay buffer was added and incubated for about 1 hr at room temperature. 3,3',5,5'-tetramethylbenzidine (TMB) substrate was used to develop the colorimetric readouts after washing the ELISA plates 3 times.

For anti-gp41 ELISA, recombinant gp41 was directly immobilized on 384 well ELISA plates by adding 1 μg/ml and incubating at 4° C. overnight, followed by blocking with BSA-containing assay buffer. The rest of the assay protocol was similar to that for anti-gp120 ELISA.

Hits from the ELISA assay were identified in a singlet screen based on optical density (OD) values above 3× assay background. A serial titration standard curve of control antibody was included on each plate.

Example 4: Neutralization Assay for Screening Antibodies Against Pseudotyped HIV Viruses The neutralization assay approach has been described previously (Binley J M, et al., (2004). Comprehensive Cross-Clade Neutralization Analysis of a Panel of Anti-Human Immunodeficiency Virus Type 1 Monoclonal Antibodies. *J. Virol.* 78: 13232-13252) and was modified and standardized for implementation in 384-well format.

Neutralization by monoclonal antibodies and patient sera was performed using a single round of replication pseudovirus assay. (Richman, D. D., et al. *Proc Natl Acad Sci USA* 100, 4144-4149 (2003)). Pseudovirus neutralization assays were performed using HIV-1$_{JR\text{-}CSF}$ alanine mutants as described in Pantophlet, R., et al. *J Virol* 77, 642-658 (2003). Neutralization activity was measured as a reduction in viral infectivity compared to an antibody-free control using a TZM-BL assay. (Li, M., et al. *J Virol* 79, 10108-10125 (2005)). Monoclonal antibody neutralization assays using phytohaemgglutinin-activated peripheral blood mononuclear cells (PBMC) isolated from three healthy human donors as target cells were performed as described in Scarlatti, G. et al, (1993) *J. Infect. Dis.* 168:207-210; Polonis, V. et al, (2001) AIDS Res. Hum. Retroviruses 17:69-79. Memory B cell supernatants were screened in a micro-neutralization assay against HIV-1 SF162, HIV-1$_{JR\text{-}CSF}$, and SIVmac239 (negative control). This assay was based on the 96-well pseudotyped HIV-1 neutralization assay (Monogram Biosciences) and was modified for screening 15 μl B cell culture supernatants in a 384-well format.

Pseudotyped virus from SF162 and JR-CSF isolates of HIV-1 and SIV mac239 (control virus) were generated by co-transfecting Human Embryonic Kidney 293 cells (293 cells) with 2 plasmids encoding the Envelope cDNA sequence and the rest of the HIV genome separately. In the HIV genome encoding vector, the Env gene was replaced by the firefly luciferase gene. Transfectant supernatants containing pseudotyped virus were co-incubated overnight (18 hours) with B cell supernatants derived from activation of an infected donor's primary peripheral blood mononuclear cells (PBMCs). U87 cells stably transfected with and expressing CD4 plus the CCR5 and CXCR4 coreceptors were added to the mixture and incubated for 3 days at 37° C. Infected cells were quantified by luminometry. SIVmac239 was used as the negative control virus.

The neutralization index was expressed as the ratio of normalized relative luminescence units (RLU) of the test viral strain to that of the control virus SIVmac239 derived from the same test B cell culture supernatant. The cut-off values used to distinguish neutralizing hits were determined by the neutralization index of a large number of "negative control wells" containing B cell culture supernatants derived from healthy donors. The false positive rate using the cut-off value of 1.5 was very low (1-3%; FIG. 5A), and it was reduced to zero if the cut-off value of 2.0 was used (FIG. 5B).

FIG. 5 summarizes the screening results from which B cell cultures were selected for antibody rescue and the monoclonal antibodies 1496_C09 (PG9), 1443_C16 (PG16), 1456_P20 (PG20), 1460_G14 (PGG14), and 1495_C14 (PGC14) were derived. The results reveal that the majority of neutralizing B cell culture supernatants did not have binding reactivity to soluble recombinant gp120 or gp41 proteins.

Lightest grey: suggested H &L pair for monoclonal antibody per priority well.

Medium grey with black lettering: Denotes clones derived from same recombinant H or L chain pool of the priority well with identical sequences.

Bolded: 1496_C09 λ3 clone 024 is likely a cross-contaminant in the recombinant DNA pool as it is identical to 1443_C16 λ2 019 in sequence. 1496_C09 λ2 017 sequence represents 21/22 clones in the pool.

*Anti-gp120 and anti-gp41 concentrations were extrapolated from b12 and 2F5 standard curves in quantitative ELISA, respectively.

N/A=not applicable because these hits were neither gp-120- nor gp-41 positive in B cell culture. ND=not done.

The purified monoclonal antibodies 1496_C09 (PG9), 1443_C16 (PG16), 1456_P20 (PG20), 1460_G14 (PGG14), and 1495_C14 (PGC14) were tested for neutralization of 6 additional HIV strains from clades A (94UG103), B (92BR020, JR-CSF), C (93IN905, IAVI_C22), and CRF01_AE (92TH021) (FIG. 30). The antibodies 1496_C09 (PG9), 1443_C16 (PG16) and 1495_C14 (PGC14) showed neutralization profile similar to that obtained with the donor sera neutralization profile. The pseudoviruses were preincubated with each monoclonal antibody for 1 hour or 18 hours prior to the infection of target cells. IC$_{50}$ values derived from 1 or 18 hours preincubation were similar. Therefore, in further neutralization assays testing purified monoclonal antibodies, 1 hour of preincubation was used.

FIG. 31A shows the neutralization profiles for the 5 monoclonal antibodies 1496_C09 (PG9), 1443_C16 (PG16), 1456_P20 (PG20), 1460_G14 (PGG14), and 1495_C14 (PGC14) in IC$_{50}$ values on an extended panel of 16 pseudoviruses, together with known cross-clade neutralizing antibodies b12, 2G12, 2F5 and 4E10. FIG. 31B shows the IC90 of two monoclonal antibodies, 1443_C16 (PG16) and 1496_C09 (PG9) on the same expanded diverse panel of 16 HIV pseudoviruses from different clades, together with known cross-clade neutralizing antibodies b12, 2G12, 2F5 and 4E10. FIG. 4 shows neutralization activity of monoclonal antibodies 1443_C16 (PG16) and 1496_C09 (PG9) to 3 other pseudoviruses not included in FIG. 30.

Example 5: Binding Specificity of Monoclonal Antibodies for HIV Gp120 by ELISA Assay The purified anti-gp120 monoclonal antibodies, 1456_P20 (PG20), 1460_G14 (PGG14), and 1495_C14 (PGC14), were confirmed for binding reactivity to gp120 in ELISA assays. When titrated in serial dilutions, all three antibodies exhibited similar binding profiles that suggest significantly higher relative avidity than control anti-gp120 (b12). MAb b12 is directed against an epitope overlapping the CD4 binding site. (Burton D R et al. 1994. Efficient neutralization of primary isolates of HIV-1 by a recombinant human monoclonal antibody. *Science* 266:1024-1027).

FIG. 5 shows dose response curves of 1456_P20 (PG20), 1460_G14 (PGG14), and 1495_C14 (PGC14) binding to recombinant gp120 in ELISA as compared to control anti-gp120 (b12). Data shown represented average OD values of triplicate ELISA wells obtained on the same plate.

The monoclonal antibodies 1443_C16 (PG16) and 1496_C09 (PG9) were tested for binding to soluble recombinant envelope proteins derived from several HIV strains in ELISA assay. ELISA assays were performed as described in Pantophlet, R., et al. *J Virol* 77, 642-658 (2003). For antigen binding ELISAs, serial dilutions of PG9 were added to antigen coated wells and binding was probed with alkaline phosphatase-conjugated goat anti-human immunoglobulin G (IgG) F(ab')2 Ab (Pierce). For competition ELISAs, competitor mAbs were added to ELISA wells and incubated for 15 min prior to adding 15 µg/mL biotinylated PG9 to each well. Biotinylated PG9 was detected using alkaline phosphatase conjugated streptavidin (Pierce) and visualized using p-nitrophenol phosphate substrate (Sigma). HIV-HXB2 gp120 was used for competition ELISA assays.

FIG. 6 shows results from ELISA binding assays of monoclonal antibodies 1443_C16 (PG16) and 1496_C09 (PG9) to HIV-1 YU2 gp140, JR-CSFgp120, membrane-proximal external regions (MPER) peptide of gp41 and V3 polypeptide. Specificity of the monoclonal antibodies 1443_C16 (PG16) and 1496_C09 (PG9) for gp120 was then confirmed, but it was noted that the binding to soluble envelope glycoprotein was weak.

Example 6: Binding Reactivity of Monoclonal Antibodies 1443_C16 (PG16) and 1496_C09 (PG9) to Envelope Proteins Expressed on Transfected Cell Surface and Competition by Soluble CD4 (sCD4)

MAb cell binding assays were performed as described in Pancera, M. & Wyatt, R. *Virology* 332, 145-156 (2005). Titrating amounts of PG9 and PG16 were added to HIV-1 Env transfected 293T cells, incubated for 1 hr at 4° C., washed with FACS buffer, and stained with goat anti-human IgG F(ab') 2 conjugated to phycoerythin. For competition assays, competitor antibodies were added to the cells 15 min prior to adding 0.1 µg/mL biotinylated PG9 or PG16. For sCD4 inhibition assays, 40 µg/mL sCD4 was added to the cells and incubated for 1 h at 4° C. prior to adding titrating amounts of antibodies. Binding was analyzed using flow cytometry, and binding curves were generated by plotting the mean fluorescence intensity of antigen binding as a function of antibody concentration.

Ninety-six-well ELISA plates were coated overnight at 4° C. with 50 µL PBS containing 100 ng gp120 or gp140 per well. The wells were washed four times with PBS containing 0.025% Tween 20 and blocked with 3% BSA at room temperature for 1 h. Serial dilutions of PG9 were added to antigen coated wells, incubated for 1 h at room temperature, and washed 4× with PBS supplemented with 0.025% Tween 20. Binding was probed with alkaline phosphatase-conjugated goat anti-human immunoglobulin G (IgG) F(ab')2 Ab (Pierce) diluted 1:1000 in PBS containing 1% BSA and 0.025% Tween 20. The plate was incubated at room temperature for 1 h, washed four times, and the plate was developed by adding 50 µL of alkaline phosphatase substrate (Sigma) to 5 mL alkaline phosphatase staining buffer (pH 9.8), according to the manufacturer's instructions. The optical density at 405 nm was read on a microplate reader (Molecular Devices). For competition ELISAs, competitor mAbs were added to $gp120_{HxB2}$ or $gp140Yu2$ coated ELISA wells and incubated for 15 min prior to adding 15 µg/mL biotinylated PG9 to each well. Biotinylated PG9 was detected using alkaline phosphatase conjugated streptavidin (Pierce) and visualized using p-nitrophenol phosphate substrate (Sigma). For sCD4 inhibition ELISAs, 5 µg/mL sCD4 was added to antigen-coated wells and incubated for 15 min at room temperature prior to adding titrating amounts of PG9. A FACSArray™ plate reader (BD Biosciences, San Jose, Calif.) was used for flow cytometric analysis and FlowJo™ software was used for data interpretation.

HIV gp160 derived from YU2 was transfected in 293 cells. Binding of monoclonal antibodies 1443_C16 (PG16) and 1496_C09 (PG9) were detected in transfected cells (FIG. 7). The preincubation of transfected cells with soluble CD4 (sCD4) partially inhibited binding of monoclonal antibody for 1496_C09 (PG9), and for 1443_C16 (PG16) suggesting the antibody binding is effected by the presence of sCD4. Binding is inhibited by at least 15%, at least 20%, at least 25%, or at least 30%. Binding of monoclonal antibodies 1443_C16 (PG16) and 1496_C09 (PG9) to 293 cells transfected with gp160 derived from JR-CSF and ADA strains was also detected (FIG. 8). The binding of both monoclonal antibodies 1443_C16 (PG16) and 1496_C09 (PG9) to JR-CSF transfected cells was blocked by sCD4. Results further confirm that binding activities of monoclonal antibodies 1443_C16 (PG16) and 1496_C09 (PG9) are affected by the presence of sCD4.

Example 7: Binding Reactivity of Monoclonal Antibodies 1443_C16 (PG16) and 1496_C09 (PG9) to Pseudoviruses In vitro virus capture assay was used to test if monoclonal antibodies 1443_C16 (PG16) and 1496_C09 (PG9) bind to intact entry competent pseudoviruses. The monoclonal antibodies 1443_C16 (PG16) and 1496_C09 (PG9) were coated at the bottom of 96-well plate via anti-human Fc. JR-CSF pseudovirus was added and captured by the monoclonal antibody 1443_C16 (PG16) or 1496_C09 (PG9) in a dose dependent manner. Target cells were added to initiate infection. Infection measured in RLU then represented the binding and capture activity of monoclonal antibodies 1443_C16 (PG16) and 1496_C09 (PG9). FIG. 9 shows the binding and capture of JR-CSF pseudovirus by both monoclonal antibodies 1443_C16 (PG16) and 1496_C09 (PG9) in a dose dependent manner, which is similar or better than another known broad and potent neutralizing antibody 2G12.

Example 8: Monoclonal Antibodies 1443_C16 (PG16) and 1496_C09 (PG9) Cross-Compete with Each Other and with sCD4 in Binding to JR-CSF Pseudovirus In a competition version of virus capture assay where JR-CSF pseudovirus was captured by monoclonal antibodies 1443_C16 (PG16), competition of the capture by either monoclonal antibodies 1443_C16 (PG16), 1496_C09 (PG9) and sCD4 was measured. FIG. 10B shows that binding of monoclonal antibody 1443_C16 (PG16) to JR-CSF pseudovirus was blocked by itself, monoclonal antibody 1496_C09 (PG9) and sCD4 in a dose dependent manner. In a corresponding manner, FIG. 10B shows that binding of monoclonal antibody 1496_C09 (PG9) to JR-CSF pseudovirus was blocked by itself, monoclonal antibody 1443_C16 (PG16) and sCD4 in a dose dependent manner. Results indicated that the monoclonal antibodies 1443_C16 (PG16) and 1496_C09 (PG9) bind to closely related epitopes on gp120 and their binding is affected by the presence of sCD4 presumably due to conformational changes induced on HIV-1 envelope by sCD4.

Example 9: Antigen Binding Properties of PG9 and PG16

Figure 11A:
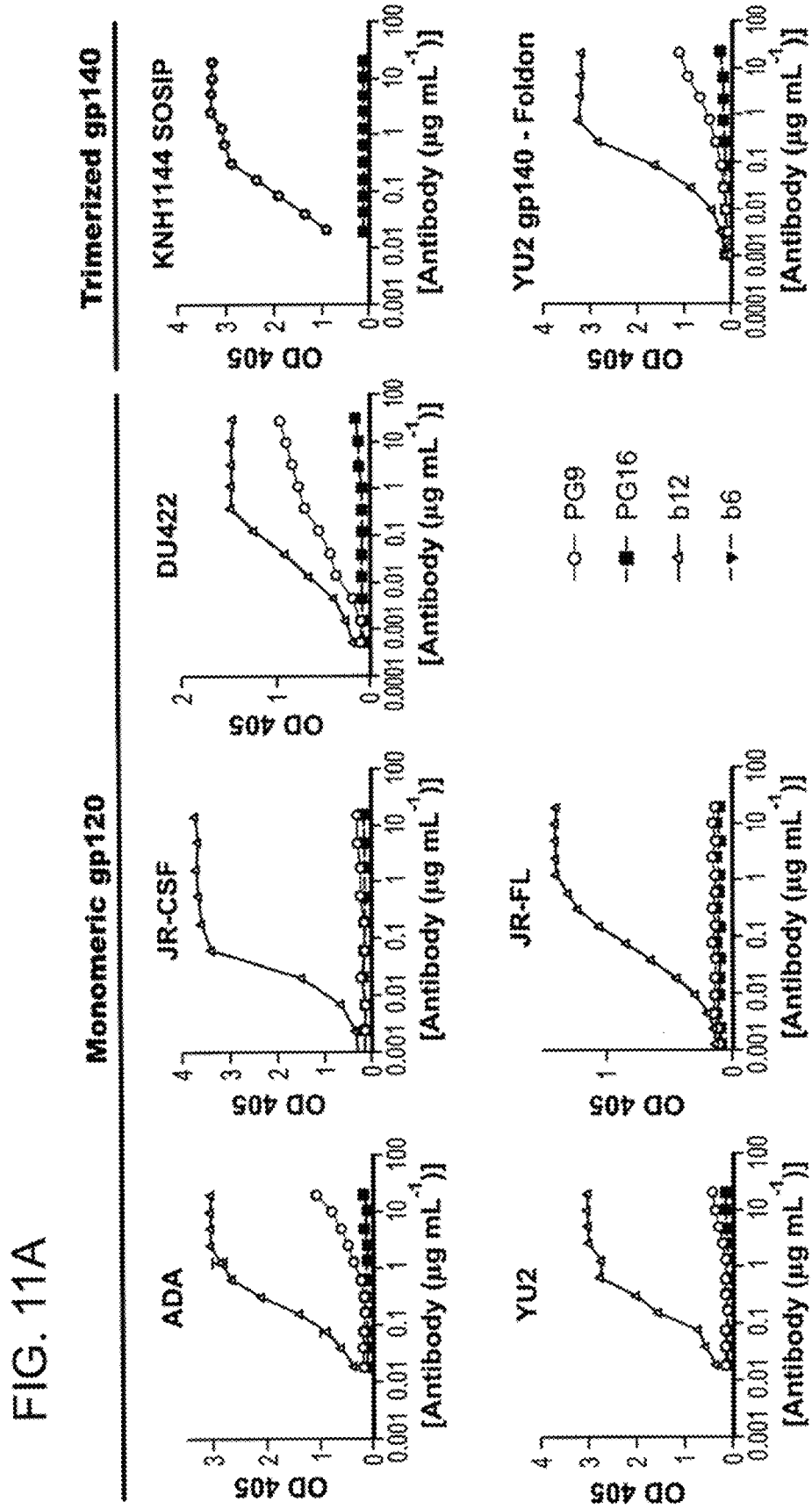
FIG. 11A is a series of graphs depicting the results of a binding assay using PG9 and PG16. The data show that PG9 and PG16 bind to monomeric gp120 and artificially trimerized gp140 constructs as determined by ELISA. IgG b12 was used as a control for ELISA assays.
Figure 11B:
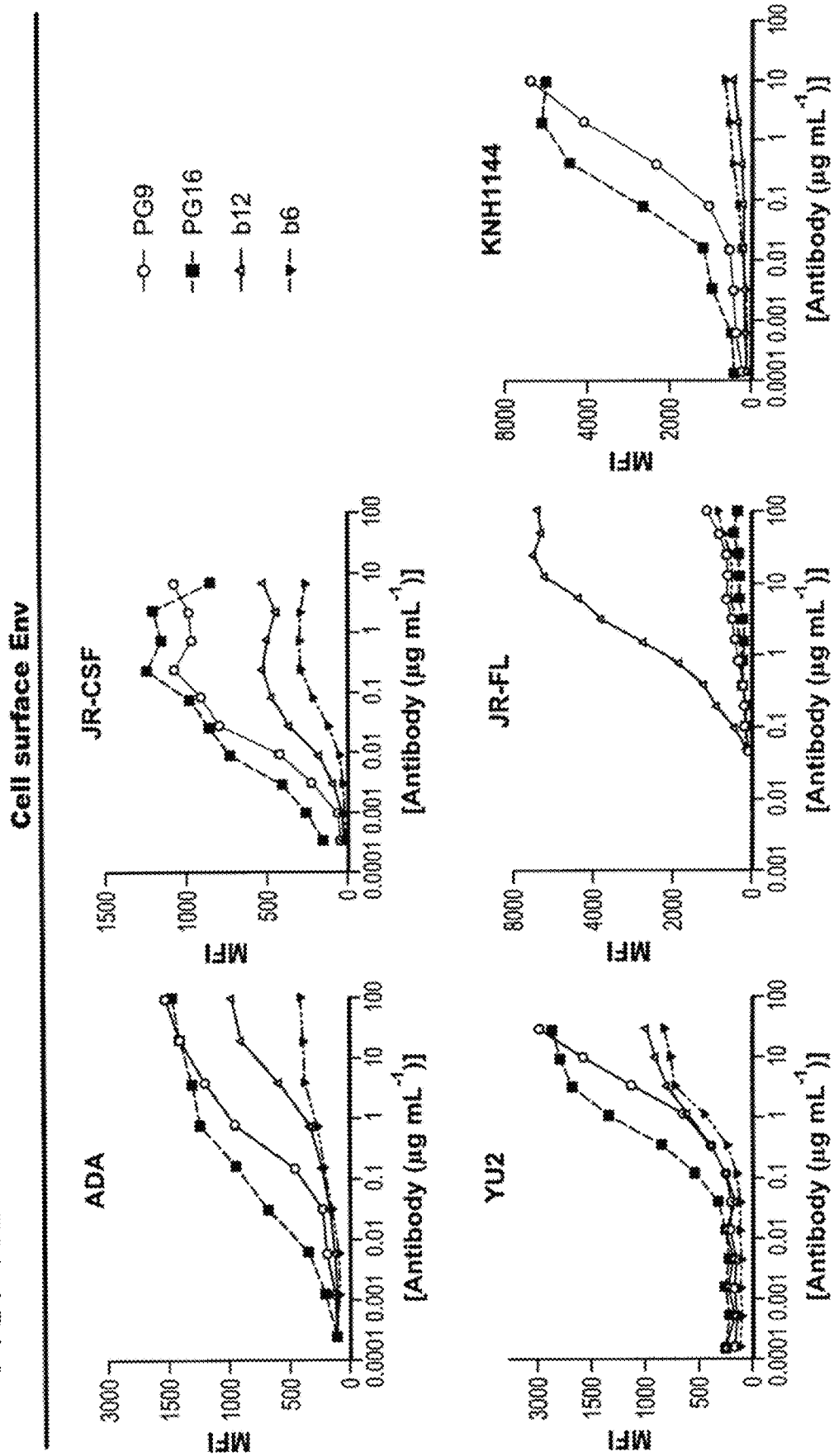
FIG. 11B is a series of graphs depicting the results of a binding assay using PG9 and PG16. The data show that PG9 and PG16 bind to Env expressed on the surface of 293T cells as determined by flow cytometry. The bNAb b12 and the non-neutralizing antibody b6 are included in the cell surface binding assays to show the expected percentages of cleaved and uncleaved Env expressed on the cell surface.
Figure 12:
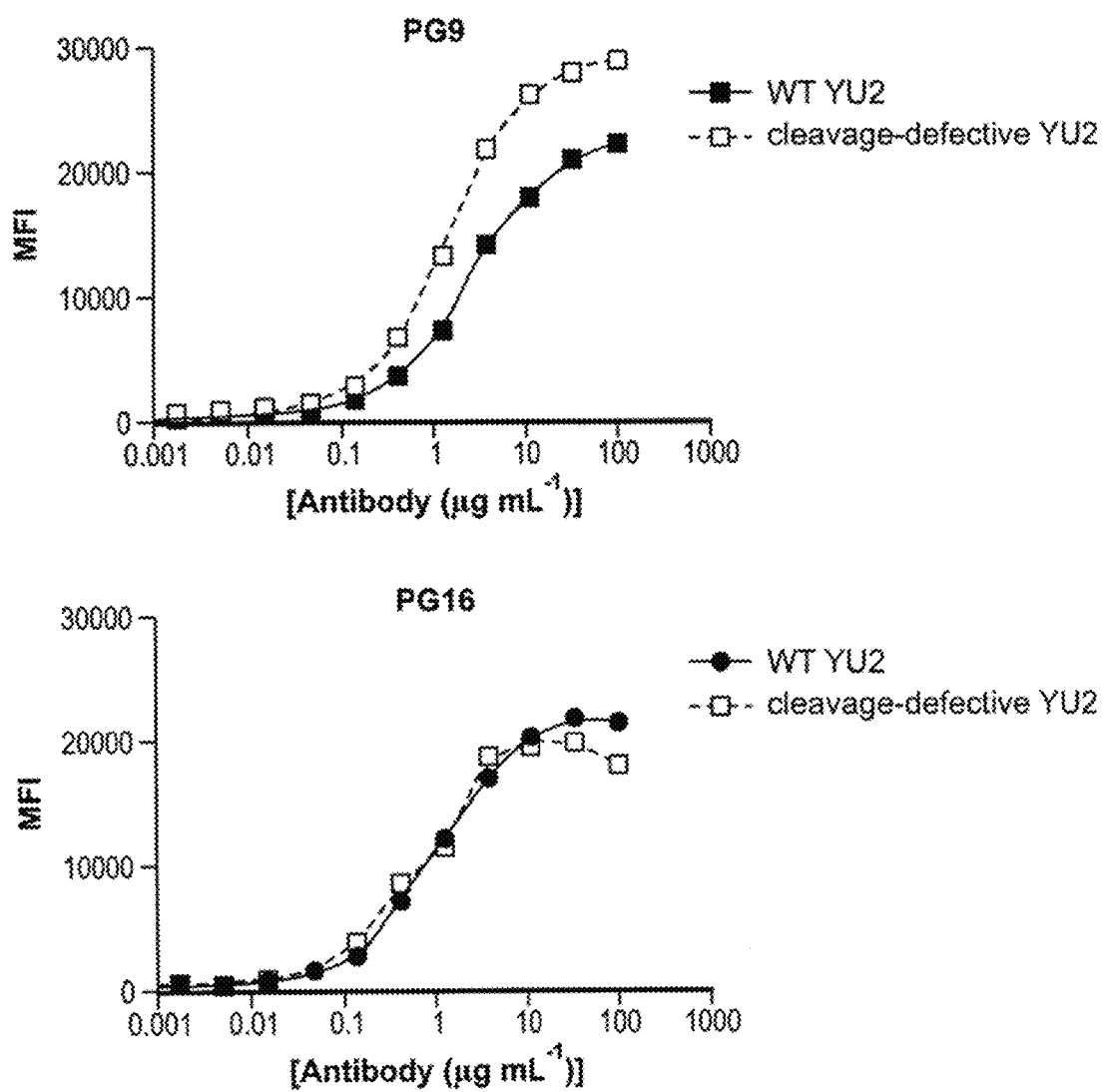
FIG. 12 is a series of graphs depicting the results of a binding assay using PG9 and PG16 and cleavage-defective HIV-1YU2 trimers. PG9 and PG16 bind with high affinity to cleavage-defective HIV-1YU2 trimers as determined by flow cytometry. Binding curves were generated by plotting the MFI of antigen binding as a function of antibody concentration.

Antigen binding properties of PG9 and PG16 were determined by ELISA assays as shown in FIG. 11A-B. Binding of PG9 and PG16 to monomeric gp120 and artificially trimerized gp140 constructs were determined (FIG. 11A). Binding of PG9 and PG16 to Env expressed on the surface of 293T cells as determined by flow cytometry. (FIG. 11B). b12 was used as a control for ELISA assays. The bNAb b12 and the non-neutralizing antibody b6 were included in the cell surface binding assays to show the expected percentages of cleaved and uncleaved Env expressed on the cell surface.

Example 10: Binding of PG9 and PG16 to Cleavage-Defective HIV-1Yu2 Trimers

Binding of PG9 and PG16 to cleavage-defective HIV-$1_{YU2}$ trimers was determined by flow cytometry. PG9 and PG16 bind with high affinity to cleavage-defective HIV-$1_{YU2}$ trimers as shown in FIG. 12. Binding curves were generated by plotting the mean fluorescence intensity (MFI) of antigen binding as a function of antibody concentration.

Example 11: Mapping the PG9 and PG16 Epitopes

Mapping the epitopes of PG9 and PG16 epitopes was performed by a competitive binding assay as shown in FIG. 13. PG9 and PG16 competed with each other for cell surface Env binding and neither antibody competed with the CD4bs antibody b12 for Env binding. Competitor antibody is indicated at the top of each graph. (FIG. 13A). Ligation of cell surface Env with sCD4 diminished binding of PG9 and PG16. 2G12 was included to control for CD4-induced shedding of gp120. (FIG. 13B). sCD4 inhibited binding of PG9 to artificially trimerized gp140$_{JR-CSF}$ as determined by ELISA. (FIG. 13C). PG9 competed with 10/76b (anti-V2), F425/b4e8 (anti-V3) and X5 (CD4i) for gp120 binding in competition ELISA assays. (FIG. 13D). PG9 and PG16 failed to bind variable loop deleted HIV-1 JR-CSF variants expressed on the surface of 293T cells. 2G12 was included to control for cell surface Env expression. (FIG. 13E).

Example 12: Competition ELISA Assays Using PG9

When competition ELISA assays using PG9 were performed, PG9 competed with c108 g (anti-V2) and partially competed with 17b (CD4i). No competition was observed with A32 (anti-C1/C2/C4/CD4i), C11 (C1), 2G12 (glycan shield), b6 (CD4bs), b3 (CD4bs) or 23b (C1/C5) for gp120$_{HxB2}$ binding as shown in FIG. 14.

Example 13: Binding of PG9 and PG16 to HIV-$1_{JR-FL}$ E168K

Figure 15:
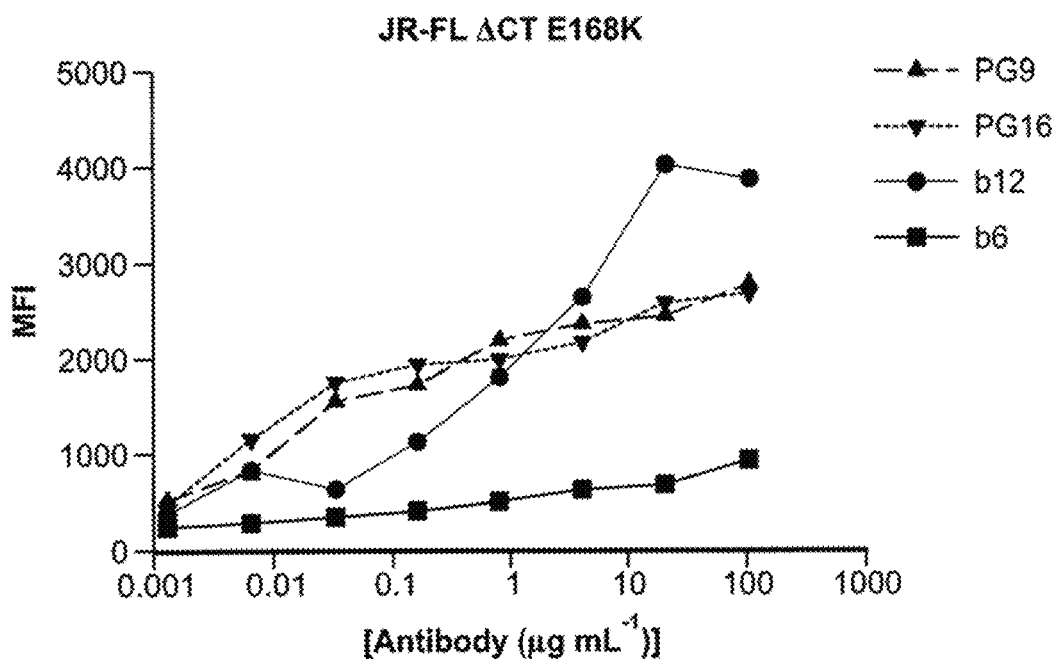
FIG. 15 is a graph depicting monoclonal antibody binding, PG9 or PG16, to HIV-1JR-FLACT E168K Env expressed on the surface of 293T cells as determined by flow cytometry.

Antibody binding to HIV-1JR-FLACT E168K Env expressed on the surface of 293T cells as determined by flow cytometry is shown in FIG. 15. A cytoplasmic tail deleted construct was used to increase cell surface expression. The bNAb b12 and the non-neutralizing antibody b6 were included in the cell surface binding assays to show the expected percentages of cleaved and uncleaved Env expressed on the cell surface. (Pancera M., et al. *Virology* 332:145 (2005). HIV-1JR-FL E168K was generated by site-directed mutagenesis. Binding curves were generated by plotting the MFI of antigen binding as a function of antibody concentration.

Figure 16:
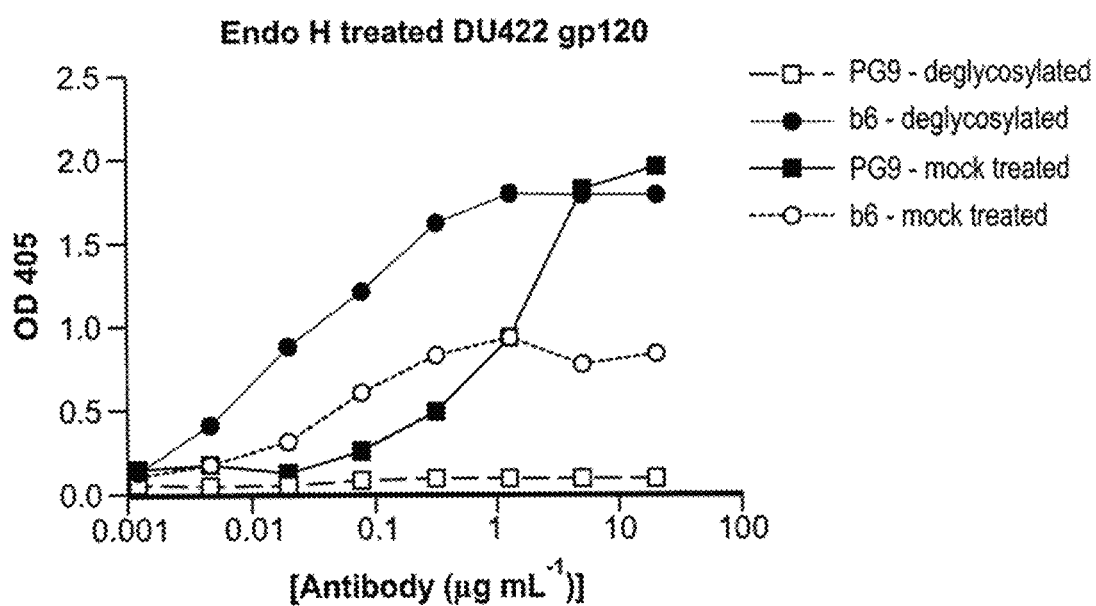
FIG. 16 is a graph depicting monoclonal antibody PG9 binding to deglycosylated gp120.

Example 14: PG9 Binding to Deglycosylated Gp120 gp120Du422 was treated with 40 mU/µg Endoglycosidase H (Endo H, New England Biolabs) in sodium acetate buffer for 24 hr at 37° C. Mock treated gp120 was treated under same conditions, but the enzyme was omitted from the reaction. Binding of PG9 and b6 to EndoH treated and mock treated gp120 was determined by ELISA as shown in FIG. 16.

Example 15: Neutralization Activity Against HIV-$1_{SF162}$ K160N

Neutralization activity of PG9 and PG16 against HIV-1SF162 and HIV-1SF162 K160N was determined using a single-round replication luciferase reporter assay of pseudotyped virus. HIV-$1_{SF162}$ K160N was generated by site-directed mutagenesis as shown in FIG. 17.

Example 16: Binding of PG9 and PG16 to Mixed Trimers

Alanine substitutions at positions 160 and 299 were introduced into HIV-1Yu2 Env to abolish binding of PG9 and PG16. An alanine substitution at position 295 was also introduced into the same construct to abrogate binding of 2G12. Co-transfection of 293T cells with WT and mutant plasmids in a 1:2 ratio resulted in the expression of 29% mutant homotrimers, 44% heterotrimers with two mutant subunits, 23% heterotrimers with one mutant subunit, and 4% wild-type homotrimers. These proportions were calculated using the formula described in Yang, X., Kurteva, S., Lee, S., and J. Sodroski, *J Virol* 79(6):3500-3508 (March 2005), and assumes that mutant and wild-type gp120s mix randomly to form trimers. Binding of mAbs to Env trimers was determined by flow cytometry as shown in FIG. 18. b12 was included as control for Env cell surface expression.

Example 17: PG9 or PG16 Neutralization Activity on HIV with Alanine Mutations within Gp120

Alanine mutations within gp120 of HIV decrease PG9 or PG16 neutralization activity as shown in FIG. 35. In the figure, amino acid numbering is based on the sequence of HIV-$1_{HxB2}$. Boxes are color coded as follows: white, the amino acid is identical among 0 to 49% of all HIV-1 isolates; light grey, the amino acid is identical among 50 to 90% of isolates; dark grey, the amino acid is identical among 90 to 100% of isolates. Amino acid identity was determined based on a sequence alignment of HIV-1 isolates listed in the HIV sequence database at hiv-web.lanl.gov/content/hiv-db/mainpage.html. C refers to constant domains and V refers to variable loops. Neutralization activity is reported as fold increase in $IC_{50}$ value relative to WT JR-CSF and was calculated using the equation ($IC_{50}$ mutant/$IC_{50}$ WT). Boxes are color coded as follows: white, substitutions which had a negative effect on neutralization activity; light grey, 4-9 fold $IC_{50}$ increase; medium grey, 10-100 fold $IC_{50}$ increase; dark grey, >100 fold $IC_{50}$ increase. Experiments were performed in triplicate and values represent an average of at least three independent experiments.

Example 18: Identification of 14443 C16 (PG16) Sister Clones

1443_C16 sister clones were identified by screening clonal transfection of rescued variable region genes for JR-CSR neutralization. Thus, antibodies that were identified as sister clones of 1443_C16 (PG16) have the similar HIV neutralization profiles as the human monoclonal 1443_C16 (PG16). Moreover, the nucleic acid or amino acid sequences of the sister clone antibodies are at least 50%, 55%, 60%, 70%, 75%, 80%, 85%, 90%, 95%, 99%, 100% or any percentage point in between, identical to those of 1443_C16 (PG16).

Example 19: 1443_C16 (PG16) Antibody Sister Clones and the 1443_C16 (PG16) Antibody Exhibit Similar Neutralization Specificity Antibodies 1456_A12, 1503 H05, 1489 113 and 1469 M23 were tested for neutralization activity against several pseudoviruses containing distinct mutations that map the reactivity epitope of 1443_C16 (PG16) on gp120 in a standard TZM-b1 assay (Table 23). Like 1443_C16 (PG16), which does not bind or neutralize wild-type JR-FL, but instead, neutralizes JR-FL with the E168K mutation, all 1443_C16 (PG16) sister clones neutralize JR-FL(E168K) with low IC50 values. Similarly, all 1443_C16 (PG16) sister clones do not neutralize the Y318A mutants and 1309A mutants of JR-CSF, where the part of the putative binding epitope is mapped on the V3 tip.

TABLE 23

Neutralization specificity of 1443 C16 (PG16) sister clones as shown with specific mutations on gp120.

| | IC50 (ug/ml) | | | | | |
|---|---|---|---|---|---|---|
| mAb | JR-CSF | JR-CSF (Y318A) | JR-CSF (I309A) | JR-FL (E168K) | ADA | 92RW020 |
| 1503 H05 | 0.001 | >1.0 | >1.0 | 0.002 | 0.003 | 0.020 |
| 1456 A12 | 0.001 | >1.0 | >1.0 | 0.003 | 0.005 | 0.050 |
| 1469 M23 | 0.002 | >1.0 | >1.0 | 0.005 | 0.005 | 0.050 |
| 1489 I13 | 0.002 | >1.0 | >1.0 | 0.005 | 0.008 | 0.030 |
| 1443 C16 | 0.001 | >1.0 | >1.0 | 0.006 | 0.004 | 0.090 |
| 1496 C09 | 0.006 | 0.001 | 0.001 | 0.020 | 0.200 | 0.100 |

Example 20: 1443_C16 (PG16) Sister Clones Exhibit Similar Neutralization Breadth and Potency as 1443_C16 (PG16) for Clade B and Clade C Viruses The antibodies 1456_A12, 1503 H05, 1489 113 and 1469 M23 exhibit neutralization activity against a panel of clade B and clade C pseudoviruses with similar breadth as does 1443 C16 (PG16) in a standard TZM-b1 assay (Table 24). The neutralization potency of each sister clone for each pseudovirus is comparable to that for 1443_C16 (PG16). When the IC50 value is determined, the value for the sister clone is within a 0.5 log range from that for 1443_C16 (PG16).

TABLE 24

Neutralization breadth and potency of 1443 C16 (PG16) sister clones.

| | | IC50 (ug/ml) | | | | |
|---|---|---|---|---|---|---|
| | Virus | 1443 C16 | 1456 Al2 | 1469 M23 | 1503 H05 | 1489 I13 |
| Clade B | CAAN | 6.37 | 10.61 | 17.72 | 13.46 | 24.87 |
| | REJO4541 | <0.01 | <0.01 | 0.39 | 0.22 | 0.34 |
| | THRO.18 | 2.19 | 2.08 | 7.01 | 4.12 | 7.41 |
| | PVO.4 | 12.3 | 10.42 | 21.25 | 11.01 | 20.57 |
| | TR0.11 | 3.61 | 3.05 | 7.52 | 4.30 | 10.94 |
| | AC10 | <0.01 | <0.01 | <0.01 | <0.01 | <0.01 |
| Clade C | DU156 | <0.01 | <0.01 | <0.01 | <0.01 | <0.01 |
| | DU422 | 0.59 | 0.36 | 0.97 | 0.71 | 1.87 |
| | Du172 | <0.01 | <0.01 | <0.01 | <0.01 | <0.01 |
| | ZM214 | >25 | >25 | >25 | >25 | >25 |
| | ZM233 | <0.01 | <0.01 | <0.01 | <0.01 | <0.01 |
| | CAP45 | <0.01 | <0.01 | <0.01 | <0.01 | <0.01 |
| | ZM249 | <0.01 | <0.01 | <0.01 | <0.01 | <0.01 |
| Control | MuLV | >25 | >25 | >25 | >25 | >25 |

Other Embodiments

Although specific embodiments of the invention have been described herein for purposes of illustration, various modifications may be made without deviating from the spirit and scope of the invention. Accordingly, the invention is not limited except as by the appended claims. While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A non-naturally occurring anti-HIV-1 PGC14 monoclonal antibody or antigen binding portion thereof comprising (a) a light chain variable region comprising complementarity determining regions having the amino acid sequences of SEQ ID NOS: 120, 121, and 44 and (b) a heavy chain variable region comprising complementarity determining regions having the amino acid sequences of SEQ ID NOS: 116, 117, and 118.

2. A non-naturally occurring anti-HIV-1 PGC14 monoclonal antibody or antigen binding portion thereof comprising a light chain variable region comprising the amino acid sequence of SEQ ID NO: 38 and a heavy chain variable region comprising the amino acid sequence of SEQ ID NO: 37.

3. A non-naturally occurring anti-HIV-1 PGC14 monoclonal antibody or antigen binding portion thereof comprising (a) a heavy chain sequence comprising the amino acid sequence of SEQ ID NO.: 24 and (b) a light chain sequence comprising the amino acid sequence of SEQ ID NO.: 26.

4. A pharmaceutical composition comprising the antibody of any one of claims 1 to 3 and a pharmaceutically acceptable carrier,
wherein the carrier is selected from the group consisting of a buffer, organic acid, antioxidant, preservative, alkyl paraben, oligopeptide, protein, amino acid, hydrophilic polymer, carbohydrate, chelating agent, tonicifier, sugar, and surfactant.

5. The composition according to claim 4, wherein the buffer is acetate, Tris, phosphate, or citrate.

6. The composition according to claim 4, wherein the antioxidant is ascorbic acid or methionine.

7. The composition according to claim 4, wherein the preservative is octadecyldimethylbenzene, ammonium chloride, hexamethonium chloride, benzalkonium chloride, benzethonium chloride, hexamethonium chloride, benzalkonium chloride, phenol, butyl alcohol, or benzyl alcohol.

8. The composition according to claim 4, wherein the alkyl paraben is methyl paraben, propyl paraben, catechol, resorcinol, cyclohexanol, 3-pentanol, or m-cresol.

9. The composition according to claim 4, wherein the oligopeptide comprises at most ten residues.

10. The composition according to claim 4, wherein the protein is an immunoglobulin, gelatin, or serum albumin.

11. The composition according to claim 4, wherein the amino acid is glycine, glutamine, asparagine, histidine, arginine, or lysine.

12. The composition according to claim 4, wherein the hydrophilic polymer is polyvinylpyrrolidone.

13. The composition according to claim 4, wherein the carbohydrate is a monosaccharide, disaccharide, dextrin, glucose, or mannose.

14. The composition according to claim 4, wherein the chelating agent is EDTA.

15. The composition according to claim 4, wherein the tonicifier is trehalose or sodium chloride.

16. The composition according to claim 4, wherein the sugar is sucrose, mannitol, trehalose, or sorbitol.

17. The composition according to claim 4, wherein the surfactant is polysorbate.

18. The composition according to claim 4, wherein said composition comprises a lyophilized formulation.

19. The composition according to claim 4, wherein said composition comprises an aqueous solution.

20. The composition according to claim 4, wherein the antibody is present at a concentration between 5-200 mg/mL.

21. The composition according to claim 4, wherein the antibody is present at a concentration between 10-100 mg/mL.

22. The composition according to claim 4, further comprising at least one therapeutic agent.

23. The composition of claim 22, wherein the therapeutic agent is a second antibody.

24. The composition of claim 22, wherein the therapeutic agent is an anti-viral agent.

25. The composition of claim 22, wherein the therapeutic agent is an anti-infective agent.

26. The composition of claim 22, wherein the therapeutic agent is a cardioprotectant.

27. The composition of claim 22, wherein the antibody is present at a concentration between 5-200 mg/mL.

28. The composition of claim 22, wherein the antibody is present at a concentration between 10-100 mg/mL.

29. The composition according to claim 4, wherein the antibody is encapsulated in microcapsules.

30. The composition of claim 22, wherein the antibody and the therapeutic agent are encapsulated in microcapsules.

31. The antibody of any one of claims 1-3, wherein the antigen is gp120.

* * * * *

```
                              SEQUENCE LISTING

<160> NUMBER OF SEQ ID NOS: 142

<210> SEQ ID NO 1
   <211> LENGTH: 11
   <212> TYPE: PRT
   <213> ORGANISM: Homo sapiens

<400> SEQUENCE: 1

Ser Ser Leu Thr Asp Arg Ser His Arg Ile Phe
   1               5                   10

<210> SEQ ID NO 2
   <211> LENGTH: 11
   <212> TYPE: PRT
   <213> ORGANISM: Homo sapiens

<400> SEQUENCE: 2

Lys Ser Leu Thr Ser Thr Arg Arg Arg Val Phe
   1               5                   10

<210> SEQ ID NO 3
   <211> LENGTH: 8
   <212> TYPE: PRT
   <213> ORGANISM: Homo sapiens

<400> SEQUENCE: 3

Ser Tyr Ser Thr Pro Arg Thr Phe
   1               5

<210> SEQ ID NO 4
   <211> LENGTH: 8
   <212> TYPE: PRT
   <213> ORGANISM: Homo sapiens

<400> SEQUENCE: 4

Ser Phe Ser Thr Pro Arg Thr Phe
   1               5

<210> SEQ ID NO 5
   <211> LENGTH: 12
   <212> TYPE: PRT
   <213> ORGANISM: Homo sapiens

<400> SEQUENCE: 5

Ala Trp Glu Thr Thr Thr Thr Thr Phe Val Phe Phe
   1               5                   10

<210> SEQ ID NO 6
   <211> LENGTH: 28
   <212> TYPE: PRT
   <213> ORGANISM: Homo sapiens

<400> SEQUENCE: 6

Glu Ala Gly Gly Pro Ile Trp His Asp Asp Val Lys Tyr Asp Phe
   1               5                   10                  15

Asn Asp Gly Tyr Tyr Asn Tyr His Tyr Met Asp Val
                   20                  25
```

<210> SEQ ID NO 7
<211> LENGTH: 28
<212> TYPE: PRT
<213> ORGANISM: Homo sapiens

<400> SEQUENCE: 7

Glu Ala Gly Gly Pro Asp Tyr Arg Asn Gly Tyr Asn Tyr Tyr Asp Phe
1               5                   10                  15
Tyr Asp Gly Tyr Tyr Asn Tyr His Tyr Met Asp Val
            20                  25

<210> SEQ ID NO 8
<211> LENGTH: 15
<212> TYPE: PRT
<213> ORGANISM: Homo sapiens

<400> SEQUENCE: 8

Asp Arg Arg Val Val Pro Met Ala Thr Asp Asn Trp Leu Asp Pro
1               5                   10                  15

<210> SEQ ID NO 9
<211> LENGTH: 15
<212> TYPE: PRT
<213> ORGANISM: Homo sapiens

<400> SEQUENCE: 9

Asp Arg Arg Ala Val Pro Ile Ala Thr Asp Asn Trp Leu Asp Pro
1               5                   10                  15

<210> SEQ ID NO 10
<211> LENGTH: 13
<212> TYPE: PRT
<213> ORGANISM: Homo sapiens

<400> SEQUENCE: 10

Gly Ala Val Gly Ala Asp Ser Gly Ser Trp Phe Asp Pro
1               5                   10

<210> SEQ ID NO 11
<211> LENGTH: 1461
<212> TYPE: DNA
<213> ORGANISM: Homo sapiens

<400> SEQUENCE: 11

| | | | | | |
|---|---|---|---|---|---|
| atggagtttg | ggctgagctg | ggttttcctc | gcaactctgt | taagagttgt | gaagtgtcag | 60 |
| gaacaactgg | tggagtctgg | gggaggcgtg | gtccagccgg | gggggtccct | gagactctcc | 120 |
| tgtttagcgt | ctggattcac | gtttcacaaa | tatggcatgc | actgggtccg | ccaggctcca | 180 |
| ggcaagggcc | tggagtgggt | ggcactcatc | tcagatgacg | gaatgaggaa | atatcattca | 240 |
| gactccatgt | ggggccgagt | caccatctcc | agagacaatt | ccaagaacac | tctttatctg | 300 |
| caattcagca | gcctgaaagt | cgaagacacg | gctatgttct | tctgtgcgag | agaggctggt | 360 |
| gggccaatct | ggcatgacga | cgtcaaatat | tacgatttta | tgacggctac | tacaactac | 420 |
| cactacatgg | acgtctgggg | caaggggacc | acggtcaccg | tctcgagcgc | ctccaccaag | 480 |
| ggcccatcgg | tcttccccct | ggcaccctcc | tccaagagca | cctctggggg | cacagcggcc | 540 |
| ctgggctgcc | tggtcaagga | ctacttcccc | gaaccggtga | cggtgtcgtg | gaactcaggc | 600 |
| gccctgacca | gcggcgtgca | caccttcccg | gctgtcctac | agtcctcagg | actctactcc | 660 |
| ctcagcagcg | tggtgaccgt | gccctccagc | agcttgggca | cccagaccta | catctgcaac | 720 |

```
gtgaatcaca agcccagcaa caccaaggtg acaagagag ttgagcccaa atcttgtgac      780
aaaactcaca catgcccacc gtgcccagca cctgaactcc tggggggacc gtcagtcttc      840
ctcttccccc caaaacccaa ggacaccctc atgatctccc ggacccctga ggtcacatgc      900
gtggtggtgg acgtgagcca cgaagaccct gaggtcaagt tcaactggta cgtggacggc      960
gtggaggtgc ataatgccaa gacaaagccg cgggaggagc agtacaacag cacgtaccgt     1020
gtggtcagcg tcctcaccgt cctgcaccag gactggctga atggcaagga gtacaagtgc     1080
aaggtctcca acaaagccct cccagccccc atcgagaaaa ccatctccaa agccaaaggg     1140
cagccccgag aaccacaggt gtacaccctg cccccatccc gggaggagat gaccaagaac     1200
caggtcagcc tgacctgcct ggtcaaaggc ttctatccca gcgacatcgc cgtggagtgg     1260
gagagcaatg ggcagccgga gaacaactac aagaccacgc ctcccgtgct ggactccgac     1320
ggctccttct tcctctatag caagctcacc gtggacaaga gcaggtggca gcagggaac      1380 gtcttctcat gctccgtgat gcatgaggct ctgcacaacc actacacgca gaagagcctc     1440
tccctgtctc cgggtaaatg a                                               1461
```

<210> SEQ ID NO 12
<211> LENGTH: 467
<212> TYPE: PRT
<213> ORGANISM: Homo sapiens

<400> SEQUENCE: 12

```
Gln Glu Gln Leu Val Glu Ser Gly Gly Gly Val Val Gln Pro Gly Gly
1               5                   10                  15

Ser Leu Arg Leu Ser Cys Leu Ala Ser Gly Phe Thr Phe His Lys Tyr
            20                  25                  30

Gly Met His Trp Val Arg Gln Ala Pro Gly Lys Gly Leu Glu Trp Val
        35                  40                  45

Ala Leu Ile Ser Asp Asp Gly Met Arg Lys Tyr His Ser Asp Ser Met
    50                  55                  60

Trp Gly Arg Val Thr Ile Ser Arg Asp Asn Ser Lys Asn Thr Leu Tyr
65                  70                  75                  80

Leu Gln Phe Ser Ser Leu Lys Val Glu Asp Thr Ala Met Phe Phe Cys
                85                  90                  95

Ala Arg Glu Ala Gly Gly Pro Ile Trp His Asp Asp Val Lys Tyr Tyr
            100                 105                 110

Asp Phe Asn Asp Gly Tyr Tyr Asn Tyr His Tyr Met Asp Val Trp Gly
        115                 120                 125

Lys Gly Thr Thr Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Arg Val Glu Pro Lys Ser Cys
225                 230                 235                 240
```

Asp Lys Thr His Thr Cys Pro Pro Cys Pro Ala Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
            275                 280                 285

Glu Asp Pro Glu Val Lys Phe Asn Trp Tyr Val Asp Gly Val Glu Val
        290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 13
<211> LENGTH: 708
<212> TYPE: DNA
<213> ORGANISM: Homo sapiens

<400> SEQUENCE: 13
atggcctggg ctctgctatt cctcaccctc ttcactcagg gcacagggtc ctggggccag      60
tctgccctga ctcagcctgc ctccgtgtct gggtctcctg gacagacgat caccatctcc     120
tgcaatggaa ccagcagtga cgttggtgga tttgactctg tctcctggta ccaacaatcc     180
ccagggaaag cccccaaagt catggttttt gatgtcagtc atcggccctc aggtatctct     240
aatcgcttct ctggctccaa gtccggcaac acggcctccc tgaccatctc tgggctccac     300
attgaggacg agggcgatta tttctgctct tcactgacag acagaagcca tcgcatattc     360
ggcggcggga ccaaggtgac cgttctaggt cagcccaagg ctgccccctc ggtcactctg     420
ttcccgccct cctctgagga gcttcaagcc aacaaggcca cactggtgtg tctcataagt     480
gacttctacc cgggagccgt gacagtggcc tggaaggcag atagcagccc cgtcaaggcg     540
ggagtggaga ccaccacacc ctccaaacaa agcaacaaca gtacgcggc cagcagctac     600 ctgagcctga cgcctgagca gtggaagtcc cacaaaagct acagctgcca ggtcacgcat     660
gaagggagca ccgtggagaa gacagtggcc cctacagaat gttcatag              708

<210> SEQ ID NO 14

<211> LENGTH: 216
<212> TYPE: PRT
<213> ORGANISM: Homo sapiens

<400> SEQUENCE: 14

Gln Ser Ala Leu Thr Gln Pro Ala Ser Val Ser Gly Ser Pro Gly Gln
1               5                   10                  15

Thr Ile Thr Ile Ser Cys Asn Gly Thr Ser Ser Asp Val Gly Gly Phe
            20                  25                  30

Asp Ser Val Ser Trp Tyr Gln Gln Ser Pro Gly Lys Ala Pro Lys Val
        35                  40                  45

Met Val Phe Asp Val Ser His Arg Pro Ser Gly Ile Ser Asn Arg Phe
    50                  55                  60

Ser Gly Ser Lys Ser Gly Asn Thr Ala Ser Leu Thr Ile Ser Gly Leu
65              70                  75                  80

His Ile Glu Asp Glu Gly Asp Tyr Phe Cys Ser Ser Leu Thr Asp Arg
                85                  90                  95

Ser His Arg Ile Phe Gly Gly Gly Thr Lys Val Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Lys Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 15
<211> LENGTH: 1422
<212> TYPE: DNA
<213> ORGANISM: Homo sapiens

<400> SEQUENCE: 15
atggactgga tttggaggtt cctctttgtg gtggcagcag ctacaggtgt ccagtcccag      60
gtccgcctgg tacagtctgg gcctgaggtg aagaagcctg gtcctcggt gacggtctcc     120 tgccaggctt ctgaggcac cttcagcagt tatgctttca cctgggtgcg ccaggccccc     180
ggacaaggtc ttgagtggtt gggcatggtc accccaatct ttggtgaggc caagtactca     240
caaagattcg agggcagagt caccatcacc gcggacgaat ccacgagcac aacctccata     300
gaattgagag gcctgacatc cgaagacacg gccatttatt actgtgcgcg agatcggcgc     360
gcggttccaa ttgccacgga caactggtta dccctgggg ccaggggac cctggtcacc     420 gtctcgagcg cctccaccaa gggcccatcg gtcttccccc tggcaccctc ctccaagagc     480
acctctgggg gcacagcggc cctgggctgc ctggtcaagg actacttccc cgaaccggtg     540
acggtgtcgt ggaactcagg cgccctgacc agcggcgtgc acaccttccc ggctgtccta     600
cagtcctcag gactctactc cctcagcagc gtggtgaccg tgccctccag cagcttgggc     660
acccagacct acatctgcaa cgtgaatcac aagcccagca acaccaaggt ggacaagaga     720

```
gttgagccca atcttgtga caaaactcac acatgccac cgtgcccagc acctgaactc      780
ctggggggac cgtcagtctt cctcttcccc ccaaaaccca aggacaccct catgatctcc     840 cggaccctg aggtcacatg cgtggtggtg gacgtgagcc acgaagaccc tgaggtcaag      900
ttcaactggt acgtggacgg cgtggaggtg cataatgcca agacaaagcc gcggaggag      960 cagtacaaca gcacgtaccg tgtggtcagc gtcctcaccg tcctgcacca ggactggctg    1020
aatggcaagg agtacaagtg caaggtctcc aacaaagccc tcccagcccc catcgagaaa    1080
accatctcca agccaaagg gcagccccga gaaccacagg tgtacaccct gcccccatcc     1140
cgggaggaga tgaccaagaa ccaggtcagc ctgacctgcc tggtcaaagg cttctatccc    1200
agcgacatcg ccgtggagtg ggagagcaat gggcagccgg agaacaacta caagaccacg    1260
cctcccgtgc tggactccga cggctccttc ttcctctata gcaagctcac cgtggacaag    1320
agcaggtggc agcaggggaa cgtcttctca tgctccgtga tgcatgaggc tctgcacaac    1380
cactacacgc agaagagcct ctccctgtct ccgggtaaat ga                       1422
```

<210> SEQ ID NO 16
<211> LENGTH: 454
<212> TYPE: PRT
<213> ORGANISM: Homo sapiens

<400> SEQUENCE: 16

```
Gln Val Arg Leu Val Gln Ser Gly Pro Glu Val Lys Lys Pro Gly Ser
1               5                   10                  15

Ser Val Thr Val Ser Cys Gln Ala Ser Gly Gly Thr Phe Ser Ser Tyr
            20                  25                  30

Ala Phe Thr Trp Val Arg Gln Ala Pro Gly Gln Gly Leu Glu Trp Leu
        35                  40                  45

Gly Met Val Thr Pro Ile Phe Gly Glu Ala Lys Tyr Ser Gln Arg Phe
    50                  55                  60

Glu Gly Arg Val Thr Ile Thr Ala Asp Glu Ser Thr Ser Thr Thr Ser
65                  70                  75                  80

Ile Glu Leu Arg Gly Leu Thr Ser Glu Asp Thr Ala Ile Tyr Tyr Cys
                85                  90                  95

Ala Arg Asp Arg Arg Ala Val Pro Ile Ala Thr Asp Asn Trp Leu Asp
            100                 105                 110

Pro Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
```

```
            245                 250                 255
Thr Leu Met Ile Ser Arg Thr Pro Glu Val Thr Cys Val Val Asp
        260                 265                 270

Val Ser His Glu Asp Pro Glu Val Lys Phe Asn Trp Tyr Val Asp Gly
    275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450
```

<210> SEQ ID NO 17
<211> LENGTH: 711
<212> TYPE: DNA
<213> ORGANISM: Homo sapiens

<400> SEQUENCE: 17

```
atggacatga gggtccccgc tcagctcctg gggctcctgc tactctggct ccgaggtgcc      60
agatgtgaca tccagttgac ccagtctcca tcctccctgt ctgcatctgt tggcgacaga     120
gtctccatca cttgccgggc gagtcagacc attaacaact acttaaattg gtatcaacag     180
acacccggga agcccctaa actcctgatc tatggtgcct ccaatttgca aaatggggtc      240
ccatcaaggt tcagcggcag tggctctggg acagacttca ctctcaccat cagcagtctg     300
caacctgagg attttgcaac ttactactgt caacagagtt tcagtactcc gaggaccttc     360
ggccaaggga cacgactgga tattaaacgt acggtggctg caccatctgt cttcatcttc     420
ccgccatctg atgagcagtt gaaatctgga actgcctctg ttgtgtgcct gctgaataac     480
ttctatccca gagaggccaa agtacagtgg aaggtggata acgccctcca atcgggtaac     540
tcccaggaga gtgtcacaga gcaggacagc aaggacagca cctacagcct cagcagcacc     600
ctgacgctga gcaaagcaga ctacgagaaa cacaaagtct acgcctgcga agtcacccat     660
cagggcctga gctcgcccgt cacaaagagc ttcaacaggg gagagtgtta g              711
```

<210> SEQ ID NO 18
<211> LENGTH: 214
<212> TYPE: PRT
<213> ORGANISM: Homo sapiens

<400> SEQUENCE: 18

```
Asp Ile Gln Leu Thr Gln Ser Pro Ser Leu Ser Ala Ser Val Gly
1               5                   10                  15
Asp Arg Val Ser Ile Thr Cys Arg Ala Ser Gln Thr Ile Asn Asn Tyr
            20                  25                  30
Leu Asn Trp Tyr Gln Gln Thr Pro Gly Lys Ala Pro Lys Leu Leu Ile
        35                  40                  45
Tyr Gly Ala Ser Asn Leu Gln Asn Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Phe Ser Thr Pro Arg
                85                  90                  95
Thr Phe Gly Gln Gly Thr Arg Leu Asp Ile Lys Arg Thr Val Ala Ala
                100                 105                 110
Pro Ser Val Phe Ile Phe Pro Pro Ser Asp Glu Gln Leu Lys Ser Gly
            115                 120                 125
Thr Ala Ser Val Val Cys Leu Leu Asn Asn Phe Tyr Pro Arg Glu Ala
        130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
                180                 185                 190
Ala Cys Glu Val Thr His Gln Gly Leu Ser Ser Pro Val Thr Lys Ser
            195                 200                 205
Phe Asn Arg Gly Glu Cys
            210

<210> SEQ ID NO 19
<211> LENGTH: 1422
<212> TYPE: DNA
<213> ORGANISM: Homo sapiens

<400> SEQUENCE: 19
atggactgga tttggaggtt cctcttggtg gtggcagcag ctacaggtgt ccagtcccag      60
gtcctgctgg tgcagtctgg gactgaggtg aagaagcctg gtcctcggt gaaggtctcc     120
tgtcaggctt ctgaggcgc cttcagtagt tatgctttca gctgggtgcg acaggcccct     180
ggacagggc ttgaatggat gggcatgatc acccctgtct ttggtgagac taaatatgca     240
ccgaggttcc agggcagact cacacttacc gcggaagaat ccttgagcac acctacatg     300
gaattgagaa gcctgacatc tgatgacacg gcctttatt attgtacgag agatcggcgc     360
gtagttccaa tggccacaga caactggtta gaccctggg gccagggac gctggtcacc     420
gtctcgagcg cctccaccaa gggcccatcg gtcttccccc tggcaccctc ctccaagagc     480
acctctgggg gcacagcggc cctgggctgc ctggtcaagg actacttccc cgaaccggtg     540
acggtgtcgt ggaactcagg cgccctgacc agcggcgtgc acaccttccc ggctgtccta     600
cagtcctcag gactctactc cctcagcagc gtggtgaccg tgccctccag cagcttgggc     660
acccagacct acatctgcaa cgtgaatcac aagcccagca acaccaaggt ggacaagaga     720
gttgagccca aatcttgtga caaaactcac acatgcccac cgtgcccagc acctgaactc     780
ctggggggac cgtcagtctt cctcttcccc ccaaaaccca aggacaccct catgatctcc     840
```

```
cggacccctg aggtcacatg cgtggtggtg gacgtgagcc acgaagaccc tgaggtcaag      900
ttcaactggt acgtggacgg cgtggaggtg cataatgcca agacaaagcc gcgggaggag      960
cagtacaaca gcacgtaccg tgtggtcagc gtcctcaccg tcctgcacca ggactggctg     1020
aatggcaagg agtacaagtg caaggtctcc aacaaagccc tcccagcccc catcgagaaa     1080
accatctcca aagccaaagg gcagcccga gaaccacagg tgtacaccct gcccccatcc      1140
cgggaggaga tgaccaagaa ccaggtcagc ctgacctgcc tggtcaaagg cttctatccc     1200
agcgacatcg ccgtggagtg ggagagcaat gggcagccgg agaacaacta caagaccacg     1260
cctcccgtgc tggactccga cggctccttc ttcctctata gcaagctcac cgtggacaag     1320
agcaggtggc agcaggggaa cgtcttctca tgctccgtga tgcatgaggc tctgcacaac     1380
cactacacgc agaagagcct ctccctgtct ccgggtaaat ga                        1422
```

<210> SEQ ID NO 20
<211> LENGTH: 453
<212> TYPE: PRT
<213> ORGANISM: Homo sapiens

<400> SEQUENCE: 20

```
Gln Val Leu Leu Val Gln Ser Gly Thr Glu Val Lys Lys Pro Gly Ser
1               5                   10                  15

Ser Val Lys Val Ser Cys Gln Ala Ser Gly Gly Ala Phe Ser Ser Tyr
            20                  25                  30

Ala Phe Ser Trp Val Arg Gln Ala Pro Gly Gln Gly Leu Glu Trp Met
        35                  40                  45

Gly Met Ile Thr Pro Val Phe Gly Glu Thr Lys Tyr Ala Pro Arg Phe
    50                  55                  60

Gln Gly Arg Leu Thr Leu Thr Ala Glu Glu Ser Leu Ser Thr Thr Tyr
65                  70                  75                  80

Met Glu Leu Arg Ser Leu Thr Ser Asp Asp Thr Ala Phe Tyr Tyr Cys
                85                  90                  95

Thr Arg Asp Arg Arg Val Val Pro Met Ala Thr Asp Asn Trp Leu Asp
            100                 105                 110

Pro Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270
```

Val Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr Asn
        290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450

<210> SEQ ID NO 21
<211> LENGTH: 711
<212> TYPE: DNA
<213> ORGANISM: Homo sapiens

<400> SEQUENCE: 21
atggacatga gggtccccgc tcagctcctg gggctcctgc tcctctggct ccgaggtgcc      60
acatgtgaca tccagttgac ccagtctcca tcctccctgt ctgcatctgt aggagacagg     120
gtcaccgtca cttgccgggc gagtcagacc atacacacct atttaaattg gtatcagcaa     180
attccaggaa aagcccctaa gctcctgatc tatggtgcct ccaccttgca aagtggggtc     240
ccgtcaaggt tcagtggcag tggatctggg acagatttca ctctcaccat caacagtctc     300
caacctgagg actttgcaac ttactactgt caacagagtt acagtacccc aaggaccttc     360
ggccaaggga cacgactgga tattaaacgt acggtggctg caccatctgt cttcatcttc     420
ccgccatctg atgagcagtt gaaatctgga actgcctctg ttgtgtgcct gctgaataac     480
ttctatccca gagaggccaa agtacagtgg aaggtggata acgccctcca atcgggtaac     540
tcccaggaga gtgtcacaga gcaggacagc aaggacagca cctacagcct cagcagcacc     600
ctgacgctga gcaaagcaga ctacgagaaa cacaaagtct acgcctgcga agtcacccat     660
cagggcctga gctcgcccgt cacaaagagc ttcaacaggg gagagtgtta g              711

<210> SEQ ID NO 22
<211> LENGTH: 214
<212> TYPE: PRT
<213> ORGANISM: Homo sapiens

<400> SEQUENCE: 22

Asp Ile Gln Leu Thr Gln Ser Pro Ser Ser Leu Ser Ala Ser Val Gly
1               5                   10                  15

```
Asp Arg Val Thr Val Thr Cys Arg Ala Ser Gln Thr Ile His Thr Tyr
            20                  25                  30

Leu Asn Trp Tyr Gln Gln Ile Pro Gly Lys Ala Pro Lys Leu Leu Ile
        35                  40                  45

Tyr Gly Ala Ser Thr Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Gln Gln Ser Tyr Ser Thr Pro Arg
                85                  90                  95

Thr Phe Gly Gln Gly Thr Arg Leu Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 23
<211> LENGTH: 1416
<212> TYPE: DNA
<213> ORGANISM: Homo sapiens

<400> SEQUENCE: 23
atggactgga tttggaggat cctcctcttg gtggcagcag ctacaggcac cctcgccgac     60
ggccacctgg ttcagtctgg ggttgaggtg aagaagactg ggctacagt caaaatctcc    120 tgcaaggttt ctggatacag cttcatcgac tactaccttc attgggtgca acgggcccct    180
ggaaaaggcc ttgagtgggt gggacttatt gatcctgaaa atggtgaggc tcgatatgca    240
gagaagttcc agggcagagt caccataatc gcggacacgt ctatagatac aggctacatg    300
gaaatgagga gcctgaaatc tgaggacacg gccgtgtatt tctgtgcagc aggtgccgtg    360
ggggctgatt ccgggagctg gttcgacccc tggggccagg gaactctggt caccgtctcg    420
agcgcctcca ccaagggccc atcggtcttc ccctggcac cctcctccaa gagcacctct    480
gggggcacag cggccctggg ctgcctggtc aaggactact ccccgaacc ggtgacggtg    540 tcgtggaact caggcgccct gaccagcggc gtgcacacct tcccggctgt cctacagtcc    600
tcaggactct actccctcag cagcgtggtg accgtgccct ccagcagctt gggcacccag    660
acctacatct gcaacgtgaa tcacaagccc agcaacacca aggtggacaa gagagttgag    720
cccaaatctt gtgacaaaac tcacacatgc ccaccgtgcc cagcacctga actcctgggg    780
ggaccgtcag tcttcctctt ccccccaaaa cccaaggaca cctcatgat ctcccggacc    840 cctgaggtca catgcgtggt ggtggacgtg agccacgaag accctgaggt caagttcaac    900
tggtacgtgg acggcgtgga ggtgcataat gccaagacaa agccgcggga ggagcagtac    960
```

```
aacagcacgt accgtgtggt cagcgtcctc accgtcctgc accaggactg gctgaatggc    1020
aaggagtaca agtgcaaggt ctccaacaaa gccctcccag cccccatcga gaaaaccatc    1080
tccaaagcca aagggcagcc ccgagaacca caggtgtaca ccctgccccc atcccgggag    1140
gagatgacca gaaccaggt cagcctgacc tgcctggtca aaggcttcta tcccagcgac    1200
atcgccgtgg agtgggagag caatgggcag ccggagaaca actacaagac cacgcctccc    1260
gtgctggact ccgacggctc cttcttcctc tatagcaagc tcaccgtgga caagagcagg    1320
tggcagcagg ggaacgtctt ctcatgctcc gtgatgcatg aggctctgca caaccactac    1380
acgcagaaga gcctctccct gtctccgggt aaatga                              1416
```

<210> SEQ ID NO 24
<211> LENGTH: 452
<212> TYPE: PRT
<213> ORGANISM: Homo sapiens

<400> SEQUENCE: 24

```
Asp Gly His Leu Val Gln Ser Gly Val Glu Val Lys Lys Thr Gly Ala
1               5                   10                  15

Thr Val Lys Ile Ser Cys Lys Val Ser Gly Tyr Ser Phe Ile Asp Tyr
            20                  25                  30

Tyr Leu His Trp Val Gln Arg Ala Pro Gly Lys Gly Leu Glu Trp Val
        35                  40                  45

Gly Leu Ile Asp Pro Glu Asn Gly Glu Ala Arg Tyr Ala Glu Lys Phe
    50                  55                  60

Gln Gly Arg Val Thr Ile Ile Ala Asp Thr Ser Ile Asp Thr Gly Tyr
65                  70                  75                  80

Met Glu Met Arg Ser Leu Lys Ser Glu Asp Thr Ala Val Tyr Phe Cys
                85                  90                  95

Ala Ala Gly Ala Val Gly Ala Asp Ser Gly Ser Trp Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285
```

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
435                 440                 445

Ser Pro Gly Lys
    450

<210> SEQ ID NO 25
<211> LENGTH: 705
<212> TYPE: DNA
<213> ORGANISM: Homo sapiens

<400> SEQUENCE: 25

```
atggcctgga tccctctctt cctcggcgtc cttgcttact gcacagattc cgtagtctcc      60
tatgaactga ctcagccacc ctcagtgtcc gtgtccccag acagacagc cagcatcacc      120
tgttctggat ctaaattggg ggataaatat gtttcctggt atcaactgag gccaggccag     180
tcccccatac tggtcatgta tgaaaatgac aggcggccct ccgggatccc tgagcgattc     240
tccggttcca attctggcga cactgccact ctgaccatca gcgggaccca ggctttggat     300
gaggctgact ctactgtca ggcgtgggag accaccacca ccacttttgt tttcttcggc     360
ggagggaccc agctgaccgt tctaggtcag cccaaggctg cccctcggt cactctgttc      420
ccgcccctcct ctgaggagct tcaagccaac aaggccacac tggtgtgtct cataagtgac     480
ttctacccgg gagccgtgac agtggcctgg aaggcagata gcagccccgt caaggcggga     540
gtggagacca ccacaccctc caaacaaagc aacaacaagt acgcggccag cagctacctg     600
agcctgacgc tgagcagtg gaagtccac aaaaagctaca gctgccaggt cacgcatgaa      660
gggagcaccg tggagaagac agtggcccct acagaatgtt catag                     705
```

<210> SEQ ID NO 26
<211> LENGTH: 215
<212> TYPE: PRT
<213> ORGANISM: Homo sapiens

<400> SEQUENCE: 26

Ser Tyr Glu Leu Thr Gln Pro Pro Ser Val Ser Val Ser Pro Gly Gln
1               5                   10                  15

Thr Ala Ser Ile Thr Cys Ser Gly Ser Lys Leu Gly Asp Lys Tyr Val
            20                  25                  30

Ser Trp Tyr Gln Leu Arg Pro Gly Gln Ser Pro Ile Leu Val Met Tyr
        35                  40                  45

Glu Asn Asp Arg Arg Pro Ser Gly Ile Pro Glu Arg Phe Ser Gly Ser
 50                      55                  60

Asn Ser Gly Asp Thr Ala Thr Leu Thr Ile Ser Gly Thr Gln Ala Leu
 65                  70                  75                  80

Asp Glu Ala Asp Phe Tyr Cys Gln Ala Trp Glu Thr Thr Thr Thr
                85                  90                  95

Phe Val Phe Phe Gly Gly Gly Thr Gln Leu Thr Val Leu Gly Gln Pro
                100                 105                 110

Lys Ala Ala Pro Ser Val Thr Leu Phe Pro Pro Ser Ser Glu Glu Leu
            115                 120                 125

Gln Ala Asn Lys Ala Thr Leu Val Cys Leu Ile Ser Asp Phe Tyr Pro
130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Lys
                180                 185                 190

Ser Tyr Ser Cys Gln Val Thr His Glu Gly Ser Thr Val Glu Lys Thr
            195                 200                 205

Val Ala Pro Thr Glu Cys Ser
        210                 215

<210> SEQ ID NO 27
<211> LENGTH: 1458
<212> TYPE: DNA
<213> ORGANISM: Homo sapiens

<400> SEQUENCE: 27
atggagtttg ggctgagctg ggttttcctc gttgctttct taagaggtgt ccagtgtcag     60
cgattagtgg agtctggggg aggcgtggtc cagcctgggt cgtccctgag actctcctgt    120
gcagcgtccg gattcgactt cagtagacaa ggcatgcact gggtccgcca ggctccaggc    180
caggggctgg agtgggtggc atttattaaa tatgatggaa gtgagaaata tcatgctgac    240
tccgtatggg gccgactcag catctccaga gacaattcca aggatacgct ttatctccaa    300
atgaatagcc tgagagtcga ggacacggct acatattttt gtgtgagaga ggctggtggg    360
cccgactacc gtaatgggta caactattac gatttctatg atggttatta taactaccac    420
tatatggacg tctggggcaa agggaccacg gtcaccgtct cgagcgcctc caccaagggc    480
ccatcggtct tccccctggc accctcctcc aagagcacct ctgggggcac agcggccctg    540
ggctgcctgg tcaaggacta cttccccgaa ccggtgacgg tgtcgtggaa ctcaggcgcc    600
ctgaccagcg gcgtgcacac cttcccggct gtcctacagt cctcaggact ctactccctc    660
agcagcgtgg tgaccgtgcc ctccagcagc ttgggcaccc agacctacat ctgcaacgtg    720
aatcacaagc ccagcaacac caaggtggac aagagagttg agcccaaatc ttgtgacaaa    780
actcacacat gcccaccgtg cccagcacct gaactcctgg ggggaccgtc agtcttcctc    840
ttccccccaa aacccaagga caccctcatg atctcccgga cccctgaggt cacatgcgtg    900
gtggtggacg tgagccacga agaccctgag gtcaagttca actggtacgt ggacggcgtg    960
gaggtgcata atgccaagac aaagccgcgg gaggagcagt acaacagcac gtaccgtgtg   1020
gtcagcgtcc tcaccgtcct gcaccaggac tggctgaatg gcaaggagta caagtgcaag   1080

-continued

```
gtctccaaca aagccctccc agccccatc gagaaaacca tctccaaagc caaagggcag       1140
ccccgagaac cacaggtgta cacctgccc ccatcccggg aggagatgac caagaaccag       1200
gtcagcctga cctgcctggt caaaggcttc tatcccagcg acatcgccgt ggagtgggag       1260
agcaatgggc agccggagaa caactacaag accacgcctc ccgtgctgga ctccgacggc       1320
tccttcttcc tctatagcaa gctcaccgtg gacaagagca ggtggcagca ggggaacgtc       1380
ttctcatgct ccgtgatgca tgaggctctg cacaaccact acacgcagaa gagcctctcc       1440
ctgtctccgg gtaaatga                                                    1458
```

<210> SEQ ID NO 28
<211> LENGTH: 466
<212> TYPE: PRT
<213> ORGANISM: Homo sapiens

<400> SEQUENCE: 28

```
Gln Arg Leu Val Glu Ser Gly Gly Val Val Gln Pro Gly Ser Ser
1               5                   10                  15

Leu Arg Leu Ser Cys Ala Ala Ser Gly Phe Asp Phe Ser Arg Gln Gly
            20                  25                  30

Met His Trp Val Arg Gln Ala Pro Gly Gln Gly Leu Glu Trp Val Ala
        35                  40                  45

Phe Ile Lys Tyr Asp Gly Ser Glu Lys Tyr His Ala Asp Ser Val Trp
    50                  55                  60

Gly Arg Leu Ser Ile Ser Arg Asp Asn Ser Lys Asp Thr Leu Tyr Leu
65                  70                  75                  80

Gln Met Asn Ser Leu Arg Val Glu Asp Thr Ala Thr Tyr Phe Cys Val
                85                  90                  95

Arg Glu Ala Gly Gly Pro Asp Tyr Arg Asn Gly Tyr Asn Tyr Tyr Asp
            100                 105                 110

Phe Tyr Asp Gly Tyr Tyr Asn Tyr His Tyr Met Asp Val Trp Gly Lys
        115                 120                 125

Gly Thr Thr Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Arg Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300
```

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465

<210> SEQ ID NO 29
<211> LENGTH: 708
<212> TYPE: DNA
<213> ORGANISM: Homo sapiens

<400> SEQUENCE: 29

```
atggcctggg ctctgctttt cctcaccctc ctcactcagg gcacagggtc ctgggcccag      60
tctgccctga ctcagcctgc ctccgtgtct gggtctcctg gacagtcgat caccatctcc     120
tgcaatggaa ccagcaatga tgttggtggc tatgaatctg tctcctggta ccaacaacat     180
cccggcaaag cccccaaagt cgtgatttat gatgtcagta acggccctca gggggtttct     240
aatcgcttct ctggctccaa gtccggcaac acggcctccc tgaccatctc tgggctccag     300
gctgaggacg agggtgacta ttactgcaag tctctgacaa gcacgagacg tcgggttttc     360
ggcactggga ccaagctgac cgttctaggt cagcccaagg ctgccccctc ggtcactctg     420
ttcccgccct cctctgagga gcttcaagcc aacaaggcca cactggtgtg tctcataagt     480
gacttctacc cgggagccgt gacagtggcc tggaaggcag atagcagccc cgtcaaggcg     540
ggagtggaga ccaccacacc ctccaaacaa agcaacaaca gctacgcggc cagcagctac     600
ctgagcctga cgcctgagca gtggaagtcc cacaaaagct acagctgcca ggtcacgcat     660
gaagggagca ccgtggagaa gacagtggcc cctacagaat gttcatag                   708
```

<210> SEQ ID NO 30
<211> LENGTH: 216
<212> TYPE: PRT
<213> ORGANISM: Homo sapiens

<400> SEQUENCE: 30

Gln Ser Ala Leu Thr Gln Pro Ala Ser Val Ser Gly Ser Pro Gly Gln
1               5                   10                  15

Ser Ile Thr Ile Ser Cys Asn Gly Thr Ser Asn Asp Val Gly Gly Tyr
            20                  25                  30

Glu Ser Val Ser Trp Tyr Gln Gln His Pro Gly Lys Ala Pro Lys Val
                35                  40                  45

Val Ile Tyr Asp Val Ser Lys Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Gly Asp Tyr Tyr Cys Lys Ser Leu Thr Ser Thr
                 85                  90                  95

Arg Arg Arg Val Phe Gly Thr Gly Thr Lys Leu Thr Val Leu Gly Gln
                100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Lys Ser Tyr Ser Cys Gln Val Thr His Glu Gly Ser Thr Val Glu Lys
            195                 200                 205

Thr Val Ala Pro Thr Glu Cys Ser
210                 215

<210> SEQ ID NO 31
<211> LENGTH: 137
<212> TYPE: PRT
<213> ORGANISM: Homo sapiens

<400> SEQUENCE: 31

Gln Glu Gln Leu Val Glu Ser Gly Gly Gly Val Gln Pro Gly Gly
 1               5                  10                  15

Ser Leu Arg Leu Ser Cys Leu Ala Ser Gly Phe Thr Phe His Lys Tyr
             20                  25                  30

Gly Met His Trp Val Arg Gln Ala Pro Gly Lys Gly Leu Glu Trp Val
             35                  40                  45

Ala Leu Ile Ser Asp Asp Gly Met Arg Lys Tyr His Ser Asp Ser Met
 50                  55                  60

Trp Gly Arg Val Thr Ile Ser Arg Asp Asn Ser Lys Asn Thr Leu Tyr
 65                  70                  75                  80

Leu Gln Phe Ser Ser Leu Lys Val Glu Asp Thr Ala Met Phe Phe Cys
                 85                  90                  95

Ala Arg Glu Ala Gly Gly Pro Ile Trp His Asp Val Lys Tyr Tyr
                100                 105                 110

Asp Phe Asn Asp Gly Tyr Tyr Asn Tyr His Tyr Met Asp Val Trp Gly
            115                 120                 125

Lys Gly Thr Thr Val Thr Val Ser Ser
130                 135

<210> SEQ ID NO 32
<211> LENGTH: 110
<212> TYPE: PRT
<213> ORGANISM: Homo sapiens

<400> SEQUENCE: 32

```
Gln Ser Ala Leu Thr Gln Pro Ala Ser Val Ser Gly Ser Pro Gly Gln
1               5                   10                  15

Thr Ile Thr Ile Ser Cys Asn Gly Thr Ser Ser Asp Val Gly Gly Phe
            20                  25                  30

Asp Ser Val Ser Trp Tyr Gln Gln Ser Pro Gly Lys Ala Pro Lys Val
        35                  40                  45

Met Val Phe Asp Val Ser His Arg Pro Ser Gly Ile Ser Asn Arg Phe
50                  55                  60

Ser Gly Ser Lys Ser Gly Asn Thr Ala Ser Leu Thr Ile Ser Gly Leu
65                  70                  75                  80

His Ile Glu Asp Glu Gly Asp Tyr Phe Cys Ser Ser Leu Thr Asp Arg
                85                  90                  95

Ser His Arg Ile Phe Gly Gly Gly Thr Lys Val Thr Val Leu
            100                 105                 110

<210> SEQ ID NO 33
<211> LENGTH: 124
<212> TYPE: PRT
<213> ORGANISM: Homo sapiens

<400> SEQUENCE: 33

Gln Val Arg Leu Val Gln Ser Gly Pro Glu Val Lys Lys Pro Gly Ser
1               5                   10                  15

Ser Val Thr Val Ser Cys Gln Ala Ser Gly Gly Thr Phe Ser Ser Tyr
            20                  25                  30

Ala Phe Thr Trp Val Arg Gln Ala Pro Gly Gln Gly Leu Glu Trp Leu
        35                  40                  45

Gly Met Val Thr Pro Ile Phe Gly Glu Ala Lys Tyr Ser Gln Arg Phe
50                  55                  60

Glu Gly Arg Val Thr Ile Thr Ala Asp Glu Ser Thr Ser Thr Thr Ser
65                  70                  75                  80

Ile Glu Leu Arg Gly Leu Thr Ser Glu Asp Thr Ala Ile Tyr Tyr Cys
                85                  90                  95

Ala Arg Asp Arg Arg Ala Val Pro Ile Ala Thr Asp Asn Trp Leu Asp
            100                 105                 110

Pro Trp Gly Gln Gly Thr Leu Val Thr Val Ser Ser
        115                 120

<210> SEQ ID NO 34
<211> LENGTH: 107
<212> TYPE: PRT
<213> ORGANISM: Homo sapiens

<400> SEQUENCE: 34

Asp Ile Gln Leu Thr Gln Ser Pro Ser Ser Leu Ser Ala Ser Val Gly
1               5                   10                  15

Asp Arg Val Ser Ile Thr Cys Arg Ala Ser Gln Thr Ile Asn Asn Tyr
            20                  25                  30

Leu Asn Trp Tyr Gln Gln Thr Pro Gly Lys Ala Pro Lys Leu Leu Ile
        35                  40                  45

Tyr Gly Ala Ser Asn Leu Gln Asn Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Phe Ser Thr Pro Arg
                85                  90                  95
```

```
Thr Phe Gly Gln Gly Thr Arg Leu Asp Ile Lys
            100                 105

<210> SEQ ID NO 35
<211> LENGTH: 124
<212> TYPE: PRT
<213> ORGANISM: Homo sapiens

<400> SEQUENCE: 35

Gln Val Leu Leu Val Gln Ser Gly Thr Glu Val Lys Lys Pro Gly Ser
1               5                   10                  15

Ser Val Lys Val Ser Cys Gln Ala Ser Gly Gly Ala Phe Ser Ser Tyr
            20                  25                  30

Ala Phe Ser Trp Val Arg Gln Ala Pro Gly Gln Gly Leu Glu Trp Met
        35                  40                  45

Gly Met Ile Thr Pro Val Phe Gly Glu Thr Lys Tyr Ala Pro Arg Phe
    50                  55                  60

Gln Gly Arg Leu Thr Leu Thr Ala Glu Glu Ser Leu Ser Thr Thr Tyr
65                  70                  75                  80

Met Glu Leu Arg Ser Leu Thr Ser Asp Thr Ala Phe Tyr Tyr Cys
                85                  90                  95

Thr Arg Asp Arg Arg Val Val Pro Met Ala Thr Asp Asn Trp Leu Asp
            100                 105                 110

Pro Trp Gly Gln Gly Thr Leu Val Thr Val Ser Ser
            115                 120

<210> SEQ ID NO 36
<211> LENGTH: 107
<212> TYPE: PRT
<213> ORGANISM: Homo sapiens

<400> SEQUENCE: 36

Asp Ile Gln Leu Thr Gln Ser Pro Ser Ser Leu Ser Ala Ser Val Gly
1               5                   10                  15

Asp Arg Val Thr Val Thr Cys Arg Ala Ser Gln Thr Ile His Thr Tyr
            20                  25                  30

Leu Asn Trp Tyr Gln Gln Ile Pro Gly Lys Ala Pro Lys Leu Leu Ile
        35                  40                  45

Tyr Gly Ala Ser Thr Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Gln Gln Ser Tyr Ser Thr Pro Arg
                85                  90                  95

Thr Phe Gly Gln Gly Thr Arg Leu Asp Ile Lys
            100                 105

<210> SEQ ID NO 37
<211> LENGTH: 122
<212> TYPE: PRT
<213> ORGANISM: Homo sapiens

<400> SEQUENCE: 37

Asp Gly His Leu Val Gln Ser Gly Val Glu Val Lys Lys Thr Gly Ala
1               5                   10                  15

Thr Val Lys Ile Ser Cys Lys Val Ser Gly Tyr Ser Phe Ile Asp Tyr
            20                  25                  30
```

Tyr Leu His Trp Val Gln Arg Ala Pro Gly Lys Gly Leu Glu Trp Val
            35                  40                  45

Gly Leu Ile Asp Pro Glu Asn Gly Glu Ala Arg Tyr Ala Glu Lys Phe
 50                  55                  60

Gln Gly Arg Val Thr Ile Ile Ala Asp Thr Ser Ile Asp Thr Gly Tyr
 65                  70                  75                  80

Met Glu Met Arg Ser Leu Lys Ser Glu Asp Thr Ala Val Tyr Phe Cys
                 85                  90                  95

Ala Ala Gly Ala Val Gly Ala Asp Ser Gly Ser Trp Phe Asp Pro Trp
                100                 105                 110

Gly Gln Gly Thr Leu Val Thr Val Ser Ser
                115                 120

<210> SEQ ID NO 38
<211> LENGTH: 109
<212> TYPE: PRT
<213> ORGANISM: Homo sapiens

<400> SEQUENCE: 38

Ser Tyr Glu Leu Thr Gln Pro Pro Ser Val Ser Val Ser Pro Gly Gln
 1               5                  10                  15

Thr Ala Ser Ile Thr Cys Ser Gly Ser Lys Leu Gly Asp Lys Tyr Val
                 20                  25                  30

Ser Trp Tyr Gln Leu Arg Pro Gly Gln Ser Pro Ile Leu Val Met Tyr
             35                  40                  45

Glu Asn Asp Arg Arg Pro Ser Gly Ile Pro Glu Arg Phe Ser Gly Ser
 50                  55                  60

Asn Ser Gly Asp Thr Ala Thr Leu Thr Ile Ser Gly Thr Gln Ala Leu
 65                  70                  75                  80

Asp Glu Ala Asp Phe Tyr Cys Gln Ala Trp Glu Thr Thr Thr Thr Thr
                 85                  90                  95

Phe Val Phe Phe Gly Gly Gly Thr Gln Leu Thr Val Leu
                100                 105

<210> SEQ ID NO 39
<211> LENGTH: 136
<212> TYPE: PRT
<213> ORGANISM: Homo sapiens

<400> SEQUENCE: 39

Gln Arg Leu Val Glu Ser Gly Gly Val Val Gln Pro Gly Ser Ser
 1               5                  10                  15

Leu Arg Leu Ser Cys Ala Ala Ser Gly Phe Asp Phe Ser Arg Gln Gly
                 20                  25                  30

Met His Trp Val Arg Gln Ala Pro Gly Gln Gly Leu Glu Trp Val Ala
             35                  40                  45

Phe Ile Lys Tyr Asp Gly Ser Glu Lys Tyr His Ala Asp Ser Val Trp
 50                  55                  60

Gly Arg Leu Ser Ile Ser Arg Asp Asn Ser Lys Asp Thr Leu Tyr Leu
 65                  70                  75                  80

Gln Met Asn Ser Leu Arg Val Glu Asp Thr Ala Thr Tyr Phe Cys Val
                 85                  90                  95

Arg Glu Ala Gly Gly Pro Asp Tyr Arg Asn Gly Tyr Asn Tyr Tyr Asp
                100                 105                 110

Phe Tyr Asp Gly Tyr Tyr Asn Tyr His Tyr Met Asp Val Trp Gly Lys
            115                 120                 125

```
Gly Thr Thr Val Thr Val Ser Ser
    130                 135

<210> SEQ ID NO 40
<211> LENGTH: 110
<212> TYPE: PRT
<213> ORGANISM: Homo sapiens

<400> SEQUENCE: 40

Gln Ser Ala Leu Thr Gln Pro Ala Ser Val Ser Gly Ser Pro Gly Gln
1               5                   10                  15

Ser Ile Thr Ile Ser Cys Asn Gly Thr Ser Asn Asp Val Gly Gly Tyr
            20                  25                  30

Glu Ser Val Ser Trp Tyr Gln Gln His Pro Gly Lys Ala Pro Lys Val
        35                  40                  45

Val Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Gly Asp Tyr Tyr Cys Lys Ser Leu Thr Ser Thr
                85                  90                  95

Arg Arg Arg Val Phe Gly Thr Gly Thr Lys Leu Thr Val Leu
            100                 105                 110

<210> SEQ ID NO 41
<211> LENGTH: 10
<212> TYPE: PRT
<213> ORGANISM: Homo sapiens

<400> SEQUENCE: 41

Ser Ser Leu Thr Asp Arg Ser His Arg Ile
1               5                   10

<210> SEQ ID NO 42
<211> LENGTH: 9
<212> TYPE: PRT
<213> ORGANISM: Homo sapiens

<400> SEQUENCE: 42

Gln Gln Ser Phe Ser Thr Pro Arg Thr
1               5

<210> SEQ ID NO 43
<211> LENGTH: 9
<212> TYPE: PRT
<213> ORGANISM: Homo sapiens

<400> SEQUENCE: 43

Gln Gln Ser Tyr Ser Thr Pro Arg Thr
1               5

<210> SEQ ID NO 44
<211> LENGTH: 12
<212> TYPE: PRT
<213> ORGANISM: Homo sapiens

<400> SEQUENCE: 44

Gln Ala Trp Glu Thr Thr Thr Thr Phe Val Phe
1               5                   10

<210> SEQ ID NO 45
<211> LENGTH: 10
```

<210> SEQ ID NO 45
<211> LENGTH: 11
<212> TYPE: PRT
<213> ORGANISM: Homo sapiens

<400> SEQUENCE: 45

Lys Ser Leu Thr Ser Thr Arg Arg Arg Val
1               5                   10

<210> SEQ ID NO 46
<211> LENGTH: 1461
<212> TYPE: DNA
<213> ORGANISM: Homo sapiens

<400> SEQUENCE: 46

```
atggagtttg ggctgagctg ggttttcctc gcaactctgt taagagttgt gaagtgtcac     60
gaacaactgg tggaggccgg gggaggcgtg gtccagccgg ggggtccct gagactctcc     120
tgtttagcgt ctggattcac gtttcacaaa tatggcatgc actgggtccg ccaggctcca    180
ggcaagggcc tggagtgggt ggcactcatc tcagatgacg gaatgaggaa atatcattca    240
gactccatgt ggggccgagt caccatctcc agagacaatt ccaagaacac tctttatctg    300
caattcagca gcctgagagt cgaagacacg gctatgttct tctgtgcgag agaggccggt    360
gggccaatct ggcatgacga cgtcaaatat tacgatttta tgacggcta ctacaactat    420
cactacatgg acgtctgggg caaggggacc aaggtcaccg tctcctcagc gtcgaccaag    480
ggcccatcgg tcttccctct ggcaccatca tccaagtcga cctctggggg cacagcggcc    540
ctgggctgcc tggtcaagga ctacttcccc gaaccggtga cggtgtcgtg aactcaggc    600
gccctgacca gcggcgtgca caccttccg gctgtcctac agtcctcagg actctactcc     660
ctcagcagcg tggtgaccgt gccctccagc agcttgggca cccagaccta catctgcaac    720
gtgaatcaca agcccagcaa caccaaggtg gacaagagag ttgagcccaa atcttgtgac    780
aaaactcaca catgcccacc gtgcccagca cctgaactcc tggggggacc gtcagtcttc    840
ctcttccccc caaaacccaa ggacaccctc atgatctccc ggacccctga ggtcacatgc    900
gtggtggtgg acgtgagcca cgaagaccct gaggtcaagt tcaactggta cgtggacggc    960
gtggaggtgc ataatgccaa gacaaagccg cgggaggagc agtacaacag cacgtaccgt    1020
gtggtcagcg tcctcaccgt cctgcaccag gactggctga atggcaagga gtacaagtgc    1080
aaggtctccaa caaagccct cccagccccc atcgagaaaa ccatctccaa agccaaaggg    1140
cagccccgag aaccacaggt gtacaccctg cccccatccc gggaggagat gaccaagaac    1200
caggtcagcc tgacctgcct ggtcaaaggc ttctatccca gcgacatcgc cgtggagtgg    1260
gagagcaatg ggcagccgga gaacaactac aagaccacgc ctcccgtgct ggactccgac    1320
ggctccttct cctctatag caagctcacc gtggacaaga gcaggtggca gcaggggaac    1380
gtcttctcat gctccgtgat gcatgaggct ctgcacaacc actacacgca gaagagcctc    1440
tccctgtctc cgggtaaatg a                                              1461
```

<210> SEQ ID NO 47
<211> LENGTH: 467
<212> TYPE: PRT
<213> ORGANISM: Homo sapiens

<400> SEQUENCE: 47

His Glu Gln Leu Val Glu Ala Gly Gly Gly Val Val Gln Pro Gly Gly
1               5                   10                  15

Ser Leu Arg Leu Ser Cys Leu Ala Ser Gly Phe Thr Phe His Lys Tyr
            20                  25                  30

Gly Met His Trp Val Arg Gln Ala Pro Gly Lys Gly Leu Glu Trp Val
            35                  40                  45

Ala Leu Ile Ser Asp Asp Gly Met Arg Lys Tyr His Ser Asp Ser Met
 50                  55                  60

Trp Gly Arg Val Thr Ile Ser Arg Asp Asn Ser Lys Asn Thr Leu Tyr
 65                  70                  75                  80

Leu Gln Phe Ser Ser Leu Arg Val Glu Asp Thr Ala Met Phe Phe Cys
                85                  90                  95

Ala Arg Glu Ala Gly Gly Pro Ile Trp His Asp Asp Val Lys Tyr Tyr
                100                 105                 110

Asp Phe Asn Asp Gly Tyr Tyr Asn Tyr His Tyr Met Asp Val Trp Gly
            115                 120                 125

Lys Gly Thr Lys Val Thr Val Ser Ser Ala Ser Thr Lys Gly Pro Ser
            130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
                180                 185                 190

Val Leu Gln Ser Ser Gly Leu Tyr Ser Leu Ser Ser Val Val Thr Val
                195                 200                 205

Pro Ser Ser Ser Leu Gly Thr Gln Thr Tyr Ile Cys Asn Val Asn His
            210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
                260                 265                 270

Ile Ser Arg Thr Pro Glu Val Thr Cys Val Val Val Asp Val Ser His
            275                 280                 285

Glu Asp Pro Glu Val Lys Phe Asn Trp Tyr Val Asp Gly Val Glu Val
            290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
                340                 345                 350

Glu Lys Thr Ile Ser Lys Ala Lys Gly Gln Pro Arg Glu Pro Gln Val
                355                 360                 365

Tyr Thr Leu Pro Pro Ser Arg Glu Glu Met Thr Lys Asn Gln Val Ser
 370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
                420                 425                 430

Asp Lys Ser Arg Trp Gln Gln Gly Asn Val Phe Ser Cys Ser Val Met
                435                 440                 445

His Glu Ala Leu His Asn His Tyr Thr Gln Lys Ser Leu Ser Leu Ser
            450                 455                 460
Pro Gly Lys
465

<210> SEQ ID NO 48
<211> LENGTH: 137
<212> TYPE: PRT
<213> ORGANISM: Homo sapiens

<400> SEQUENCE: 48

His Glu Gln Leu Val Glu Ala Gly Gly Val Val Gln Pro Gly Gly
1               5                   10                  15

Ser Leu Arg Leu Ser Cys Leu Ala Ser Gly Phe Thr Phe His Lys Tyr
            20                  25                  30

Gly Met His Trp Val Arg Gln Ala Pro Gly Lys Gly Leu Glu Trp Val
        35                  40                  45

Ala Leu Ile Ser Asp Asp Gly Met Arg Lys Tyr His Ser Asp Ser Met
    50                  55                  60

Trp Gly Arg Val Thr Ile Ser Arg Asp Asn Ser Lys Asn Thr Leu Tyr
65                  70                  75                  80

Leu Gln Phe Ser Ser Leu Arg Val Glu Asp Thr Ala Met Phe Phe Cys
                85                  90                  95

Ala Arg Glu Ala Gly Gly Pro Ile Trp His Asp Val Lys Tyr Tyr
            100                 105                 110

Asp Phe Asn Asp Gly Tyr Tyr Asn Tyr His Tyr Met Asp Val Trp Gly
        115                 120                 125

Lys Gly Thr Lys Val Thr Val Ser Ser
        130                 135

<210> SEQ ID NO 49
<211> LENGTH: 707
<212> TYPE: DNA
<213> ORGANISM: Homo sapiens

<400> SEQUENCE: 49
atggcctggg cttgctattc ctcaccctct tcactcaggg cacagggtcc tggggccagt     60
ctgccctgac tcagcctgcc tccgtgtctg ggtctcctgg acagacgatc accatctcct    120
gcaatggaac cagccgtgac gttggtggat ttgactctgt ctcctggtat caacaatccc    180
cagggaaagc ccccaaagtc atggtttttg atgtcagtca tcggccctca ggtatgtcta    240
atcgcttctc tggctccaag tccggcaaca cggcctccct gaccatttct gggctccaca    300
ttgaggacga gggcgattat ttctgctctt cattgacaga cagaagccat cgcatattcg    360
gcggcgggac caagctgacc gttctaggtc agcccaaggc tgccccctcg gtcactctgt    420
tcccgccctc ctctgaggag cttcaagcca acaaggccac actggtgtgt ctcataagtg    480
acttctaccc gggagccgtg acagtggcct ggaaggcaga tagcagcccc gtcaaggcgg    540
gagtggagac caccacaccc tccaaacaaa gcaacaacaa gtacgcggcc agcagctacc    600
tgagcctgac gcctgagcag tggaagtccc acaaaagcta cagctgccag gtcacgcatg    660
aagggagcac cgtggagaag acagtggccc ctacagaatg ttcatag                 707

<210> SEQ ID NO 50
<211> LENGTH: 216
<212> TYPE: PRT
<213> ORGANISM: Homo sapiens -continued

```
<400> SEQUENCE: 50

Gln Ser Ala Leu Thr Gln Pro Ala Ser Val Ser Gly Ser Pro Gly Gln
1               5                   10                  15

Thr Ile Thr Ile Ser Cys Asn Gly Thr Ser Arg Asp Val Gly Gly Phe
            20                  25                  30

Asp Ser Val Ser Trp Tyr Gln Gln Ser Pro Gly Lys Ala Pro Lys Val
        35                  40                  45

Met Val Phe Asp Val Ser His Arg Pro Ser Gly Met Ser Asn Arg Phe
    50                  55                  60

Ser Gly Ser Lys Ser Gly Asn Thr Ala Ser Leu Thr Ile Ser Gly Leu
65                  70                  75                  80

His Ile Glu Asp Glu Gly Asp Tyr Phe Cys Ser Ser Leu Thr Asp Arg
                85                  90                  95

Ser His Arg Ile Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Lys Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 51
<211> LENGTH: 110
<212> TYPE: PRT
<213> ORGANISM: Homo sapiens

<400> SEQUENCE: 51

Gln Ser Ala Leu Thr Gln Pro Ala Ser Val Ser Gly Ser Pro Gly Gln
1               5                   10                  15

Thr Ile Thr Ile Ser Cys Asn Gly Thr Ser Arg Asp Val Gly Gly Phe
            20                  25                  30

Asp Ser Val Ser Trp Tyr Gln Gln Ser Pro Gly Lys Ala Pro Lys Val
        35                  40                  45

Met Val Phe Asp Val Ser His Arg Pro Ser Gly Met Ser Asn Arg Phe
    50                  55                  60

Ser Gly Ser Lys Ser Gly Asn Thr Ala Ser Leu Thr Ile Ser Gly Leu
65                  70                  75                  80

His Ile Glu Asp Glu Gly Asp Tyr Phe Cys Ser Ser Leu Thr Asp Arg
                85                  90                  95

Ser His Arg Ile Phe Gly Gly Gly Thr Lys Leu Thr Val Leu
            100                 105                 110

<210> SEQ ID NO 52
<211> LENGTH: 1460
<212> TYPE: DNA
<213> ORGANISM: Homo sapiens
```

-continued

<400> SEQUENCE: 52

```
atggagtttg gctgagctgg gttttcctcg caactctgtt aagagttgtg aagtgtcagg      60
aaaaactggt ggagtctggg ggaggcgtgg tccagccggg ggggtccctg agactctcct     120
gtttagcgtc tggattcacc tttcacaaat atggcatgca ctgggtccgc caggctccag     180
gcaagggcct ggagtgggtg gcactcatct cagatgacgg aatgaggaaa tatcattcag     240
actccatgtg gggccgagtc accatctcca gagacaattc caagaacact ttatatctgc     300
aattcagcag cctgaaagtc gaagacacgg ctatgttctt ctgtgcgaga gaggctggtg     360
ggccaatctg gcatgacgac gtcaaatatt acgattttaa tgacggctac tacaattacc     420
actacatgga cgtctggggc aaggggacca ttgtcaccgt ctcctcagcg tcgaccaagg     480
gcccatcggt cttccctctg gcaccatcat ccaagtcgac ctctgggggc acagcggccc     540
tgggctgcct ggtcaaggac tacttccccg aaccggtgac ggtgtcgtgg aactcaggcg     600
ccctgaccag cggcgtgcac accttccggg ctgtcctaca gtcctcagga ctctactccc     660
tcagcagcgt ggtgaccgtg ccctccagca gcttgggcac ccagacctac atctgcaacg     720
tgaatcacaa gcccagcaac accaaggtgg acaagagagt tgagcccaaa tcttgtgaca     780
aaactcacac atgcccaccg tgcccagcac ctgaactcct ggggggaccg tcagtcttcc     840
tcttcccccc aaaacccaag gacaccctca tgatctcccg gacccctgag gtcacatgcg     900
tggtggtgga cgtgagccac gaagaccctg aggtcaagtt caactggtac gtggacggcg     960
tggaggtgca taatgccaag acaaagccgc gggaggagca gtacaacagc acgtaccgtg    1020
tggtcagcgt cctcaccgtc ctgcaccagg actggctgaa tggcaaggag tacaagtgca    1080
aggtctccaa caaagccctc ccagccccca tcgagaaaac catctccaaa gccaagggc     1140
agccccgaga accacaggtg tacaccctgc ccccatcccg ggaggagatg accaagaacc    1200
aggtcagcct gacctgcctg gtcaaaggct tctatcccag cgacatcgcc gtggagtggg    1260
agagcaatgg gcagccggag aacaactaca agaccacgcc tcccgtgctg gactccgacg    1320
gctccttctt cctctatagc aagctcaccg tggacaagag caggtggcag caggggaacg    1380
tcttctcatg ctccgtgatg catgaggctc tgcacaacca ctacacgcag aagagcctct    1440
ccctgtctcc gggtaaatga                                                1460
```

<210> SEQ ID NO 53
<211> LENGTH: 467
<212> TYPE: PRT
<213> ORGANISM: Homo sapiens

<400> SEQUENCE: 53

```
Gln Glu Lys Leu Val Glu Ser Gly Gly Gly Val Val Gln Pro Gly Gly
1               5                   10                  15

Ser Leu Arg Leu Ser Cys Leu Ala Ser Gly Phe Thr Phe His Lys Tyr
            20                  25                  30

Gly Met His Trp Val Arg Gln Ala Pro Gly Lys Gly Leu Glu Trp Val
        35                  40                  45

Ala Leu Ile Ser Asp Asp Gly Met Arg Lys Tyr His Ser Asp Ser Met
    50                  55                  60

Trp Gly Arg Val Thr Ile Ser Arg Asp Asn Ser Lys Asn Thr Leu Tyr
65                  70                  75                  80

Leu Gln Phe Ser Ser Leu Lys Val Glu Asp Thr Ala Met Phe Phe Cys
                85                  90                  95

Ala Arg Glu Ala Gly Gly Pro Ile Trp His Asp Asp Val Lys Tyr Tyr
```

```
                100             105             110
Asp Phe Asn Asp Gly Tyr Tyr Asn Tyr His Tyr Met Asp Val Trp Gly
            115                 120                 125
Lys Gly Thr Ile Val Thr Val Ser Ser Ala Ser Thr Lys Gly Pro Ser
130                 135                 140
Val Phe Pro Leu Ala Pro Ser Ser Lys Ser Thr Ser Gly Gly Thr Ala
145                 150                 155                 160
Ala Leu Gly Cys Leu Val Lys Asp Tyr Phe Pro Glu Pro Val Thr Val
            165                 170                 175
Ser Trp Asn Ser Gly Ala Leu Thr Ser Gly Val His Thr Phe Pro Ala
            180                 185                 190
Val Leu Gln Ser Ser Gly Leu Tyr Ser Leu Ser Ser Val Val Thr Val
            195                 200                 205
Pro Ser Ser Ser Leu Gly Thr Gln Thr Tyr Ile Cys Asn Val Asn His
            210                 215                 220
Lys Pro Ser Asn Thr Lys Val Asp Lys Arg Val Glu Pro Lys Ser Cys
225                 230                 235                 240
Asp Lys Thr His Thr Cys Pro Pro Cys Pro Ala Pro Glu Leu Leu Gly
            245                 250                 255
Gly Pro Ser Val Phe Leu Phe Pro Pro Lys Pro Lys Asp Thr Leu Met
            260                 265                 270
Ile Ser Arg Thr Pro Glu Val Thr Cys Val Val Val Asp Val Ser His
            275                 280                 285
Glu Asp Pro Glu Val Lys Phe Asn Trp Tyr Val Asp Gly Val Glu Val
            290                 295                 300
His Asn Ala Lys Thr Lys Pro Arg Glu Glu Gln Tyr Asn Ser Thr Tyr
305                 310                 315                 320
Arg Val Val Ser Val Leu Thr Val Leu His Gln Asp Trp Leu Asn Gly
            325                 330                 335
Lys Glu Tyr Lys Cys Lys Val Ser Asn Lys Ala Leu Pro Ala Pro Ile
            340                 345                 350
Glu Lys Thr Ile Ser Lys Ala Lys Gly Gln Pro Arg Glu Pro Gln Val
            355                 360                 365
Tyr Thr Leu Pro Pro Ser Arg Glu Glu Met Thr Lys Asn Gln Val Ser
370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
            405                 410                 415
Val Leu Asp Ser Asp Gly Ser Phe Phe Leu Tyr Ser Lys Leu Thr Val
            420                 425                 430
Asp Lys Ser Arg Trp Gln Gln Gly Asn Val Phe Ser Cys Ser Val Met
            435                 440                 445
His Glu Ala Leu His Asn His Tyr Thr Gln Lys Ser Leu Ser Leu Ser
            450                 455                 460
Pro Gly Lys
465

<210> SEQ ID NO 54
<211> LENGTH: 137
<212> TYPE: PRT
<213> ORGANISM: Homo sapiens

<400> SEQUENCE: 54
```

-continued

Gln Glu Lys Leu Val Glu Ser Gly Gly Val Val Gln Pro Gly Gly
1               5                   10                  15

Ser Leu Arg Leu Ser Cys Leu Ala Ser Gly Phe Thr Phe His Lys Tyr
            20                  25                  30

Gly Met His Trp Val Arg Gln Ala Pro Gly Lys Gly Leu Glu Trp Val
            35                  40                  45

Ala Leu Ile Ser Asp Asp Gly Met Arg Lys Tyr His Ser Asp Ser Met
        50                  55                  60

Trp Gly Arg Val Thr Ile Ser Arg Asp Asn Ser Lys Asn Thr Leu Tyr
65                  70                  75                  80

Leu Gln Phe Ser Ser Leu Lys Val Glu Asp Thr Ala Met Phe Phe Cys
                85                  90                  95

Ala Arg Glu Ala Gly Gly Pro Ile Trp His Asp Asp Val Lys Tyr Tyr
            100                 105                 110

Asp Phe Asn Asp Gly Tyr Tyr Asn Tyr His Tyr Met Asp Val Trp Gly
            115                 120                 125

Lys Gly Thr Ile Val Thr Val Ser Ser
            130                 135

<210> SEQ ID NO 55
<211> LENGTH: 707
<212> TYPE: DNA
<213> ORGANISM: Homo sapiens

<400> SEQUENCE: 55
atggcctggg cttgctattc ctcaccctct tcactcaggg cacagggtcc tggggccagt      60
ctgccctgac tcagcctgcc tccgtgtctg ggtctcctgg acagacgatc accatctcct     120
gcaatggaac cagaagtgac gttggtggat tgactctgt ctcctggtac caacaatccc     180
cagggaaagc ccccaaagtc atggtttttg atgtcagtca tcggccctca ggtatctcta     240
atcgcttctc tggctccaag tccggcaaca cggcctccct gaccatctct ggctccaca     300
ttgaggacga gggcgattat ttctgctctt cactgacaga cagaagccat cgcatattcg     360
gcggcgggac caaggtgacc gttctaggtc agcccaaggc tgcccctcg gtcactctgt     420
tcccgccctc ctctgaggag cttcaagcca acaaggccac actggtgtgt ctcataagtg     480
acttctaccc gggagccgtg acagtggcct ggaaggcaga tagcagcccc gtcaaggcgg     540
gagtggagac caccacaccc tccaaacaaa gcaacaacaa gtacgcggcc agcagctacc     600
tgagcctgac gcctgagcag tggaagtccc acaaaagcta cagctgccag gtcacgcatg     660
aagggagcac cgtggagaag acagtggccc ctacagaatg ttcatag                   707

<210> SEQ ID NO 56
<211> LENGTH: 216
<212> TYPE: PRT
<213> ORGANISM: Homo sapiens

<400> SEQUENCE: 56

Gln Ser Ala Leu Thr Gln Pro Ala Ser Val Ser Gly Ser Pro Gly Gln
1               5                   10                  15

Thr Ile Thr Ile Ser Cys Asn Gly Thr Arg Ser Asp Val Gly Gly Phe
            20                  25                  30

Asp Ser Val Ser Trp Tyr Gln Gln Ser Pro Gly Lys Ala Pro Lys Val
        35                  40                  45

Met Val Phe Asp Val Ser His Arg Pro Ser Gly Ile Ser Asn Arg Phe
    50                  55                  60

Ser Gly Ser Lys Ser Gly Asn Thr Ala Ser Leu Thr Ile Ser Gly Leu
65                  70                  75                  80

His Ile Glu Asp Glu Gly Asp Tyr Phe Cys Ser Ser Leu Thr Asp Arg
                85                  90                  95

Ser His Arg Ile Phe Gly Gly Gly Thr Lys Val Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Lys Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 57
<211> LENGTH: 110
<212> TYPE: PRT
<213> ORGANISM: Homo sapiens

<400> SEQUENCE: 57

Gln Ser Ala Leu Thr Gln Pro Ala Ser Val Ser Gly Ser Pro Gly Gln
1               5                   10                  15

Thr Ile Thr Ile Ser Cys Asn Gly Thr Arg Ser Asp Val Gly Gly Phe
                20                  25                  30

Asp Ser Val Ser Trp Tyr Gln Gln Ser Pro Gly Lys Ala Pro Lys Val
            35                  40                  45

Met Val Phe Asp Val Ser His Arg Pro Ser Gly Ile Ser Asn Arg Phe
        50                  55                  60

Ser Gly Ser Lys Ser Gly Asn Thr Ala Ser Leu Thr Ile Ser Gly Leu
65                  70                  75                  80

His Ile Glu Asp Glu Gly Asp Tyr Phe Cys Ser Ser Leu Thr Asp Arg
                85                  90                  95

Ser His Arg Ile Phe Gly Gly Gly Thr Lys Val Thr Val Leu
            100                 105                 110

<210> SEQ ID NO 58
<211> LENGTH: 1461
<212> TYPE: DNA
<213> ORGANISM: Homo sapiens

<400> SEQUENCE: 58
atggagtttg ggctgagctg gttttcctc gcaactctgt taagagttgt gaagtgtcag       60
gaacaactgt tggagtctgg gggaggcgtg gtccagccgg ggggtccct gagactctcc      120 tgtttagcgt ctggattcac gtttcacaaa tatggcatgc actgggtccg ccaggctcca     180
ggcaagggcc tggagtgggt ggcactcatc tcagatgacg gaatgaggaa atatcattca     240
aactccatgt ggggccgagt caccatctcc agagacaatt ccaagaacac tctttatctg     300
caattcagca gcctgaaagt cgaagacacg gctatgttct tctgtgcgag agaggctggt     360

```
gggccaatct ggcatgacga cgtcaaatat tacgattta atgacggcta ctacaactac    420
cactacatgg acgtctgggg caaggggacc acggtcaccg tctcctcagc gtcgaccaag    480
ggcccatcgg tcttccctct ggcaccatca tccaagtcga cctctggggg cacagcggcc    540
ctgggctgcc tggtcaagga ctacttcccc gaaccggtga cggtgtcgtg gaactcaggc    600
gccctgacca gcggcgtgca caccttcccg gctgtcctac agtcctcagg actctactcc    660
ctcagcagcg tggtgaccgt gccctccagc agcttgggca cccagaccta catctgcaac    720
gtgaatcaca agcccagcaa caccaaggtg gacaagagag ttgagcccaa atcttgtgac    780
aaaactcaca catgcccacc gtgcccagca cctgaactcc tggggggacc gtcagtcttc    840
ctcttccccc caaaacccaa ggacaccctc atgatctccc ggacccctga ggtcacatgc    900
gtggtggtgg acgtgagcca cgaagaccct gaggtcaagt tcaactggta cgtggacggc    960
gtggaggtgc ataatgccaa gacaaagccg cgggaggagc agtacaacag cacgtaccgt   1020
gtggtcagcg tcctcaccgt cctgcaccag gactggctga atggcaagga gtacaagtgc   1080
aaggtctcca acaaagccct cccagccccc atcgagaaaa ccatctccaa agccaaaggg   1140
cagccccgag aaccacaggt gtacaccctg cccccatccc gggaggagat gaccaagaac   1200
caggtcagcc tgacctgcct ggtcaaaggc ttctatccca gcgacatcgc cgtggagtgg   1260
gagagcaatg ggcagccgga gaacaactac aagaccacgc ctcccgtgct ggactccgac   1320
ggctccttct tcctctatag caagctcacc gtggacaaga gcaggtggca gcaggggaac   1380
gtcttctcat gctccgtgat gcatgaggct ctgcacaacc actacacgca gaagagcctc   1440
tccctgtctc cgggtaaatg a                                             1461
```

<210> SEQ ID NO 59
<211> LENGTH: 467
<212> TYPE: PRT
<213> ORGANISM: Homo sapiens

<400> SEQUENCE: 59

Gln Glu Gln Leu Leu Glu Ser Gly Gly Gly Val Val Gln Pro Gly Gly
1               5                   10                  15

Ser Leu Arg Leu Ser Cys Leu Ala Ser Gly Phe Thr Phe His Lys Tyr
            20                  25                  30

Gly Met His Trp Val Arg Gln Ala Pro Gly Lys Gly Leu Glu Trp Val
        35                  40                  45

Ala Leu Ile Ser Asp Asp Gly Met Arg Lys Tyr His Ser Asn Ser Met
    50                  55                  60

Trp Gly Arg Val Thr Ile Ser Arg Asp Asn Ser Lys Asn Thr Leu Tyr
65                  70                  75                  80

Leu Gln Phe Ser Ser Leu Lys Val Glu Asp Thr Ala Met Phe Phe Cys
                85                  90                  95

Ala Arg Glu Ala Gly Gly Pro Ile Trp His Asp Asp Val Lys Tyr Tyr
            100                 105                 110

Asp Phe Asn Asp Gly Tyr Tyr Asn Tyr His Tyr Met Asp Val Trp Gly
        115                 120                 125

Lys Gly Thr Thr Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

```
Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
            245                 250                 255

Gly Pro Ser Val Phe Leu Phe Pro Pro Lys Pro Lys Asp Thr Leu Met
        260                 265                 270

Ile Ser Arg Thr Pro Glu Val Thr Cys Val Val Val Asp Val Ser His
    275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
            325                 330                 335

Lys Glu Tyr Lys Cys Lys Val Ser Asn Lys Ala Leu Pro Ala Pro Ile
        340                 345                 350

Glu Lys Thr Ile Ser Lys Ala Lys Gly Gln Pro Arg Glu Pro Gln Val
    355                 360                 365

Tyr Thr Leu Pro Pro Ser Arg Glu Glu Met Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
            405                 410                 415

Val Leu Asp Ser Asp Gly Ser Phe Phe Leu Tyr Ser Lys Leu Thr Val
        420                 425                 430

Asp Lys Ser Arg Trp Gln Gln Gly Asn Val Phe Ser Cys Ser Val Met
    435                 440                 445

His Glu Ala Leu His Asn His Tyr Thr Gln Lys Ser Leu Ser Leu Ser
    450                 455                 460

Pro Gly Lys
465

<210> SEQ ID NO 60
<211> LENGTH: 137
<212> TYPE: PRT
<213> ORGANISM: Homo sapiens

<400> SEQUENCE: 60

Gln Glu Gln Leu Leu Glu Ser Gly Gly Gly Val Val Gln Pro Gly Gly
1               5                   10                  15

Ser Leu Arg Leu Ser Cys Leu Ala Ser Gly Phe Thr Phe His Lys Tyr
            20                  25                  30

Gly Met His Trp Val Arg Gln Ala Pro Gly Lys Gly Leu Glu Trp Val
        35                  40                  45

Ala Leu Ile Ser Asp Asp Gly Met Arg Lys Tyr His Ser Asn Ser Met
    50                  55                  60

Trp Gly Arg Val Thr Ile Ser Arg Asp Asn Ser Lys Asn Thr Leu Tyr
65                  70                  75                  80
```

```
Leu Gln Phe Ser Ser Leu Lys Val Glu Asp Thr Ala Met Phe Phe Cys
                85                  90                  95

Ala Arg Glu Ala Gly Gly Pro Ile Trp His Asp Val Lys Tyr Tyr
            100                 105                 110

Asp Phe Asn Asp Gly Tyr Tyr Asn Tyr His Tyr Met Asp Val Trp Gly
        115                 120                 125

Lys Gly Thr Thr Val Thr Val Ser Ser
    130                 135

<210> SEQ ID NO 61
<211> LENGTH: 708
<212> TYPE: DNA
<213> ORGANISM: Homo sapiens

<400> SEQUENCE: 61
atggcctggg ctctgctatt cctcaccctc ttcactcagg gcacagggtc ccggggccag    60
tctgccctga ctcagcctgc ctccgtgtct gggtctcctg gacagacgat caccatctcc   120
tgcaatggaa ccagcagtga cgttggtgga tttgactctg tctcctggta tcaacaatcc   180
ccagggaaag cccccaaagt catggttttt gatgtcagtc atcggccctc aggtatctct   240
aatcgcttct ctggctccaa gtccggcaac acggcctccc tgaccatctc tgggctccac   300
attgaggacg agggcgatta tttctgctct tcactgacag acagaagcca tcgcatattc   360
ggcggcggga ccaaggtgac cgttctaggt cagcccaagg ctgccccctc ggtcactctg   420
ttcccgccct cctctgagga gcttcaagcc aacaaggcca cactggtgtg tctcataagt   480
gacttctacc cgggagccgt gacagtggcc tggaaggcag atagcagccc cgtcaaggcg   540
ggagtggaga ccaccacacc ctccaaacaa agcaacaaca gtacgcggc cagcagctac   600 ctgagcctga cgcctgagca gtggaagtcc cacaaaagct acagctgcca ggtcacgcat   660
gaagggagca ccgtggagaa gacagtggcc cctacagaat gttcatag               708

<210> SEQ ID NO 62

<400> SEQUENCE: 62

000

<210> SEQ ID NO 63

<400> SEQUENCE: 63

000

<210> SEQ ID NO 64
<211> LENGTH: 1460
<212> TYPE: DNA
<213> ORGANISM: Homo sapiens

<400> SEQUENCE: 64
atggagtttg gctgagctgg gttttcctcg caactctgtt aagagttgtg aagtgtcagg    60
aacaactggt ggagtctggg ggaggcgtgg tccagccggg ggggtccctg agactctcct   120
gtttagcgtc tggattcacg tttcacaaat atggcatgca ctgggtccgc caggctccag   180
gcaagggcct ggagtgggtg gcactcatct cagatgacgg aatgaggaaa tatcattcag   240
actccatgtg gggccgagtc accatctcca gagacaattc caagaacact ctttatctgc   300
aattcagcag cctgaaagtc gaagacacgg ctatgttctt ctgtgcgaga gaggctggtg   360
```

-continued

```
ggccaatctg gcatgacgac gtcaaatatt acgattttaa tgacggctac tacaactacc    420
actacatgga cgtctgggc aaggggacca cggtcaccgt ctcctcagcg tcgaccaagg    480
gcccatcggt cttccctctg gcaccatcat ccaagtcgac ctctggggc acagcggccc    540 tgggctgcct ggtcaaggac tacttccccg aaccggtgac ggtgtcgtgg aactcaggcg    600
ccctgaccag cggcgtgcac accttcccgg ctgtcctaca gtcctcagga ctctactccc    660
tcagcagcgt ggtgaccgtg ccctccagca gcttgggcac ccagacctac atctgcaacg    720
tgaatcacaa gcccagcaac accaaggtgg acaagagagt tgagcccaaa tcttgtgaca    780
aaactcacac atgcccaccg tgcccagcac ctgaactcct gggggaccg tcagtcttcc    840 tcttcccccc aaaacccaag gacaccctca tgatctcccg gacccctgag gtcacatgcg    900
tggtggtgga cgtgagccac gaagaccctg aggtcaagtt caactggtac gtggacggcg    960
tggaggtgca taatgccaag acaaagccgc gggaggagca gtacaacagc acgtaccgtg   1020
tggtcagcgt cctcaccgtc ctgcaccagg actggctgaa tggcaaggag tacaagtgca   1080
aggtctccaa caaagccctc ccagcccca tcgagaaaac catctccaaa gccaagggc    1140 agccccgaga accacaggtg tacaccctgc ccccatcccg ggaggagatg accaagaacc   1200
aggtcagcct gacctgcctg gtcaaaggct tctatcccag cgacatcgcc gtggagtggg   1260
agagcaatgg gcagccggag aacaactaca agaccacgcc tcccgtgctg gactccgacg   1320
gctccttctt cctctatagc aagctcaccg tggacaagag caggtggcag caggggaacg   1380
tcttctcatg ctccgtgatg catgaggctc tgcacaacca ctacacgcag aagagcctct   1440
ccctgtctcc gggtaaatga                                               1460
```

<210> SEQ ID NO 65
<211> LENGTH: 467
<212> TYPE: PRT
<213> ORGANISM: Homo sapiens

<400> SEQUENCE: 65

```
Gln Glu Gln Leu Val Glu Ser Gly Gly Gly Val Val Gln Pro Gly Gly
1               5                   10                  15

Ser Leu Arg Leu Ser Cys Leu Ala Ser Gly Phe Thr Phe His Lys Tyr
            20                  25                  30

Gly Met His Trp Val Arg Gln Ala Pro Gly Lys Gly Leu Glu Trp Val
        35                  40                  45

Ala Leu Ile Ser Asp Asp Gly Met Arg Lys Tyr His Ser Asp Ser Met
    50                  55                  60

Trp Gly Arg Val Thr Ile Ser Arg Asp Asn Ser Lys Asn Thr Leu Tyr
65                  70                  75                  80

Leu Gln Phe Ser Ser Leu Lys Val Glu Asp Thr Ala Met Phe Phe Cys
                85                  90                  95

Ala Arg Glu Ala Gly Gly Pro Ile Trp His Asp Asp Val Lys Tyr Tyr
            100                 105                 110

Asp Phe Asn Asp Gly Tyr Tyr Asn Tyr His Tyr Met Asp Val Trp Gly
        115                 120                 125

Lys Gly Thr Thr Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175
```

```
Ser Trp Asn Ser Gly Ala Leu Thr Ser Gly Val His Thr Phe Pro Ala
                180                 185                 190

Val Leu Gln Ser Ser Gly Leu Tyr Ser Leu Ser Ser Val Val Thr Val
            195                 200                 205

Pro Ser Ser Ser Leu Gly Thr Gln Thr Tyr Ile Cys Asn Val Asn His
        210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
450                 455                 460

Pro Gly Lys
465

<210> SEQ ID NO 66

<400> SEQUENCE: 66

000

<210> SEQ ID NO 67
<211> LENGTH: 708
<212> TYPE: DNA
<213> ORGANISM: Homo sapiens

<400> SEQUENCE: 67
atggcctggg ctctgctatt cgtcaccctc ctcactcagg gcacagggtc ctggggccag      60
tctgccctga ctcagcctgc ctccgtgtct gggtctcctg gacagacgat caccatctcc     120
tgcaatggaa ccagcagtga cgttggtgga tttgactctg tcctggta tcaacaatcc       180 ccagggaaag cccccaaagt catggttttt gatgtcagtc atcggccctc aggtatctct     240
```

```
aatcgcttct ctggctccaa gtccggcaac acggcctccc tgaccatctc tgggctccac    300
attgaggacg agggcgatta tttctgctct tcactgacag acagaagcca tcgcatattc    360
ggcggcggga ccaaggtgac cgttctaggt cagcccaagg ctgccccctc ggtcactctg    420
ttcccgccct cctctgagga gcttcaagcc aacaaggcca cactggtgtg tctcataagt    480
gacttctacc cgggagccgt gacagtggcc tggaaggcag atagcagccc cgtcaaggcg    540
ggagtggaga ccaccacacc ctccaaacaa agcaacaaca agtacgcggc cagcagctac    600
ctgagcctga cgcctgagca gtggaagtcc cacaaaagct acagctgcca ggtcacgcat    660
gaagggagca ccgtggagaa gacagtggcc cctacagaat gttcatag                 708
```

<210> SEQ ID NO 68
<211> LENGTH: 33
<212> TYPE: DNA
<213> ORGANISM: Homo sapiens

<400> SEQUENCE: 68
tctggattca cgtttcacaa atatggcatg cac    33

<210> SEQ ID NO 69
<211> LENGTH: 33
<212> TYPE: DNA
<213> ORGANISM: Homo sapiens

<400> SEQUENCE: 69
tctggattca cctttcacaa atatggcatg cac    33

<210> SEQ ID NO 70
<211> LENGTH: 33
<212> TYPE: DNA
<213> ORGANISM: Homo sapiens

<400> SEQUENCE: 70
tctggattca cctttcacaa atatggcatg cac    33

<210> SEQ ID NO 71
<211> LENGTH: 33
<212> TYPE: DNA
<213> ORGANISM: Homo sapiens
<220> FEATURE:
<221> NAME/KEY: misc_feature
<222> LOCATION: (12)..(12)
<223> OTHER INFORMATION: Wherein n is either c or g.

<400> SEQUENCE: 71
tctggattca cntttcacaa atatggcatg cac    33

<210> SEQ ID NO 72
<211> LENGTH: 48
<212> TYPE: DNA
<213> ORGANISM: Homo sapiens

<400> SEQUENCE: 72
ctcatctcag atgacggaat gaggaaatat cattcagact ccatgtgg    48

<210> SEQ ID NO 73
<211> LENGTH: 48
<212> TYPE: DNA
<213> ORGANISM: Homo sapiens

<400> SEQUENCE: 73

```
ctcatctcag atgacggaat gaggaaatat cattcaaact ccatgtgg                 48
```

<210> SEQ ID NO 74
<211> LENGTH: 48
<212> TYPE: DNA
<213> ORGANISM: Homo sapiens
<220> FEATURE:
<221> NAME/KEY: misc_feature
<222> LOCATION: (37)..(37)
<223> OTHER INFORMATION: Wherein n is a or g.

<400> SEQUENCE: 74

```
ctcatctcag atgacggaat gaggaaatat cattcanact ccatgtgg                 48
```

<210> SEQ ID NO 75
<211> LENGTH: 84
<212> TYPE: DNA
<213> ORGANISM: Homo sapiens

<400> SEQUENCE: 75

```
gaggctggtg ggccaatctg gcatgacgac gtcaaatatt acgattttaa tgacggctac    60
tacaactacc actacatgga cgtc                                           84
```

<210> SEQ ID NO 76
<211> LENGTH: 84
<212> TYPE: DNA
<213> ORGANISM: Homo sapiens
<220> FEATURE:
<221> NAME/KEY: misc_feature
<222> LOCATION: (6)..(6)
<223> OTHER INFORMATION: Wherein n is t, c, or g.

<400> SEQUENCE: 76

```
gaggcnggtg ggccaatctg gcatgacgac gtcaaatatt acgattttaa tgacggctac    60
tacaactatc actacatgga cgtc                                           84
```

<210> SEQ ID NO 77
<211> LENGTH: 84
<212> TYPE: DNA
<213> ORGANISM: Homo sapiens

<400> SEQUENCE: 77

```
gaggccggtg ggccaatctg gcatgacgac gtcaaatatt acgattttaa tgacggctac    60
tacaactatc actacatgga cgtc                                           84
```

<210> SEQ ID NO 78
<211> LENGTH: 84
<212> TYPE: DNA
<213> ORGANISM: Homo sapiens

<400> SEQUENCE: 78

```
gaggcgggtg ggccaatctg gcatgacgac gtcaaatatt acgattttaa tgacggctac    60
tacaactatc actacatgga cgtc                                           84
```

<210> SEQ ID NO 79

<400> SEQUENCE: 79

000

<210> SEQ ID NO 80
<211> LENGTH: 42
<212> TYPE: DNA

```
<213> ORGANISM: Homo sapiens

<400> SEQUENCE: 80
aatggaacca gcagtgacgt tggtggattt gactctgtct cc                              42

<210> SEQ ID NO 81
<211> LENGTH: 42
<212> TYPE: DNA
<213> ORGANISM: Homo sapiens
<220> FEATURE:
<221> NAME/KEY: misc_feature
<222> LOCATION: (12)..(12)
<223> OTHER INFORMATION: Wherein n is c or a.
<220> FEATURE:
<221> NAME/KEY: misc_feature
<222> LOCATION: (13)..(13)
<223> OTHER INFORMATION: Wherein n is c or a.

<400> SEQUENCE: 81
aatggaacca gnngtgacgt tggtggattt gactctgtct cc                              42

<210> SEQ ID NO 82
<211> LENGTH: 42
<212> TYPE: DNA
<213> ORGANISM: Homo sapiens

<400> SEQUENCE: 82
aatggaacca gaagtgacgt tggtggattt gactctgtct cc                              42

<210> SEQ ID NO 83
<211> LENGTH: 42
<212> TYPE: DNA
<213> ORGANISM: Homo sapiens

<400> SEQUENCE: 83
aatggaacca gccgtgacgt tggtggattt gactctgtct cc                              42

<210> SEQ ID NO 84
<211> LENGTH: 24
<212> TYPE: DNA
<213> ORGANISM: Homo sapiens

<400> SEQUENCE: 84
gatgtcagtc atcggccctc aggt                                                  24

<210> SEQ ID NO 85
<211> LENGTH: 30
<212> TYPE: DNA
<213> ORGANISM: Homo sapiens

<400> SEQUENCE: 85
tcttcactga cagacagaag ccatcgcata                                            30

<210> SEQ ID NO 86
<211> LENGTH: 30
<212> TYPE: DNA
<213> ORGANISM: Homo sapiens

<400> SEQUENCE: 86
tcttcattga cagacagaag ccatcgcata                                            30

<210> SEQ ID NO 87
<211> LENGTH: 30
<212> TYPE: DNA
<213> ORGANISM: Homo sapiens
```

```
<220> FEATURE:
<221> NAME/KEY: misc_feature
<222> LOCATION: (7)..(7)
<223> OTHER INFORMATION: Wherein n is c or t.

<400> SEQUENCE: 87
tcttcantga cagacagaag ccatcgcata                                          30

<210> SEQ ID NO 88
<211> LENGTH: 11
<212> TYPE: PRT
<213> ORGANISM: Homo sapiens

<400> SEQUENCE: 88

Ser Gly Phe Thr Phe His Lys Tyr Gly Met His
1               5                   10

<210> SEQ ID NO 89
<211> LENGTH: 16
<212> TYPE: PRT
<213> ORGANISM: Homo sapiens

<400> SEQUENCE: 89

Leu Ile Ser Asp Asp Gly Met Arg Lys Tyr His Ser Asp Ser Met Trp
1               5                   10                  15

<210> SEQ ID NO 90

<400> SEQUENCE: 90

000

<210> SEQ ID NO 91
<211> LENGTH: 16
<212> TYPE: PRT
<213> ORGANISM: Homo sapiens
<220> FEATURE:
<221> NAME/KEY: MISC_FEATURE
<222> LOCATION: (13)..(13)
<223> OTHER INFORMATION: Wherein X is D or N.

<400> SEQUENCE: 91

Leu Ile Ser Asp Asp Gly Met Arg Lys Tyr His Ser Xaa Ser Met Trp
1               5                   10                  15

<210> SEQ ID NO 92
<211> LENGTH: 14
<212> TYPE: PRT
<213> ORGANISM: Homo sapiens

<400> SEQUENCE: 92

Asn Gly Thr Arg Ser Asp Val Gly Gly Phe Asp Ser Val Ser
1               5                   10

<210> SEQ ID NO 93
<211> LENGTH: 14
<212> TYPE: PRT
<213> ORGANISM: Homo sapiens

<400> SEQUENCE: 93

Asn Gly Thr Ser Arg Asp Val Gly Gly Phe Asp Ser Val Ser
1               5                   10

<210> SEQ ID NO 94
<211> LENGTH: 14
<212> TYPE: PRT
```

```
<213> ORGANISM: Homo sapiens
<220> FEATURE:
<221> NAME/KEY: MISC_FEATURE
<222> LOCATION: (4)..(4)
<223> OTHER INFORMATION: Wherein X is S or R.
<220> FEATURE:
<221> NAME/KEY: MISC_FEATURE
<222> LOCATION: (5)..(5)
<223> OTHER INFORMATION: Wherein X is S or R.

<400> SEQUENCE: 94

Asn Gly Thr Xaa Xaa Asp Val Gly Gly Phe Asp Ser Val Ser
1               5                   10

<210> SEQ ID NO 95
<211> LENGTH: 8
<212> TYPE: PRT
<213> ORGANISM: Homo sapiens

<400> SEQUENCE: 95

Asp Val Ser His Arg Pro Ser Gly
1               5

<210> SEQ ID NO 96
<211> LENGTH: 110
<212> TYPE: PRT
<213> ORGANISM: Homo sapiens

<400> SEQUENCE: 96

Gln Ser Ala Leu Thr Gln Pro Ala Ser Val Ser Gly Ser Pro Gly Gln
1               5                   10                  15

Thr Ile Thr Ile Ser Cys Asn Gly Thr Arg Ser Asp Val Gly Gly Phe
            20                  25                  30

Asp Ser Val Ser Trp Tyr Gln Gln Ser Pro Gly Arg Ala Pro Lys Val
        35                  40                  45

Met Val Phe Asp Val Ser His Arg Pro Ser Gly Ile Ser Asn Arg Phe
    50                  55                  60

Ser Gly Ser Lys Ser Gly Asn Thr Ala Ser Leu Thr Ile Ser Gly Leu
65                  70                  75                  80

His Ile Glu Asp Glu Gly Asp Tyr Phe Cys Ser Ser Leu Thr Asp Arg
                85                  90                  95

Ser His Arg Ile Phe Gly Gly Gly Thr Lys Leu Thr Val Leu
            100                 105                 110

<210> SEQ ID NO 97
<211> LENGTH: 14
<212> TYPE: PRT
<213> ORGANISM: Homo sapiens

<400> SEQUENCE: 97

Asn Gly Thr Ser Ser Asp Val Gly Gly Phe Asp Ser Val Ser
1               5                   10

<210> SEQ ID NO 98
<211> LENGTH: 16
<212> TYPE: PRT
<213> ORGANISM: Homo sapiens

<400> SEQUENCE: 98

Leu Ile Ser Asp Asp Gly Met Arg Lys Tyr His Ser Asn Ser Met Trp
1               5                   10                  15

<210> SEQ ID NO 99
```

```
<211> LENGTH: 411
<212> TYPE: DNA
<213> ORGANISM: Homo sapiens

<400> SEQUENCE: 99
caggaacaac tggtggagtc tgggggaggc gtggtccagc cggggggtc cctgagactc      60 tcctgtttag cgtctggatt cacgtttcac aaatatggca tgcactgggt ccgccaggct    120
ccaggcaagg gcctggagtg gtggcactc atctcagatg acggaatgag gaaatatcat    180
tcagactcca tgtggggccg agtcaccatc tccagagaca attccaagaa cactctttat    240
ctgcaattca gcagcctgaa agtcgaagac acggctatgt tcttctgtgc gagagaggct    300
ggtgggccaa tctggcatga cgacgtcaaa tattacgatt ttaatgacgg ctactacaac    360
taccactaca tggacgtctg ggcaagggg accacggtca ccgtctcgag c              411

<210> SEQ ID NO 100
<211> LENGTH: 330
<212> TYPE: DNA
<213> ORGANISM: Homo sapiens

<400> SEQUENCE: 100
cagtctgccc tgactcagcc tgcctccgtg tctgggtctc ctggacagac gatcaccatc     60
tcctgcaatg gaaccagcag tgacgttggt ggatttgact ctgtctcctg gtaccaacaa   120
tccccaggga aagcccccaa agtcatggtt tttgatgtca gtcatcggcc ctcaggtatc   180
tctaatcgct tctctggctc caagtccggc aacacggcct ccctgaccat ctctgggctc   240
cacattgagg acgagggcga ttatttctgc tcttcactga cagacagaag ccatcgcata   300
ttcggcggcg ggaccaaggt gaccgttcta                                    330

<210> SEQ ID NO 101
<211> LENGTH: 372
<212> TYPE: DNA
<213> ORGANISM: Homo sapiens

<400> SEQUENCE: 101
caggtccgcc tggtacagtc tgggcctgag gtgaagaagc ctgggtcctc ggtgacggtc     60
tcctgccagg cttctggagg caccttcagc agttatgctt tcacctgggt gcgccaggcc   120
cccggacaag gtcttgagtg gttgggcatg gtcaccccaa tctttggtga ggccaagtac   180
tcacaaagat tcgagggcag agtcaccatc accgcggacg aatccacgag cacaacctcc   240
atagaattga gaggcctgac atccgaagac acggccattt attactgtgc gcgagatcgg   300
cgcgcggttc caattgccac ggacaactgg ttagaccct ggggccaggg gaccctggtc    360
accgtctcga gc                                                       372

<210> SEQ ID NO 102
<211> LENGTH: 13
<212> TYPE: PRT
<213> ORGANISM: Homo sapiens

<400> SEQUENCE: 102

Arg Ala Val Pro Ile Ala Thr Asp Asn Trp Leu Asp Pro
1               5                   10

<210> SEQ ID NO 103
<211> LENGTH: 14
<212> TYPE: PRT
<213> ORGANISM: Homo sapiens
```

<400> SEQUENCE: 103

Arg Arg Ala Val Pro Ile Ala Thr Asp Asn Trp Leu Asp Pro
1               5                   10

<210> SEQ ID NO 104
<211> LENGTH: 11
<212> TYPE: PRT
<213> ORGANISM: Homo sapiens

<400> SEQUENCE: 104

Ser Gly Gly Thr Phe Ser Ser Tyr Ala Phe Thr
1               5                   10

<210> SEQ ID NO 105
<211> LENGTH: 16
<212> TYPE: PRT
<213> ORGANISM: Homo sapiens

<400> SEQUENCE: 105

Met Val Thr Pro Ile Phe Gly Glu Ala Lys Tyr Ser Gln Arg Phe Glu
1               5                   10                  15

<210> SEQ ID NO 106
<211> LENGTH: 321
<212> TYPE: DNA
<213> ORGANISM: Homo sapiens

<400> SEQUENCE: 106
gacatccagt tgacccagtc tccatcctcc ctgtctgcat ctgttggcga cagagtctcc      60
atcacttgcc gggcgagtca gaccattaac aactacttaa attggtatca acagacaccc    120
gggaaagccc ctaaactcct gatctatggt gcctccaatt tgcaaaatgg ggtcccatca    180
aggttcagcg gcagtggctc tgggacagac ttcactctca ccatcagcag tctgcaacct    240
gaggattttg caacttacta ctgtcaacag agtttcagta ctccgaggac cttcggccaa    300
gggacacgac tggatattaa a                                              321

<210> SEQ ID NO 107
<211> LENGTH: 11
<212> TYPE: PRT
<213> ORGANISM: Homo sapiens

<400> SEQUENCE: 107

Arg Ala Ser Gln Thr Ile Asn Asn Tyr Leu Asn
1               5                   10

<210> SEQ ID NO 108
<211> LENGTH: 8
<212> TYPE: PRT
<213> ORGANISM: Homo sapiens

<400> SEQUENCE: 108

Gly Ala Ser Asn Leu Gln Asn Gly
1               5

<210> SEQ ID NO 109
<211> LENGTH: 372
<212> TYPE: DNA
<213> ORGANISM: Homo sapiens

<400> SEQUENCE: 109
caggtcctgc tggtgcagtc tgggactgag gtgaagaagc ctgggtcctc ggtgaaggtc       60

```
tcctgtcagg cttctggagg cgccttcagt agttatgctt tcagctgggt gcgacaggcc    120
cctggacagg ggcttgaatg gatgggcatg atcacccctg tctttggtga gactaaatat    180
gcaccgaggt tccagggcag actcacactt accgcggaag aatccttgag caccacctac    240
atggaattga aagcctgac  atctgatgac acggcctttt attattgtac gagagatcgg    300
cgcgtagttc aatggccac  agacaactgg ttagacccct ggggccaggg gacgctggtc    360
accgtctcga gc                                                         372
```

<210> SEQ ID NO 110
<211> LENGTH: 11
<212> TYPE: PRT
<213> ORGANISM: Homo sapiens

<400> SEQUENCE: 110

Ser Gly Gly Ala Phe Ser Ser Tyr Ala Phe Ser
1               5                   10

<210> SEQ ID NO 111
<211> LENGTH: 16
<212> TYPE: PRT
<213> ORGANISM: Homo sapiens

<400> SEQUENCE: 111

Met Ile Thr Pro Val Phe Gly Glu Thr Lys Tyr Ala Pro Arg Phe Gln
1               5                   10                  15

<210> SEQ ID NO 112
<211> LENGTH: 321
<212> TYPE: DNA
<213> ORGANISM: Homo sapiens

<400> SEQUENCE: 112

```
gacatccagt tgacccagtc tccatcctcc ctgtctgcat ctgtaggaga cagggtcacc    60
gtcacttgcc gggcgagtca gaccatacac acctatttaa attggtatca gcaaattcca    120
ggaaaagccc ctaagctcct gatctatggt gcctccacct tgcaaagtgg ggtcccgtca    180
aggttcagtg gcagtggatc tgggacagat ttcactctca ccatcaacag tctccaacct    240
gaggactttg caacttacta ctgtcaacag agttacagta ccccaaggac cttcggccaa    300
gggacacgac tggatattaa a                                               321
```

<210> SEQ ID NO 113
<211> LENGTH: 10
<212> TYPE: PRT
<213> ORGANISM: Homo sapiens

<400> SEQUENCE: 113

Arg Ala Ser Gln Thr Ile His Thr Tyr Leu
1               5                   10

<210> SEQ ID NO 114
<211> LENGTH: 8
<212> TYPE: PRT
<213> ORGANISM: Homo sapiens

<400> SEQUENCE: 114

Gly Ala Ser Thr Leu Gln Ser Gly
1               5

<210> SEQ ID NO 115
<211> LENGTH: 366

```
<212> TYPE: DNA
<213> ORGANISM: Homo sapiens

<400> SEQUENCE: 115
gacggccacc tggttcagtc tggggttgag gtgaagaaga ctggggctac agtcaaaatc      60
tcctgcaagg tttctggata cagcttcatc gactactacc ttcattgggt gcaacgggcc     120
cctggaaaag gccttgagtg ggtgggactt attgatcctg aaaatggtga ggctcgatat     180
gcagagaagt tccagggcag agtcaccata atcgcggaca cgtctataga tacaggctac     240
atggaaatga ggagcctgaa atctgaggac acggccgtgt atttctgtgc agcaggtgcc     300 gtggggctg attccgggag ctggttcgac ccctggggcc agggaactct ggtcaccgtc      360
tcgagc                                                               366

<210> SEQ ID NO 116
<211> LENGTH: 11
<212> TYPE: PRT
<213> ORGANISM: Homo sapiens

<400> SEQUENCE: 116

Ser Gly Tyr Ser Phe Ile Asp Tyr Tyr Leu His
1               5                   10

<210> SEQ ID NO 117
<211> LENGTH: 16
<212> TYPE: PRT
<213> ORGANISM: Homo sapiens

<400> SEQUENCE: 117

Leu Ile Asp Pro Glu Asn Gly Glu Ala Arg Tyr Ala Glu Lys Phe Gln
1               5                   10                  15

<210> SEQ ID NO 118
<211> LENGTH: 12
<212> TYPE: PRT
<213> ORGANISM: Homo sapiens

<400> SEQUENCE: 118

Ala Val Gly Ala Asp Ser Gly Ser Trp Phe Asp Pro
1               5                   10

<210> SEQ ID NO 119
<211> LENGTH: 327
<212> TYPE: DNA
<213> ORGANISM: Homo sapiens

<400> SEQUENCE: 119
tcctatgaac tgactcagcc accctcagtg tccgtgtccc caggacagac agccagcatc      60
acctgttctg gatctaaatt gggggataaa tatgtttcct ggtatcaact gaggccaggc     120
cagtccccca tactggtcat gtatgaaaat gacaggcggc cctccgggat ccctgagcga     180
ttctccggtt ccaattctgg cgacactgcc actctgacca tcagcgggac ccaggctttg     240
gatgaggctg acttctactg tcaggcgtgg gagaccacca ccaccacttt tgttttcttc     300
ggcggaggga cccagctgac cgttcta                                        327

<210> SEQ ID NO 120
<211> LENGTH: 11
<212> TYPE: PRT
<213> ORGANISM: Homo sapiens

<400> SEQUENCE: 120
```

Ser Gly Ser Lys Leu Gly Asp Lys Tyr Val Ser
1               5                   10

<210> SEQ ID NO 121
<211> LENGTH: 8
<212> TYPE: PRT
<213> ORGANISM: Homo sapiens

<400> SEQUENCE: 121

Glu Asn Asp Arg Arg Pro Ser Gly
1               5

<210> SEQ ID NO 122
<211> LENGTH: 408
<212> TYPE: DNA
<213> ORGANISM: Homo sapiens

<400> SEQUENCE: 122
cagcgattag tggagtctgg gggaggcgtg gtccagcctg gtcgtccct gagactctcc      60 tgtgcagcgt ccggattcga cttcagtaga caaggcatgc actgggtccg ccaggctcca   120
ggccaggggc tggagtgggt ggcatttatt aaatatgatg gaagtgagaa atatcatgct   180
gactccgtat ggggccgact cagcatctcc agagacaatt ccaaggatac gctttatctc   240
caaatgaata gcctgagagt cgaggacacg gctacatatt tttgtgtgag agaggctggt   300
gggcccgact accgtaatgg gtacaactat tacgatttct atgatggtta ttataactac   360
cactatatgg acgtctgggg caaagggacc acggtcaccg tctcgagc                408

<210> SEQ ID NO 123
<211> LENGTH: 11
<212> TYPE: PRT
<213> ORGANISM: Homo sapiens

<400> SEQUENCE: 123

Ser Gly Phe Asp Phe Ser Arg Gln Gly Met His
1               5                   10

<210> SEQ ID NO 124
<211> LENGTH: 16
<212> TYPE: PRT
<213> ORGANISM: Homo sapiens

<400> SEQUENCE: 124

Phe Ile Lys Tyr Asp Gly Ser Glu Lys Tyr His Ala Asp Ser Val Trp
1               5                   10                  15

<210> SEQ ID NO 125
<211> LENGTH: 330
<212> TYPE: DNA
<213> ORGANISM: Homo sapiens

<400> SEQUENCE: 125
cagtctgccc tgactcagcc tgcctccgtg tctgggtctc ctggacagtc gatcaccatc      60
tcctgcaatg gaaccagcaa tgatgttggt ggctatgaat ctgtctcctg gtaccaacaa   120
catcccggca agcccccaa agtcgtgatt tatgatgtca gtaaacggcc ctcaggggtt   180
tctaatcgct tctctggctc caagtccggc aacacggcct ccctgaccat ctctgggctc   240
caggctgagg acgagggtga ctattactgc aagtctctga caagcacgag acgtcgggtt   300
ttcggcactg ggaccaagct gaccgttcta                                    330

<210> SEQ ID NO 126
<211> LENGTH: 14
<212> TYPE: PRT
<213> ORGANISM: Homo sapiens

<400> SEQUENCE: 126

Asn Gly Thr Ser Asn Asp Val Gly Gly Tyr Glu Ser Val Ser
1               5                   10

<210> SEQ ID NO 127
<211> LENGTH: 8
<212> TYPE: PRT
<213> ORGANISM: Homo sapiens

<400> SEQUENCE: 127

Asp Val Ser Lys Arg Pro Ser Gly
1               5

<210> SEQ ID NO 128
<211> LENGTH: 411
<212> TYPE: DNA
<213> ORGANISM: Homo sapiens

<400> SEQUENCE: 128
caggaaaaac tggtggagtc tggggggaggc gtggtccagc cggggggtc cctgagactc      60
tcctgtttag cgtctggatt caccttttcac aaatatggca tgcactgggt ccgccaggct    120
ccaggcaagg gcctggagtg ggtggcactc atctcagatg acggaatgag gaaatatcat    180
tcagactcca tgtggggccg agtcaccatc tccagagaca attccaagaa cactctatat    240
ctgcaattca gcagcctgaa agtcgaagac acggctatgt tcttctgtgc gagagaggct    300
ggtgggccaa tctggcatga cgacgtcaaa tattacgatt ttaatgacgg ctactacaac    360
taccactaca tggacgtctg ggcaagggg accacggtca ccgtctcctc a              411

<210> SEQ ID NO 129
<211> LENGTH: 330
<212> TYPE: DNA
<213> ORGANISM: Homo sapiens

<400> SEQUENCE: 129
cagtctgccc tgactcagcc tgcctccgtg tctgggtctc ctggacagac gatcaccatc      60
tcctgcaatg gaaccagaag tgacgttggt ggatttgact ctgtctcctg gtaccaacaa    120
tccccaggga gagcccccaa agtcatggtt tttgatgtca gtcatcggcc tcaggtatc     180
tctaatcgct tctctggctc caagtccggc aacacggcct ccctgaccat ctctgggctc    240
cacattgagg acgagggcga ttatttctgc tcttcactga cagacagaag ccatcgcata    300
ttcggcggcg ggaccaagct gaccgttcta                                     330

<210> SEQ ID NO 130
<211> LENGTH: 411
<212> TYPE: DNA
<213> ORGANISM: Homo sapiens

<400> SEQUENCE: 130
cacgaacaac tggtggaggc cggggggaggc gtggtccagc cggggggtc cctgagactc     60
tcctgtttag cgtctggatt cacgtttcac aaatatggca tgcactgggt ccgccaggct    120
ccaggcaagg gcctggagtg ggtggcactc atctcagatg acggaatgag gaaatatcat    180
tcagactcca tgtggggccg agtcaccatc tccagagaca attccaagaa cactctttat    240

```
ctgcaattca gcagcctgag agtcgaagac acggctatgt tcttctgtgc gagagaggcc    300
ggtgggccaa tctggcatga cgacgtcaaa tattacgatt ttaatgacgg ctactacaac    360
tatcactaca tggacgtctg gggcaagggg accaaggtca ccgtctcctc a             411
```

<210> SEQ ID NO 131
<211> LENGTH: 330
<212> TYPE: DNA
<213> ORGANISM: Homo sapiens

<400> SEQUENCE: 131

```
cagtctgccc tgactcagcc tgcctccgtg tctgggtctc ctggacagac gatcaccatc    60
tcctgcaatg gaaccagccg tgacgttggt ggatttgact ctgtctcctg gtatcaacaa    120
tccccaggga aagcccccaa agtcatggtt tttgatgtca gtcatcggcc ctcaggtatg    180
tctaatcgct tctctggctc caagtccggc aacacggcct ccctgaccat ttctgggctc    240
cacattgagg acgagggcga ttatttctgc tcttcattga cagacagaag ccatcgcata    300
ttcggcggcg ggaccaagct gaccgttcta                                     330
```

<210> SEQ ID NO 132
<211> LENGTH: 411
<212> TYPE: DNA
<213> ORGANISM: Homo sapiens

<400> SEQUENCE: 132

```
caggaaaaac tggtggagtc tggggaggc gtggtccagc cggggggtc cctgagactc      60 tcctgtttag cgtctggatt caccttcac aaatatggca tgcactgggt ccgccaggct     120
ccaggcaagg gcctggagtg ggtggcactc atctcagatg acggaatgag gaaatatcat    180
tcagactcca tgtggggccg agtcaccatc tccagagaca attccaagaa cactttatat    240
ctgcaattca gcagcctgaa agtcgaagac acggctatgt tcttctgtgc gagagaggct    300
ggtgggccaa tctggcatga cgacgtcaaa tattacgatt ttaatgacgg ctactacaat    360
taccactaca tggacgtctg gggcaagggg accattgtca ccgtctcctc a             411
```

<210> SEQ ID NO 133
<211> LENGTH: 330
<212> TYPE: DNA
<213> ORGANISM: Homo sapiens

<400> SEQUENCE: 133

```
cagtctgccc tgactcagcc tgcctccgtg tctgggtctc ctggacagac gatcaccatc    60
tcctgcaatg gaaccagaag tgacgttggt ggatttgact ctgtctcctg gtaccaacaa    120
tccccaggga aagcccccaa agtcatggtt tttgatgtca gtcatcggcc ctcaggtatc    180
tctaatcgct tctctggctc caagtccggc aacacggcct ccctgaccat ctctgggctc    240
cacattgagg acgagggcga ttatttctgc tcttcactga cagacagaag ccatcgcata    300
ttcggcggcg ggaccaaggt gaccgttcta                                     330
```

<210> SEQ ID NO 134
<211> LENGTH: 411
<212> TYPE: DNA
<213> ORGANISM: Homo sapiens

<400> SEQUENCE: 134

```
caggaacaac tgttggagtc tggggaggc gtggtccagc cggggggtc cctgagactc      60
```

```
tcctgtttag cgtctggatt cacgtttcac aaatatggca tgcactgggt ccgccaggct    120
ccaggcaagg gcctggagtg gtggcactc atctcagatg acggaatgag gaaatatcat     180
tcaaactcca tgtggggccg agtcaccatc tccagagaca attccaagaa cactctttat    240
ctgcaattca gcagcctgaa agtcgaagac acggctatgt tcttctgtgc gagagaggct    300
ggtgggccaa tctggcatga cgacgtcaaa tattacgatt ttaatgacgg ctactacaac    360
taccactaca tggacgtctg ggcaaggggg accacggtca ccgtctcctc a             411
```

<210> SEQ ID NO 135
<211> LENGTH: 330
<212> TYPE: DNA
<213> ORGANISM: Homo sapiens

<400> SEQUENCE: 135

```
cagtctgccc tgactcagcc tgcctccgtg tctgggtctc ctggacagac gatcaccatc    60
tcctgcaatg gaaccagcag tgacgttggt ggatttgact ctgtctcctg gtatcaacaa    120
tccccaggga agccccccaa agtcatggtt tttgatgtca gtcatcggcc ctcaggtatc    180
tctaatcgct tctctggctc caagtccggc aacacggcct ccctgaccat ctctgggctc    240
cacattgagg acgagggcga ttatttctgc tcttcactga cagacagaag ccatcgcata    300
ttcggcggcg ggaccaaggt gaccgttcta                                     330
```

<210> SEQ ID NO 136
<211> LENGTH: 411
<212> TYPE: DNA
<213> ORGANISM: Homo sapiens

<400> SEQUENCE: 136

```
caggaacaac tggtggagtc tgggggaggc gtggtccagc cggggggggtc cctgagactc    60 tcctgtttag cgtctggatt cacgtttcac aaatatggca tgcactgggt ccgccaggct    120
ccaggcaagg gcctggagtg gtggcactc atctcagatg acggaatgag gaaatatcat     180
tcagactcca tgtggggccg agtcaccatc tccagagaca attccaagaa cactctttat    240
ctgcaattca gcagcctgaa agtcgaagac acggctatgt tcttctgtgc gagagaggct    300
ggtgggccaa tctggcatga cgacgtcaaa tattacgatt ttaatgacgg ctactacaac    360
taccactaca tggacgtctg ggcaaggggg accacggtca ccgtctcctc a             411
```

<210> SEQ ID NO 137
<211> LENGTH: 330
<212> TYPE: DNA
<213> ORGANISM: Homo sapiens

<400> SEQUENCE: 137

```
cagtctgccc tgactcagcc tgcctccgtg tctgggtctc ctggacagac gatcaccatc    60
tcctgcaatg gaaccagcag tgacgttggt ggatttgact ctgtctcctg gtatcaacaa    120
tccccaggga agccccccaa agtcatggtt tttgatgtca gtcatcggcc ctcaggtatc    180
tctaatcgct tctctggctc caagtccggc aacacggcct ccctgaccat ctctgggctc    240
cacattgagg acgagggcga ttatttctgc tcttcactga cagacagaag ccatcgcata    300
ttcggcggcg ggaccaaggt gaccgttcta                                     330
```

<210> SEQ ID NO 138
<211> LENGTH: 1461
<212> TYPE: DNA
<213> ORGANISM: Homo sapiens

<400> SEQUENCE: 138

```
atggagtttg ggctgagctg ggttttcctc gcaactctgt taagagttgt gaagtgtcag     60
gaaaaactgg tggagtctgg gggaggcgtg gtccagccgg gggggtccct gagactctcc    120
tgtttagcgt ctggattcac ctttcacaaa tatggcatgc actgggtccg ccaggctcca    180
ggcaagggcc tggagtgggt ggcactcatc tcagatgacg gaatgaggaa atatcattca    240
gactccatgt ggggccgagt caccatctcc agagacaatt ccaagaacac tctatatctg    300
caattcagca gcctgaaagt cgaagacacg gctatgttct tctgtgcgag agaggctggt    360
gggccaatct ggcatgacga cgtcaaatat tacgatttta atgacggcta ctacaactac    420
cactacatgg acgtctgggg caaggggacc acggtcaccg tctcctcagc gtcgaccaag    480
ggcccatcgg tcttccctct ggcaccatca tccaagtcga cctctggggg cacagcggcc    540
ctgggctgcc tggtcaagga ctacttcccc gaaccggtga cggtgtcgtg gaactcaggc    600
gccctgacca gcggcgtgca caccttcccg gctgtcctac agtcctcagg actctactcc    660
ctcagcagcg tggtgaccgt gccctccagc agcttgggca cccagaccta catctgcaac    720
gtgaatcaca agcccagcaa caccaaggtg gacaagagag ttgagcccaa atcttgtgac    780
aaaactcaca catgcccacc gtgcccagca cctgaactcc tggggggacc gtcagtcttc    840
ctcttccccc caaaacccaa ggacaccctc atgatctccc ggacccctga ggtcacatgc    900
gtggtggtgg acgtgagcca cgaagaccct gaggtcaagt tcaactggta cgtggacggc    960
gtggaggtgc ataatgccaa gacaaagccg cgggaggagc agtacaacag cacgtaccgt   1020
gtggtcagcg tcctcaccgt cctgcaccag gactggctga atggcaagga gtacaagtgc   1080
aaggtctcca acaaagccct cccagccccc atcgagaaaa ccatctccaa agccaaaggg   1140
cagccccgag aaccacaggt gtacaccctg cccccatccc gggaggagat gaccaagaac   1200
caggtcagcc tgacctgcct ggtcaaaggc ttctatccca gcgacatcgc cgtggagtgg   1260
gagagcaatg ggcagccgga gaacaactac aagaccacgc ctcccgtgct ggactccgac   1320
ggctccttct cctctatag caagctcacc gtggacaaga gcaggtggca gcagggaac   1380
gtcttctcat gctccgtgat gcatgaggct ctgcacaacc actacacgca gaagagcctc   1440
tccctgtctc cgggtaaatg a                                             1461
```

<210> SEQ ID NO 139
<211> LENGTH: 467
<212> TYPE: PRT
<213> ORGANISM: Homo sapiens

<400> SEQUENCE: 139

```
Gln Glu Lys Leu Val Glu Ser Gly Gly Val Val Gln Pro Gly Gly
1               5                   10                  15

Ser Leu Arg Leu Ser Cys Leu Ala Ser Gly Phe Thr Phe His Lys Tyr
            20                  25                  30

Gly Met His Trp Val Arg Gln Ala Pro Gly Lys Gly Leu Glu Trp Val
        35                  40                  45

Ala Leu Ile Ser Asp Asp Gly Met Arg Lys Tyr His Ser Asp Ser Met
    50                  55                  60

Trp Gly Arg Val Thr Ile Ser Arg Asp Asn Ser Lys Asn Thr Leu Tyr
65                  70                  75                  80

Leu Gln Phe Ser Ser Leu Lys Val Glu Asp Thr Ala Met Phe Phe Cys
                85                  90                  95
```

```
Ala Arg Glu Ala Gly Gly Pro Ile Trp His Asp Val Lys Tyr Tyr
                100                 105                 110

Asp Phe Asn Asp Gly Tyr Tyr Asn Tyr His Tyr Met Asp Val Trp Gly
    115                 120                 125

Lys Gly Thr Thr Val Thr Val Ser Ser Ala Ser Thr Lys Gly Pro Ser
130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 140
<211> LENGTH: 137
<212> TYPE: PRT
<213> ORGANISM: Homo sapiens

<400> SEQUENCE: 140
```

Gln Glu Lys Leu Val Glu Ser Gly Gly Gly Val Val Gln Pro Gly Gly
1               5                   10                  15

Ser Leu Arg Leu Ser Cys Leu Ala Ser Gly Phe Thr Phe His Lys Tyr
            20                  25                  30

Gly Met His Trp Val Arg Gln Ala Pro Gly Lys Gly Leu Glu Trp Val
        35                  40                  45

Ala Leu Ile Ser Asp Asp Gly Met Arg Lys Tyr His Ser Asp Ser Met
    50                  55                  60

Trp Gly Arg Val Thr Ile Ser Arg Asp Asn Ser Lys Asn Thr Leu Tyr
65                  70                  75                  80

Leu Gln Phe Ser Ser Leu Lys Val Glu Asp Thr Ala Met Phe Phe Cys
                85                  90                  95

Ala Arg Glu Ala Gly Gly Pro Ile Trp His Asp Asp Val Lys Tyr Tyr
            100                 105                 110

Asp Phe Asn Asp Gly Tyr Tyr Asn Tyr His Tyr Met Asp Val Trp Gly
        115                 120                 125

Lys Gly Thr Thr Val Thr Val Ser Ser
            130                 135

<210> SEQ ID NO 141
<211> LENGTH: 708
<212> TYPE: DNA
<213> ORGANISM: Homo sapiens

<400> SEQUENCE: 141
atggcctggg ctctgctatt cctcaccctc ttcactcagg gcacagggtc ctggggccag      60
tctgccctga ctcagcctgc tccgtgtct gggtctcctg gacagacgat caccatctcc     120
tgcaatggaa ccagaagtga cgttggtgga tttgactctg tctcctggta ccaacaatcc     180
ccagggagag cccccaaagt catggttttt gatgtcagtc atcggccctc aggtatctct     240
aatcgcttct ctggctccaa gtccggcaac acggcctccc tgaccatctc tgggctccac     300
attgaggacg agggcgatta tttctgctct tcactgacag acagaagcca tcgcatattc     360
ggcggcggga ccaagctgac cgttctaggt cagcccaagg ctgccccctc ggtcactctg     420
ttcccgccct cctctgagga gcttcaagcc aacaaggcca cactggtgtg tctcataagt     480
gacttctacc cgggagccgt gacagtggcc tggaaggcag atagcagccc cgtcaaggcg     540
ggagtggaga ccaccacacc ctccaaacaa agcaacaaca gtacgcggc cagcagctac     600
ctgagcctga cgcctgagca gtggaagtcc cacaaaagct acagctgcca ggtcacgcat     660
gaagggagca ccgtggagaa gacagtggcc cctacagaat gttcatag              708

<210> SEQ ID NO 142
<211> LENGTH: 216
<212> TYPE: PRT
<213> ORGANISM: Homo sapiens

<400> SEQUENCE: 142

Gln Ser Ala Leu Thr Gln Pro Ala Ser Val Ser Gly Ser Pro Gly Gln
1               5                   10                  15

Thr Ile Thr Ile Ser Cys Asn Gly Thr Arg Ser Asp Val Gly Gly Phe
            20                  25                  30

Asp Ser Val Ser Trp Tyr Gln Gln Ser Pro Gly Arg Ala Pro Lys Val
        35                  40                  45

Met Val Phe Asp Val Ser His Arg Pro Ser Gly Ile Ser Asn Arg Phe
    50                  55                  60

```
Ser Gly Ser Lys Ser Gly Asn Thr Ala Ser Leu Thr Ile Ser Gly Leu
 65              70                  75                  80

His Ile Glu Asp Glu Gly Asp Tyr Phe Cys Ser Ser Leu Thr Asp Arg
                 85                  90                  95

Ser His Arg Ile Phe Gly Gly Thr Lys Leu Thr Val Leu Gly Gln
                100             105             110

Pro Lys Ala Ala Pro Ser Val Thr Leu Phe Pro Pro Ser Ser Glu Glu
            115             120             125

Leu Gln Ala Asn Lys Ala Thr Leu Val Cys Leu Ile Ser Asp Phe Tyr
        130             135             140

Pro Gly Ala Val Thr Val Ala Trp Lys Ala Asp Ser Ser Pro Val Lys
145             150             155             160

Ala Gly Val Glu Thr Thr Thr Pro Ser Lys Gln Ser Asn Asn Lys Tyr
                165             170             175

Ala Ala Ser Ser Tyr Leu Ser Leu Thr Pro Glu Gln Trp Lys Ser His
            180             185             190

Lys Ser Tyr Ser Cys Gln Val Thr His Glu Gly Ser Thr Val Glu Lys
        195             200             205

Thr Val Ala Pro Thr Glu Cys Ser
    210             215
```